US012060383B2

(12) United States Patent
Sebo et al.

(10) Patent No.: US 12,060,383 B2
(45) Date of Patent: *Aug. 13, 2024

(54) PROTECTED FLUORESCENT REAGENT COMPOUNDS

(71) Applicant: Pacific Biosciences of California, Inc., Menlo Park, CA (US)

(72) Inventors: Lubomir Sebo, Redwood City, CA (US); Jeremiah Hanes, Menlo Park, CA (US); Gene Shen, Santa Clara, CA (US); Louis Brogley, Santa Cruz, CA (US); Stephen Yue, Eugene, OR (US); Frank Zheng, Fremont, CA (US); Yuri Lapin, Newark, CA (US); John Lyle, Fremont, CA (US); Honey Osuna, San Francisco, CA (US); Andrei Fedorov, San Bruno, CA (US)

(73) Assignee: Pacific Biosciences of California, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/167,729

(22) Filed: Feb. 10, 2023

(65) Prior Publication Data

US 2023/0192749 A1 Jun. 22, 2023

Related U.S. Application Data

(63) Continuation of application No. 17/006,638, filed on Aug. 28, 2020, now Pat. No. 11,578,093, which is a continuation of application No. 15/966,334, filed on Apr. 30, 2018, now Pat. No. 10,800,805, which is a continuation of application No. 14/452,497, filed on Aug. 5, 2014, now Pat. No. 9,957,291.

(60) Provisional application No. 61/862,502, filed on Aug. 5, 2013.

(51) Int. Cl.
| C07H 19/10 | (2006.01) |
| C07F 9/6558 | (2006.01) |
| C07F 9/6561 | (2006.01) |
| C09B 23/06 | (2006.01) |
| C09B 23/08 | (2006.01) |
| C09B 69/10 | (2006.01) |
| C12Q 1/6869 | (2018.01) |

(52) U.S. Cl.
CPC ......... *C07H 19/10* (2013.01); *C07F 9/65586* (2013.01); *C07F 9/65616* (2013.01); *C09B 23/06* (2013.01); *C09B 23/083* (2013.01); *C09B 69/105* (2013.01); *C12Q 1/6869* (2013.01)

(58) Field of Classification Search
CPC .. C07H 19/10; C07F 9/65586; C07F 9/65616; C09B 23/06; C09B 23/083; C09B 69/105; C12Q 1/6869
See application file for complete search history.

(56) References Cited

U.S. PATENT DOCUMENTS

| 4,711,955 A | 12/1987 | Ward et al. |
| 5,223,384 A | 6/1993 | Ohbayashi et al. |
| 5,688,648 A | 11/1997 | Mathies et al. |
| 6,153,442 A | 11/2000 | Pirio et al. |
| 6,255,083 B1 | 7/2001 | Williams |
| 6,399,335 B1 | 6/2002 | Kao et al. |
| 6,787,308 B2 | 9/2004 | Balasubramanian et al. |
| 6,917,726 B2 | 7/2005 | Levene et al. |
| 7,013,054 B2 | 3/2006 | Levene et al. |
| 7,041,812 B2 | 5/2006 | Kumar et al. |
| 7,056,661 B2 | 6/2006 | Korlach et al. |
| 7,405,281 B2 | 7/2008 | Xu et al. |
| 7,476,503 B2 | 1/2009 | Turner et al. |
| 7,767,805 B2 | 8/2010 | Buzby |
| 7,777,013 B2 | 8/2010 | Xu et al. |
| 7,842,475 B2 | 11/2010 | Zheng et al. |
| 7,906,284 B2 | 3/2011 | Turner et al. |
| 7,968,702 B2 | 6/2011 | Wegener et al. |
| 7,973,146 B2 | 7/2011 | Shen et al. |
| 8,058,031 B2 | 11/2011 | Xu et al. |
| 8,133,672 B2 | 3/2012 | Bjornson et al. |

(Continued)

FOREIGN PATENT DOCUMENTS

| WO | 199106678 A1 | 5/1991 |
| WO | 199627025 A1 | 9/1996 |

(Continued)

OTHER PUBLICATIONS

Astruc et al. (2010) Chem. Rev. 110:1857-1959.
Baskin et al. (2007) PNAS 104:16793-16797.
Eid et al. (2009) Science 323:133-158.
Evans (2007) Aus. J. Chem. 60:384-395.
Extended European Search Report Issued Apr. 4, 2017 for European Patent Application 14834734.7.
Genisphere Poc Tech. Note (2012).
International Search Report and Written Opinion Dated Oct. 27, 2014 for Related PCT/US14/49833.

(Continued)

*Primary Examiner* — Jezia Riley
(74) *Attorney, Agent, or Firm* — VLP Law Group LLP

(57) ABSTRACT

Protected fluorescent reagent compounds and their methods of synthesis are provided. The compounds are useful in various fluorescence-based analytical methods, including the analysis of highly multiplexed optical reactions in large numbers at high densities, such as single molecule real time nucleic acid sequencing reactions. The compounds contain fluorescent dye elements, that allow the compounds to be detected with high sensitivity at desirable wavelengths, binding elements, that allow the compounds to be recognized specifically by target biomolecules, and protective shield elements, that decrease undesirable contacts between the fluorescent dye elements and the bound target biomolecules and that therefore decrease photodamage of the bound target biomolecules by the fluorescent dye elements.

31 Claims, 50 Drawing Sheets

(56) References Cited

U.S. PATENT DOCUMENTS

| | | | |
|---|---|---|---|
| 8,133,702 B2 | 3/2012 | Shen et al. | |
| 8,182,993 B2 | 5/2012 | Tomaney et al. | |
| 8,236,499 B2 | 8/2012 | Patel et al. | |
| 8,257,954 B2 | 9/2012 | Clark et al. | |
| 9,957,291 B2 * | 5/2018 | Sebo | C07H 19/10 |
| 10,800,805 B2 * | 10/2020 | Sebo | C07F 9/65616 |
| 11,578,093 B2 * | 2/2023 | Sebo | C09B 23/06 |
| 2003/0077610 A1 | 4/2003 | Nelson et al. | |
| 2003/0162213 A1 | 8/2003 | Fuller et al. | |
| 2003/0162216 A1 | 8/2003 | Gold et al. | |
| 2004/0241716 A1 | 12/2004 | Kumar et al. | |
| 2007/0249652 A1 | 10/2007 | Parenty et al. | |
| 2009/0024331 A1 | 1/2009 | Tomaney et al. | |
| 2009/0118129 A1 | 5/2009 | Turner | |
| 2009/0142316 A1 | 6/2009 | Majoral et al. | |
| 2009/0186343 A1 | 7/2009 | Wang et al. | |
| 2009/0208957 A1 | 8/2009 | Korlach et al. | |
| 2009/0325260 A1 | 12/2009 | Otto et al. | |
| 2010/0075328 A1 | 3/2010 | Bjornson et al. | |
| 2010/0136592 A1 | 6/2010 | Kong et al. | |
| 2010/0152424 A1 | 6/2010 | Korlach et al. | |
| 2010/0167299 A1 | 7/2010 | Korlach | |
| 2010/0221716 A1 | 9/2010 | Flusberg et al. | |
| 2010/0255488 A1 | 10/2010 | Kong et al. | |
| 2011/0183320 A1 | 7/2011 | Flusberg et al. | |
| 2011/0244447 A1 | 10/2011 | Korlach | |
| 2011/0256618 A1 | 10/2011 | Eid et al. | |
| 2012/0052506 A1 | 3/2012 | Yue et al. | |
| 2012/0052507 A1 | 3/2012 | Shen | |
| 2012/0058469 A1 | 3/2012 | Shen | |
| 2012/0058473 A1 | 3/2012 | Yue et al. | |
| 2012/0058482 A1 | 3/2012 | Shen et al. | |
| 2012/0077189 A1 | 3/2012 | Shen et al. | |
| 2012/0115736 A1 | 5/2012 | Bjornson et al. | |
| 2012/0122779 A1 | 5/2012 | Kirshenbaum et al. | |
| 2013/0289253 A1 | 10/2013 | Luescher et al. | |
| 2013/0316912 A1 | 11/2013 | Bjornson et al. | |
| 2014/0005404 A1 | 1/2014 | Yue et al. | |
| 2014/0080127 A1 | 3/2014 | Yue et al. | |

FOREIGN PATENT DOCUMENTS

| | | |
|---|---|---|
| WO | 2010057185 A1 | 5/2010 |
| WO | 2012027618 A2 | 3/2012 |
| WO | 2012027625 A2 | 3/2012 |
| WO | 2013123258 A1 | 8/2013 |

OTHER PUBLICATIONS

Kim et al. (2013) Biophys. J. 104:1566-1575.
Kolb et al. (2001) Angew. Chem. Int. Ed. Engl. 40:2004-20212.
Levene et al. (2003) Science 299:682-686.
PubChem CID 11341015.
PubChem CID 3514056.
Siriporn et al. (ChemComm 2009, p. 806-808).
European Examination Report dated Apr. 6, 2018, for European Patent Application 14834734.7.
European Examination Report dated Oct. 24, 2018 for European Patent Application 14834734.7.
European Examination Report dated May 22, 2019 for European Patent Application 14834734.7.
European Examination Report dated Dec. 17, 2019 for European Patent Application 14834734.7.
European Examination Report dated May 8, 2020 for European Patent Application 14834734.7.
European Examination Report dated Aug. 3, 2020 for European Patent Application 14834734.7.
Intention to Grant dated Sep. 17, 2021 for European Patent Application 14834734.7.

* cited by examiner

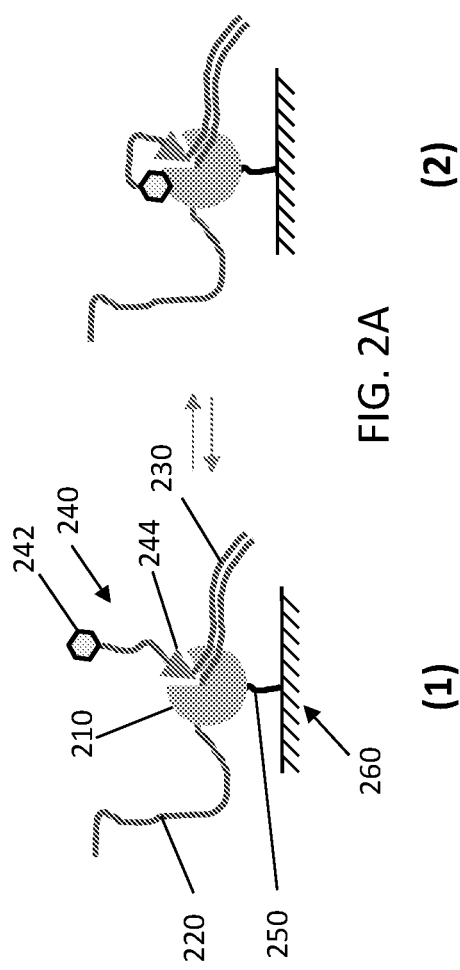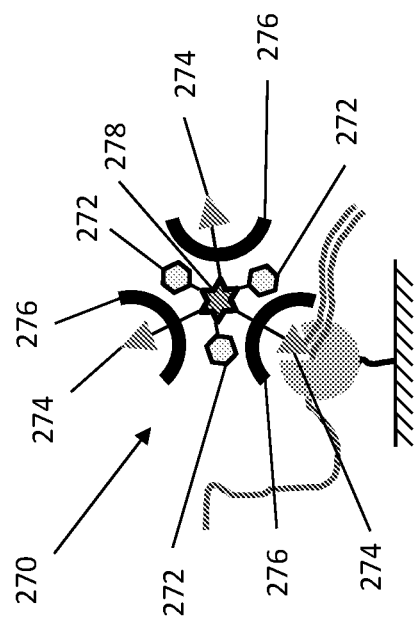
FIG. 2A
FIG. 2B

Compound 3A

Compound 3B

| SMRT Pipe | Condition 1 | Condition 2 | Condition 3 |
|---|---|---|---|
| # of Mapped Bases | 891K | 1425K | 2340K |
| Mapped Subreads | 2691 | 4107 | 5117 |
| Mean Read length | 331bp | 346bp | 457bp |
| Mean Accuracy | 78.58% | 77.82% | 77.31% |

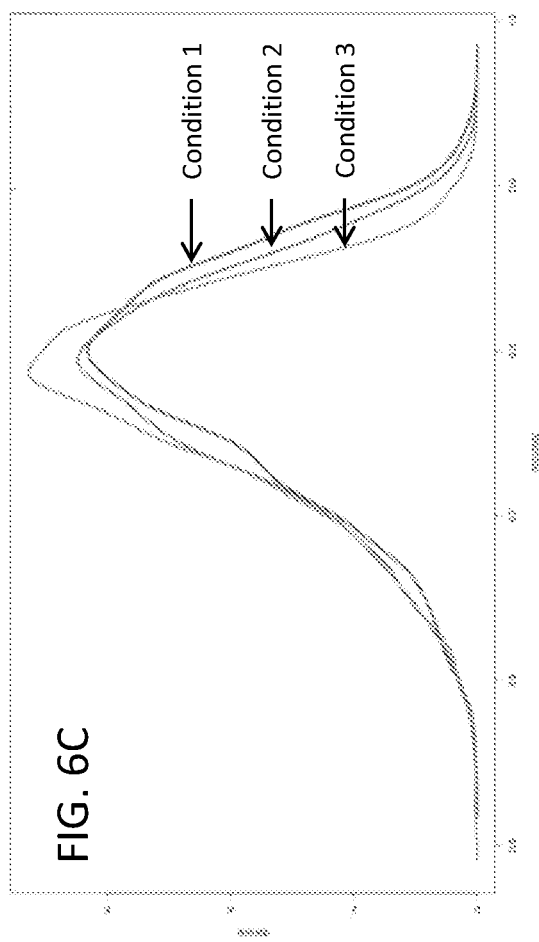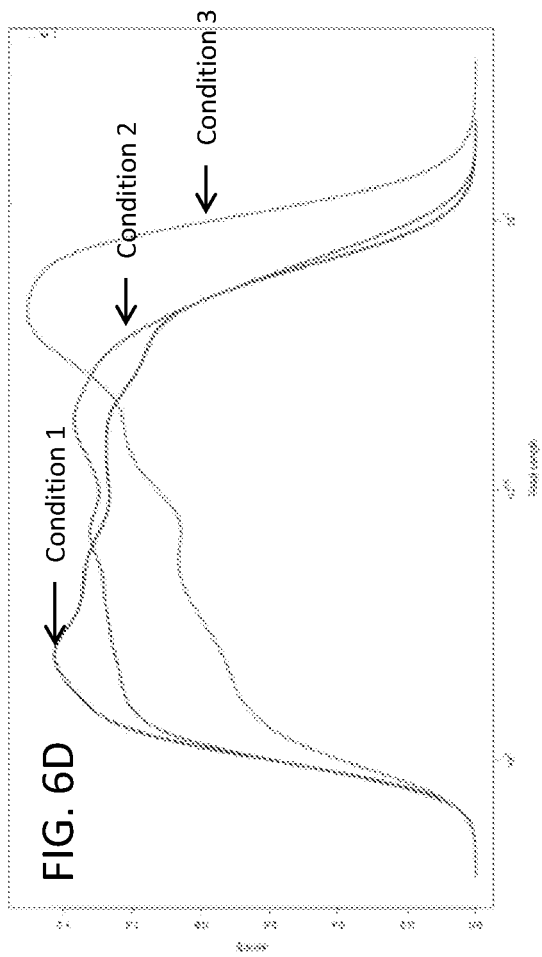
FIG. 6C
FIG. 6D

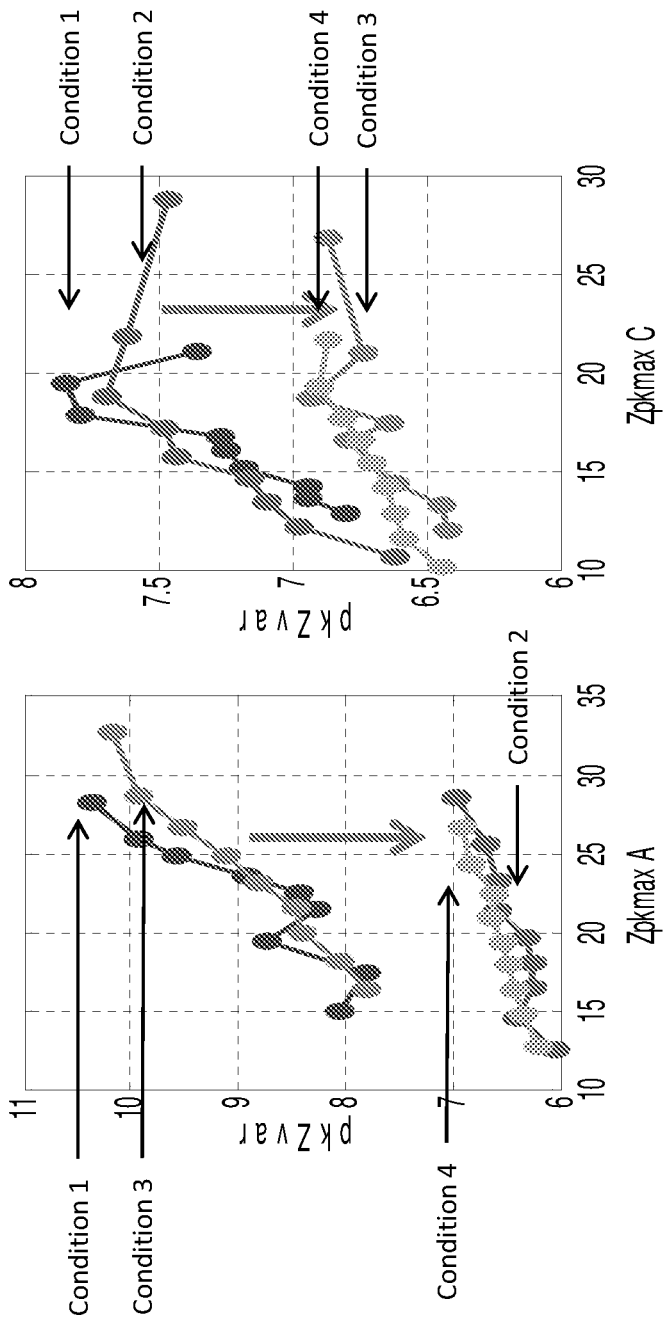

FIG. 14 Scheme 1

FIG. 15 Scheme 2

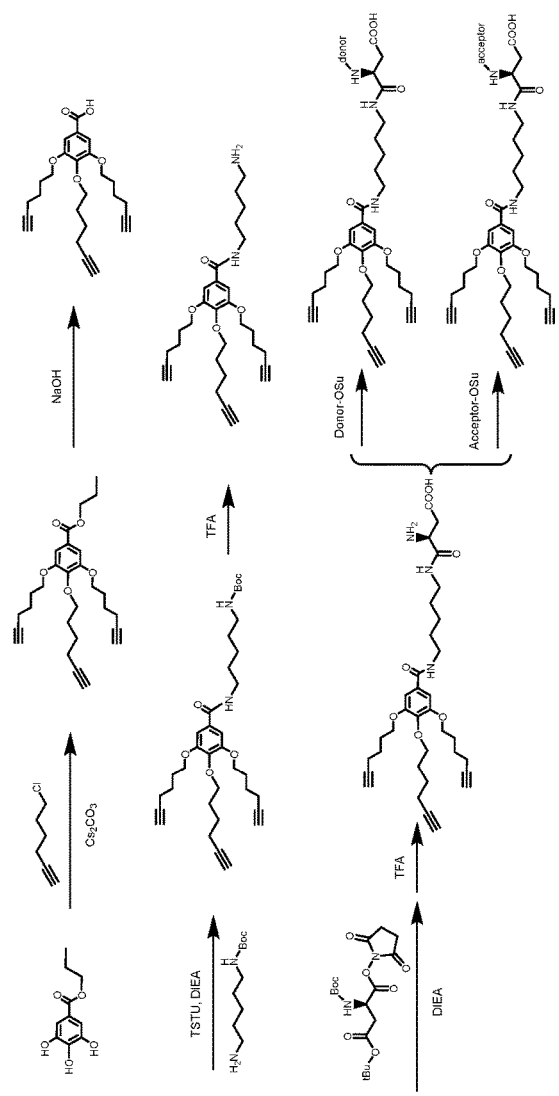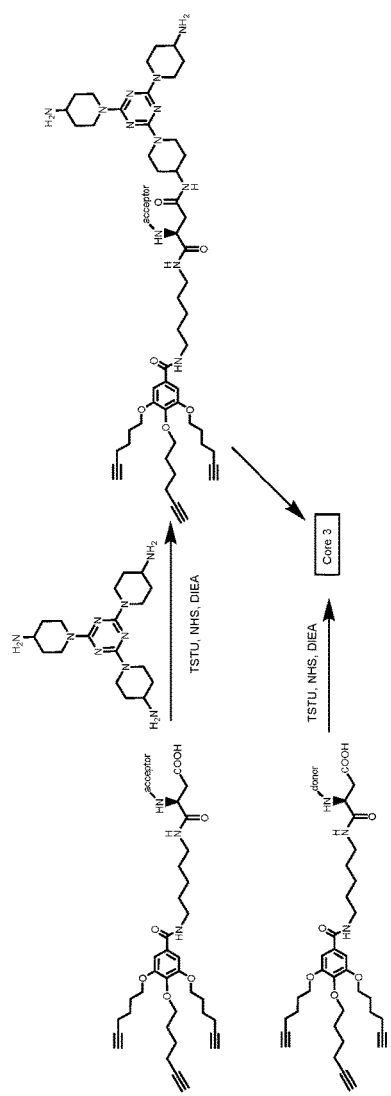
FIG. 16

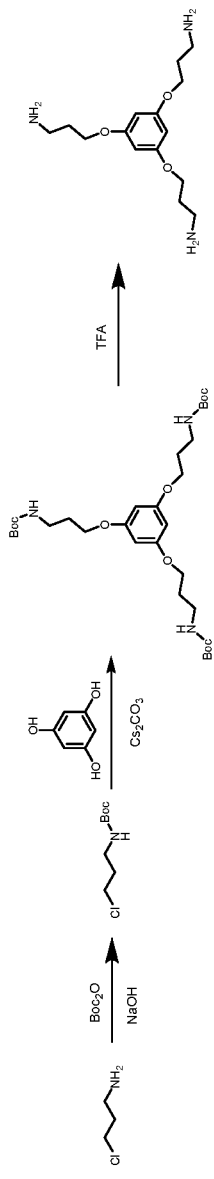
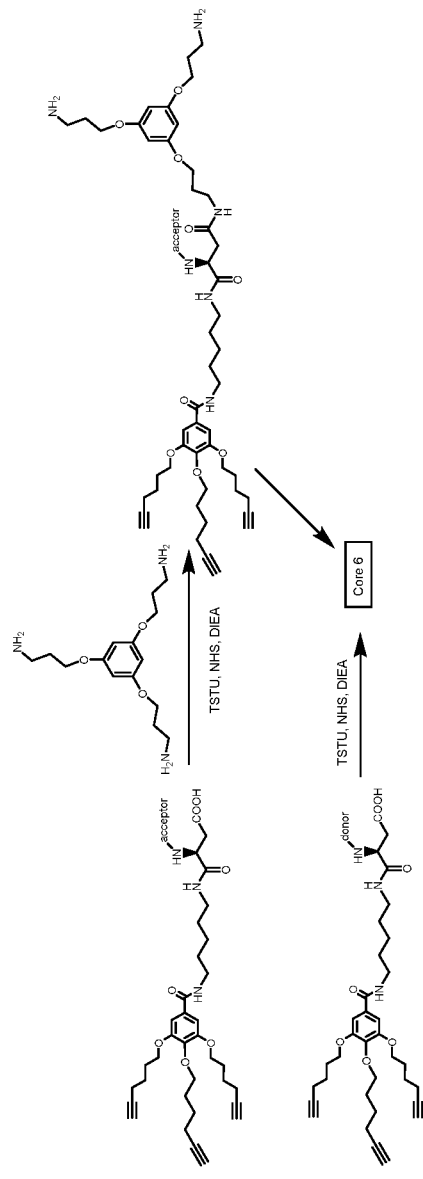
Scheme 6-3
Scheme 6-4;
FIG. 16 (cont.)

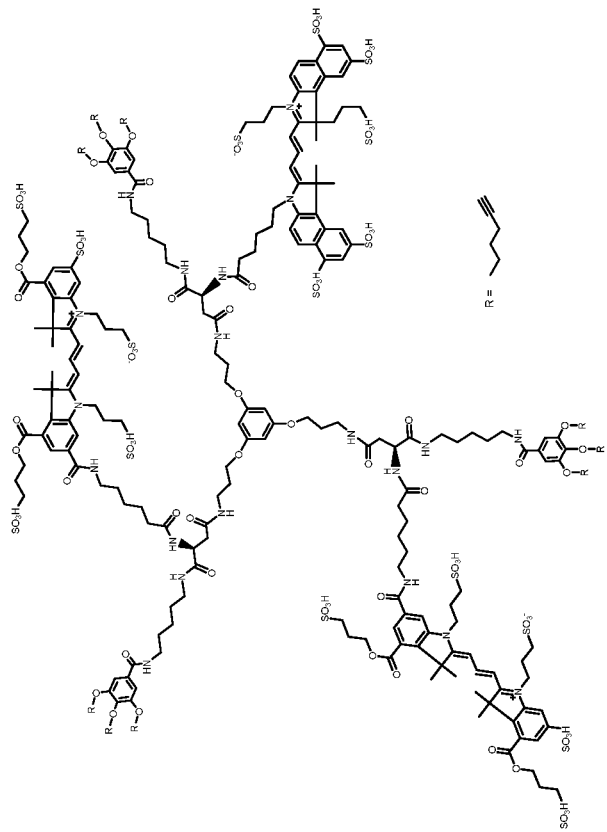
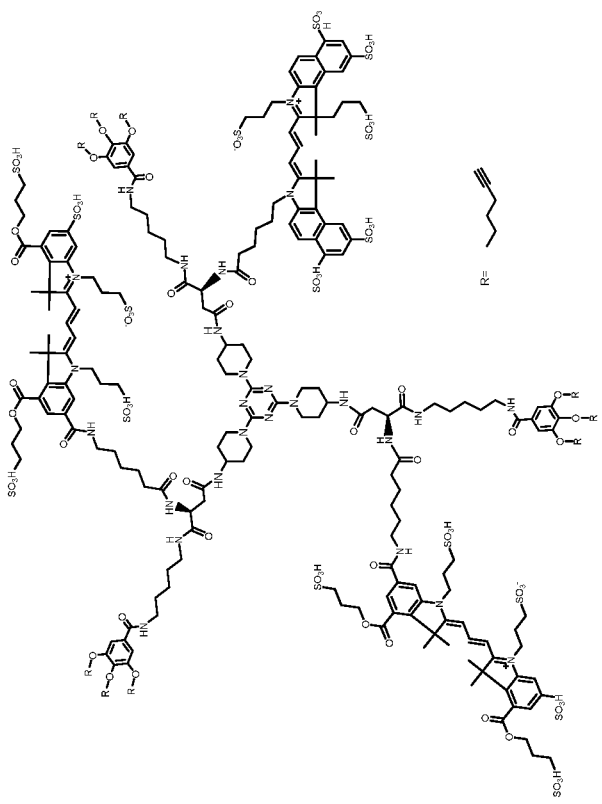
FIG. 17

Scheme 5

Scheme 18

Scheme 19
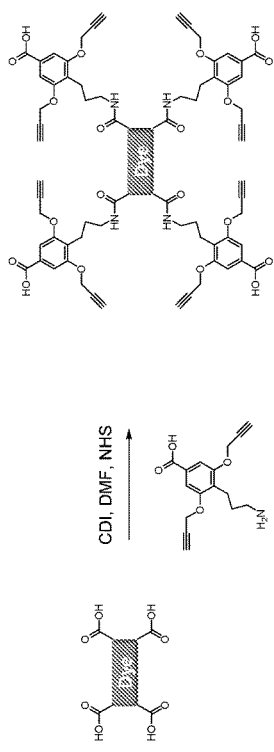
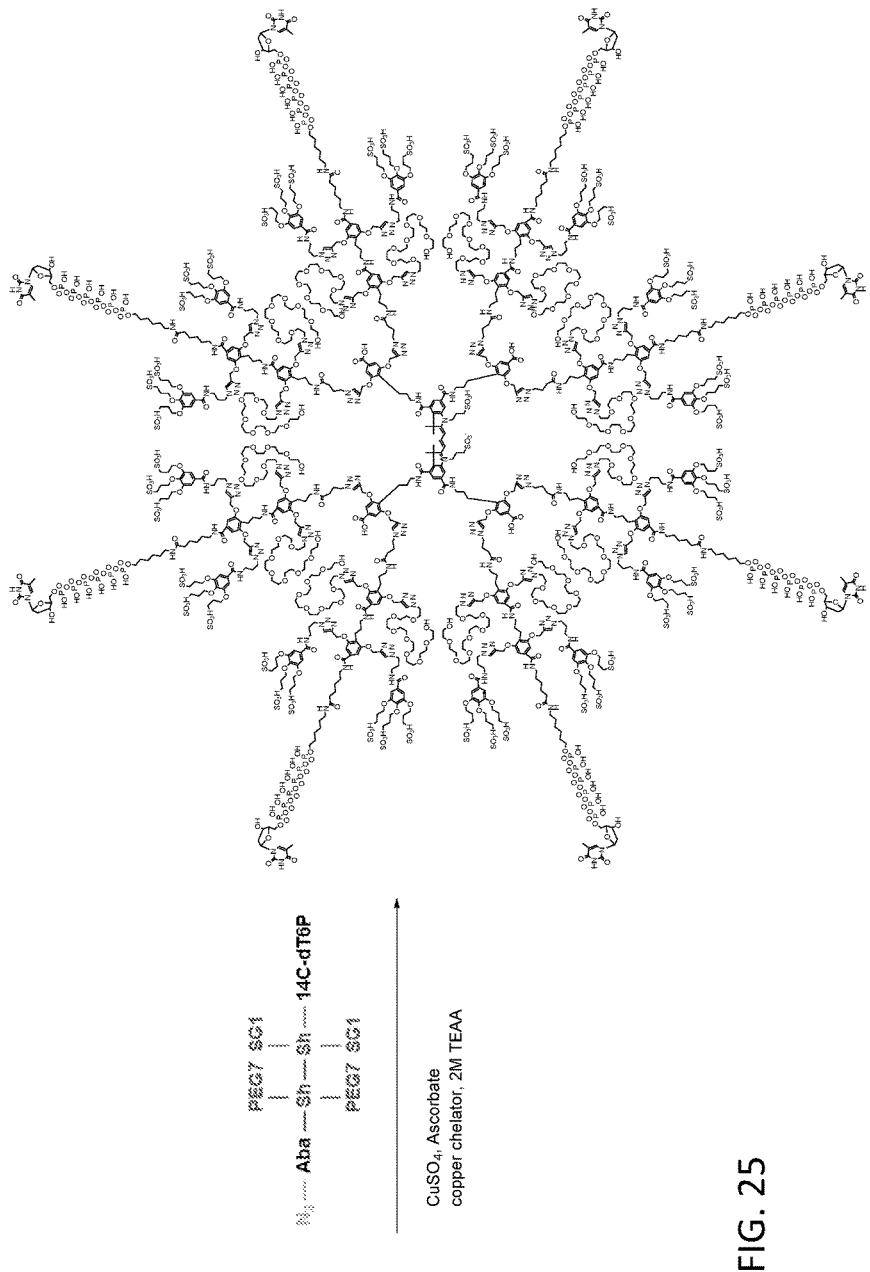
FIG. 25

Scheme 20

Scheme 23

Scheme 24

Scheme 26

Scheme 29

PROTECTED FLUORESCENT REAGENT COMPOUNDS

CROSS-REFERENCE TO RELATED APPLICATION

This application is a continuation of U.S. patent application Ser. No. 17/006,638, filed on Aug. 28, 2020, which is a continuation of U.S. patent application Ser. No. 15/966,334, filed on Apr. 30, 2018, now U.S. Pat. No. 10,800,805, which is a continuation of U.S. patent application Ser. No. 14/452,497, filed on Aug. 5, 2014, now U.S. Pat. No. 9,957,291, which claims the benefit under 35 U.S.C. § 119(e) of U.S. Provisional Application No. 61/862,502, filed on Aug. 5, 2013, the disclosures of which are incorporated herein by reference in their entireties.

BACKGROUND OF THE INVENTION

The use of fluorescent optical signals in analytical systems is extremely powerful due to the sensitivity and selectivity of the signal and the variety and adaptability of the chemistry. Furthermore, the ability to simultaneously measure signals of different wavelengths has facilitated the development of assays in which multiple reactions can be observed at the same time. For example, the use of four-color fluorescent systems in nucleotide sequencing reactions facilitates the detection of all four bases in a single reaction solution. Such methods have been employed in the "real-time" detection of incorporation events, where the act of incorporation gives rise to a signaling event that can be detected. In particularly elegant methods, labeling components are coupled to portions of the nucleotides that are removed during the incorporation event, eliminating any need to remove such labeling components before the next nucleotide is added. See, e.g., Eid, J. et al. (2009) *Science* 323:133-138.

At the same time, however, the exquisite sensitivity of fluorescent probes, and the requirement that the probes be excited to potentially unstable electronic states in order for them to be detected, means that the fluorescent probes may be damaged during the course of the reaction or may inflict damage on other components of the reaction mixture. Such damage is particularly problematic in highly processive reactions, where the reaction mixture may be exposed to excitation radiation for extended periods of time. In enzyme-mediated template-dependent DNA sequencing methods, such as fluorescent based single molecule, real time sequencing reactions, for example, the solution is exposed to excitation radiation while the sequencing reaction is occurring. If the enzyme or other components of the reaction mixture are damaged due to such irradiation, the sequencing reaction can become compromised or end. For example, the enzyme may be inactivated due to interactions with excited dyes, which are typically in close proximity to the enzyme during an incorporation event.

There is therefore a continuing need to increase the performance of fluorescence-based analytical systems. In particular, there is a continuing need to develop fluorescent reagents that are readily detectable at low concentrations and at convenient wavelengths, that are less sensitive to photo-degradation than traditional fluorescent reagents, that are less likely to photodamage or otherwise compromise other components of the analytical system, and that display other desirable characteristics.

SUMMARY OF THE INVENTION

The present disclosure addresses these and other needs by providing in one aspect protected fluorescent reagent compounds having structural formula (I):

$$Z-[S'-B']_m \quad \text{(I); wherein}$$

Z is a multivalent central core element comprising a fluorescent dye element;

each S' is independently an intermediate chemical group, wherein at least one S' comprises a shield element;

each B' is independently a terminal chemical group, wherein at least one B' comprises a binding element; and m is an integer from 2 to 24.

In some embodiments, the shield element decreases photodamage of the compound or of a biomolecule associated with the binding element, and in some embodiments, the shield element decreases contact between the fluorescent dye and the binding element.

In specific embodiments, the shield element comprises a plurality of side chains. In more specific embodiments, at least one side chain has a molecular weight of at least 300, and in even more specific embodiments, all of the side chains have a molecular weight of at least 300.

According to some embodiments, at least one side chain comprises a dendrimer, a polyethylene glycol, or a negatively-charged component. According to specific embodiments, the negatively-charged component comprises a sulfonic acid.

In some embodiments, at least one side chain comprises a substituted phenyl group, and in more specific embodiments, the at least one side chain comprises the structure:

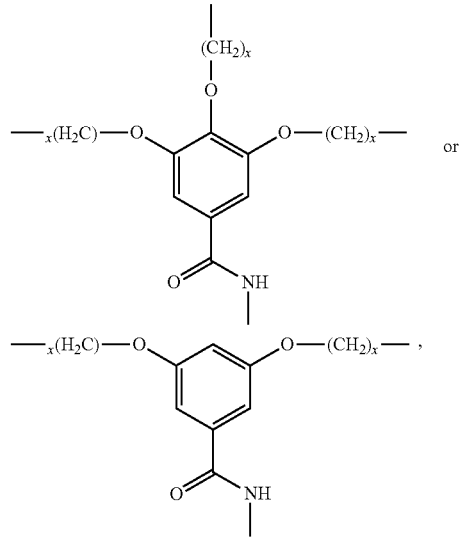

or wherein each x is independently an integer from 1 to 6, or more specifically an integer from 1 to 4. In some embodiments, at least one side chain comprises a triazole, at least one side chain comprises the structure:

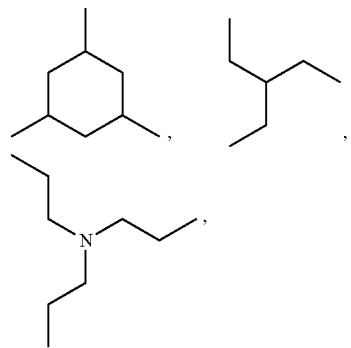

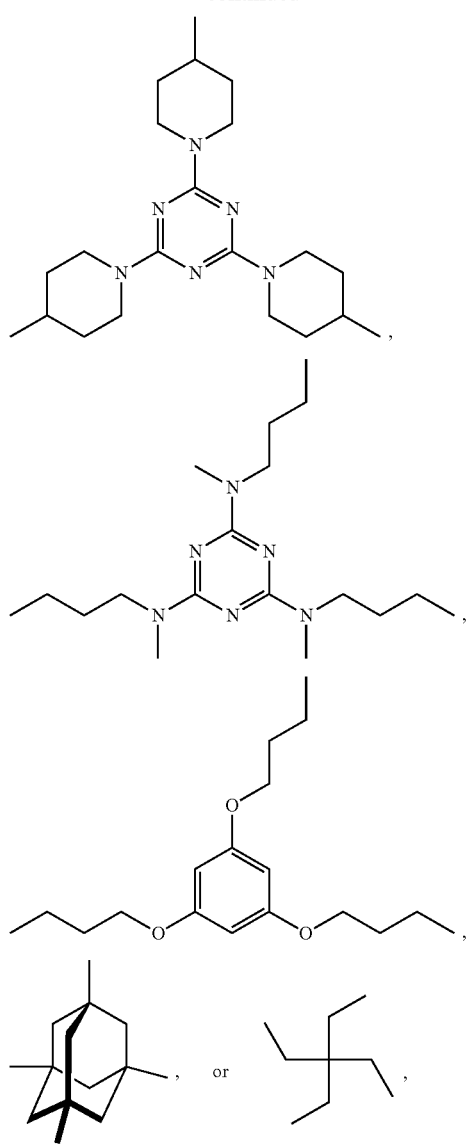
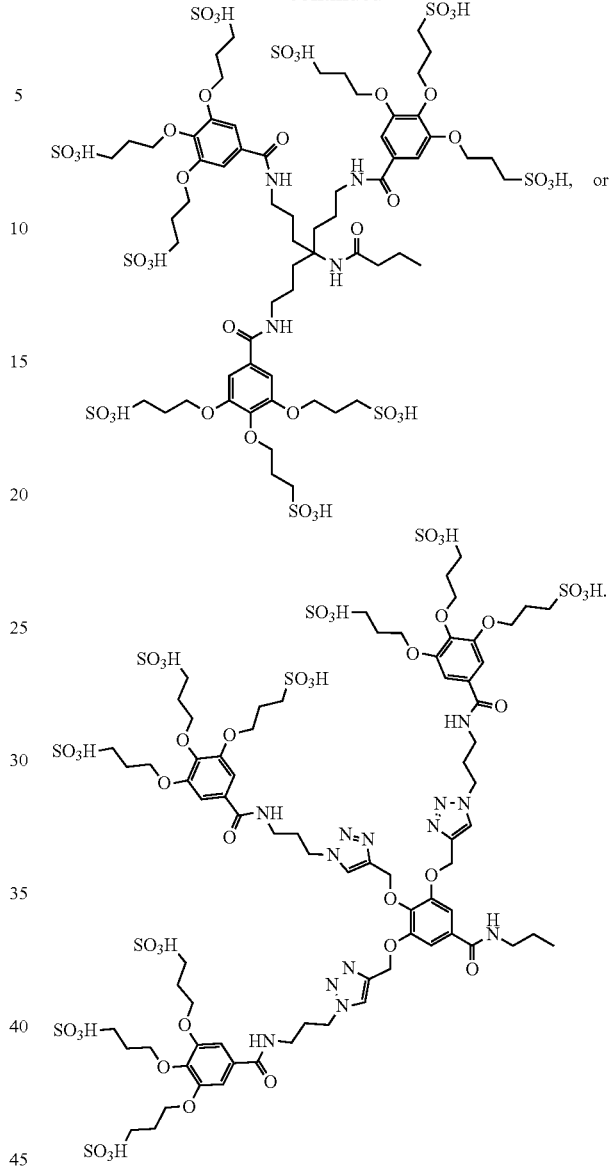
or at least one side chain comprises the structure:
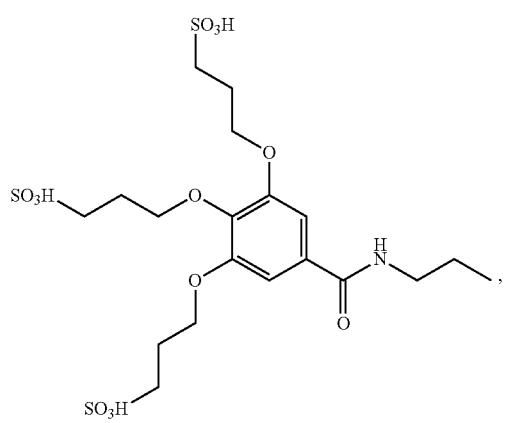
In some embodiments, the shield element comprises the structure:
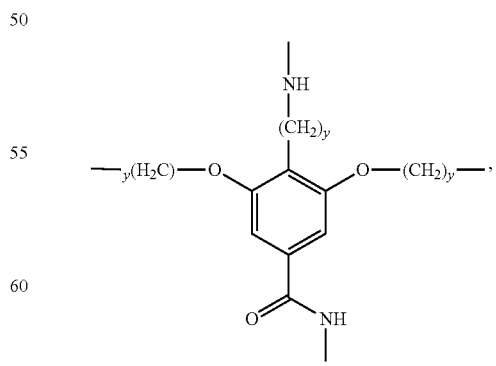
wherein each y is independently an integer from 1 to 6, and in some embodiments the shield element comprises an inner layer and an outer layer.

According to certain embodiments, at least one S'—B' group comprises the structure:
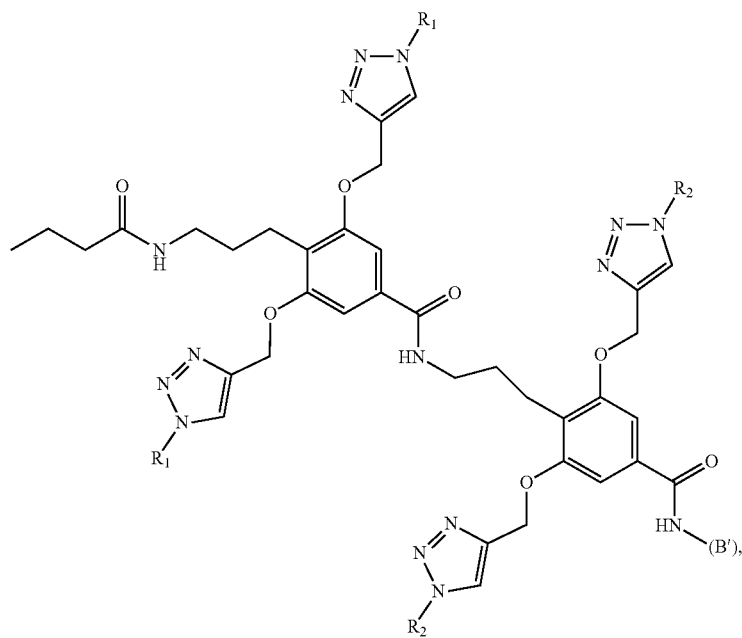
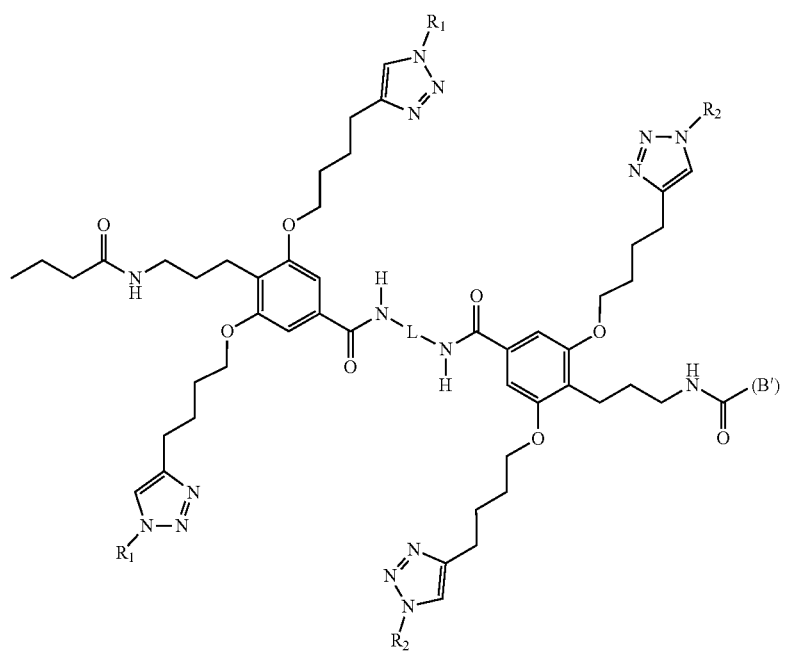

-continued
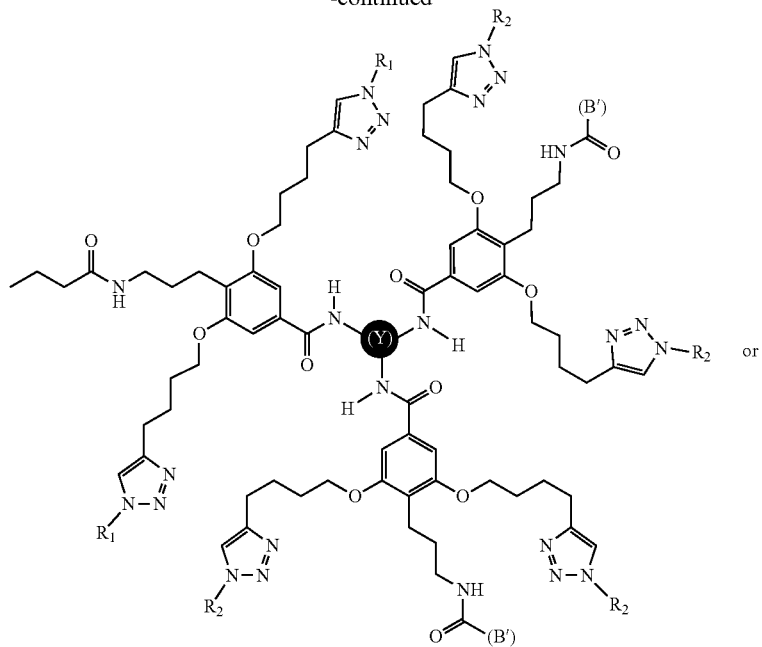
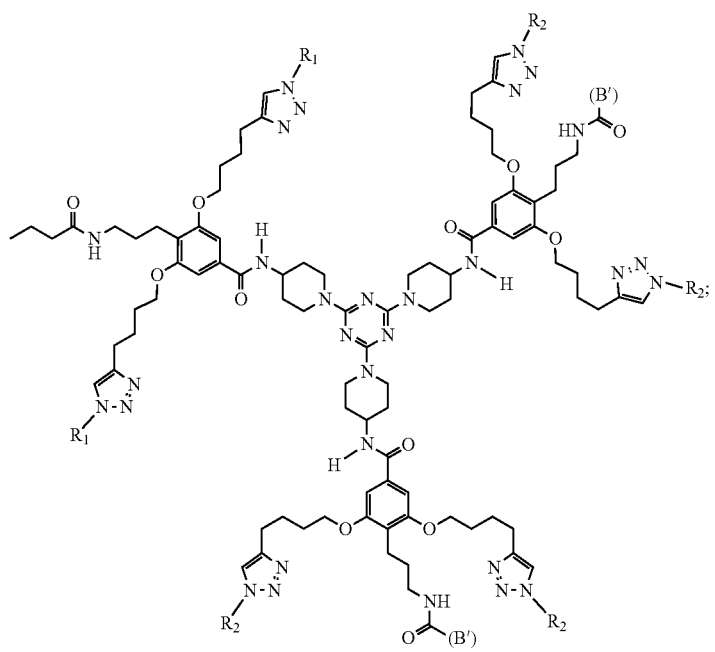
wherein R₁ and R₂ is each independently a side chain;
L is an alkyl, heteroalkyl, cycloalkyl, cycloheteroalkyl, aryl, or heteroaryl linker; and
Y is 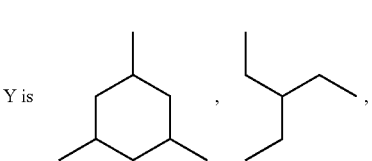,
-continued
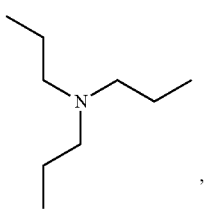,

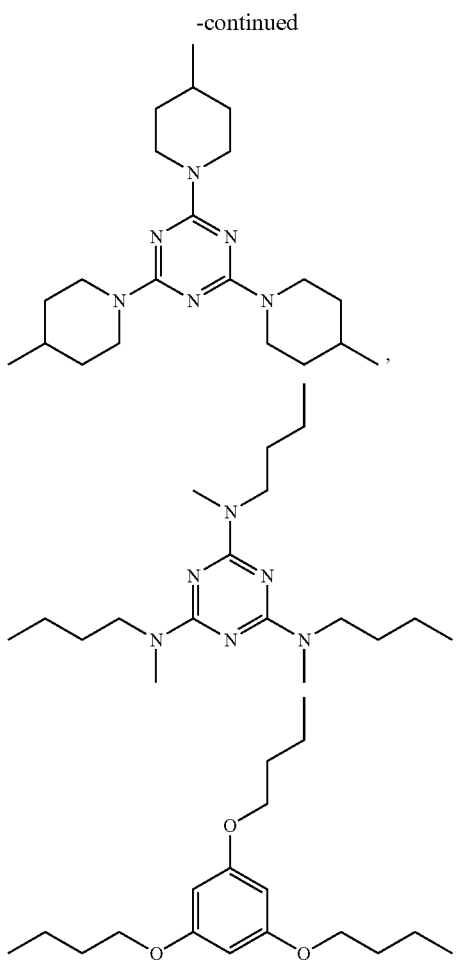

In certain embodiments, the binding element comprises a nucleotide, biotin, or a polyphosphate.

According to certain embodiments, Z may comprise a branching element, and in more specific embodiments, the branching element may comprise a substituted phenyl group or the branching element may comprise the structure:

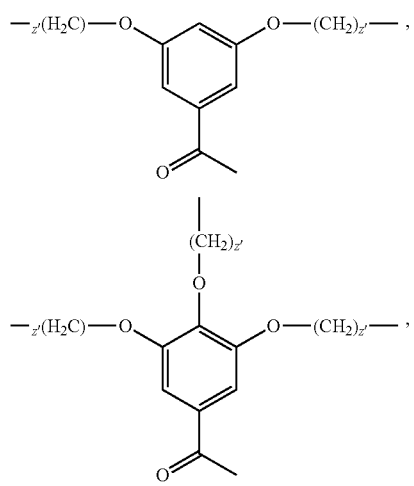

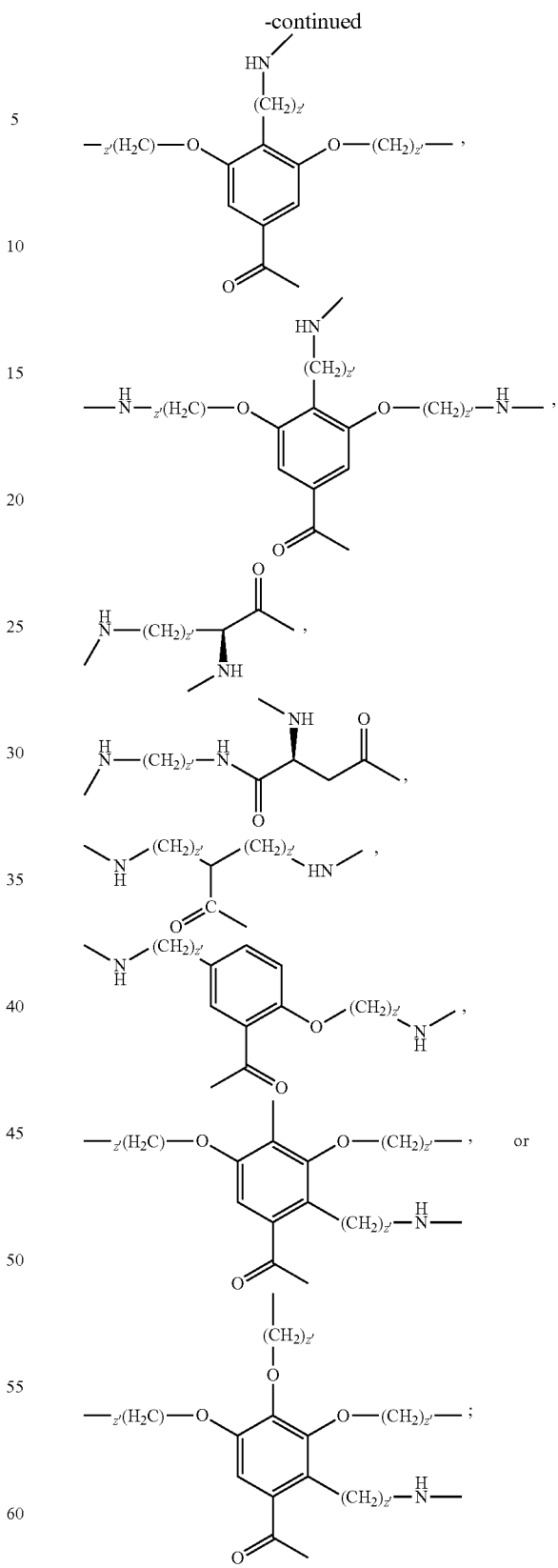

wherein each z' is independently 1 to 6.

In certain compounds of formula (I), m is an integer from 2 to 12, more specifically an integer from 2 to 8, and even more specifically an integer from 2 to 4.

According to certain embodiments, Z may comprise a multivalent fluorescent dye element, and in specific embodiments, the multivalent fluorescent dye element may be a multivalent cyanine dye.

In certain specific embodiments, the multivalent cyanine dye has the formula:

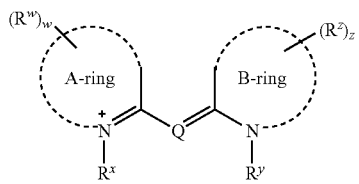

wherein the A-ring and B-ring are independently monocyclic, bicyclic or polycyclic aryl or heteroaryl moieties;
Q is —(CH=C($R_u$))$_c$—CH=), wherein c is 1, 2, 3, 4, or 5;
each $R^w$ and $R^z$ is independently a substituted or unsubstituted alkyl, heteroalkyl, aryl, or heteroaryl group that is coupled to the A-ring or B-ring either directly or through a carbonyl, amide, carbamide, ester, thioester, ether, thioether, or amino linkage;

each $R^x$ and $R^y$, is independently an alkyl or heteroalkyl group, optionally substituted with a sulfonic acid, carboxylic acid, phosphonic acid, or phosphoric acid; and
each $R^u$ is independently hydrogen, alkyl, or heteroalkyl.

In some embodiments, the compound of formula (I) has the structure:

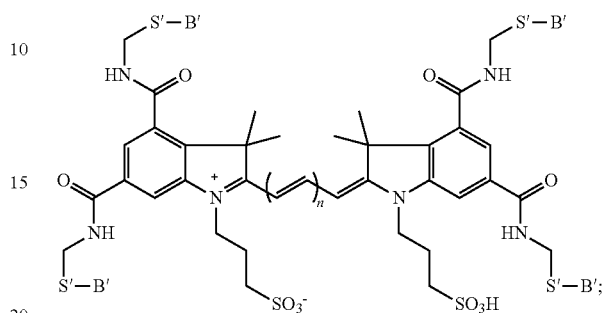

wherein
n=1 or 2. In other embodiments, the compound has the structure:

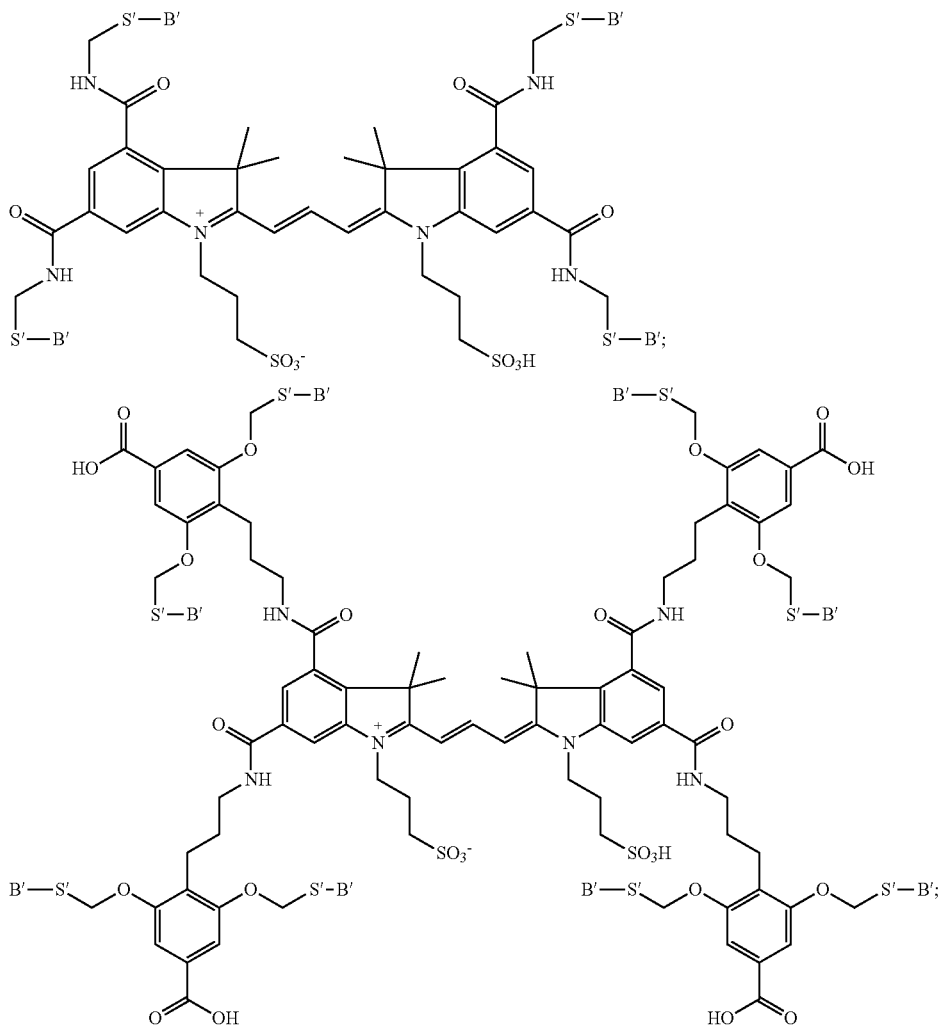

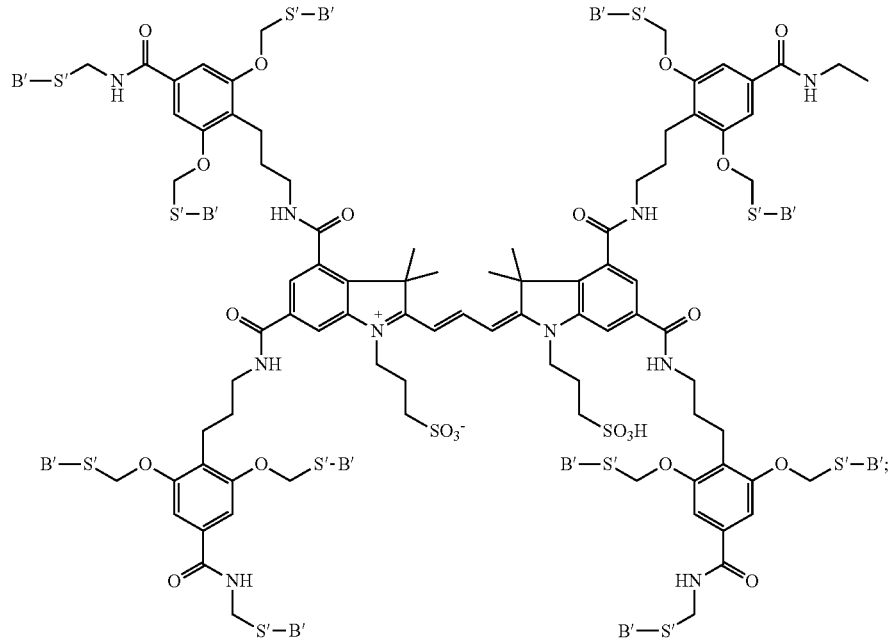
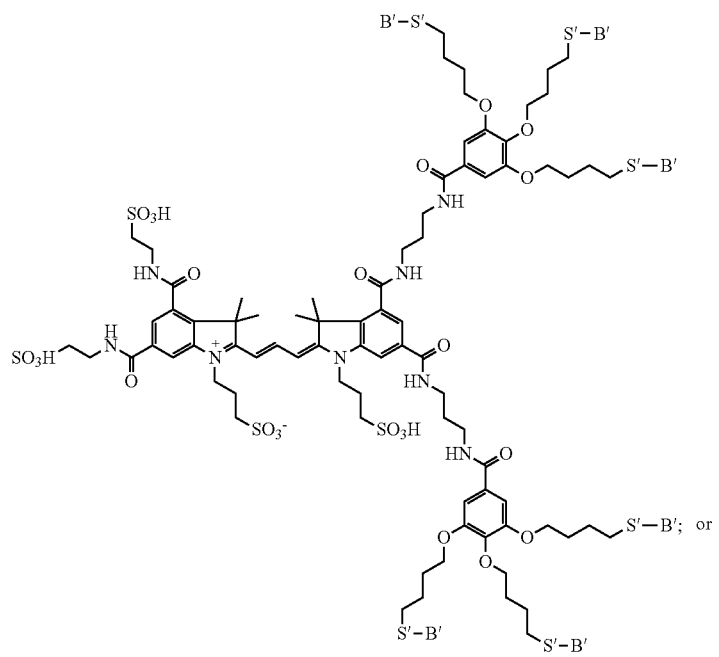

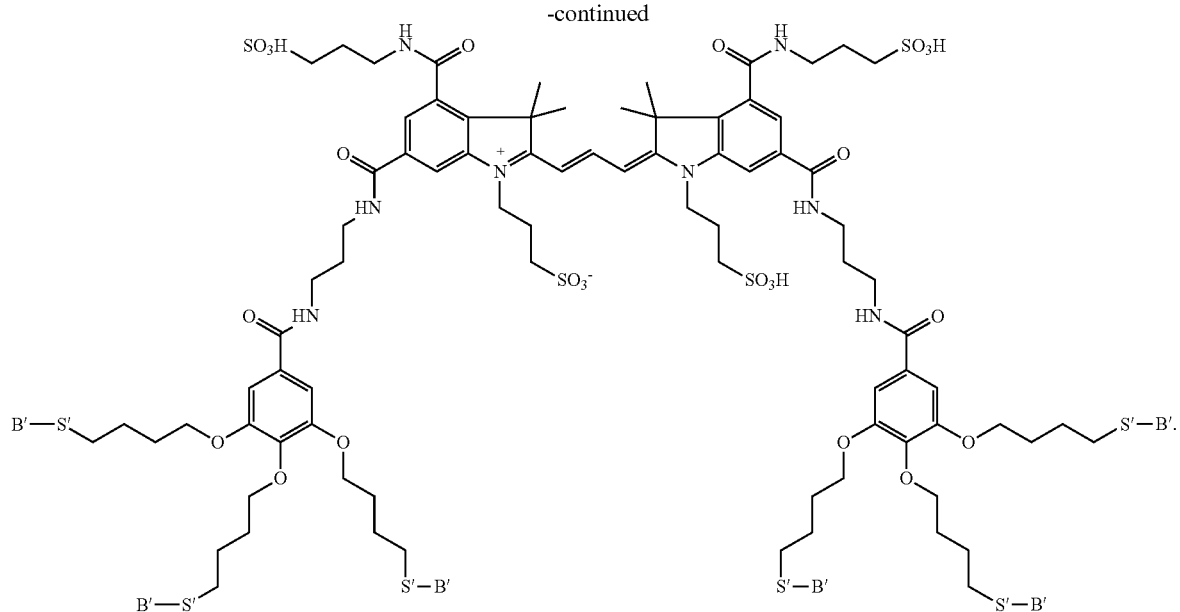

In some embodiments, the Z group of formula (I) comprises a linker group and, more specifically, the linker group may comprise a substituted phenyl group. Even more specifically, the linker group may comprise the structure:

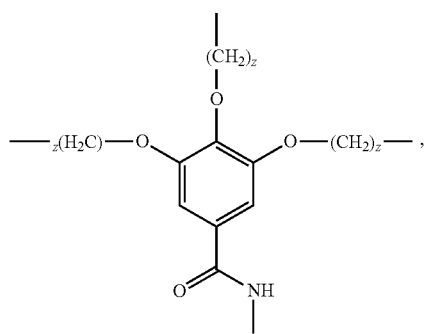

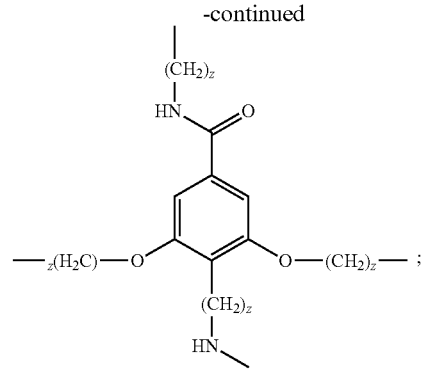

wherein each z is independently an integer from 1 to 6 or even from 1 to 4. In some embodiments, the linker group comprises a diaminoalkyl group.

According to another aspect of the invention, the disclosure provides compounds having structural formula (IIa) or (IIb):

 (IIa)

 (IIb)

wherein
X is a non-fluorescent multivalent central core element;
at least one D is a fluorescent dye element;
at least one W, if present, is a branching element;
n is an integer from 2 to 6;
each o is independently an integer from 1 to 4; and
each p is independently an integer from 1 to 4.

Also provided in another aspect of the invention are compounds having structural formula (III):

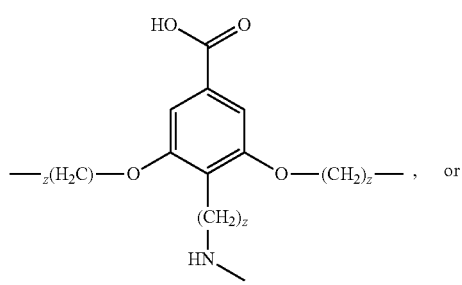

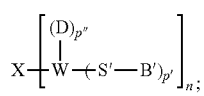
(III)

wherein
X is a non-fluorescent multivalent central core element;
at least one D is a fluorescent dye element;
at least one W is a branching element;
n is an integer from 2 to 6;
each p' is independently an integer from 1 to 4; and
each p" is independently an integer from 1 to 4.

In some embodiments of formulae (IIa), (IIb), and (III), the X group comprises a polyamine and, in more specific embodiments, the polyamine has the structure:

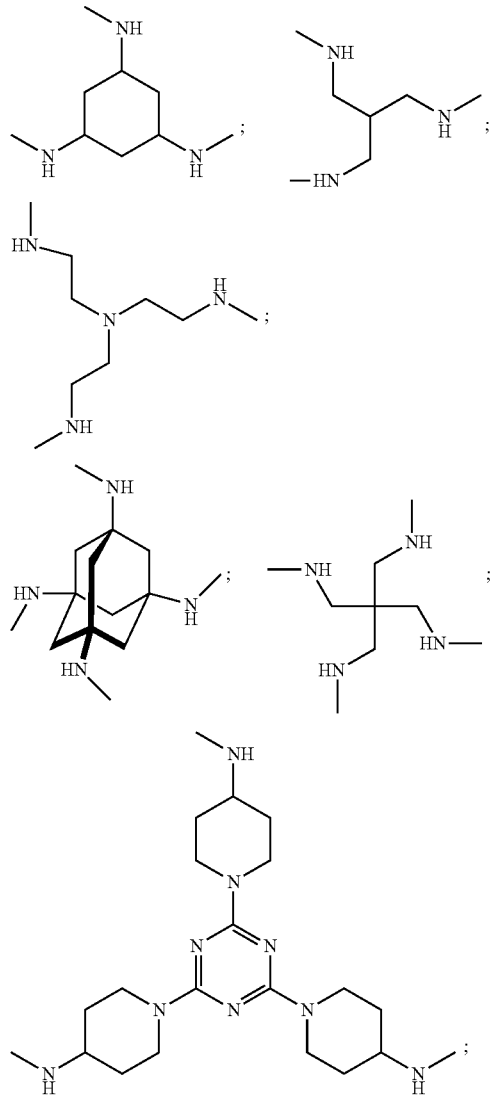

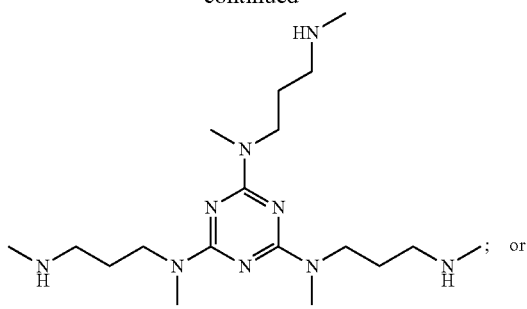

In some embodiments, the X group comprises a substituted cyclohexane, or more specifically a 1,3,5-triaminocyclohexane.

In some embodiments, the X group comprises a substituted 1,3,5-triazine.

In some embodiments, the X group comprises a substituted benzene, or more specifically the substituted benzene is

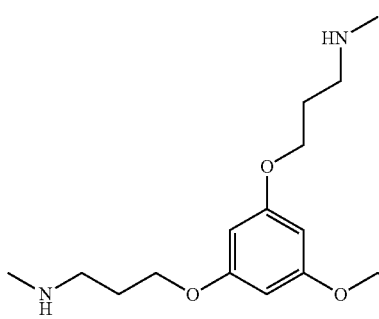

In some embodiments of these formulae, the compound comprises at least one donor fluorescent dye element and at least one acceptor fluorescent dye element.

According to other embodiments, the shield element comprises a plurality of side chains, including embodiments wherein at least one side chain has a molecular weight of at least 300, wherein all of the side chains have a molecular weight of at least 300, wherein the shield element comprises a dendrimer, and wherein at least one side chain comprises a polyethylene glycol. In some embodiments, at least one side chain comprises a negatively-charged component, including embodiments wherein the negatively-charged component comprises a sulfonic acid. In some embodiments, at least one side chain comprises a substituted phenyl group, including embodiments wherein the at least one side chain comprises the structure:

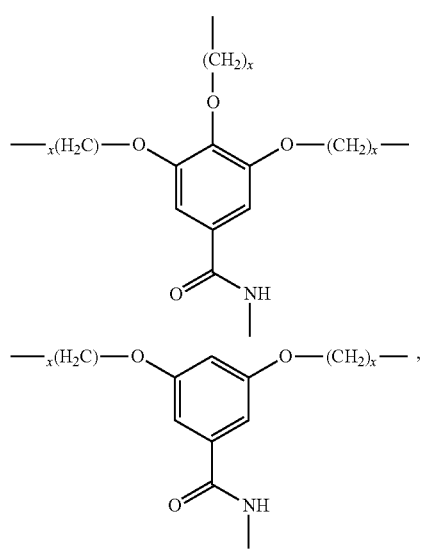
or
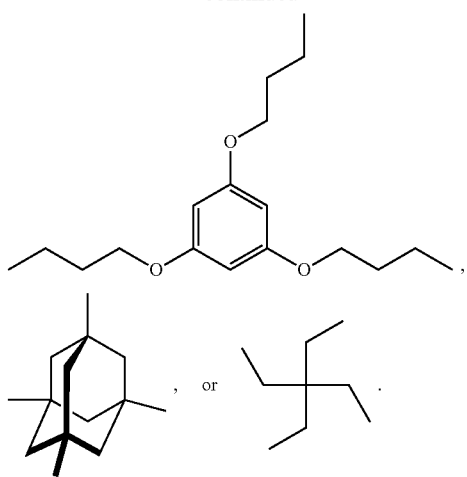
wherein each x is independently an integer from 1 to 6 or even from 1 to 4.
In some embodiments, at least one side chain comprises a triazole, and in other embodiments, at least one side chain comprises the structure:
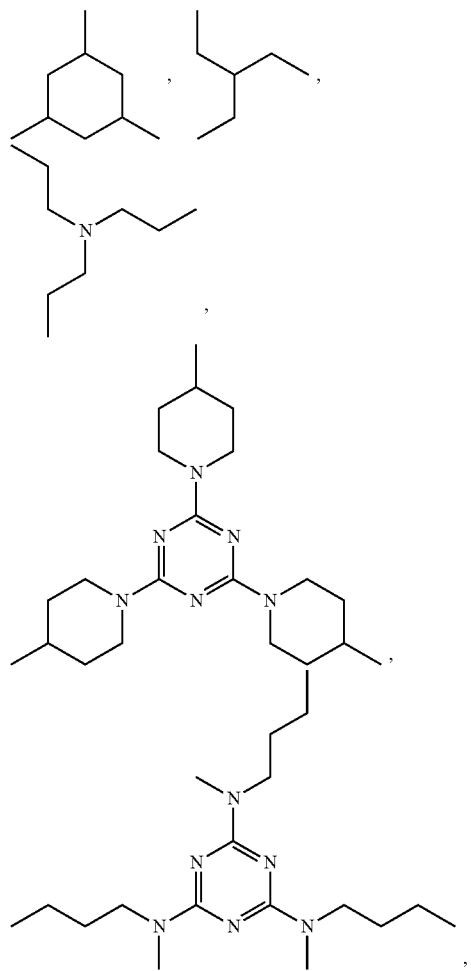
In specific embodiments, at least one side chain comprises the structure:
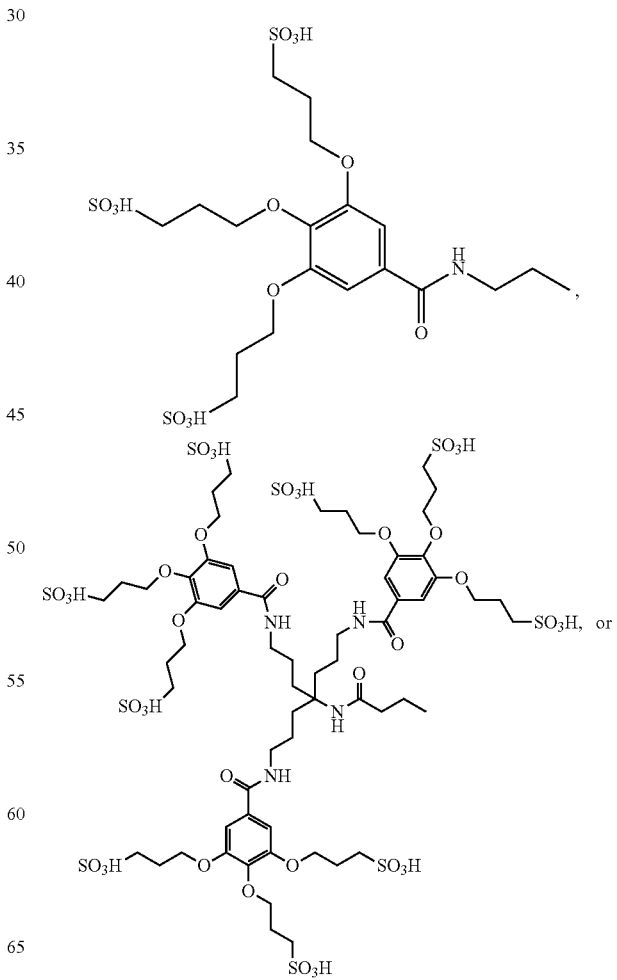

According to some embodiments, the shield element comprises the structure:
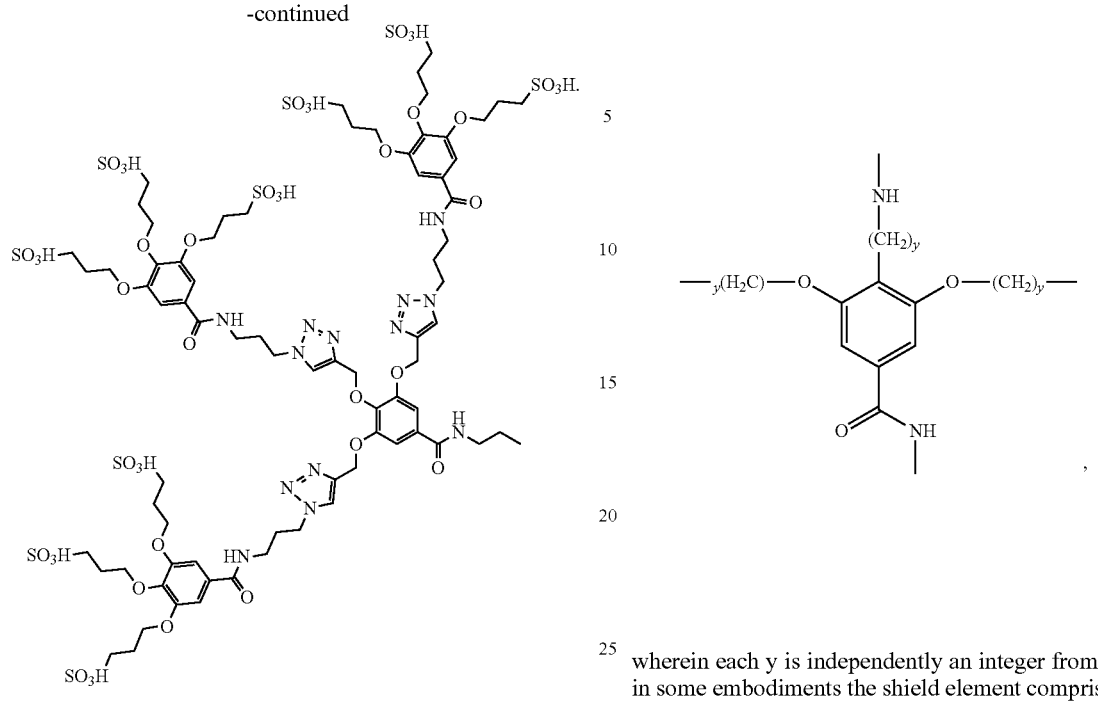
In specific embodiments, at least one S'—B' group comprises the structure:
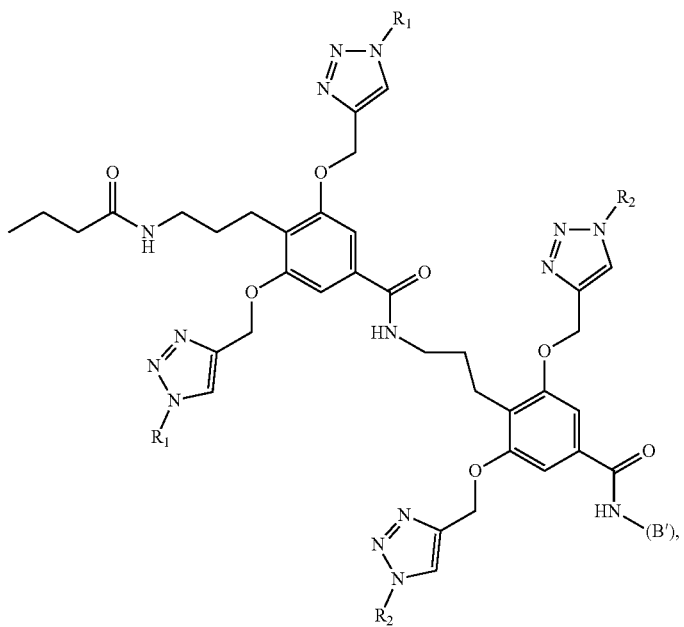
wherein each y is independently an integer from 1 to 6, and in some embodiments the shield element comprises an inner layer and an outer layer.

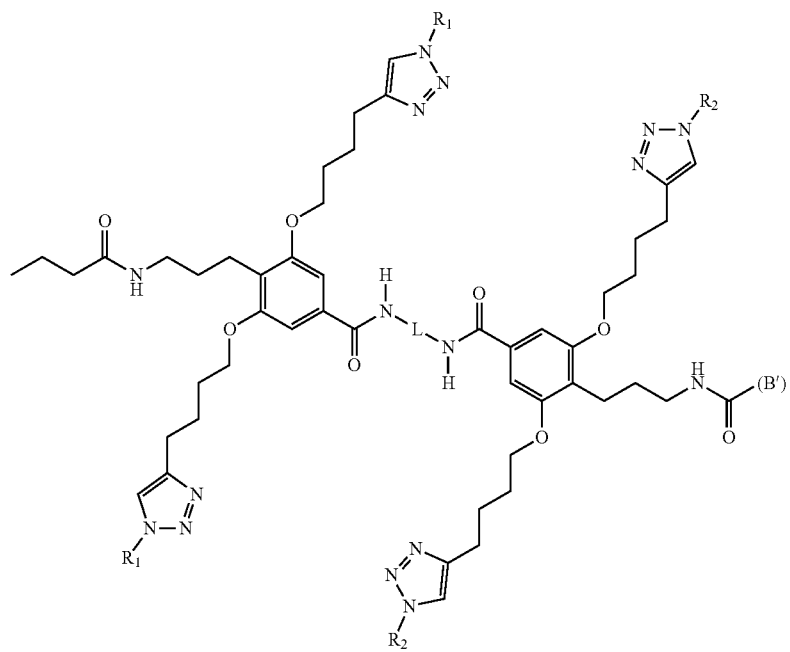
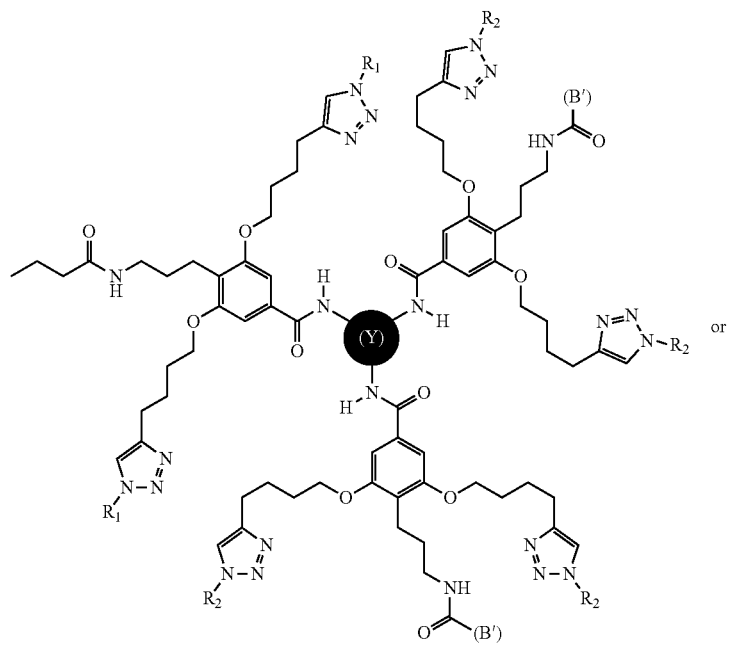

-continued

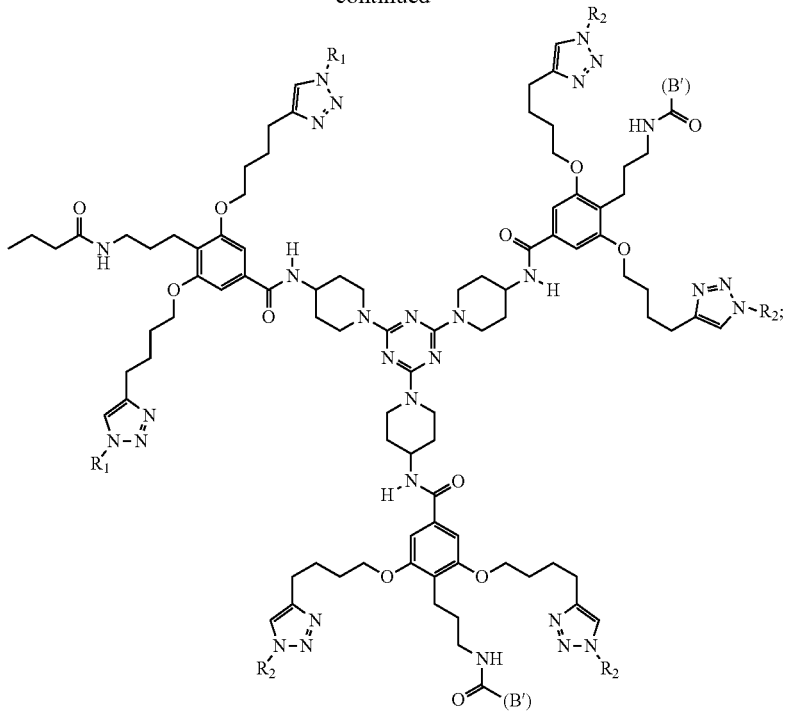

wherein $R_1$ and $R_2$ is each independently a side chain;
L is an alkyl, heteroalkyl, cycloalkyl, cycloheteroalkyl, aryl, or heteroaryl linker; and
Y is

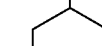

-continued

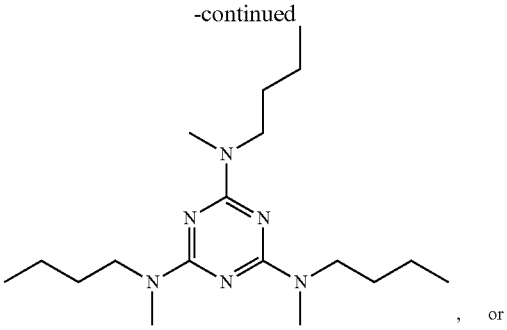

In some embodiments, the binding element comprises a nucleotide, biotin, or a polyphosphate.

In certain embodiments, the branching element comprises a substituted phenyl group, and in some embodiments the branching element comprises the structure:

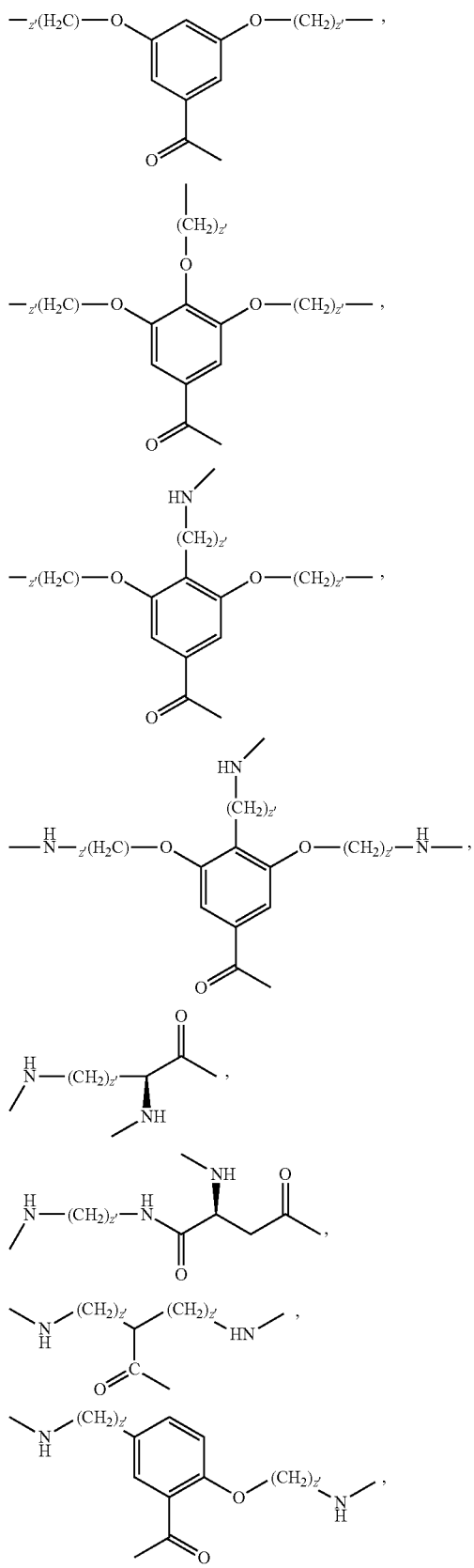

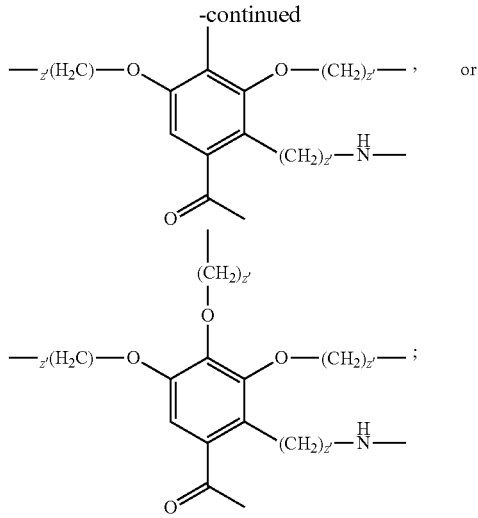

wherein each z' is independently an integer from 1 to 6, or even from 1 to 4.

According to some embodiments of the above formulae, n may be an integer from 2 to 4, each o may be independently an integer from 1 to 3, each p may be independently an integer from 1 to 3, each p' may be independently an integer from 1 to 3, or each p" may be independently an integer from 1 to 3.

BRIEF DESCRIPTION OF THE DRAWINGS

FIG. 2A illustrates single molecule real time sequencing with a Cconventional nucleotide analog. FIG. 2B illustrates an exemplary nucleic acid sequencing process making use of a protected fluorescent reagent of the invention.

FIGS. 6A-6D show a comparison of sequencing read-length and accuracy for two exemplary protected fluorescent reagent compounds compared to control, unprotected compounds.

FIGS. 8A-8B illustrate a comparison of noise level variation during incorporation reactions for the various reagent mixtures as measured in two different sequencing channels under longer sequencing times.

FIG. 16 illustrates an exemplary synthetic route for preparing exemplary alternative core elements comprising fluorescent dye elements.

FIG. 17 illustrates exemplary core structures.

FIGS. 24-26 illustrate the synthesis of exemplary protected fluorescent reagent compounds.

DETAILED DESCRIPTION OF THE INVENTION

Fluorescent reagents are used in a wide variety of different applications. Such applications may include the analysis of single molecules, and may involve observing, for example, single biomolecules in real time as they carry out reactions. For ease of discussion, such fluorescent reagents, and particularly the protected fluorescent reagents of the instant disclosure, are discussed herein in terms of a preferred application: the analysis of nucleic acid sequence information, and particularly, single molecule nucleic acid sequence analysis. The instant protected fluorescent reagents will, however, find utility for other purposes in other applications, such as, for example, other fluorescence-based analytical techniques, where non-protected fluorescent reagents are now routinely used.

In the preferred application, single molecule primer extension reactions are monitored in real-time, to identify the continued incorporation of nucleotides in the extension product to elucidate the underlying template sequence. In such single molecule real time (or SMRT™) sequencing, the process of incorporation of nucleotides in a polymerase-mediated template dependent primer extension reaction is monitored as it occurs. In preferred aspects, the template/polymerase primer complex is provided, typically immobilized, within an optically confined region, such as a zero mode waveguide (ZMW), or proximal to the surface of a transparent substrate, optical waveguide, or the like (see e.g., U.S. Pat. Nos. 6,917,726, and 7,170,050 and U.S. Patent Application Publication No. 2007/0134128, the full disclosures of which are hereby incorporated by reference herein in their entirety for all purposes). The optically confined region is illuminated with an appropriate excitation radiation for the fluorescently labeled nucleotides that are to be used. Because the complex is within an optically confined region, or very small illumination volume, only the reaction volume immediately surrounding the complex is subjected to the excitation radiation. Accordingly, those fluorescently labeled nucleotides that are interacting with the complex, e.g., during an incorporation event, are present within the illumination volume for a sufficient time to identify them as having been incorporated.

Figure 1A:
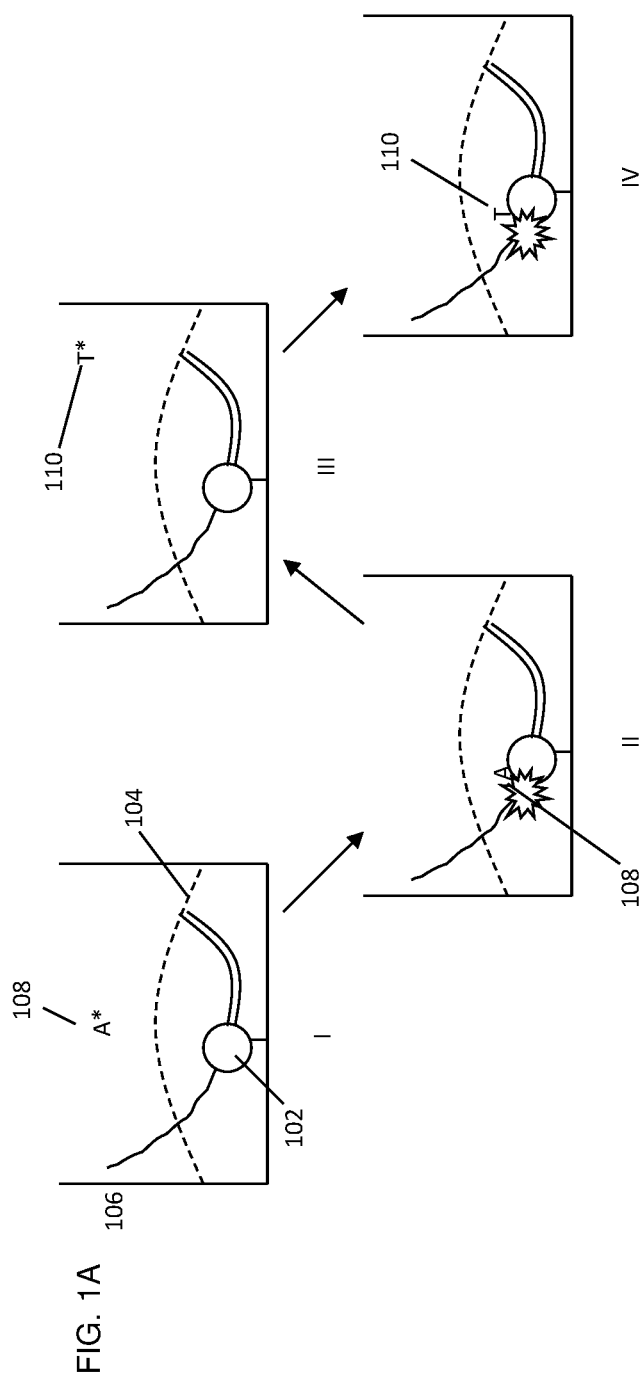
FIGS. 1A-1B schematically illustrate an exemplary nucleic acid sequencing process that can be carried out using aspects of the invention.
Figure 1B:
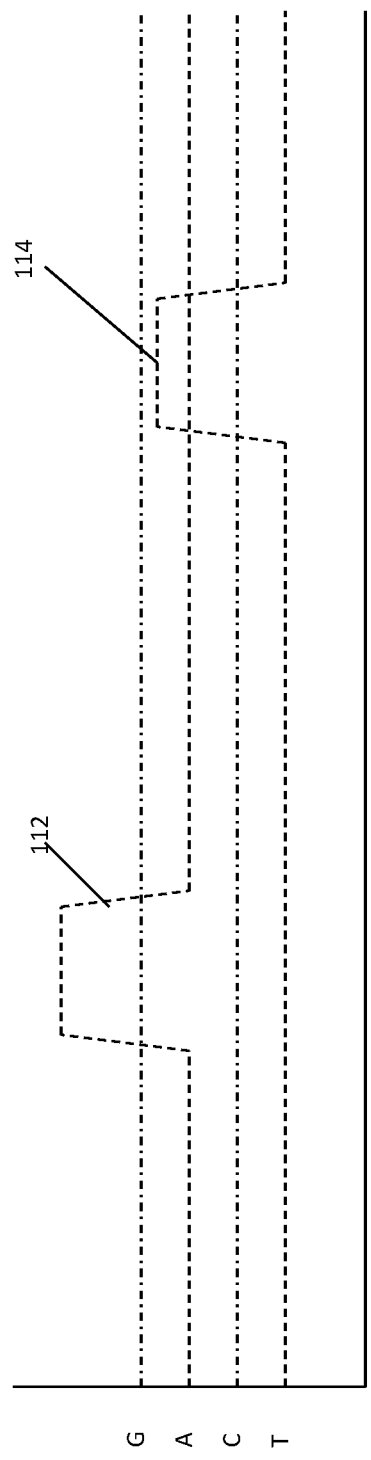

A schematic illustration of this sequencing process is shown in FIGS. 1A and 1B. As shown in FIG. 1A, an immobilized complex 102 of a polymerase enzyme, a template nucleic acid and a primer sequence are provided within an observation volume (as shown by dashed line 104) of an optical confinement, of e.g., a zero mode waveguide 106. As an appropriate nucleotide analog, e.g., nucleotide 108, is incorporated into the nascent nucleic acid strand, it is illuminated for an extended period of time corresponding to the retention time of the labeled nucleotide analog within the observation volume during incorporation which produces a signal associated with that retention, e.g., signal pulse 112 as shown by the A trace in FIG. 1B. Once incorporated, the label that was attached to the polyphosphate component of the labeled nucleotide analog, is released. When the next appropriate nucleotide analog, e.g., nucleotide 110, is contacted with the complex, it too is incorporated, giving rise to a corresponding signal 114 in the T trace of FIG. 1B. By monitoring the incorporation of bases into the nascent strand, as dictated by the underlying complementarity of the template sequence, long stretches of sequence information of the template can be obtained.

As just noted, in single-molecule real-time sequencing using fluorescence detection, the polymerase enzyme is illuminated with excitation light while a sequencing reaction is taking place. In some cases, this illumination results in photodamage which inhibits, and in some cases completely inactivates, the polymerase enzyme. This damage can thus cause the sequencing reaction to end, resulting in shorter read lengths than desired. Significantly longer read lengths can in some cases be obtained in the dark than can be obtained for the same sequencing reaction under illumination. Importantly, damage to the enzyme under illumination may be accompanied by the formation of a covalent bond between a fluorescent dye moiety on a nucleotide analog and the polymerase enzyme and/or exchange of electrons between the excited state dye and the enzyme. It is therefore believed that the stability of the enzyme can be compromised when there is contact between the enzyme and a fluorescent moiety on a nucleotide analog which is in the active site of the enzyme. In some cases, it appears that this mechanism constitutes the dominant mode of degradation. The instant disclosure addresses the problem of photodamage by providing fluorescent compounds that are less susceptible to such photodamage and that are less likely to cause photodamage to associated biomolecules, such as enzymes, that specifically bind to the fluorescent compounds.

U.S. patent application Ser. No. 13/767,619, filed Feb. 14, 2013, which is incorporated by reference herein in its entirety for all purposes, provides a novel approach to mitigating photodamage and improving sequencing read-lengths by incorporation of a shielding protein into a nucleotide analog. The nucleotide analog is constructed such that the shielding protein is disposed between the nucleotide phosphate portion and the fluorescent dye portion of the nucleotide analog. The size and position of the protein are chosen such that the fluorescent dye portion of the analog does not come into contact with the polymerase enzyme when the nucleotide portion is held within the active site of the polymerase. Preventing contact between the fluorescent dye and the polymerase prevents the formation of a covalent bond to the polymerase. By shielding the enzyme from contact with the fluorescent dye, the protein blocks a significant photodamage pathway, resulting in longer enzyme life under illumination.

The instant inventors have now discovered that photodamage can also be mitigated in fluorescent reagent compounds by the covalent incorporation of a general shield element between a fluorescent dye within the compound and a binding element moiety. These compounds may also benefit from completely surrounding the fluorescent dye moiety by a protective shell of associated shield elements. Without intending to be bound by theory, the shield element is thus understood to limit contacts between the fluorescent core and the binding element and thus to minimize photodamage, in particular photodamage to biomolecules that are specifically associated with the binding element of the protected compound. The protected fluorescent reagents of the instant disclosure can therefore be used in reactions where they are present, together with their associated biomolecular binding partners, for extended periods of time, and where photodamage and the associated inactivation of the associated biomolecules is therefore likely to be problematic. The improved performance of the instant fluorescent reagent compounds provides advantages for the use of these reagents in various fluorescent analytical techniques.

FIGS. 2A and 2B provide a schematic illustration of the role believed to be played by the shield element of the instant compounds in the context of a single-molecule real-time sequencing reaction. FIG. 2A illustrates real-time single-molecule sequencing with a conventional nucleotide analog. The polymerase enzyme 210 is bound to the surface of a substrate, such as a chip, 260, for example with a linker 250. The polymerase enzyme 210 is complexed with a template nucleic acid having a template strand 220 and a primer/growing strand 230.

Sequencing is performed by observing the enzyme while it incorporates nucleotides into the growing strand. A nucleotide analog being incorporated into the growing strand generally spends more time in the active site than a nucleotide not being incorporated, allowing for the identification of the incorporated nucleotide by its fluorescent signal. When the nucleotide is incorporated, the remainder of the nucleotide analog, including the fluorescent label, is cleaved away and the enzyme is ready for the next incorporation. By watching the incorporation of bases over time, the sequence of the template nucleic acid 220 can be determined by determining the series of nucleotides that are incorporated into the growing strand 230. Variations in the general technique, such as attaching the polymerase to other surfaces or even other media, and/or restricting movement of the polymerase complex in other ways, or even in using other types of restricted volumes, may also be contemplated in this general approach.

As just described, FIG. 2A (1) shows a conventional nucleotide analog 240, held in the enzyme prior to incorporation. The nucleotide portion of the analog 244 is held in the active site of the enzyme in position for incorporation. FIG. 2A (2) illustrates that while the nucleotide analog is associated with the enzyme, the fluorescent moiety 242 can come into contact with the enzyme. During this process, the enzyme is illuminated with excitation light to allow for observation of the fluorescent moiety. When the fluorescent moiety absorbs the excitation light, it enters into an excited state. It is believed that having the excited fluorescent moiety in the vicinity of the enzyme, and in particular when the fluorescent moiety comes into contact with the enzyme, damage to the enzyme may result, adversely affecting the sequencing reaction. The damage to the enzyme may result in slowing the enzyme, altering its effectiveness, or in completely halting the polymerase reaction.

FIG. 2B shows a protected fluorescent compound of the invention (270) having three fluorescent dyes (272), three nucleotide binding elements (274), and three shield elements (276). The compound is thus trivalent with respect to dye, trivalent with respect to binding elements, and hexavalent overall, as will be further described below. As would be understood by one of ordinary skill in the art, sequencing may be carried out with the instant protected reagent compounds by the same processes described above for conventional nucleotide analogs. As with a conventional enzyme substrate, the nucleotide portion of the protected reagent is held in the active site of the enzyme prior to incorporation. The protected reagent thus has a nucleotide binding element, 274, connected to the shield element through the phosphate portion of the nucleotide. In some embodiments, the nucleotide may be attached to the shield element through a linker group. Without intending to be bound by theory, the shielding elements are thought to prevent contact between the polymerase enzyme and the fluorescent dye moiety, 272. By shielding the enzyme from contact with the fluorescent dye moiety while the nucleotide binding element portion of the analog is in the active site of the enzyme, the enzyme is protected from photodamage due to contact with the fluorescent moiety's excited state. Although the sequencing reaction is exemplified here with a particular embodiment of the instant compounds, it should be understood that any other suitable compound embodiment could be utilized in such reactions and would be considered within the scope of the invention.

While the usefulness of the protected reagents of the invention is illustrated with the description above of SMRT™ sequencing, it is to be understood that these compounds may be used with any appropriate enzymatic or binding reaction and will thus have broader application in other analytical techniques. For example, the protected fluorescent reagents of the instant disclosure are also useful in the measurement of any type of binding interaction, not just binding interactions that result in the reaction of the reagent. While in preferred embodiments, such as single-molecule, real-time nucleic acid sequencing reactions, the reagent serves as an enzyme substrate and is chemically altered as a result of the interaction, in other embodiments, such as, for example, the binding of a protected fluorescent reagent to an antibody, a receptor, or other affinity agent, the reagent remains unaltered as a result of the interaction. Measurement of the binding interaction, or any other type of interaction, may be performed using well-known fluorescence techniques and biochemical processes. Examples of such techniques and processes include fluorescence resonance energy transfer (FRET), fluorescence cross-correlation spectroscopy, fluorescence quenching, fluorescence polarization, flow cytometry, and the like.

The instant disclosure provides chemical formulae and specific chemical structures for the inventive protected fluorescent reagents. Where chemical moieties are specified by their conventional chemical formulae, written from left to right, they optionally equally encompass the moiety which would result from writing the structure from right to left, e.g., —CH$_2$O— is intended to also recite —OCH$_2$—; —NHS(O)$_2$— is also intended to optionally represent —S(O)$_2$HN—, etc. Moreover, where compounds can be represented as free acids or free bases or salts thereof, the representation of a particular form, e.g., carboxylic or sulfonic acid, also discloses the other form, e.g., the deprotonated salt form, e.g., the carboxylate or sulfonate salt. Appropriate counterions for salts are well-known in the art, and the choice of a particular counterion for a salt of the invention is well within the abilities of those of skill in the art. Similarly, where the salt is disclosed, this structure also discloses the compound in a free acid or free base form. Methods of making salts and free acids and free bases are well-known in the art.

"Cyanine," as used herein, refers to polymethine dyes such as those based upon the cyanine, merocyanine, styryl and oxonol ring. Cyanine dyes include, for example, CY3, CY3.5, CY5 and CY5.5 type dyes.

As used herein, "nucleic acid" means any natural or non-natural nucleotide or nucleoside phosphate oligomer or polymer; e.g., DNA, RNA, single-stranded, double-stranded, triple-stranded or more highly aggregated hybridization motifs, and any chemical modifications thereof.

Exemplary modified nucleic acids include, but are not limited to, peptide nucleic acids (PNAs), those with phosphodiester group modifications (e.g., replacement of O$^-$ with OR, NR, or SR), 2'-, 3'- and 5'-position sugar modifications, modifications to the base moiety, e.g., 5-position pyrimidine modifications, 8-position purine modifications, modifications at exocyclic amines, substitution of 4-thiouridine, substitution of 5-bromo or 5-iodo-uracil; backbone modifications, i.e., substitution of P(O)O$_3$ with another moiety, methylations, unusual base-pairing combinations such as the isobases, isocytidine and isoguanidine and the like. Nucleic acids can also include non-natural bases, e.g., nitroindole. Non-natural bases include bases that are modified with a minor groove binder, an intercalating agent, a hybridization enhancer, a chelating agent, a metal chelate, a quencher, a fluorophore, a fluorogenic compound, etc. Modifications within the scope of "nucleic acid" also include 3' and 5' modifications with one or more of the species described above.

Nucleic acids, nucleotides and nucleosides contain nucleobases. In addition to the naturally occurring nucleobases of deoxyribonucleic acids, i.e., adenine, cytosine, guanine, and thymine, the compounds of the invention may optionally include modified bases. These components may also include modified sugars. For example, the nucleic acids, nucleotides, or nucleosides described herein may comprise at least one modified base moiety which is selected from the group including, but not limited to, 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-d-galactosylqueosine, inosine, N$^6$-isopentenyladenine, 1-methylguanine, 1-methylinosine, 2,2-dimethylguanine, 2-methyladenine, 2-methylguanine, 3-methylcytosine, 5-methylcytosine, N$^6$-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N$^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methyl ester, uracil-5-oxyacetic acid (v), 5-methyl-2-thiouracil, 3-(3-amino-3-N-2-carboxypropyl) uracil, (acp3)w, nitroindole, and 2,6-diaminopurine.

Typically the nucleic acids, nucleotides, and nucleosides described herein may comprise either ribose (RNA) or deoxyribose (DNA). In some embodiments, the nucleic acids, nucleotides, or nucleosides may comprise a modified sugar moiety selected from the group including, but not limited to, arabinose, 2-fluoroarabinose, xylulose, and hexose. A modified sugar moiety may, for example, be present in a binding element of the instant protected compounds.

In yet other embodiments, the nucleic acids, nucleotides, and nucleosides may comprise at least one modified phosphate backbone selected from the group including, but not limited to, a peptide nucleic acid hybrid, a phosphorothioate, a phosphorodithioate, a phosphoramidothioate, a phosphoramidate, a phosphordiamidate, a methylphosphonate, an alkyl phosphotriester, and a formacetal or analog thereof. A modified phosphate backbone may, for example, be present in a binding element of the instant protected compounds.

Nucleic acids, nucleotides, and nucleotides described herein may also include species that are modified at one or more internucleotide bridges (e.g., P(O)O$_3$) by replacing or derivatizing an oxygen of the bridge atom. For example a "nucleic acid" also refers to species in which the P(O)O$_2$ moiety (the O$^-$ moiety remains unchanged or is converted to "OR") of a natural nucleic acid is replaced with a non-natural linker species, e.g., —ORP(O)O—, —ROP(O)R—, —ORP(O)OR—, —ROP(O)OR—, or —RP(O)R— in which the symbol "-" indicates the position of attachment of the linker to the 2'-, 3'- or 5'-carbon of a nucleotide sugar moiety, thus allowing the placement of the exemplified, and other, non-natural linkers between adjacent nucleoside sugar moieties. Exemplary linker subunits ("R") include substituted or unsubstituted alkyl and substituted or unsubstituted heteroalkyl moieties. Such modifications may be present in a binding element of the instant protected compounds Further exemplary nucleic acids, nucleotides, and nucleosides described herein may include a polyphosphate moiety, e.g., pyrophosphate or a higher homologue, such as the 3-mer, 4-mer, 5-mer, 6-mer, 7-mer, 8-mer and the like. The polyphosphate moieties of the instant protected reagent compounds generally comprise from 2 to 10 phosphates. In preferred embodiments, the polyphosphate moieties comprise 4, 5, 6, 7 or 8 phosphates. In other embodiments, a methylene moiety, NH moiety, or S moiety bridges two or more phosphorus atoms, replacing the OPO link with an PCH$_2$P, PNHP, or PSP link.

Furthermore, compounds of the disclosure may include species in which one or more internucleotide bridge does not include phosphorus. An exemplary bridge includes a substituted or unsubstituted alkyl or substituted or unsubstituted heteroalkyl moiety in which a carbon atom is the locus for the interconnection of two nucleoside sugar residues. The discussion above is not limited to moieties that include a carbon atom as the point of attachment; the locus may also be another appropriate linking atom, such as nitrogen or another atom.

Phosphodiester linked nucleic acids described herein may be synthesized by standard methods known in the art, e.g. by use of an automated DNA synthesizer using commercially available amidite chemistries (Ozaki et al., *Nucleic Acids Research*, 20: 5205-5214 (1992); Agrawal et al., *Nucleic Acids Research*, 18: 5419-5423 (1990); Beaucage et al., *Tetrahedron*, 48: 2223-2311 (1992); Molko et al., U.S. Pat. No. 4,980,460; Koster et al., U.S. Pat. No. 4,725,677; Caruthers et al., U.S. Pat. Nos. 4,415,732; 4,458,066; and 4,973,679). Nucleic acids bearing modified phosphodiester linking groups may be synthesized by methods known in the art. For example, phosphorothioate nucleic acids may be synthesized by the method of Stein et al. (*Nucl. Acids Res.* 16:3209 (1988)), methylphosphonate nucleic acids may be prepared by use of controlled pore glass polymer supports (Sarin et al., *Proc. Natl. Acad. Sci. U.S.A.* 85:7448-7451 (1988)). Other methods of synthesizing both phosphodiester- and modified phosphodiester-linked nucleic acids will be apparent to those of skill in the art.

The nucleotides and nucleoside phosphates of the instant protected reagent compounds are generally meant to be used as substrates for polymerase enzymes, particularly in the context of nucleic acid sequencing. Therefore, generally, any non-natural base, sugar, or phosphate of the nucleotide or nucleoside phosphate may be included as a nucleotide or nucleoside phosphate of the invention if the nucleoside phosphate is capable of acting as a substrate for any natural or modified polymerase enzyme.

"Activated derivatives of carboxyl moieties," and equivalent species, refers to a moiety on a component of the instant protected reagent compounds or their precursors or derivatives or on another reagent component in which an oxygen-containing, or other, leaving group is formally accessed through a carboxyl moiety, e.g., an active ester, acyl halide, acyl imidazolide, etc. Such activated moieties may be useful in coupling the various components of the instant compounds as they are assembled.

The term "alkyl," by itself or as part of another substituent, means, unless otherwise stated, a straight or branched chain, or cyclic hydrocarbon radical, or combination thereof, which may be fully saturated, mono- or polyunsaturated and can include mono-, di- and multivalent radicals, having the number of carbon atoms designated (i.e., $C_1$-$C_{10}$ means one to ten carbons). Examples of saturated alkyl radicals include, but are not limited to, groups such as methyl, methylene, ethyl, ethylene, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher homologs and isomers. The term "alkyl," unless otherwise noted, includes "alkylene," "alkynyl" and, optionally, those derivatives of alkyl defined in more detail below, such as "heteroalkyl".

The term "heteroalkyl," by itself or in combination with another term, means, unless otherwise stated, a stable straight or branched chain, or cyclic hydrocarbon radical, or combinations thereof, consisting of the stated number of carbon atoms and at least one heteroatom selected from the group consisting of O, N, Si, P and S, and wherein the nitrogen and sulfur atoms may optionally be oxidized and the nitrogen heteroatom may optionally be quaternized. The heteroatom(s) O, N, S, P and Si may be placed at any interior position of the heteroalkyl group or at the position at which the alkyl group is attached to the remainder of the molecule. Examples include, but are not limited to, —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, and —CH=CH—N($CH_3$)—$CH_3$. Up to two heteroatoms may be consecutive, such as, for example, —$CH_2$—NH—$OCH_3$ and —$CH_2$—O—Si($CH_3$)$_3$. Similarly, the term "heteroalkylene" by itself or as part of another substituent means a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene, alkynyl, and heteroalkylene linking groups, no orientation of the linking group is implied by the direction in which the formula of the linking group is written. For example, the formula —C(O)$_2$R'— represents both —C(O)$_2$R'— and —R'C(O)$_2$—.

The terms "cycloalkyl" and "heterocycloalkyl", by themselves or in combination with other terms, represent, unless otherwise stated, cyclic versions of "alkyl" and "heteroalkyl", respectively. Also included are di- and multi-valent species such as "cycloalkylene." Additionally, for heterocycloalkyl, a heteroatom can occupy the position at which the heterocycle is attached to the remainder of the molecule. Examples of cycloalkyl include, but are not limited to, cyclopentyl, cyclohexyl, 1-cyclohexenyl, 3-cyclohexenyl, cycloheptyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl. For example, the term "halo($C_1$-$C_4$)alkyl" is meant to include, but not be limited to, species such as trifluoromethyl, 2,2,2-trifluoroethyl, 4-chlorobutyl, 3-bromopropyl, and the like.

The term "aryl" means, unless otherwise stated, a polyunsaturated, aromatic, hydrocarbon substituent, which can be a single ring or multiple rings (preferably from 1 to 3 rings), which are fused together or linked covalently. The term "heteroaryl" refers to aryl groups (or rings) that contain from one to four heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Also included are di- and multi-valent linker species, such as "arylene." Substituents for each of the above noted aryl and heteroaryl ring systems are selected from the group of acceptable substituents described below.

For brevity, the term "aryl" when used in combination with other terms (e.g., aryloxy, arylthioxy, arylalkyl) includes both aryl and heteroaryl rings as defined above. Thus, the term "arylalkyl" is meant to include those radicals in which an aryl group is attached to an alkyl group (e.g., benzyl, phenethyl, pyridylmethyl and the like) including those alkyl groups in which a carbon atom (e.g., a methylene group) has been replaced by, for example, an oxygen atom (e.g., phenoxymethyl, 2-pyridyloxymethyl, 3-(1-naphthyloxy)propyl, and the like).

Each of the above terms (e.g., "alkyl," "heteroalkyl," "aryl" and "heteroaryl") include both substituted and unsubstituted forms of the indicated radical. Exemplary substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to: —OR', =O, =NR', =N—OR', —NR'R", —SR', -halogen, —SiR'R"R''', —OC(O)R', —C(O)R', —CO$_2$R', —CONR'R", —OC(O)NR'R", —NR"C(O)R', SO$_3$R', —NR'—C(O)NR"R''', —NR"C(O)$_2$R', —NR—C(NR'R"R''')=NR'''', —NR—C(NR'R")=NR''', —S(O)R', —S(O)$_2$R', —S(O)$_2$NR'R", —NRSO$_2$R', —CN and —NO$_2$ in a number ranging from zero to (2m'+1), where m' is the total number of carbon atoms in such radical. R', R", R''' and R'''' each preferably independently refer to hydrogen, substituted or unsubstituted heteroalkyl, substituted or unsubstituted aryl, e.g., aryl substituted with 1-3 halogens, substituted or unsubstituted alkyl, alkoxy or thioalkoxy groups, or arylalkyl groups. When a compound of the invention includes more than one R group, for example, each of the R groups is independently selected as are each R', R", R''' and R'''' groups when more than one of these groups is present. When R' and R" are attached to the same nitrogen atom, they can be combined with the nitrogen atom to form a 5-, 6-, or 7-membered ring. For example, —NR'R" is meant to include, but not be limited to, 1-pyrrolidinyl and 4-morpholinyl. Accordingly, from the above discussion of substituents, one of skill in the art will understand that the terms "substituted alkyl" and "heteroalkyl" are meant to include groups that have carbon atoms bound to groups other than hydrogen atoms, such as haloalkyl (e.g., —CF$_3$ and —CH$_2$CF$_3$) and acyl (e.g., —C(O)CH$_3$, —C(O)CF$_3$, —C(O)CH$_2$OCH$_3$, and the like).

The substituents set forth in the paragraph above are referred to herein as "alkyl group substituents."

Similar to the substituents described for the alkyl radical, substituents for the aryl and heteroaryl groups are varied and are selected from, for example: halogen, —OR', =O, =NR', =N—OR', —NR'R", —SR', -halogen, —SiR'R"R'''', —OC(O)R', —C(O)R', —CO$_2$R', —CONR'R", —OC(O)NR'R", —NR"C(O)R', —NR'—C(O)NR"R''', —NR"C(O)$_2$R', —NR—C(NR'R")=NR''', —S(O)R', —S(O)$_2$R', SO$_3$R', —S(O)$_2$NR'R", —NRSO$_2$R', —CN and —NO$_2$, —R', —N$_3$, —CH(Ph)$_2$, fluoro(C$_1$-C$_4$) alkoxy, and fluoro(C$_1$-C$_4$)alkyl, in a number ranging from zero to the total number of open valences on the aromatic ring system; and where R', R", R''' and R'''' are preferably independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl. When a compound of the invention includes more than one R group, for example, each of the R groups is independently selected as are each R', R", R''' and R'''' groups when more than one of these groups is present.

Two of the substituents on adjacent atoms of the aryl or heteroaryl ring may optionally be replaced with a substituent of the formula -T-C(O)—(CRR')$_q$—U—, wherein T and U are independently —NR—, —O—, —CRR'— or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR'— or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$-J-(CR"R''')$_d$—, where s and d are independently integers of from 0 to 3, and J is —O—, —NR'—, —S—, —S(O)—, —S(O)$_2$—, or —S(O)$_2$NR'—. The substituents R, R', R" and R''' are preferably independently selected from hydrogen or substituted or unsubstituted (C$_1$-C$_6$)-alkyl.

The substituents set forth in the two paragraphs above are referred to herein as "aryl group substituents."

When referring to components of the compounds of the invention, the term "residue derived from," refers to a residue formed by the reaction of a first reactive functional group on a first component (e.g., central core element, dye element, shield element, or a binding element) and a second reactive functional group on a second component (e.g., central core element, dye element, shield element, or a binding element) to form a covalent bond. In exemplary embodiments, an amine group on the first component is reacted with an activated carboxyl group on the second component to form a residue including one or more amide moieties. Other permutations of first and second reactive functional groups are encompassed by the invention. For example, the copper-catalyzed reaction of an azide-substituted first component with an alkyne-substituted second component results in a triazole-containing residue through the well-known "click" reaction, as would be understood by those of ordinary skill in the art. See Kolb et al. (2001) *Angew. Chem. Int. Ed. Engl.* 40:2004; Evans (2007) *Aus. J. Chem.* 60:384.

In some embodiments, a copper-free variant of the click reaction may be used to couple the first and second reactive groups. See, e.g., Baskin et al. (2007) *Proc. Natl Acad. Sci. U.S.A.* 104:16793-97. For example, an azide-substituted first component may be reacted with a cycloalkyne, ideally a cyclooctyne, attached to the second component, in the absence of a copper catalyst. Such so-called copper-free click reagents are available commercially. Examples of such cycloalkynes include, without limitation, dibenzocyclooctyne-amine, bicyclo[6.1.0]non-4-yn-9-yl, or monofluorinated cyclooctynes. Other coupling chemistries may also be usefully employed in the synthesis of the compounds of the instant disclosure, as would be understood by those of skill in the art.

It should also be understood that the attachment sites for the first and second reactive functional groups in the just-described reactions can generally be reversed if so desired, depending on the situation. For example, in the case of a "click" reaction, the first component may be azide-substituted and the second component may be alkyne-substituted, as described above, or the first component may be alkyne-substituted and the second component may be azide-substituted. Such variation in the reactions is well within the skill of those in the art.

As used herein, a listed range of integers includes each of the integers within the range. For example, an integer from 2 to 6 includes the integers 2, 3, 4, 5, and 6.

Protected Fluorescent Reagent Compounds

The instant disclosure provides fluorescent reagent compounds for use in the measurement and analysis of enzymatic reactions and other molecular recognition events, such as, for example, the single-molecule real-time sequencing of nucleic acids, the binding of fluorescent compounds to biomolecules such as receptors and antibodies, and other types of reaction and recognition events, where the target biomolecules are protected from photodamage or other detrimental reactions by the fluorescent compounds due to the specific structural design of the compounds. The protection may also extend to protection from photodamage or other detrimental reactions that may occur to the reagent compounds themselves.

Accordingly, in one aspect, the disclosure provides compounds of structural formula (I):

Z—[S'—B']$_m$ (I); wherein

Z is a multivalent central core element comprising a fluorescent dye element;

S' is an intermediate chemical group, wherein at least one S' comprises a shield element;

B' is a terminal chemical group, wherein at least one B' comprises a binding element; and m is an integer from 2 to 24.

As described in more detail elsewhere in the disclosure, it is believed that the shield element of the instant compounds protects against photodamage of biomolecules associated with the binding element of the compounds. In particular, and without intending to be bound by theory, biomolecules capable of recognizing and binding to the compounds of the disclosure, for example receptors, antibodies, enzymes, and the like, may be protected from photodamage due to steric or other effects, whereby the large shield elements within the instant compounds decrease contact between the fluorescent dyes within the compounds and a biomolecule associated with the binding element. The shield elements may alternatively, or in addition, provide a protective microenvironment for the attached fluorescent dyes that results in improved physical and chemical properties of the dyes.

It should be understood throughout the disclosure, that an intermediate chemical group, S', of the instant compounds, while potentially corresponding to any suitable intermediate chemical group, preferably comprises a shield element. It should further be understood that a terminal chemical group, B', of the instant compounds, while potentially corresponding to any suitable terminal chemical group, preferably comprises a binding element. This does not exclude the possibility, however, that in some embodiments, one or more intermediate chemical groups will not comprise a shield element or that one or more terminal chemical groups will not comprise a binding element, in any possible combination. It should also be understood that within a given protected reagent compound of the instant disclosure, the S' groups may be the same or different from one another, depending on the desired properties, the B' groups may be the same or different from one another, likewise depending on the desired properties, and the variation in S' and B' may occur in any possible combination. In preferred compound embodiments of the instant formulae, however, all S' groups are the same, and all B' groups are the same. In highly preferred compound embodiments of the instant formulae, all S' groups are the same, and they all comprise a shield element, and all B' groups are the same, and they all comprise a binding element.

Multivalent Central Core Elements

One of the advantages of the protected fluorescent compounds of the instant disclosure is the multivalency of binding elements within each compound molecule. Specifically, each compound molecule comprises a plurality of terminal chemical groups, wherein at least one of the terminal chemical groups comprises a binding element that is capable of being recognized and bound by a target of interest. In the case of enzyme targets, such as, for example, the DNA polymerase used in single-molecule real-time DNA sequencing assays, the binding element comprises a substrate component capable of being reacted upon by the enzyme. A protected reagent compound for use in a DNA polymerase-catalyzed reaction might therefore include a nucleobase such as adenine, cytosine, guanine, thymine, or a modified form of one of these bases. In the normal DNA polymerase reaction using natural NTPs, or specifically dNTPs, the bond between the alpha phosphate, attached to the nucleoside and the beta phosphate is cleaved, releasing pyrophosphate, whereas in the instant reagent compounds, turnover by the enzyme releases the rest of the protected compound from the nucleobase. Multivalency of such binding elements on the protected fluorescent reagent therefore allows the same reagent molecule to undergo multiple enzyme turnovers before the molecule loses reactivity. The multivalency thus effectively increases the concentration of enzyme substrate in the reaction. Multivalency of binding elements in the protected reagent compounds is likely to provide similar advantages in the analysis of other types of binding interactions as well.

The integer "m" in formula (I) indicates the multivalency of S'—B' groups in the compounds of this formula. In some embodiments, m is an integer from 2 to 24. In specific embodiments, m is an integer from 2 to 12. In more specific embodiments, m is an integer from 2 to 8 or from 2 to 4. It should be understood that in all of these embodiments, the value of m can include any of the integer values within the listed range.

The multivalency of binding elements in the instant protected fluorescent compounds results, at least in part, from the inclusion of a multivalent central core element within the reagent molecule. According to one aspect, the multivalent central core element of the instant fluorescent compounds comprises a multivalent fluorescent dye element. Any suitable fluorescent dye may be used in such a fluorescent multivalent central core element, Z, provided the dye contains a plurality of reactive sites suitable for attachment of the relevant intermediate chemical groups, S', and terminal chemical groups, B'. In preferred embodiments, the fluorescent dye is a cyanine dye, for example any of the cyanine dyes disclosed in co-owned PCT International Publication No. 2012/027618; U.S. Patent Application Publication No. 2012/0058469; U.S. Patent Application Publication No. 2012/0058482; U.S. Patent Application Publication No. 2012/0052506; and U.S. Patent Application No. 61/649,058, the disclosures of each of which are incorporated herein by reference in their entireties for all purposes.

As noted in the above references, exemplary cyanine dyes have the formula:

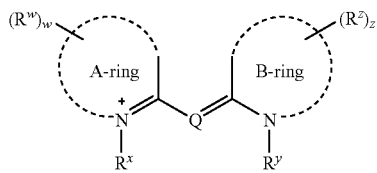

wherein the A-ring and B-ring are independently selected from monocyclic, bicyclic or polycyclic aryl or heteroaryl moieties. Q is a substituted or unsubstituted methine moiety (e.g., —(CH═C($R^u$))$_c$—CH═), in which c is an integer selected from 1, 2, 3, 4, or 5. Each $R^u$, $R^w$, $R^x$, $R^y$ and $R^z$ is independently selected from various suitable substituents, and the indices w and z are independently selected from the integers from 0 to 6. For use in a fluorescent multivalent central core element, Z, of the instant compounds, at least two of the $R^w$ and/or $R^z$ groups would be understood to contain suitable functionality to allow for the attachment of a plurality of S'—B' groups.

In some embodiments, each $R^w$ and $R^z$ is independently a substituted or unsubstituted alkyl, heteroalkyl, aryl, or heteroaryl group that is coupled to the A-ring or B-ring either directly or through a carbonyl, amide, carbamide, ester, thioester, ether, thioether, or amino linkage.

In some embodiments, each $R^x$ and $R^y$, is independently an alkyl or heteroalkyl group, optionally substituted with a sulfonic acid, carboxylic acid, phosphonic acid, or phosphoric acid.

In some embodiments, each $R^u$ is independently hydrogen, alkyl, or heteroalkyl.

Specific embodiments are described more thoroughly in the above-listed patent publications.

A specific example of a protected fluorescent reagent compounds of the instant disclosure comprising a tetravalent cyanine dye is the following structure:

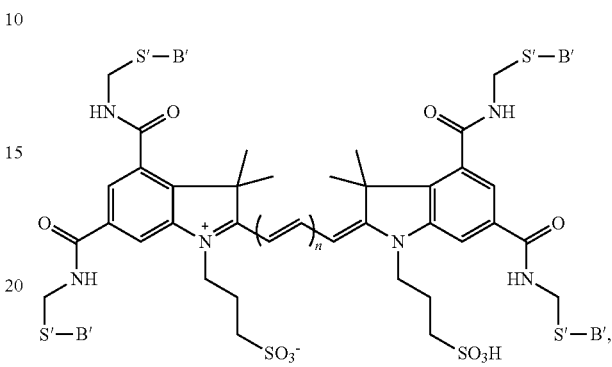

where n is 1 or 2. It should be understood that the connections between the cyanine dye and the S'—B' groups, in this, and in other related compounds, may be varied as desired. Such variation depends on the exact linking reactions used to attach the S'—B' group, as would be understood by those of ordinary skill in the art. Exemplary linkage reactions are described further below and are also described in disclosures of the above-listed, co-owned patent application publications.

Other examples of protected reagent compounds comprising multivalent cyanine dyes, including tetravalent, hexavalent, octavalent, and dodecavalent cyanine dyes, include the following non-limiting compound structures:

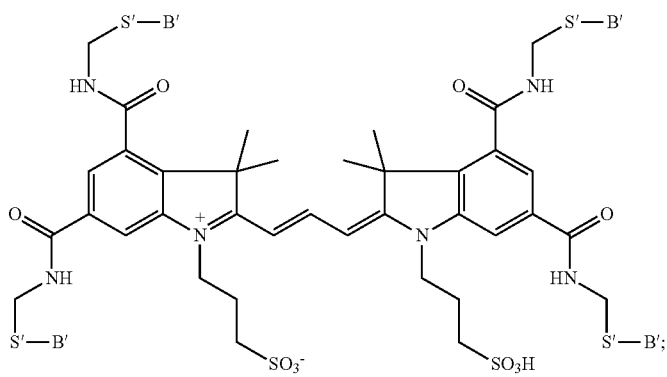

D010 (Tetravalent)

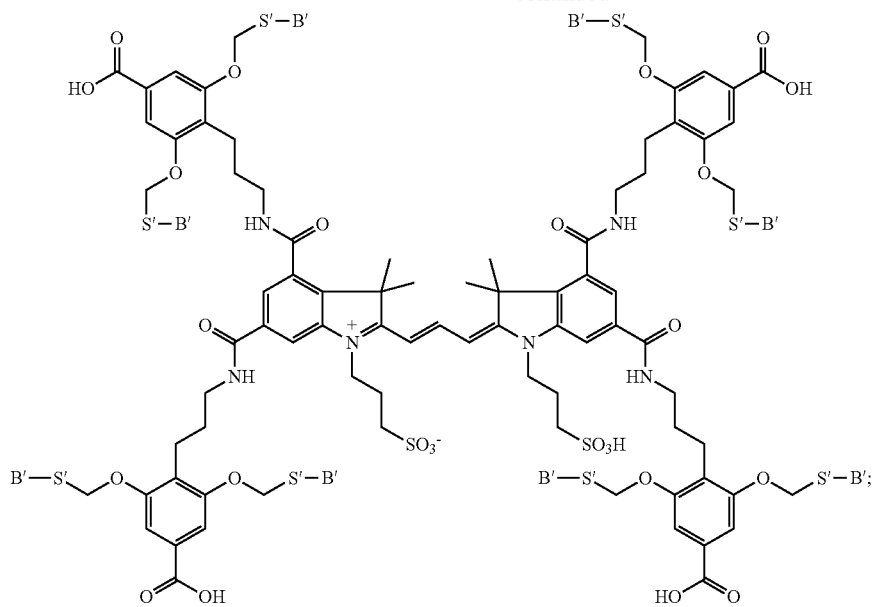
D010(Sh)₄ (Octavalent)
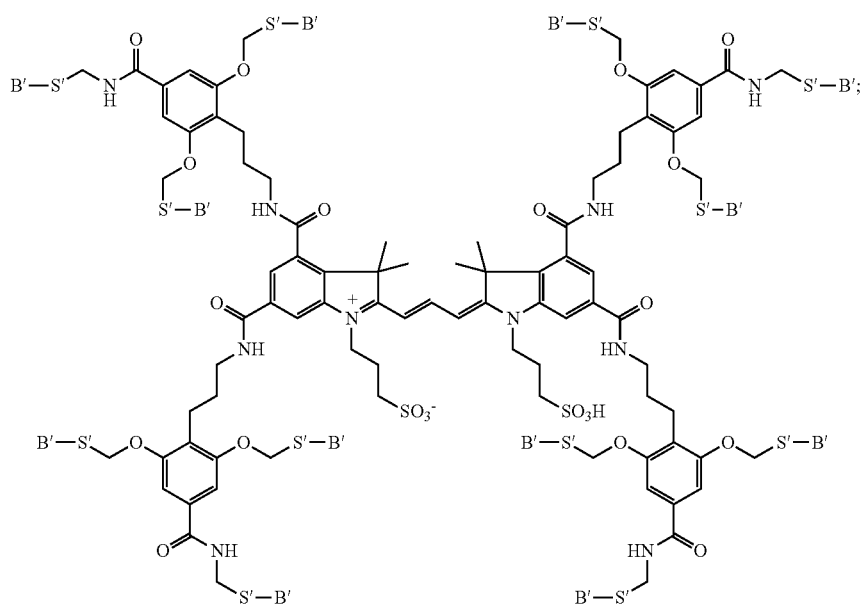
D010(Sh)₄ (Dodecavalent)

-continued
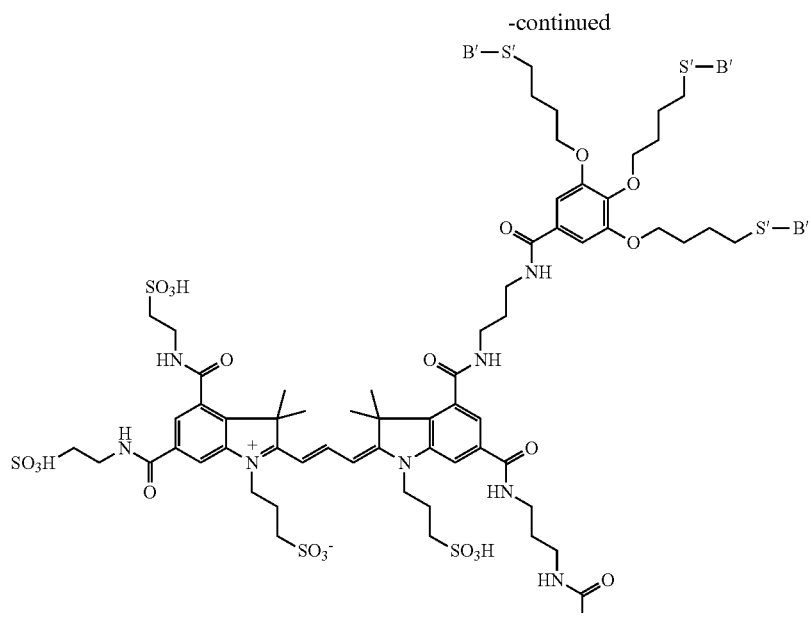
D011 (PD-Gal)₂ (Hexavalent)
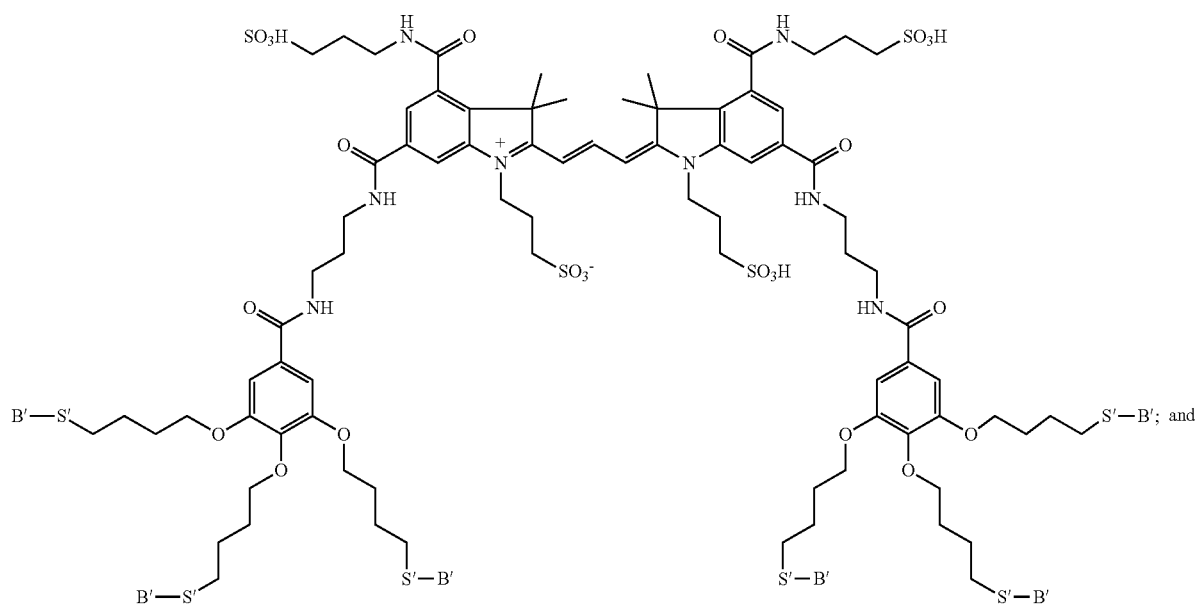
D009 (PD-Gal)₂ (Hexavalent)

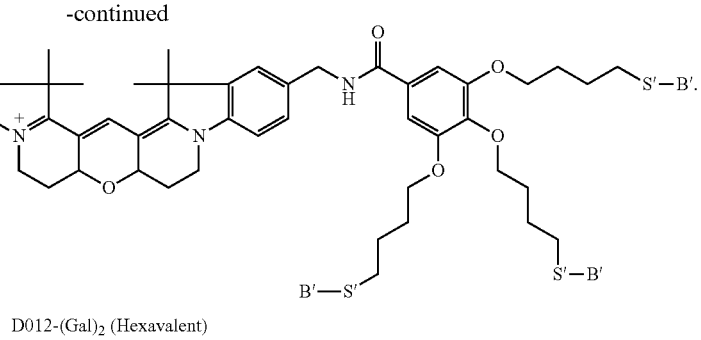

D012-(Gal)₂ (Hexavalent)

The above compound examples are labeled with the name of the specific dye that serves as the building block for the multivalent central core element and the name of the linking moiety that provides branching functionality. The S'—B' valency is indicated in parentheses for each compound. It should be understood that the linking moieties, and the functional groups used to couple them both to the central dye molecule and to the S'—B' groups may be varied as desired within the scope of the instant disclosure.

As is readily apparent upon review of the above structures, the S'—B' groups may be attached directly, or nearly directly, to the dye molecules, or they may be attached indirectly, for example, through a linker group. In some embodiments, the linker group comprises the structure:

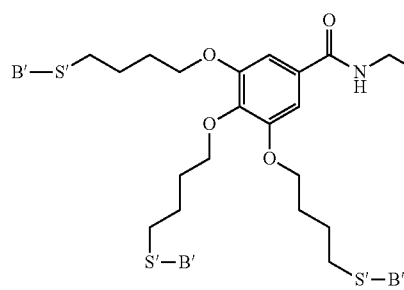

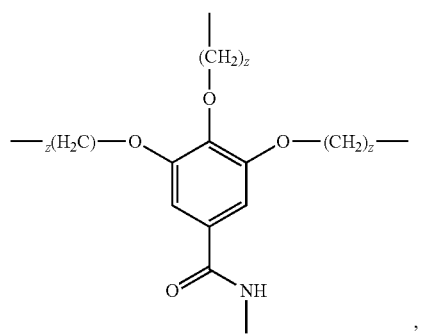

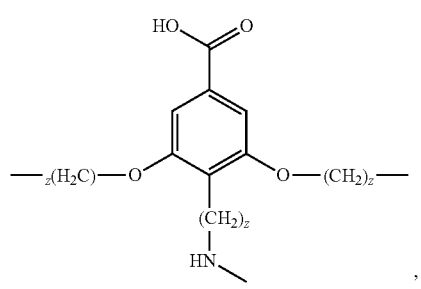

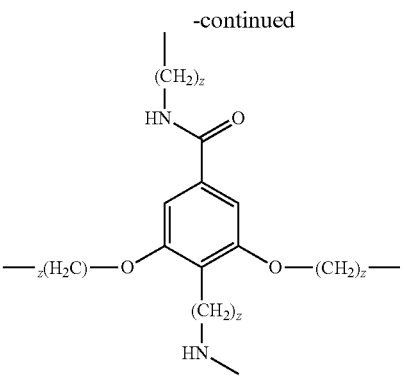

wherein each z is independently an integer from 1 to 6.

In more specific embodiments, each z is independently an integer from 1 to 4. As is apparent in some of the above-described compound examples, the linker group may further comprise an aminoalkyl group or a diaminoalkyl group. Other linker groups, for example, acylalkyl groups, diacylalkyl groups, or any other suitable linker group, may be usefully employed in the attachment of the S'—B' groups to the fluorescent multivalent central core element, as would be understood by those of ordinary skill in the art.

The linking moieties may also provide branching functionality, as is described more thoroughly below in the section entitled "Branching Elements", thus increasing the total possible valency of the fluorescent multivalent central core element.

Non-Fluorescent Multivalent Central Core Elements

According to another aspect, the instant compounds comprise a multivalent central core element that is not itself fluorescent but that rather provides sites of attachment for a plurality of fluorescent dye elements to the core element. The fluorescent dye elements themselves may be either monovalent or multivalent, depending on the intended use and desired properties. The non-fluorescent multivalent core element thus serves as a "scaffold" for assembly of the fluorescent dye elements and binding elements into the larger molecule. Exemplary scaffolds usefully employed in the protected fluorescent compounds of the instant disclosure are described in co-owned U.S. Patent Application Publication No. 2012/0077189, which is incorporated herein by reference in its entirety for all purposes.

In preferred embodiments, the non-fluorescent multivalent central core element provides for the attachment of a plurality of fluorescent dyes to the core. For example, the disclosure provides compounds of structural formula (IIa) or (IIb):

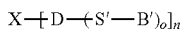 (IIa)

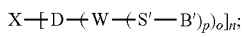 (IIb)

wherein
X is a non-fluorescent multivalent central core element;
at least one D is a fluorescent dye element;
at least one W, if present, is a branching element;
n is an integer from 2 to 6;
each o is independently an integer from 1 to 4;
each p is independently an integer from 1 to 4; and S' and B' are as defined above.

As is apparent from the above formulae, the non-fluorescent multivalent core element, X, is attached to a plurality of D groups, at least one of which is a fluorescent dye. The D groups of formulae (IIa) and (IIb) are accordingly either bivalent (e.g., in formula (IIa), and also in formula (IIb), when o=1) or have higher valency (e.g., in formula (IIb), when o≥2). The D groups thus serve as a link between the X group and the W group or groups (for formula (IIb)) or between the X group and the S'—B' group or groups (for formula (IIa).

For D groups that are fluorescent dye elements, the fluorescent dye elements are therefore either bivalent or have higher valency. Any suitable fluorescent dye may be used in the instant protected compounds, provided that the dye has proper valency and can be appropriately coupled to the relevant associated groups (X and W or S'). In preferred embodiments, the fluorescent dye is a cyanine dye, as described in detail above, including the cyanine dyes disclosed in the above-cited patent publications and in the above-depicted structures.

In other preferred embodiments, the D groups are monovalent and do not provide a connection between the non-fluorescent multivalent central core element and the S'—B' groups but are instead terminal groups that are connected to the central core element through a branching element that also serves to link the S'—B' groups to the central core element. For example, the disclosure provides protected reagent compounds of structural formula (III):

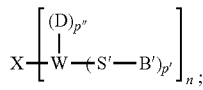 (III)

wherein
X is a non-fluorescent multivalent central core element;
at least one D is a fluorescent dye element;
at least one W is a branching element;
n is an integer from 1 to 6;
each p' is independently an integer from 1 to 4;
each p" is independently an integer from 1 to 4;
and S' and B' are as defined above.

As is evident in formula (III), the D group or groups and the S'—B' group or groups are attached to the non-fluorescent multivalent central core element through an intermediary branching element, W. Such branching elements have already been mentioned above in the context of the linker groups of the protected reagent compounds of formula (I), and they will described more thoroughly below in the section entitled "Branching Elements".

In preferred embodiments of the compounds of formulae (IIa), (IIb), and (III), all S' groups are the same and all B' groups are the same within a given reagent compound. In highly preferred embodiments, for a given reagent compound, all S' groups are the same, and each S' group comprises a shield element, and all B' groups are the same, and each B' group comprises a binding element.

As is evident in the structures of the compounds according to formulae (IIa), (IIb), and (III), the intermediate chemical group, S', and its associated terminal chemical group, B', may be either directly attached to the non-fluorescent multivalent central core element or may be attached indirectly through either an intermediary multivalent dye or through a branching element. The specific chemical linkages used in any of these attachments is not critical, so long as the linkages are stable under the conditions in which the compounds are being used, as would be understood by those of ordinary skill in the art.

As mentioned above, the non-fluorescent multivalent central core element according to this aspect of the invention serves as a scaffold for dyes, intermediate chemical groups and their associated shield elements, and terminal chemical groups and their associated binding elements in some of the disclosed compounds. In some embodiments, the non-fluorescent multivalent central core element comprises a polyamine central core element. Polyamines may be readily reacted with appropriate electrophilic reagents, such as electrophilic linker or branching elements, dye reagents, and the like, to generate intermediate compounds that may in turn be reacted with appropriate shield element and binding element reagents. It should be understood that the order of such reactions may be varied, depending on the desired outcome, as would be understood by those of ordinary skill in the art. Non-limiting examples of polyamines usefully employed in the non-fluorescent multivalent central core elements of the instant disclosure include the following:

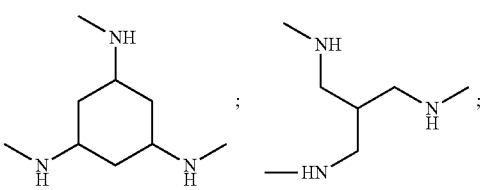

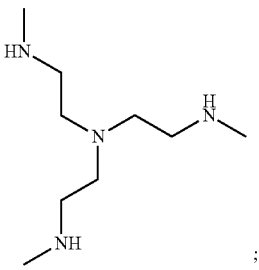

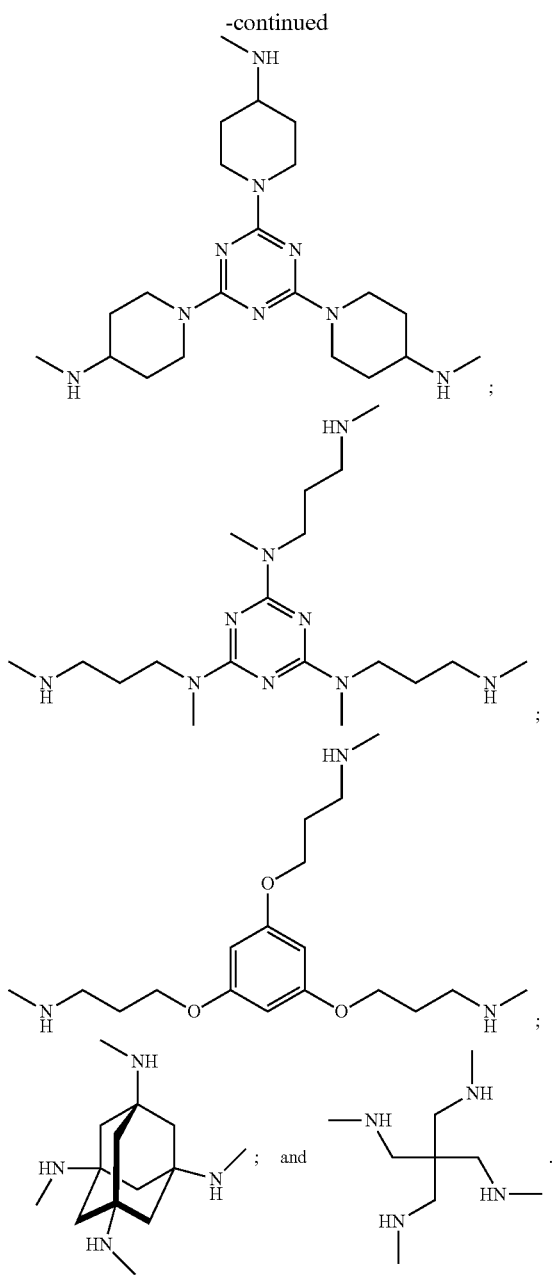

The skilled artisan would understand, however, that other polyamines could be readily utilized in the protected fluorescent compounds of the instant disclosure.

In specific embodiments, the non-fluorescent multivalent central core element comprises a substituted cyclohexane, more specifically a 1,3,5-triamino-cyclohexane.

In other specific embodiments, the non-fluorescent multivalent central core element comprises a substituted 1,3,5-triazine.

In still other specific embodiments, the non-fluorescent multivalent central core element comprises a substituted benzene.

In some embodiments the non-fluorescent multivalent central core element comprises an ether linkage. In some embodiments, the non-fluorescent multivalent central core element comprises an acyl linkage. Examples of such ether and acyl-linked central core elements include the following structures:

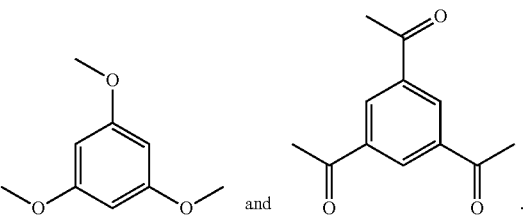

These structures may be incorporated into the instant protected reagent compounds as described in detail below. In particular, ether-linked central core elements may be modified with acetylene-containing groups, including cycloalkyne-containing groups, and the acetylene groups may then be coupled to azide-containing reagents using "click" chemistry or "copper-free click" chemistry. Likewise, carboxylate-containing central core elements may be activated using suitable reagents, and the activated acyl groups may then be coupled to appropriate nucleophilic reagents as desired. Alternatively, or in addition, the central core elements may be activated using azide-containing groups, and those groups may be coupled to acetylene-containing reagents, including cycloalkyne-containing reagents, using "click" chemistry or "copper-free click" chemistry. Such reactions are well understood by those of ordinary skill in the art.

Branching Elements

As described above, the protected reagent compounds of the instant disclosure may, in some embodiments, comprise additional linker groups that may be attached, for example, to a central core element or that may serve as an intervening linkage between a D group and S'—B' group. Such linker groups may in some embodiments serve as branching elements to allow the attachment of multiple S'—B' groups to D groups (as in Formula (IIb)) or multiple D and S'—B' groups to X groups (as in Formula (III)). In preferred embodiments, the branching elements may include acyl groups for coupling to, for example, an appropriate amino group, amino groups for coupling to, for example, an appropriate acyl group, and further reactive groups, such as, for example, acetylene groups for coupling to, for example, azide-labeled groups. Exemplary branching elements usefully employed in the protected reagent compounds of the instant disclosure include the following:

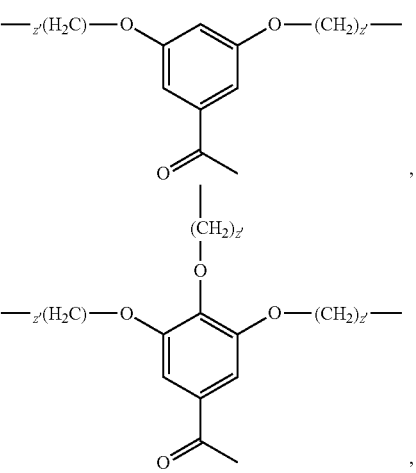

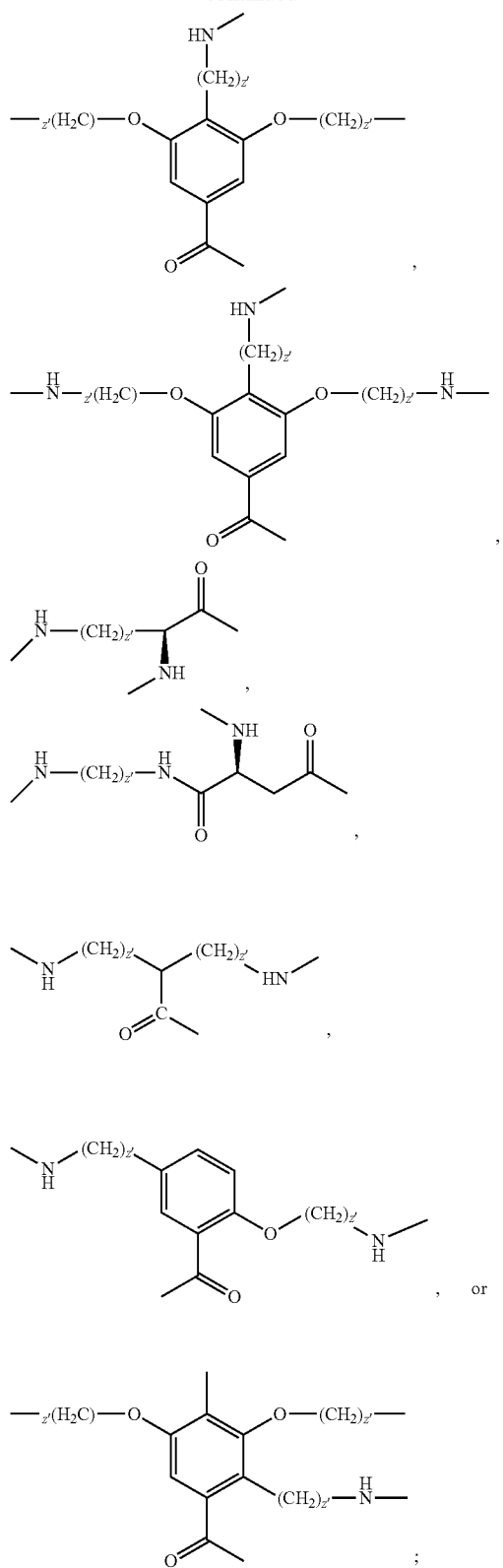
wherein each z' is independently an integer from 1 to 6. In more specific embodiments, each z' is independently an integer from 1 to 4. In some embodiments, the branching element includes the following:
In other specific embodiments, the branching element comprises the structure:
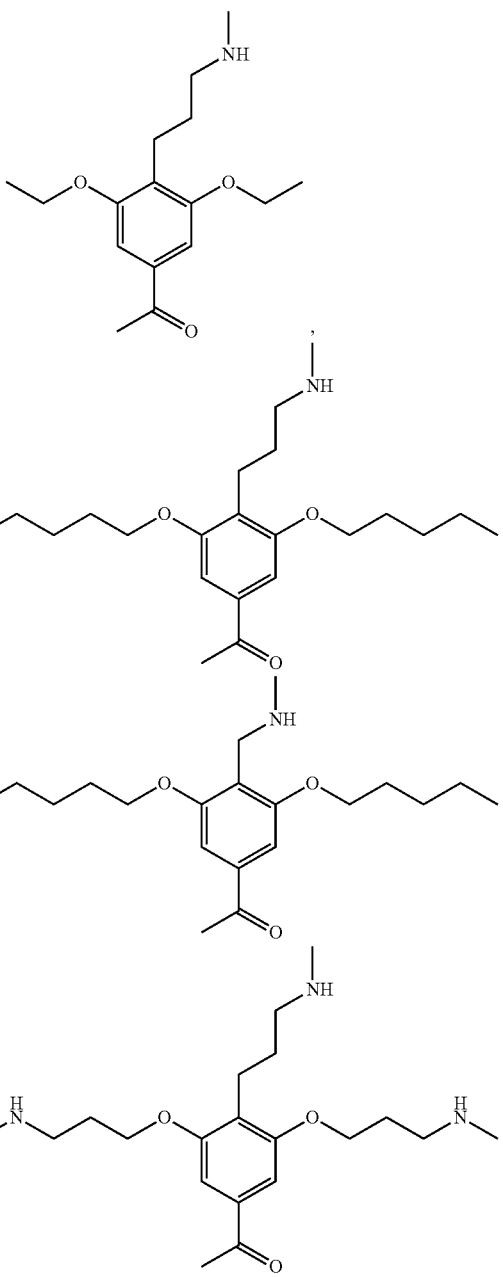

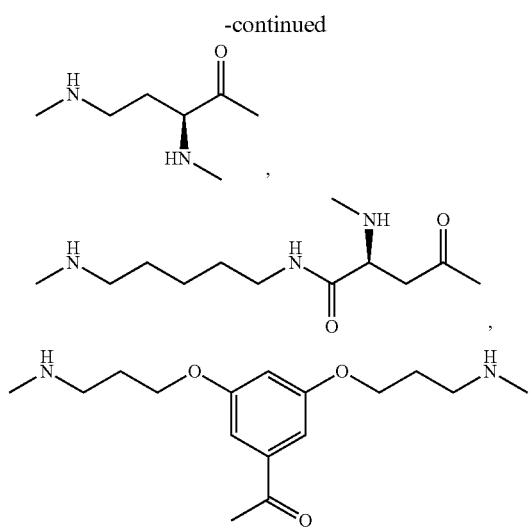

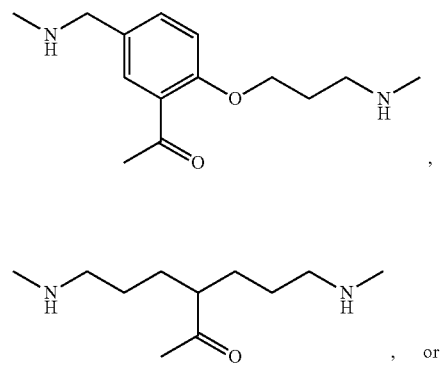

, or

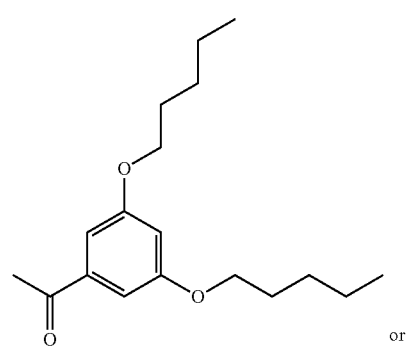

and in some embodiments comprises the structure

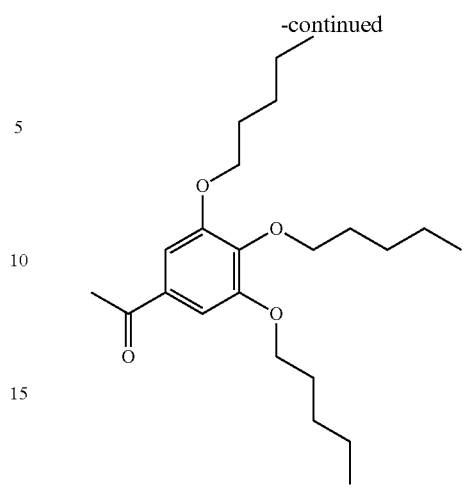

In some embodiments, the branching element comprises the structure

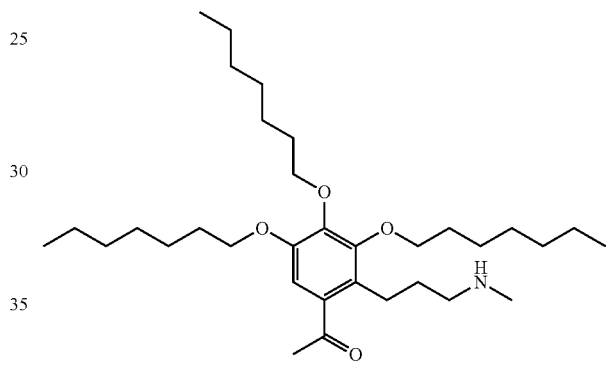

Some branching elements may contain more than one of the above structures, and different branching element structures may be present within a single molecule of the instant compounds.

As would be understood by those of ordinary skill in the art, the terminal acyl groups of the above structures are preferably linked to an amine group within a given compound, for example to an amine group in the central core element, and the terminal amino groups of the above structures are preferably linked to an acyl group within a given compound, for example to an acyl group in the D group (for compounds of formula (III)). Branching elements are typically coupled to their associated shield element-binding element (S'—B') groups using "click" chemistry, or "copper-free click" chemistry, as described more thoroughly below. The terminal methylene groups in the above structures are therefore preferably linked to the S'—B' groups through a triazole structure, although other linking chemistry should be considered within the scope of the invention.

It should be generally understood that other coupling chemistry may prove suitable in the protected compounds of the instant invention, and that the branching element structures should not, therefore, be limited to those illustrated in the exemplified compounds. Accordingly, reactions other than those exemplified in the synthetic schemes below, may be suitable for generating the protected reagent compounds of the instant invention. For example, alkylations, e.g., through the reaction of alkyl halides, acylations, and other suitable reactions may be utilized in synthesizing the instant compounds.

Intermediate Compounds

Exemplary intermediate compounds useful in the synthesis of some embodiments of the instant compounds comprise a non-fluorescent multivalent central core element with attached fluorescent dye groups. These compounds further comprise acetylene groups that may be efficiently coupled to shield elements and their associated binding elements through "click" reactions, or "copper-free click" reactions, and the like. Such synthetic intermediates include the following non-limiting examples:

"acceptor" dye. Compounds comprising donor and acceptor fluorophores thus provide for the possibility of measuring a fluorescent signal using fluorescence resonance energy transfer (FRET) techniques or the like, as would be understood by those of ordinary skill in the art. Examples of FRET-labeled nucleotides and donor-acceptor pairing are provided in U.S. Patent Application Publication Nos. 2010/0255488 and 2012/0058469, the full disclosures of which are hereby incorporated by reference herein in their entirety for all purposes. Additional long-wavelength heteroarylcya-

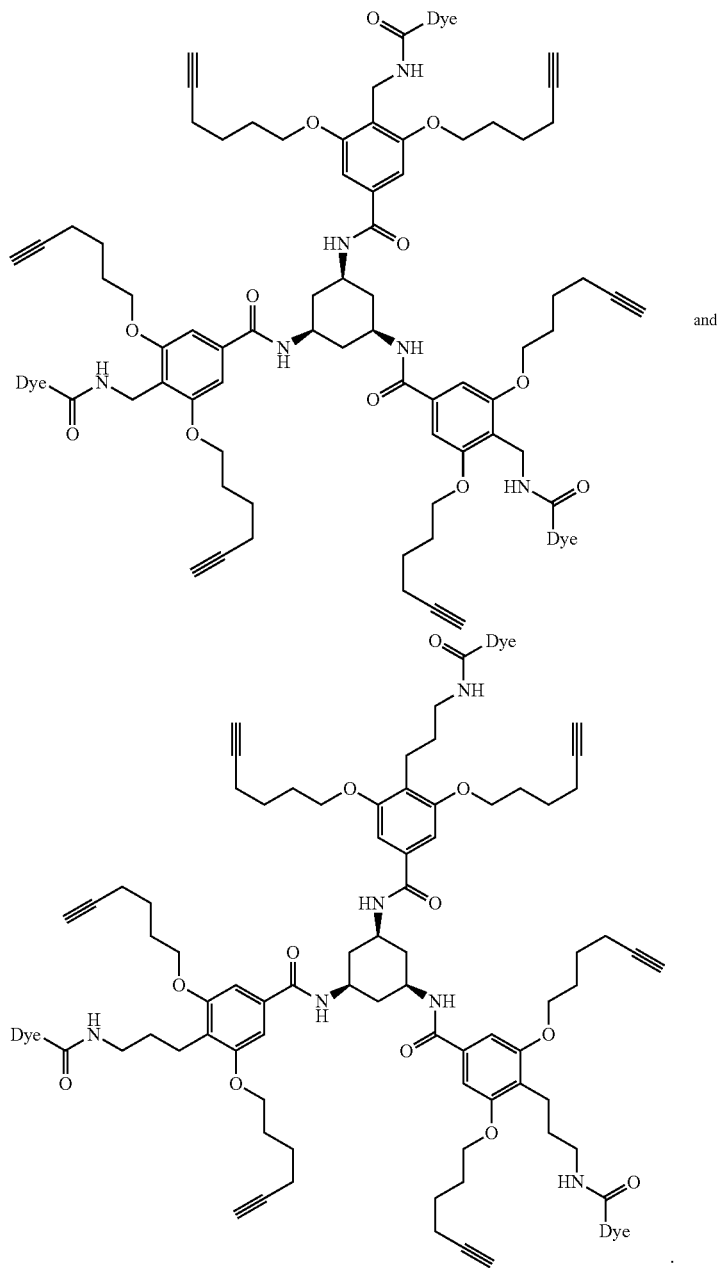

and

The "dye" groups of the previous exemplary intermediates may be the same or different fluorescent dyes within a given reagent molecule. In preferred embodiments, the dyes are different, and at least one of the dyes is an energy transfer "donor" dye and at least one of the dyes is an energy transfer nine dyes usefully incorporated into the instant protected fluorescent compounds are disclosed in U.S. patent application Ser. No. 13/898,369, filed May 20, 2013, the full disclosure of which is hereby incorporated by reference herein for all purposes.

The terms "fluorescence resonance energy transfer" and "FRET" are used herein to refer to both radiative and non-radiative energy transfer processes. For example, processes in which a photon is emitted and those involving long-range electron transfer are included within these terms. Throughout this specification, both of these phenomena are subsumed under the general term "donor-acceptor energy transfer".

Any of the dyes set forth herein can be a component of a FRET pair as either the donor or acceptor. Conjugating a donor and an acceptor through reactive functional groups on the donor, the acceptor, and, if appropriate, an appropriate linker or carrier molecule, is well within the abilities of those of skill in the art in view of the instant disclosure.

Exemplary protected fluorescent compounds having one or more donor and one or more acceptor fluorophores include the following non-limiting structures:

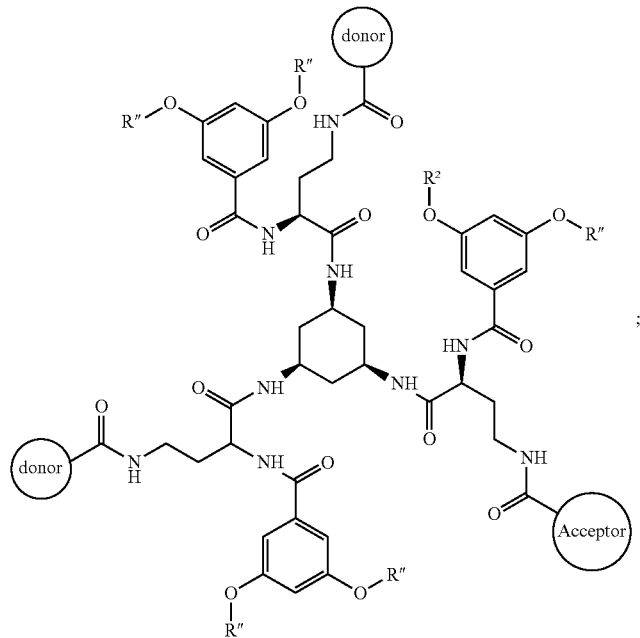

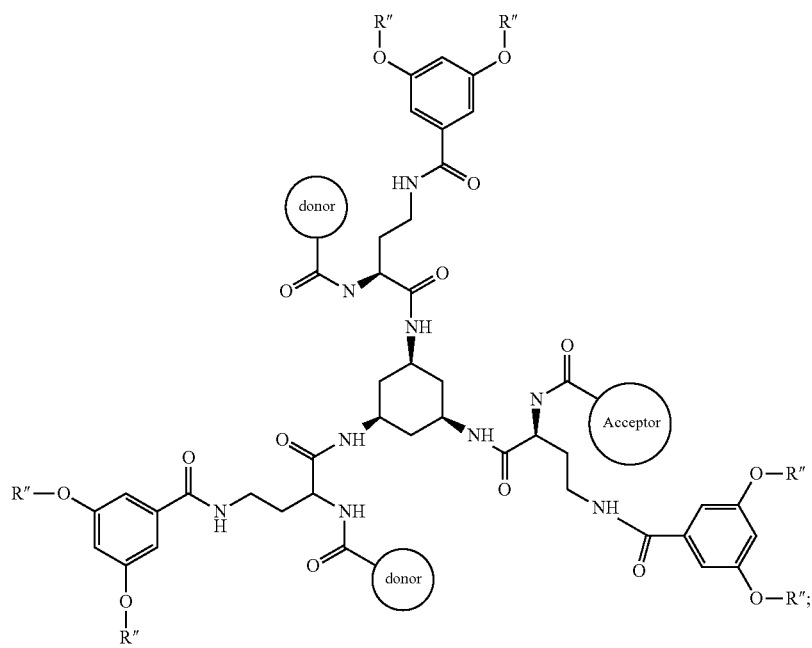

-continued
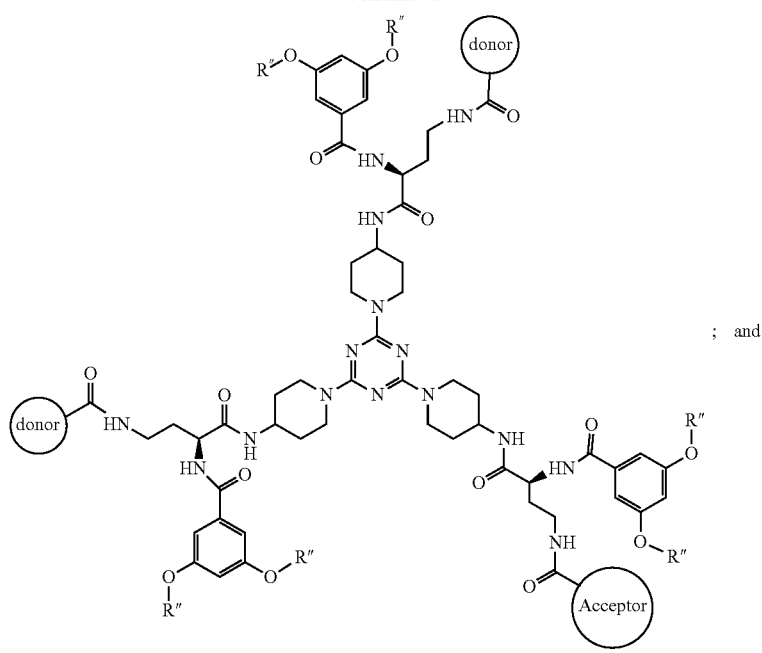
; and
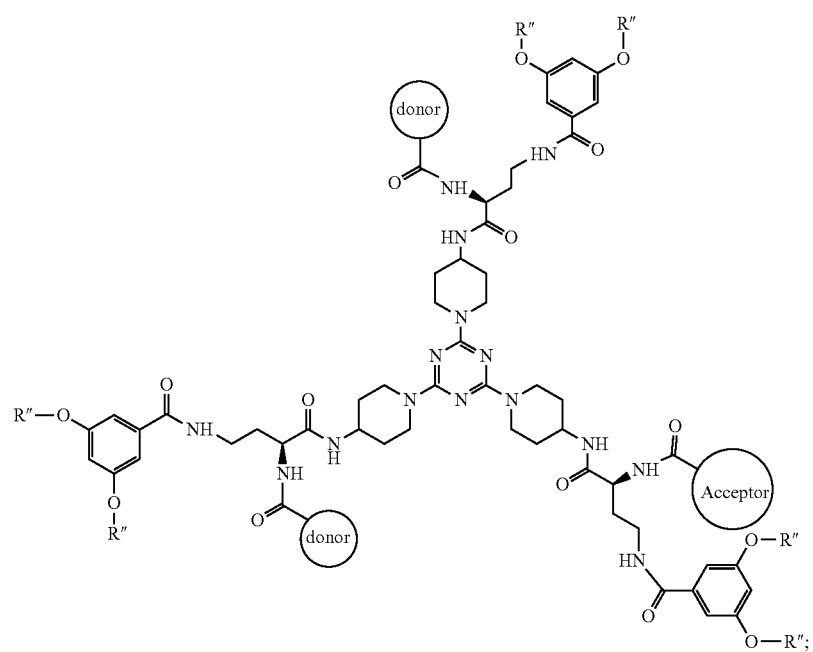

where the donor dye and acceptor dye attachment locations are as indicated, the R" groups represent locations for attachment of the S'—B' groups, and where the lower two structures comprise alternative polyamine central core elements.

Figure 11:
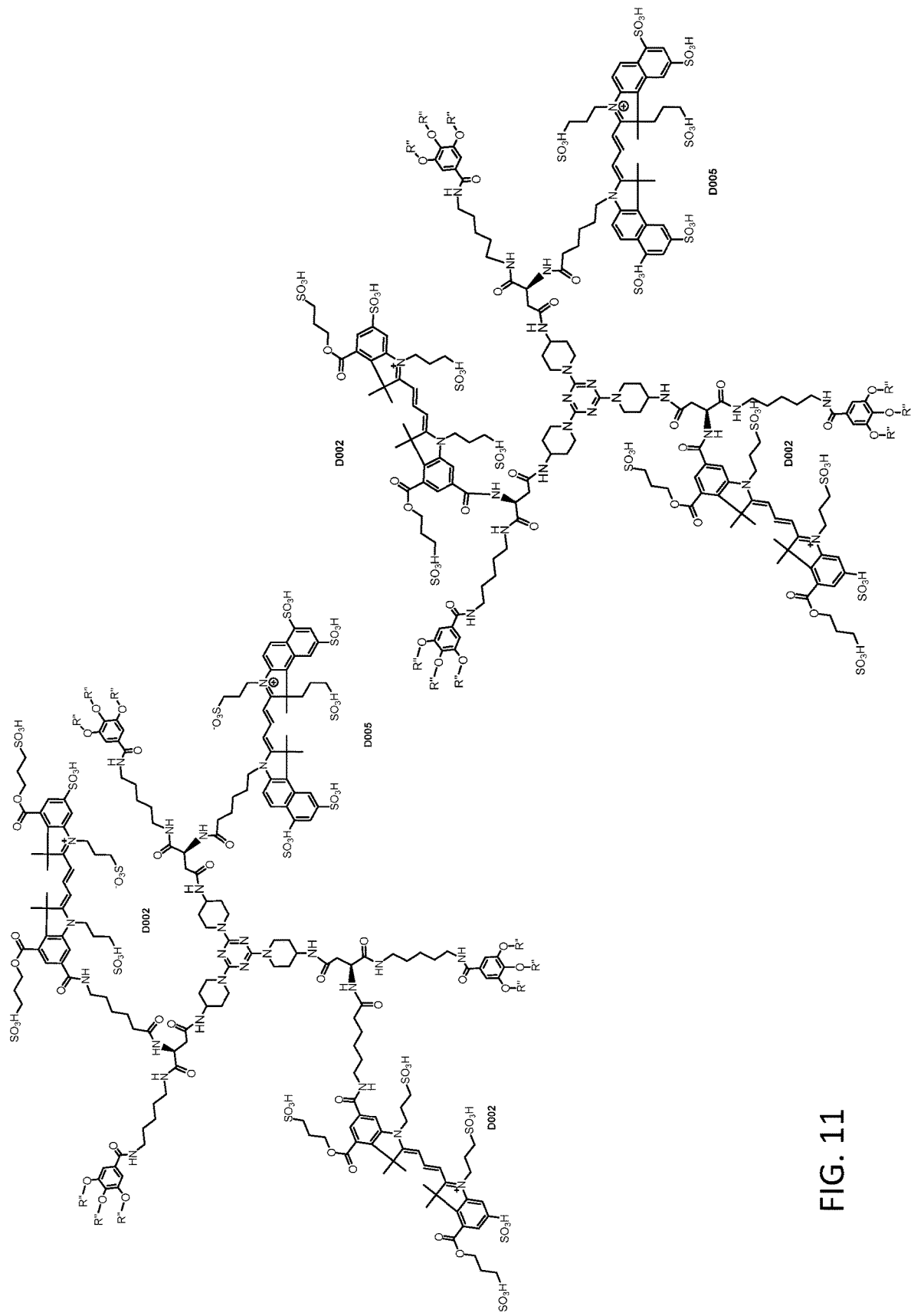
FIG. 11 illustrates exemplary protected fluorescent compounds.
Figure 11:
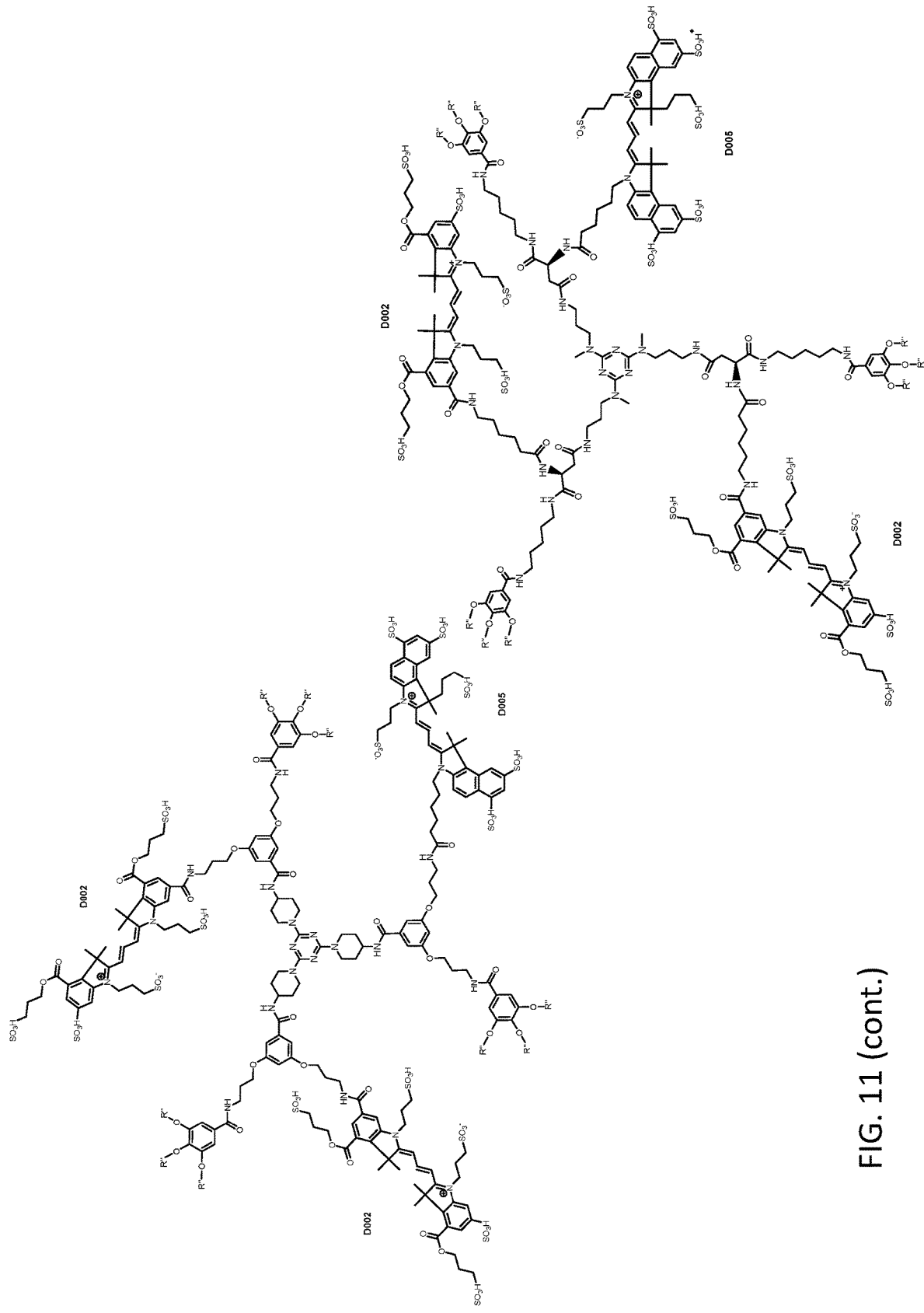
Figure 11:
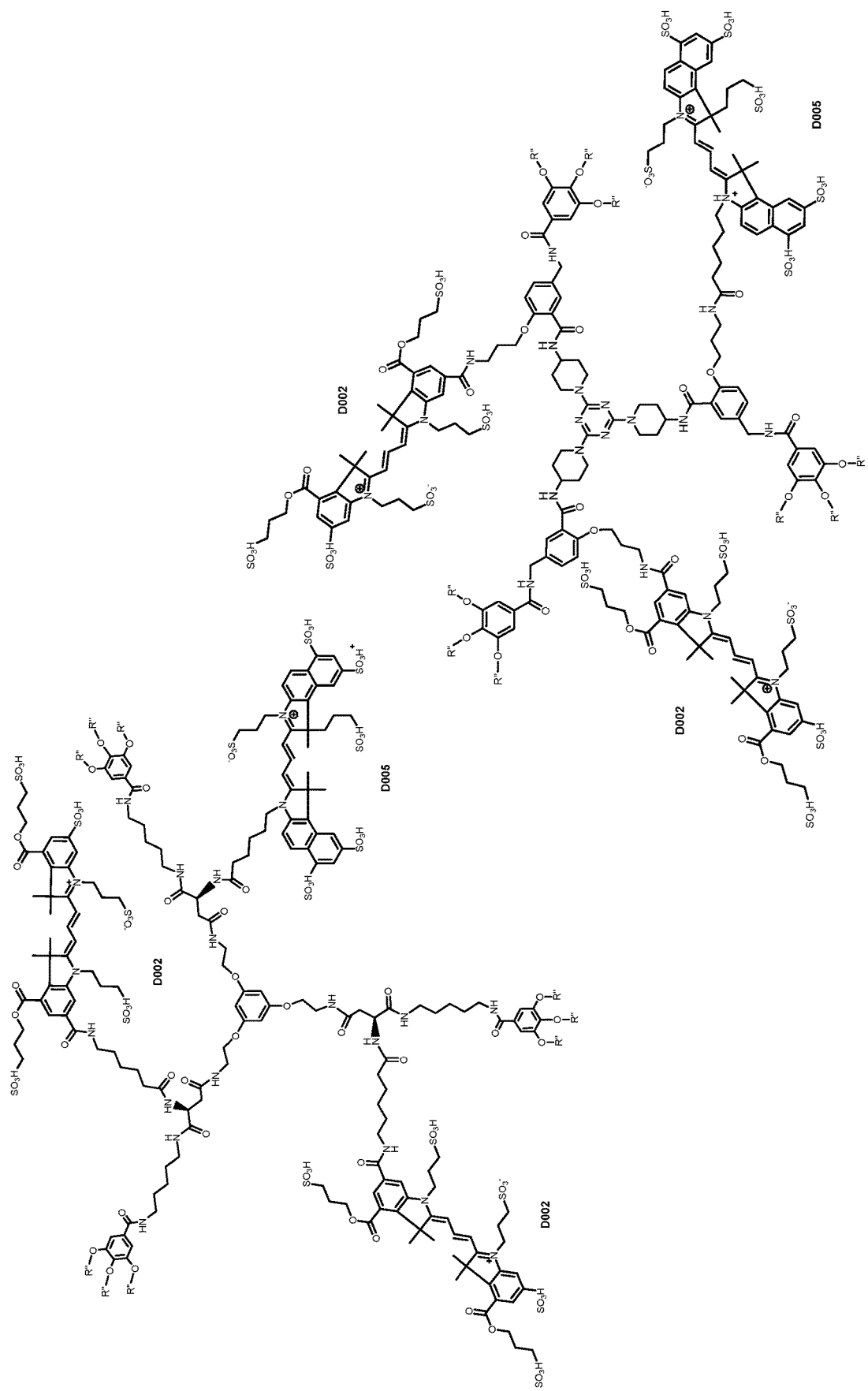

Further examples of protected fluorescent compounds according to this aspect of the instant invention include the nonlimiting structures illustrated in FIG. 11, where the R" groups represent locations for attachment of the S'—B' groups, and where the structures each include two donor fluorescent dye elements, designated "D002", and one acceptor fluorescent dye element, designated "D005".

Another example of this type of structure is the following:

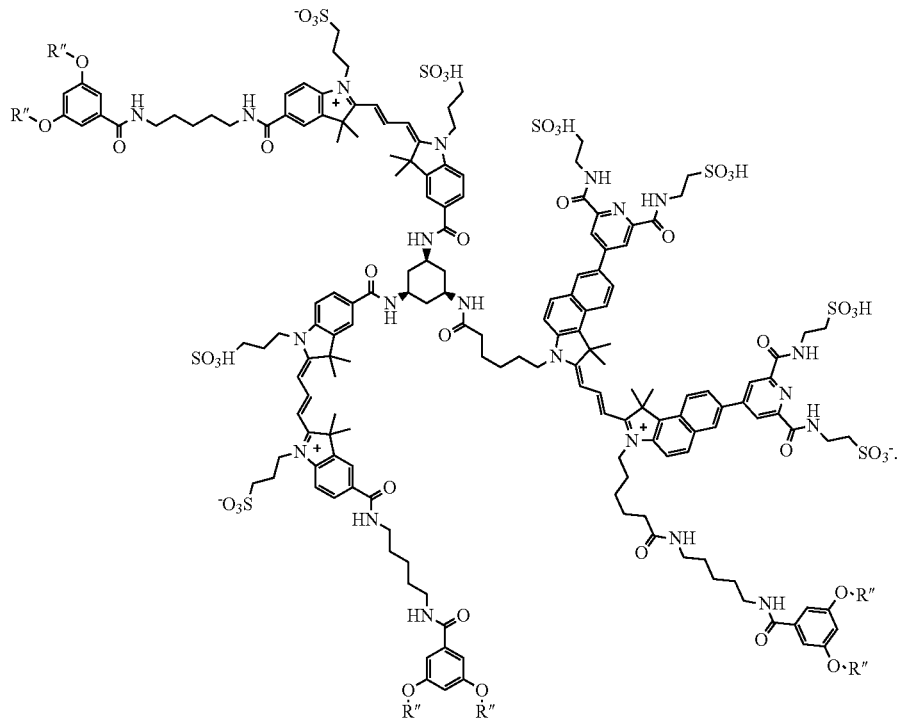

Other exemplary core structures usefully incorporated into the protected fluorescent reagent compounds of the invention include the following:

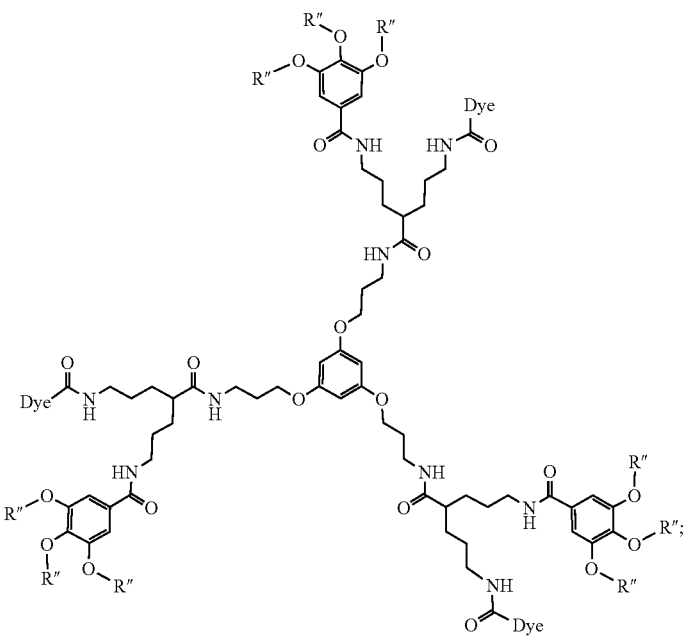

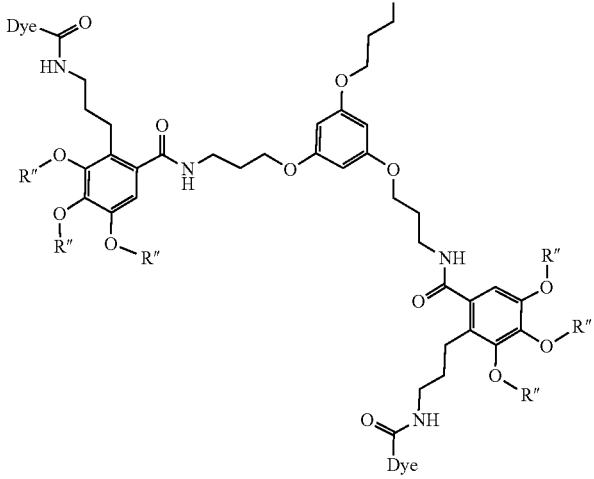

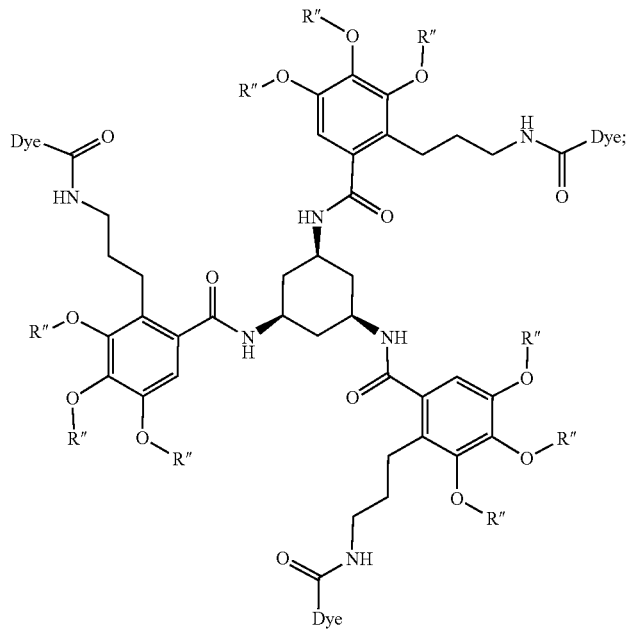

where R″ is as defined above, and "Dye" can be independently any donor or acceptor fluorescent dye element.

In some embodiments, the instant protected fluorescent compounds may include a non-fluorescent multivalent central core element with attachment sites for 5, 6, or even more fluorescent dye elements on each core. The dyes may either be the same or different, for example, if FRET donors and acceptors are used. Intermediate compounds containing the core elements with attached fluorescent dyes may be further reacted with appropriate reagents to attach shield elements and binding elements as desired, for example, as illustrated in the reaction schemes outlined below.

Exemplary intermediate compounds useful in the synthesis of the just-described embodiments include the following non-limiting examples, which comprise acetylene groups for coupling to the shield elements and their associated binding elements through "click" reactions, "copper-free click" reactions, or the like:

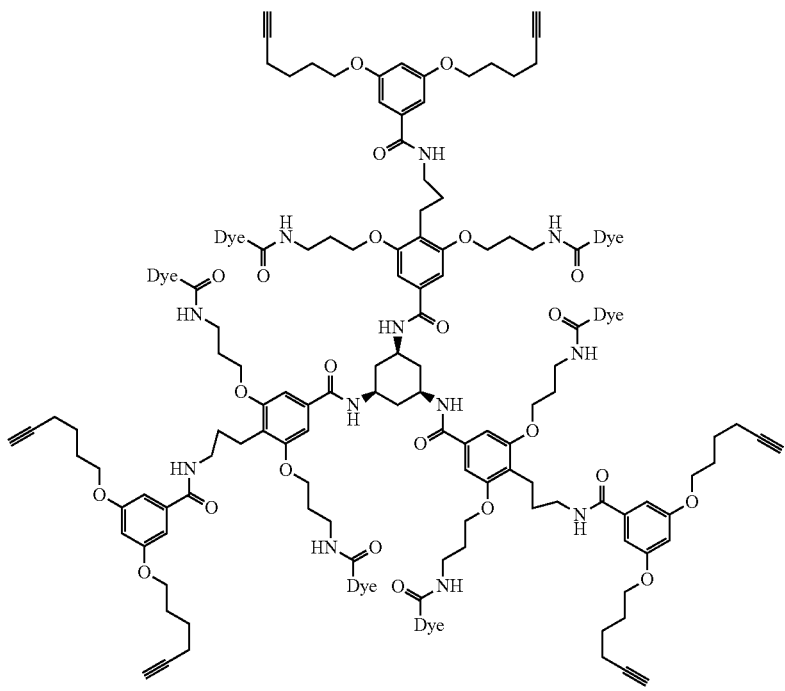
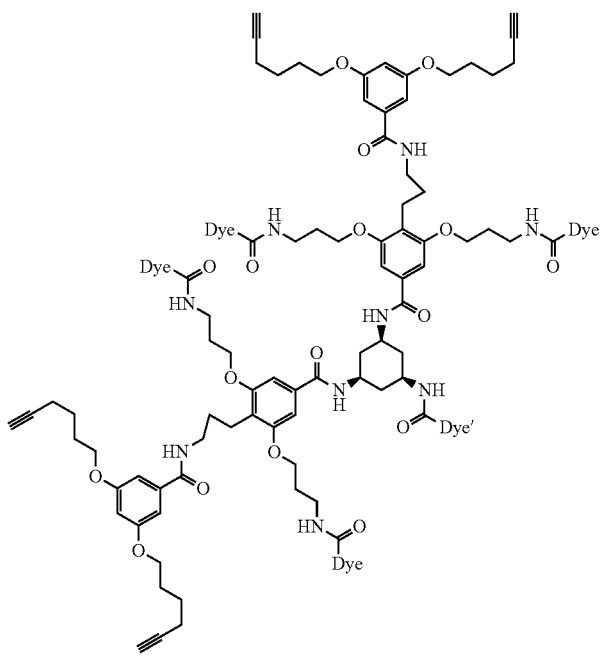

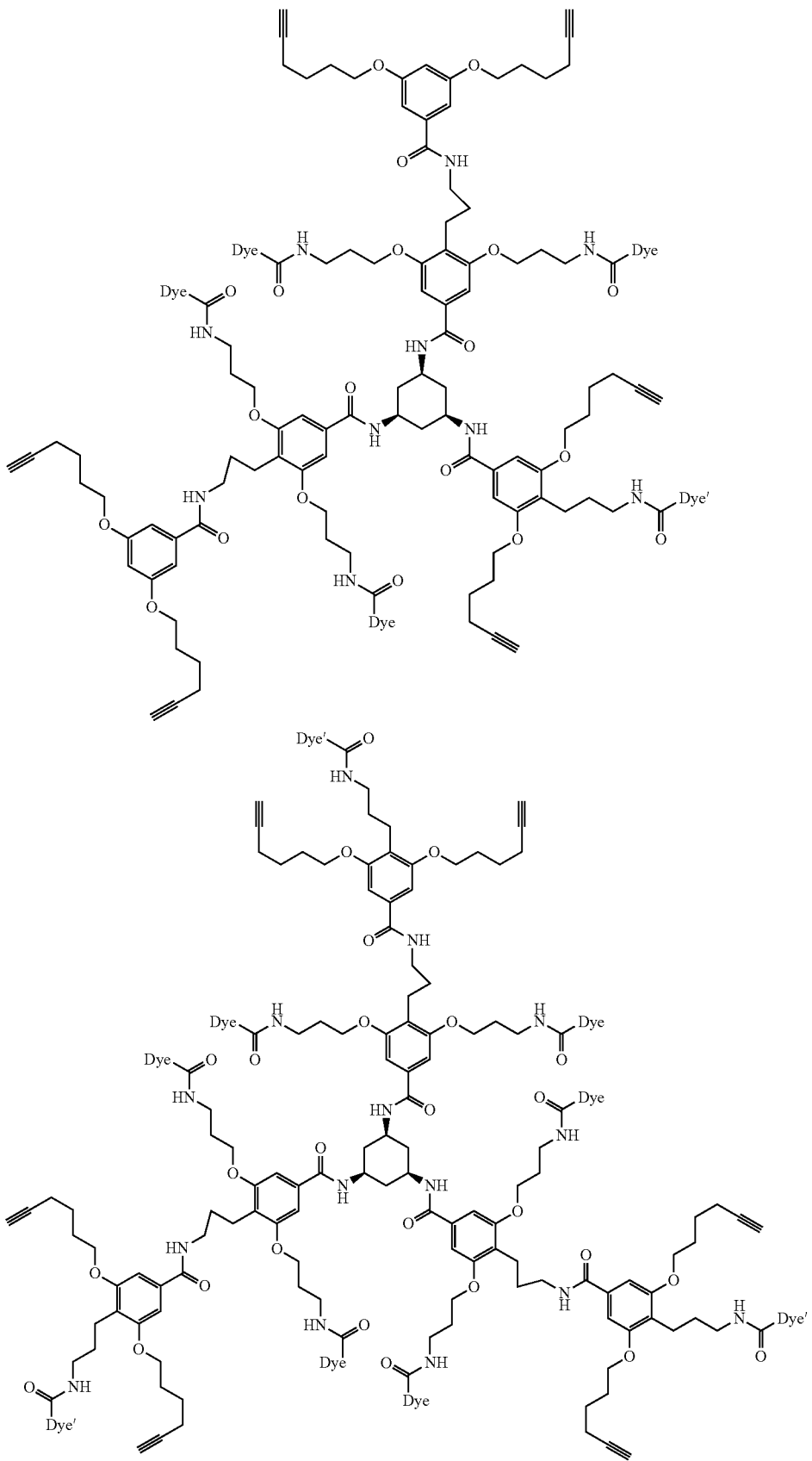

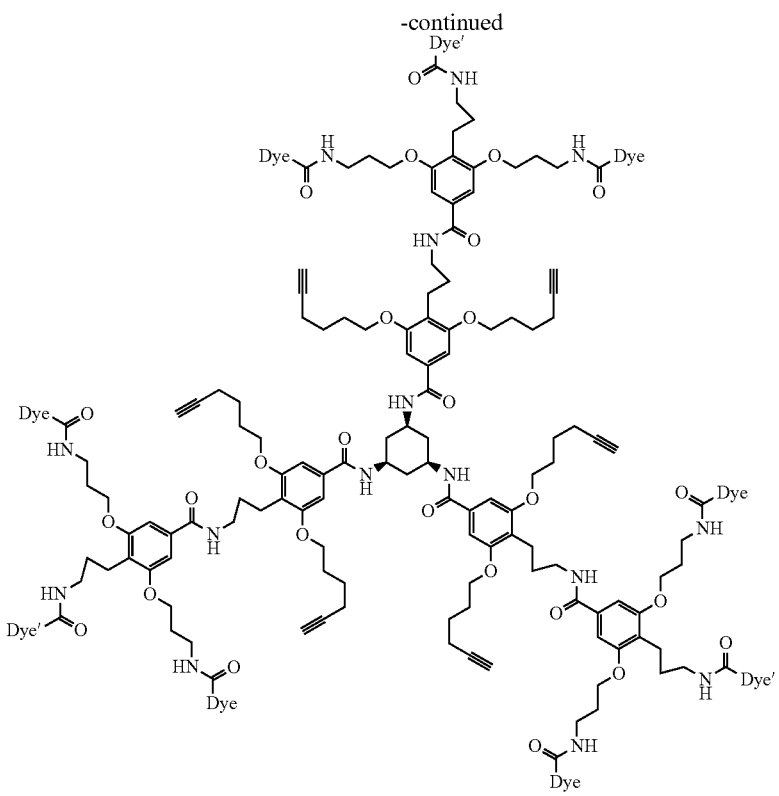

Figure 12:
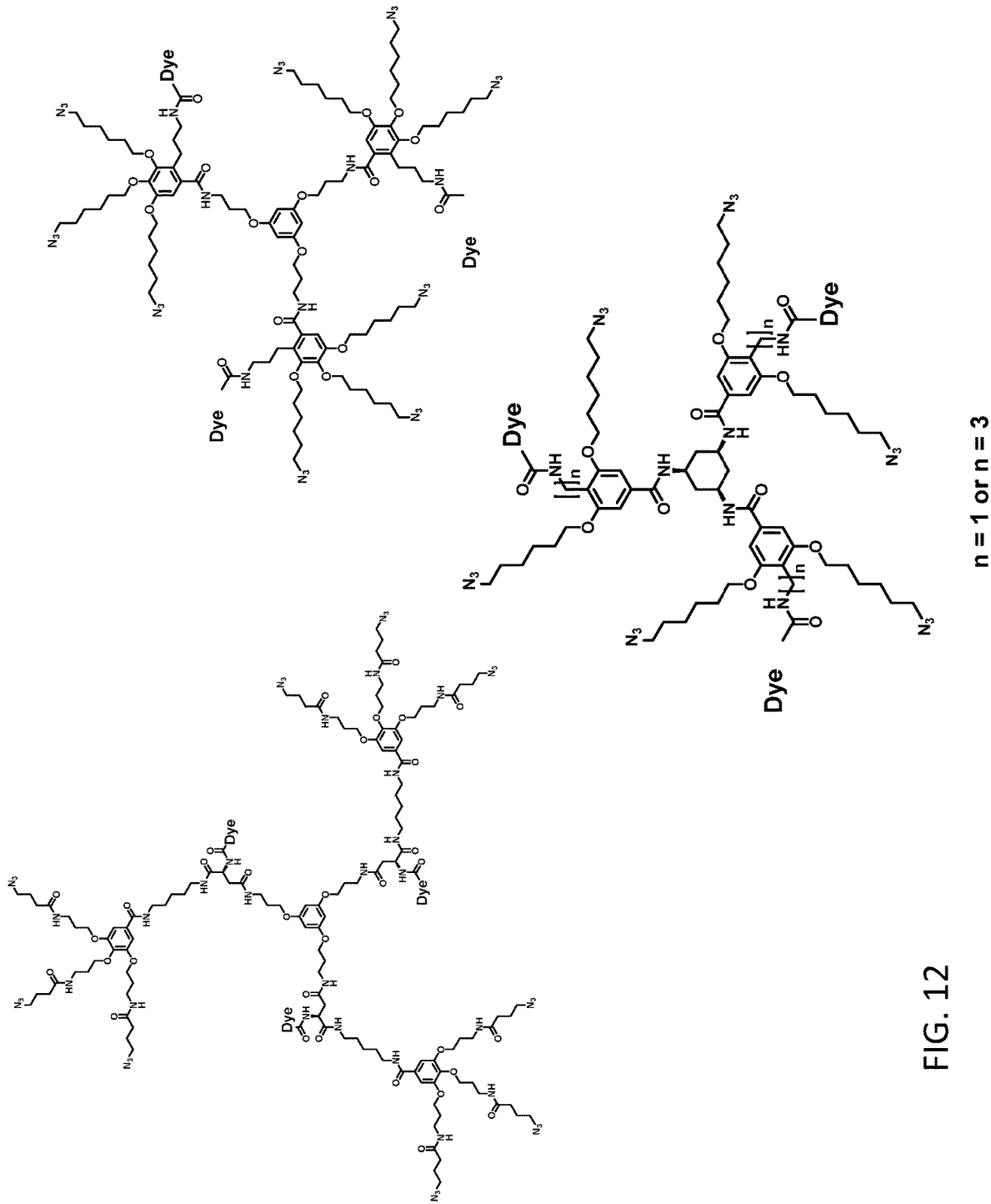
FIG. 12 illustrates non-limiting examples of azido-containing central core intermediate compounds.
Figure 12:
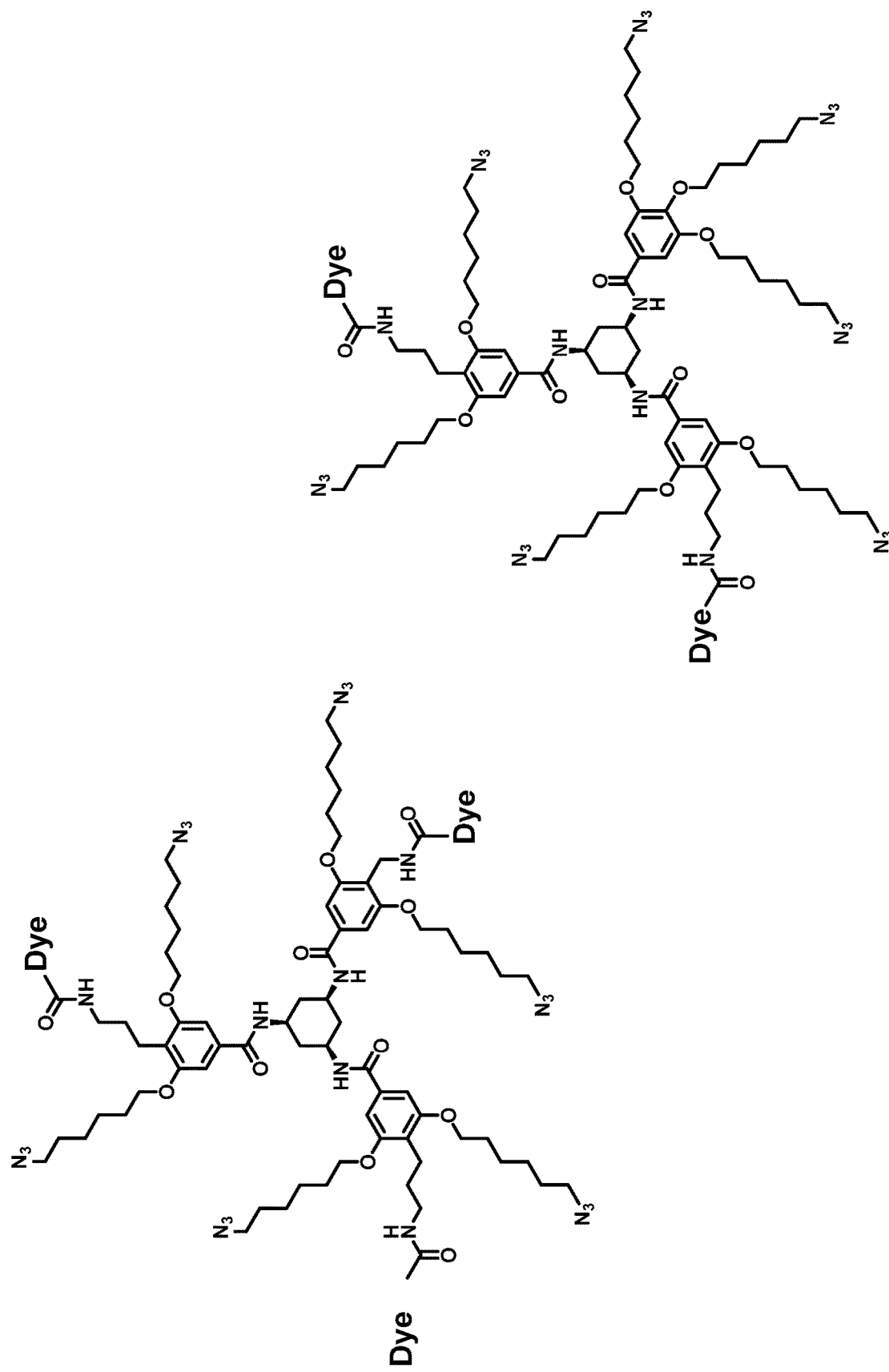

It may be advantageous under some circumstances, for example when using the Cu-free click reaction to assemble the protected reagent compounds, to include an azide group within the central core intermediate compound, rather than an alkyne group. Non-limiting examples of azido-containing central core intermediate compounds are illustrated in FIG. 12.

After reaction of the above intermediates with a cycloalkyne-containing reagent using Cu-free click chemistry, these structures include the following exemplary linkages, where the "R" group corresponds to an S'—B' group:

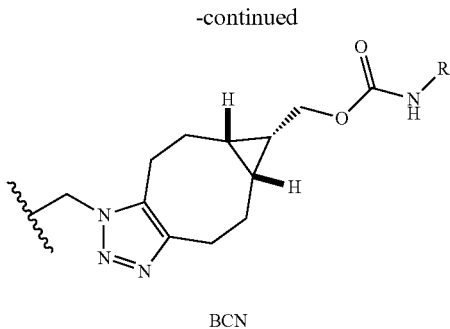

BCN

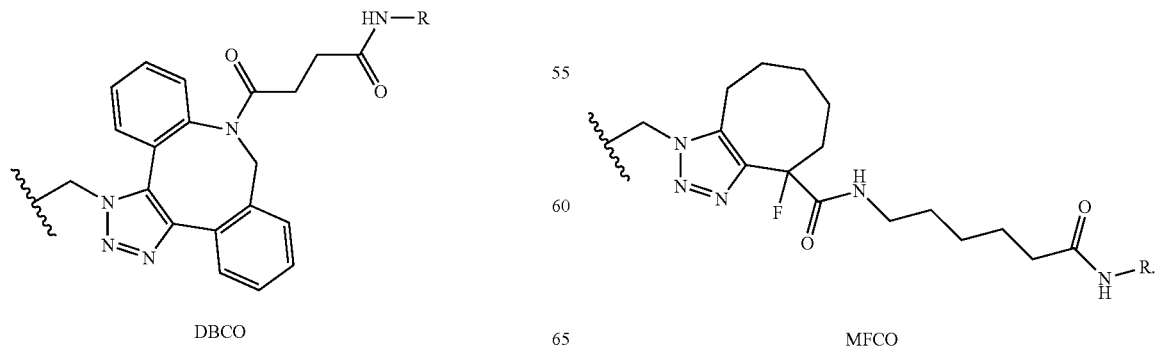

DBCO

MFCO

Variation in the above linkages, for example where the lengths of the alkyl linker groups are altered, or where heteroatoms or other intervening chemical moieties are substituted for the structures shown, are envisioned where such substitution does not interfere with the function of the linker group, as would be understood by those of ordinary skill in the art.

As noted above, the substituents labeled "Dye" and "Dye'" in these structures may be the same or different fluorescent dye elements, depending on the desired spectroscopic properties of the respective compounds.

In preferred embodiments, the non-fluorescent multivalent central core element of these compounds is a trivalent, tetravalent, pentavalent, hexavalent, octavalent, decavalent, or dodecavalent central core element.

Shield Elements

As previously noted, photodamage caused by the instantly-disclosed compounds is mitigated by the covalent incorporation of a shield element between the associated fluorescent dyes and the associated binding elements. The exact structure of the shield elements of the protected compounds disclosed herein are not believed to be critical, so long as the structures are large enough to limit contacts between the fluorescent dyes and proteins, or other molecules of interest, that bind to the instant compounds and that are sensitive to photodamage by the excited dyes. In some embodiments, the shield element comprises a protein. In some embodiments, the shield element does not comprise a protein.

In some embodiments, the shield element of the instant compounds preferably comprises a shield core element that provides multivalent attachment sites for shield element side chains, where the shield element side chains provide the primary "bulkiness" of the shield element moiety and are thus believed to be responsible for the protective effects in the compounds.

Accordingly, the shield elements may in some embodiments comprise a suitable core structure that provides for the attachment of a plurality of side chains to the shield element core. In specific embodiments, the shield element comprises the structure:

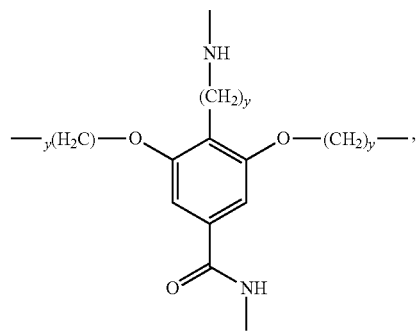

wherein each y is independently an integer from 1 to 6. In other specific embodiments, the shield element comprises one of the other branching elements described in more detail above.

In some embodiments, the shield core elements provide a "layered" multivalent structure, such that one type of side chain can be attached to the portion of the shield element facing the interior of the protected compound (i.e., the dye region) and a different side chain can be attached to the portion of the shield element facing the exterior of the protected compound (i.e., the binding element region). The inner layer is ideally designed to create a protective microenvironment for the fluorescent dyes and thus to improve their photophysical properties (e.g., their brightness) and their photochemical stabilities. The inner layer preferably comprises pairs of neutral or negatively charged groups. The outer layer defines the interactions with the solvent and the binding partner. For uses of the protected fluorescent compounds in SMRT™ sequencing reaction systems, the outer layer is preferably designed to improve solubility of the compound, to improve sequencing incorporation kinetics, and to minimize undesirable interactions with the surface of the sequencing apparatus and the enzyme. The outer layer preferably comprises pairs of negatively charged groups, although these groups may be altered as desired, depending on the intended use of the protected fluorescent compound.

Exemplary shield elements usefully incorporated into the protected fluorescent compounds of the instant disclosure include the following non-limiting structures:

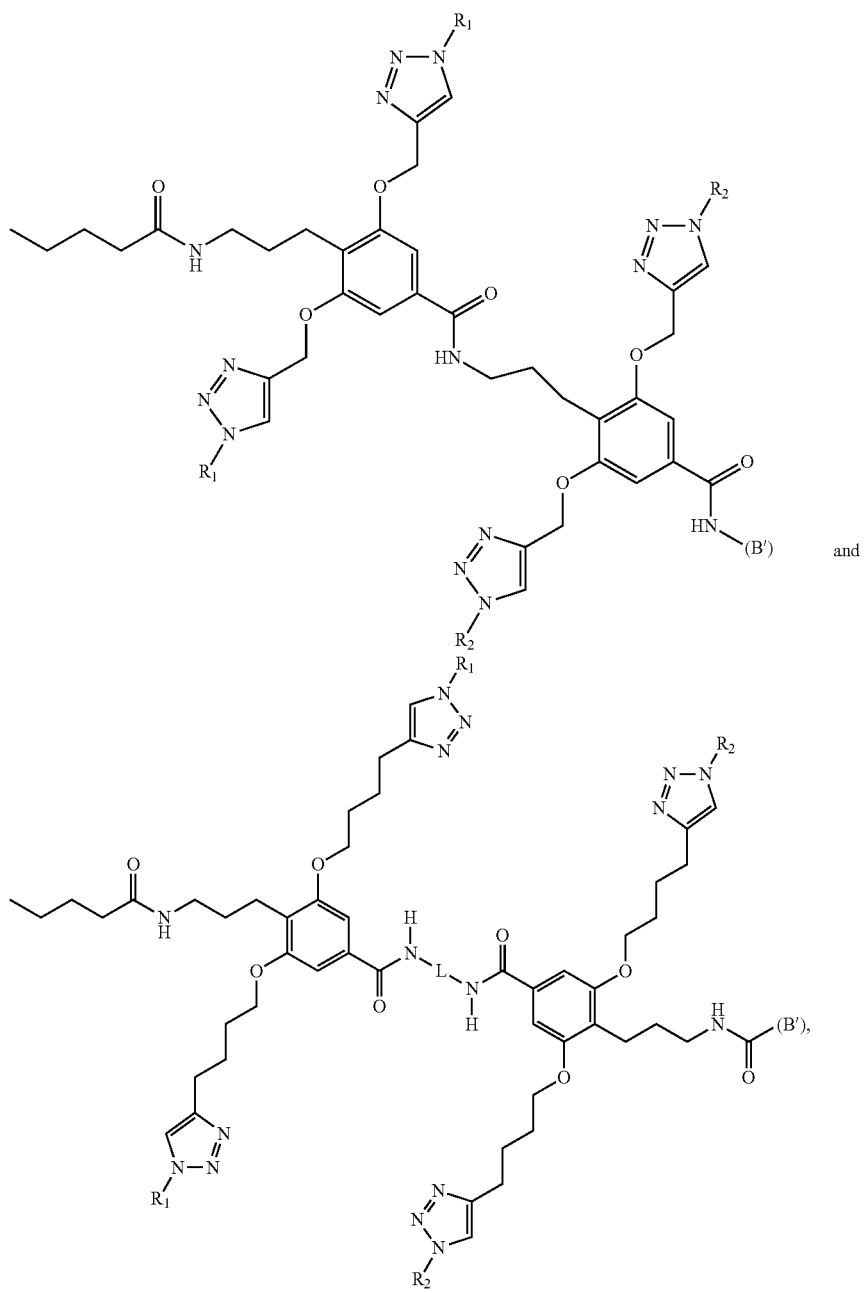

where $R_1$ and $R_2$ represent "inner" and "outer" side chains, respectively, the "B'" group is preferably a "binding element", and the remaining portion of the structure represents the shield core element, including, in some embodiments, a "linker" group, L, that bridges the shield layers in some of the shield element embodiments. This "linker" is preferably a short alkyl or cycloalkyl group, such as, for example, a hexyl or cyclohexyl linker group, but other linker moieties may be suitably employed for this purpose. For example, L may be an alkyl, heteroalkyl, cycloalkyl, cycloheteroalkyl, aryl, or heteroaryl linker. The shield element is typically attached to a multivalent central core element or to a multivalent dye element through the terminal alkyl group, typically through a triazole structure.

It should be understood that the S'—B' groups are preferably synthetically attached to central core elements using "click" reactions, or "copper-free click" reactions, as is described in further detail below. The S'—B' groups are therefore preferably labeled with an azide group that reacts with an acetylene group of the multivalent central core element or dye. It should also be understood, however, that other methods of attachment may be used to generate protected compounds within the scope of the instant invention, as would be understood by those of ordinary skill in the art.

Other shield elements may include additional multivalent "branched" cores to increase the number of side chains, as shown in the following exemplary structures:

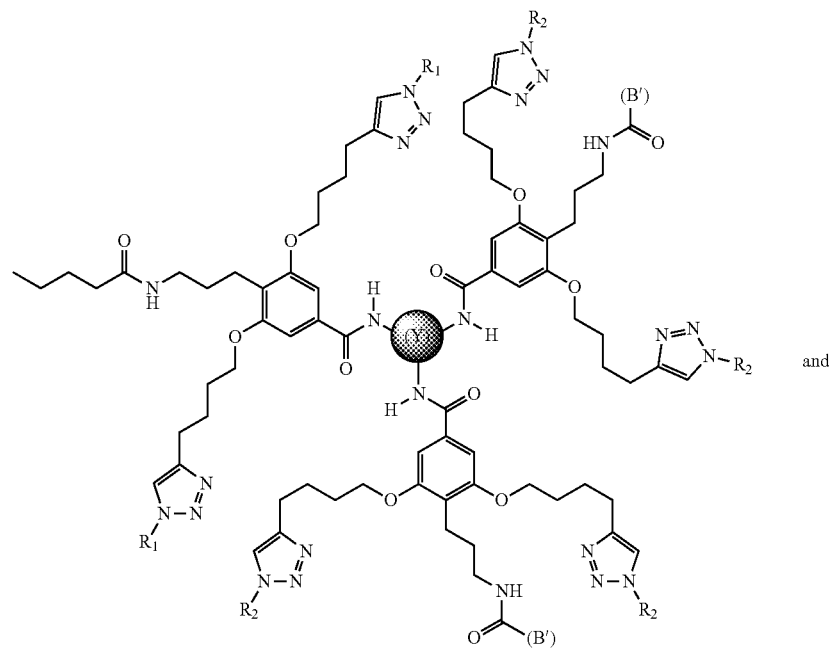
and
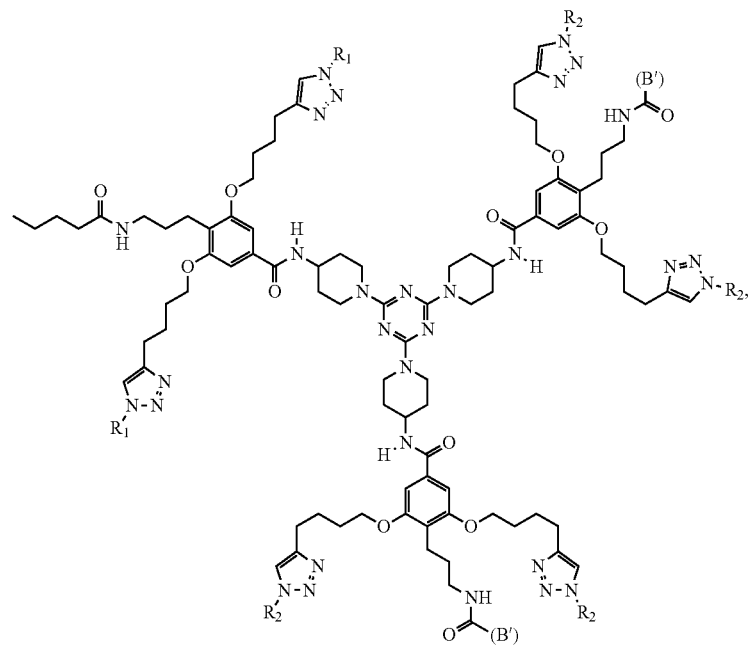

where the $R_1$, $R_2$, and B' groups have the meanings described in the previous paragraph, "Y" represents a suitable trivalent group, for example one of the trivalent groups described above in the context of the core element components, and the shield element is attached to the fluorescent central core element at the terminal alkyl chain, typically through a triazole structure. In preferred embodiments, Y is

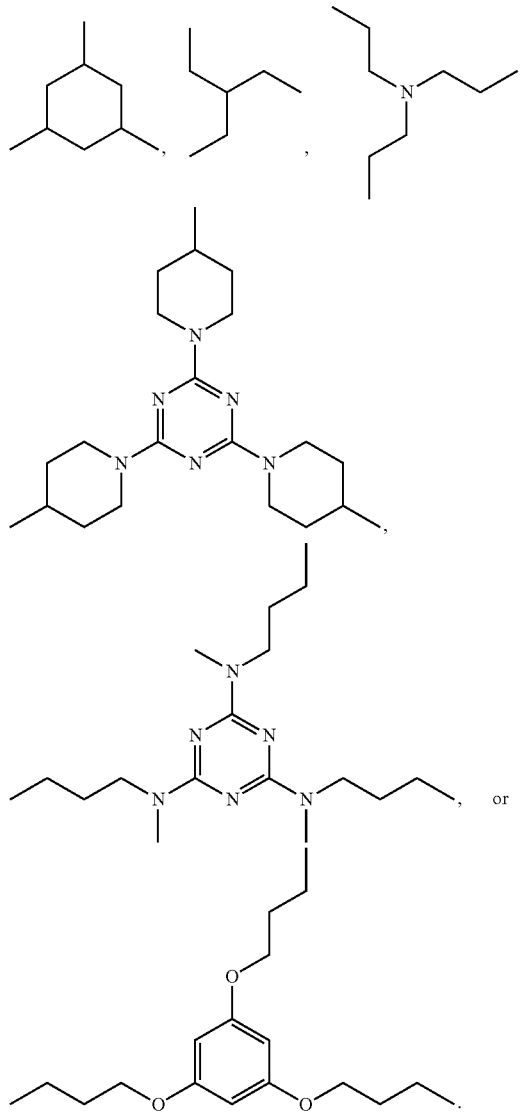

Some shield element structures may include three, four, or even more "layers" of side chains, for example as shown in the following formulae:

-Aba-Sh($R_1$)$_2$-Sh($R_2$)$_2$-Sh($R_3$)$_2$—B'; and

-Aba-Sh($R_1$)$_2$-Sh($R_2$)$_2$-Sh($R_3$)$_2$-Sh($R_4$)$_2$—B';

where "Aba" is

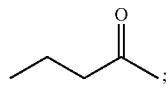

"Sh" is a shield core element, such as, for example,

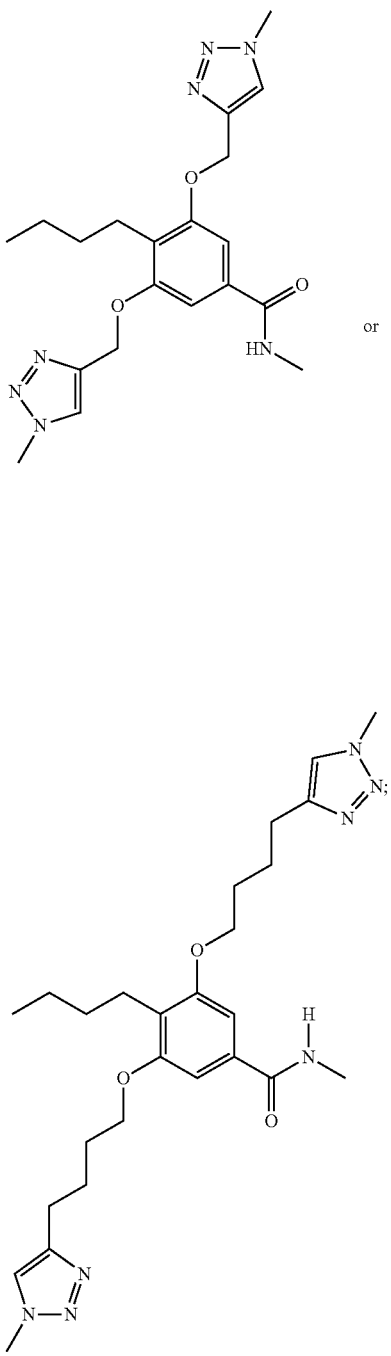

"$R_1$", "$R_2$", "$R_3$", and "$R_4$" are side chains, and "B'" is preferably a binding element. It should be understood that the "$R_1$", "$R_2$", "$R_3$", and "$R_4$" side chain groups may be the same or different side chains, in any combination, as desired to achieve protection from photodamage by the reagent compounds. The shield element is attached to a multivalent central core element or dye through the Aba group in these examples.

An exemplary cyclooctyne-labeled triple-layer shield reagent useful in the synthesis of a protected fluorescent reagent compound according to this aspect of the invention is:

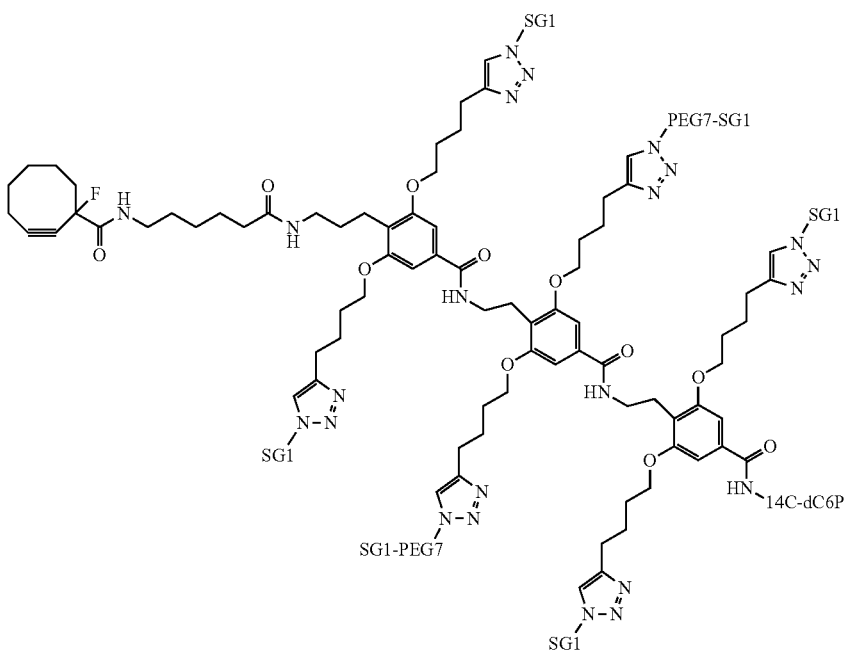

("MFCO-Sb2(SG1)2-Sb2(PEG7-SG1)2-Sb2(SG1)2-14C-dC6P"), where the SG1 and PEG7 components have the structures defined below.

As is true of the shield elements generally, the exact structures of the side chain components of the shield elements are not believed to be critical, so long as they are large enough to limit contacts between the fluorescent dyes and the target biomolecules that are associated with the binding elements of the instant protected compounds. In some embodiments, the side chain components provide a suitable microenvironment to improve the photophysical properties and/or photochemical stabilities of the attached dyes. Again, the exact structures of the side chain components are not necessarily critical, so long as they provide the desired microenvironment for the dyes.

In some embodiments, the side chains comprise polyethylene glycol. In preferred embodiments, the polyethylene glycol side chains comprise polyethylene glycol with from 3 to 20 repeating ethylene oxide units. In more preferred embodiments, the polyethylene glycol side chains comprise polyethylene glycol with from 4 to 10 repeating ethylene oxide units. In some embodiments, the side chains comprise a negatively-charged component, such as, for example, a component comprising a sulfonic acid. In some embodiments, the side chains comprise a combination of polyethylene glycol and another component, such as, for example a negatively-charged component. In preferred embodiments, the inner layer of the shield element comprises a side chain comprising polyethylene glycol, and the outer layer of the shield element comprises a side chain comprising a negatively-charged component.

The side chains may additionally comprise a core structure that provides for branching within the side chains. In some embodiments, the side chain comprises a substituted phenyl group. In specific embodiments, the side chain comprises the structure:

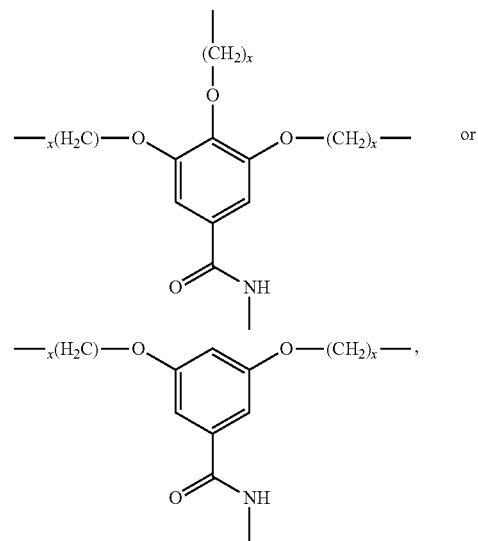

wherein each x is independently an integer from 1 to 6. In more specific embodiments, each x is independently an integer from 1 to 4. In some embodiments, the side chain comprises one of the other branching elements described in more detail below.

The side chain may, in some embodiments, comprise a dendrimer. A dendrimer (or "dendron") is a repetitively branched molecule that is typically symmetric around the core and that may adopt a spherical three-dimensional morphology. See, e.g., Astruc et al. (2010) Chem. Rev. 110:1857. Incorporation of such structures into the shield elements of the instant compounds provides for a protective effect through the steric inhibition of contacts between the fluorescent dye element or elements and one or more biomolecules associated with the binding element or elements. Refinement of the chemical and physical properties of the dendrimer through variation in primary structure of the molecule, including potential functionalization of the dendrimer surface, allows the protective effects to be adjusted as desired. Dendrimers may be synthesized by a variety of techniques using a wide range of materials and branching reactions, as is well-known in the art. Such synthetic variation allows the properties of the dendrimer to be customized as necessary.

In some embodiments, at least one side chain comprises a peptide chain.

In some embodiments, at least one side chains comprises a polysaccharide.

Non-limiting side chain examples include the following structures:

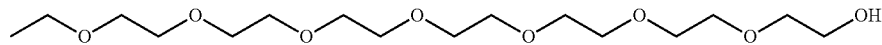 [SMILES: CCOCCOCCOCCOCCOCCOCCOCCO]

(corresponding to PEG7) and polyethylene glycols with other numbers of repeating unit;

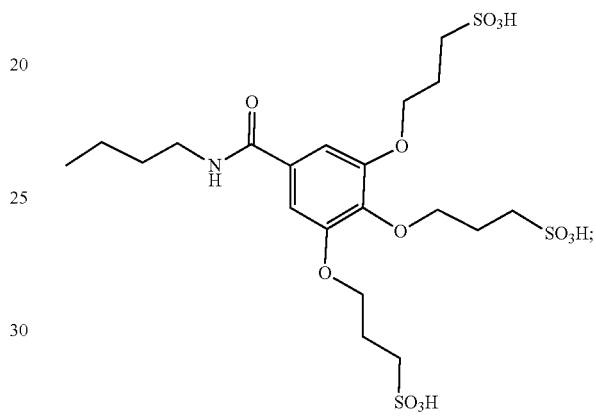

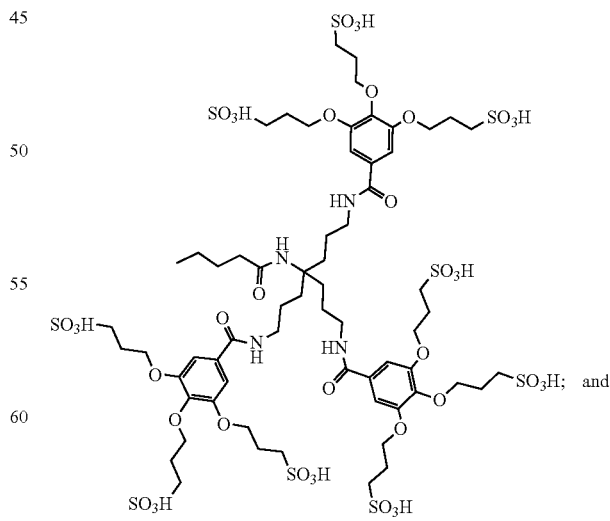

and

-continued

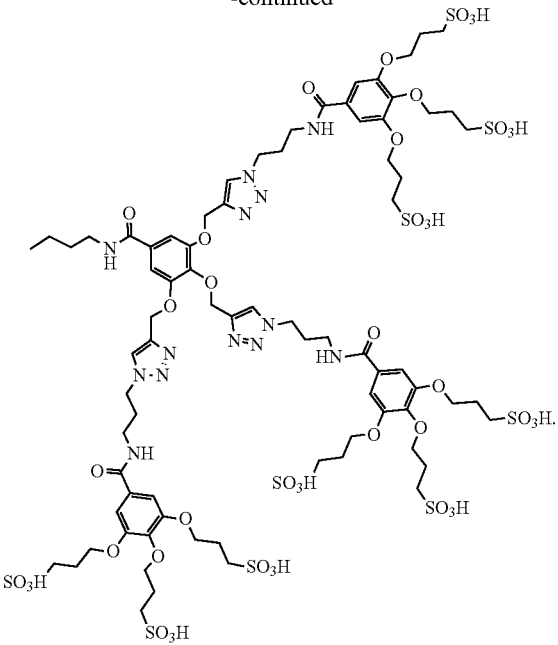

Some side chain embodiments may include combinations of any of the above components, such as, for example, the following combination of a polyethylene and a negatively-charged side chain:

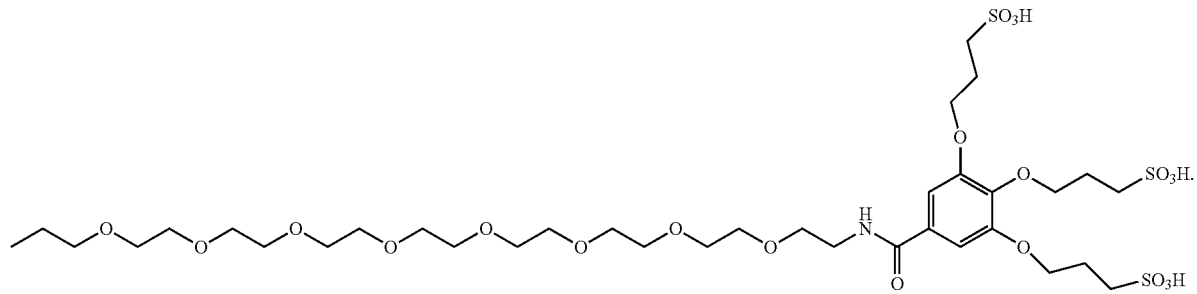 [SMILES: CCCOCCOCCOCCOCCOCCOCCOCCOCCNC(=O)c1cc(OCCCS(=O)(=O)O)c(OCCCS(=O)(=O)O)c(OCCCS(=O)(=O)O)c1]

Figure 13:
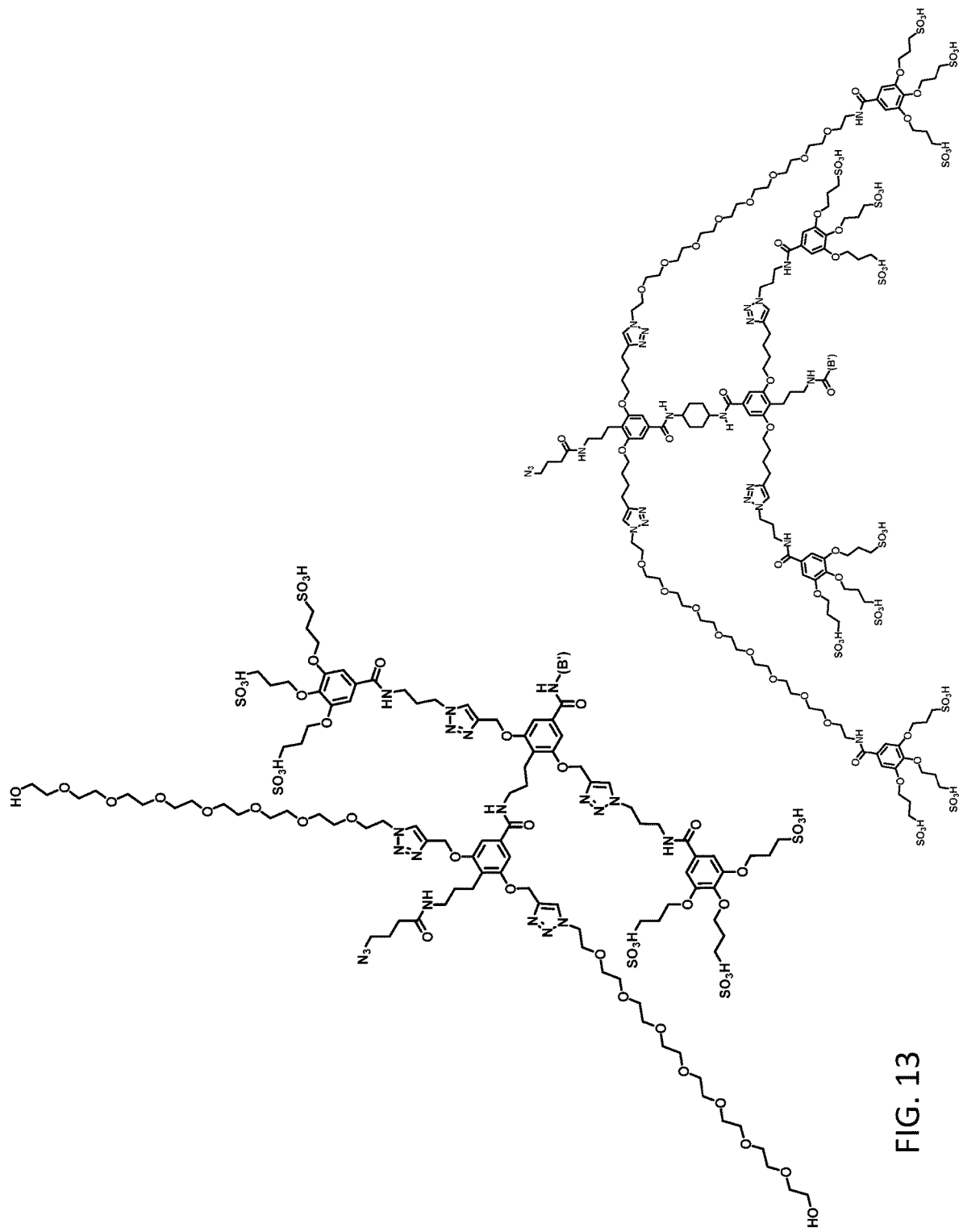
FIG. 13 illustrates exemplary shield element-binding element (S'—B') reagents.

Exemplary shield element-binding element (S'—B') reagents include the non-limiting examples illustrated in FIG. 13:
where the azide group represents the site of attachment to the multivalent central core element or multivalent dye, typically through a "click" reaction, or a "copper-free click" reaction, and "B'" is preferably a binding element.

In some embodiments, the molecular weight of the side chain is at least 300, 350, 400, 450, or even higher. In preferred embodiments, the molecular weight of the side chain is at least 300.

Binding Elements

The protected fluorescent reagent compounds of the instant disclosure further comprise at least one binding element. As already described, the binding element is responsible for recognition of a compound by a target biomolecule of interest, for example, an enzyme, such as DNA polymerase, when the fluorescent compound serves as a reagent in an enzymatic reaction. In some cases, the target biomolecule of interest may be a receptor, antibody, nucleic acid sequence, or the like, and the binding element will accordingly be selected to be specifically and efficiently recognized by that particular target molecule, as would be understood by those of ordinary skill in the art.

In the case of fluorescent reagent compounds for use in single-molecule real-time nucleic acid sequencing reactions, the binding element of the instant protected compound comprises a nucleotide. The nucleotide portion of the protected fluorescent compound is preferably attached to the shield element through a polyphosphate moiety coupled to the nucleotide at the normal 5' position. With this attachment, when the nucleotide monophosphate portion of the nucleotide analog is incorporated into the growing nucleic acid strand by the DNA polymerase, the portion of the nucleotide analog containing the shield element(s) and the fluorescent dye element(s) is cleaved from the nucleotide that is incorporated into the polynucleotide, and it diffuses away to allow for incorporation of the next nucleotide into the chain without interference from these moieties. In addition, due to the multivalency of binding elements in the instant protected compounds, the cleaved compounds can continue to be processed by the polymerase enzyme, so long as the compounds have remaining attached binding elements.

In preferred embodiments, the polyphosphate moiety of the instant compounds is coupled to the shield element through a linker moiety. The linkers are typically short alkyl, or cycloalkyl, moieties, in some cases with heteroatom substitutions, as would be understood by those of ordinary skill in the art.

As noted above, not all B' terminal chemical groups need be binding elements, and different binding elements may be present in a single protected reagent compound.

Exemplary binding elements of the instant protected reagent compounds, in particular binding elements comprising nucleotides, are described in detail above.

In some embodiments of the instant protected reagent compounds, the binding element is biotin. Suitable target biomolecules for compounds comprising biotin include, for example, avidin, streptavidin, and the like.

In some embodiments, the binding element is a nucleic acid or modified nucleic acid. Suitable target biomolecules for compounds comprising such binding elements include, for example, complementary nucleic acids.

Synthesis of the Protected Fluorescent Reagent Compounds

Figure 14:
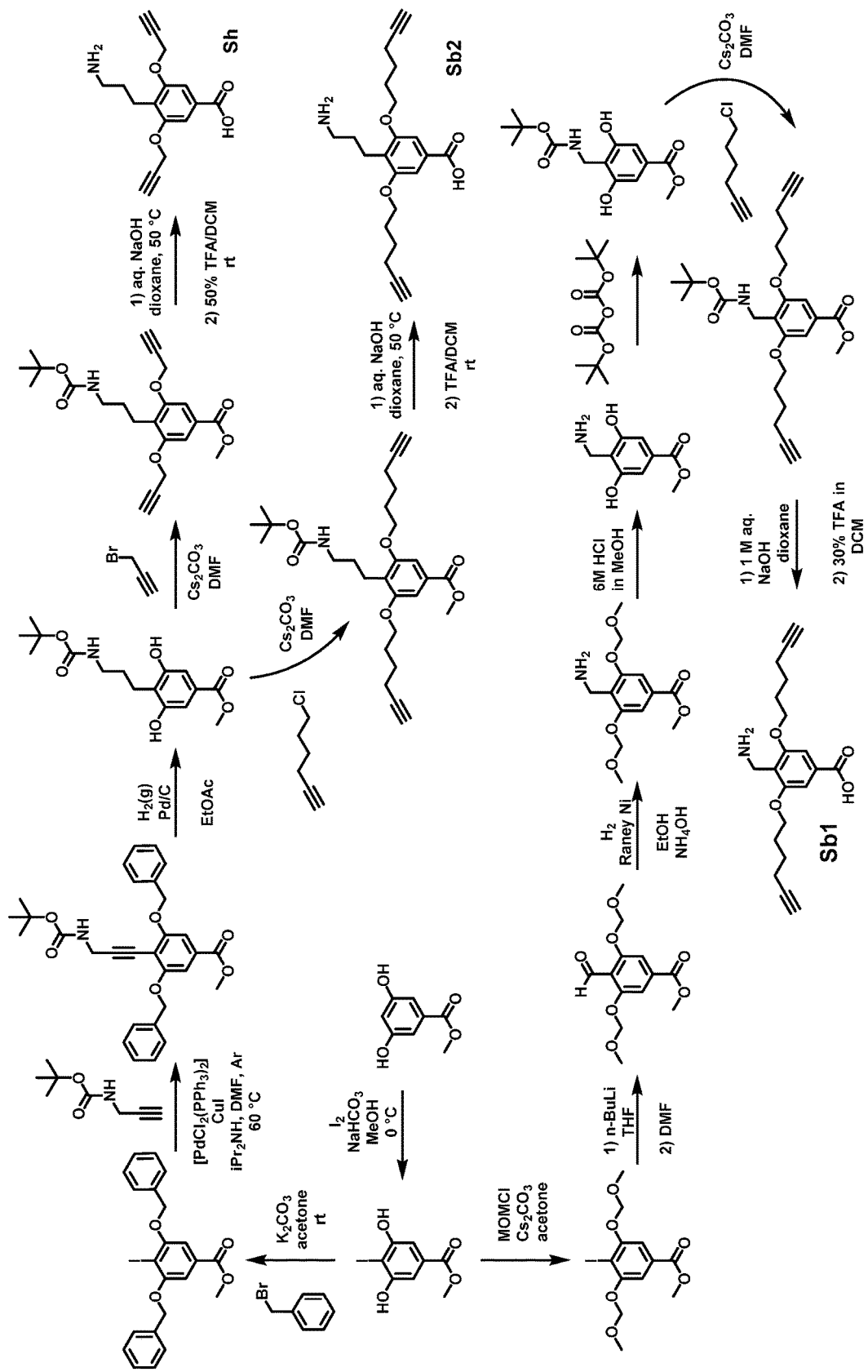
FIG. 14 illustrates an exemplary synthetic route for preparing exemplary shield core elements.
Figure 15:
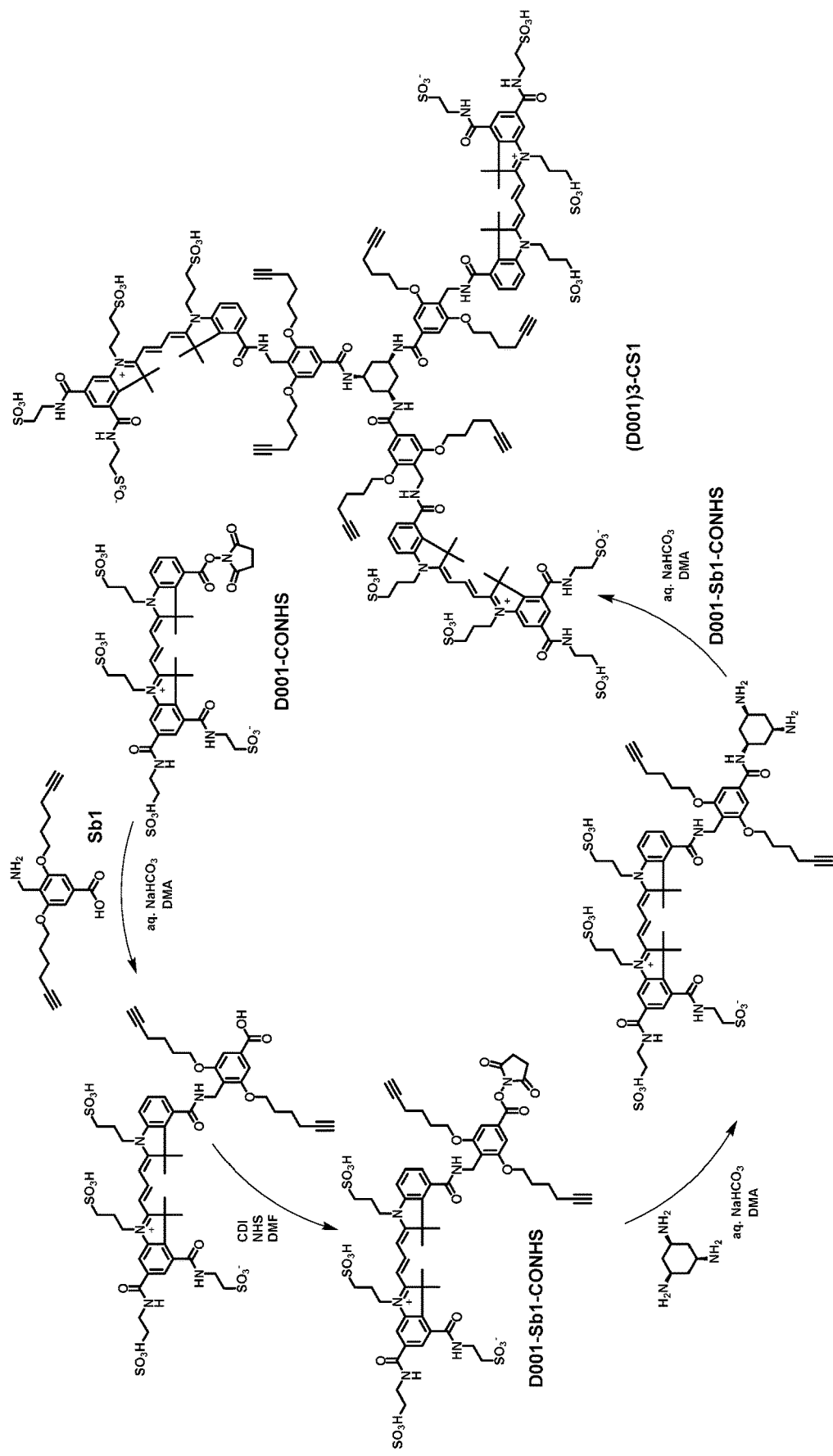
FIG. 15 illustrates an exemplary synthetic route for preparing exemplary multivalent fluorescent dye core elements.

The protected compounds of the instant disclosure are synthesized using standard chemical techniques. For example, exemplary shield core elements of the instant compounds may be synthesized according to the reactions illustrated in Scheme 1 of FIG. 14.[0176] Multivalent fluorescent dye core elements of the instant compounds may be synthesized, for example, according to the reactions illustrated in Scheme 2 of FIG. 15.

It should be understood that Scheme 2 can be readily adapted to allow synthesis of variant compounds for use in FRET analyses by substitution of one or more of the illustrated fluorophore moieties for an appropriate FRET donor or acceptor fluorophore, as would be understood by those of ordinary skill in the art.
Non-fluorescent multivalent central core elements of the instant compounds may be synthesized, for example, according to the reactions illustrated in Scheme 3:
Scheme 3
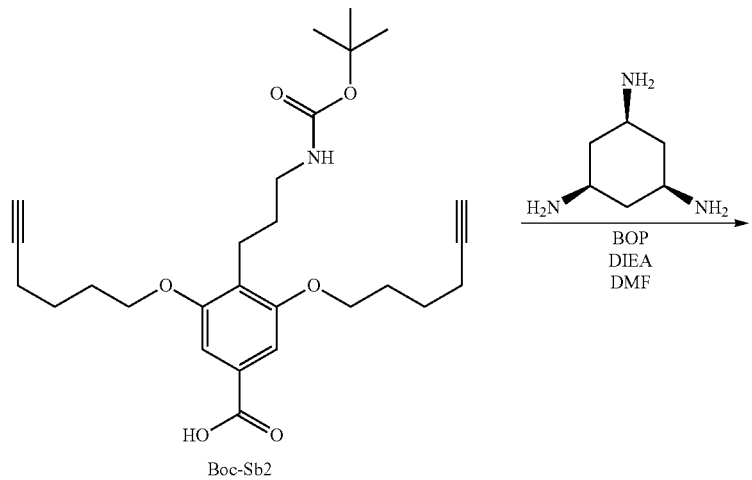
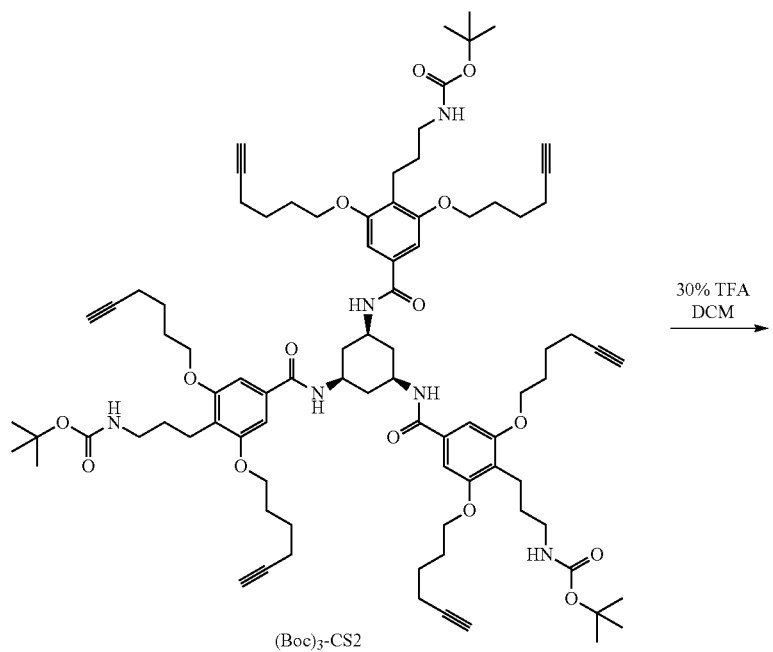

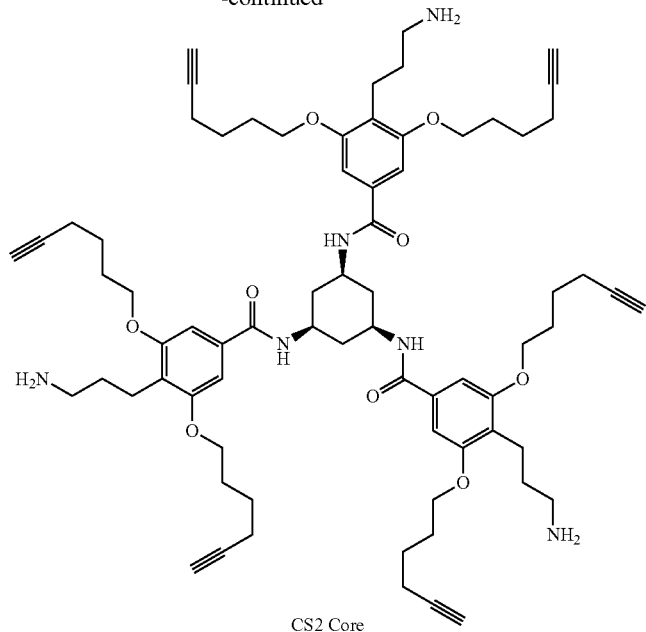

CS2 Core

Figure 19:
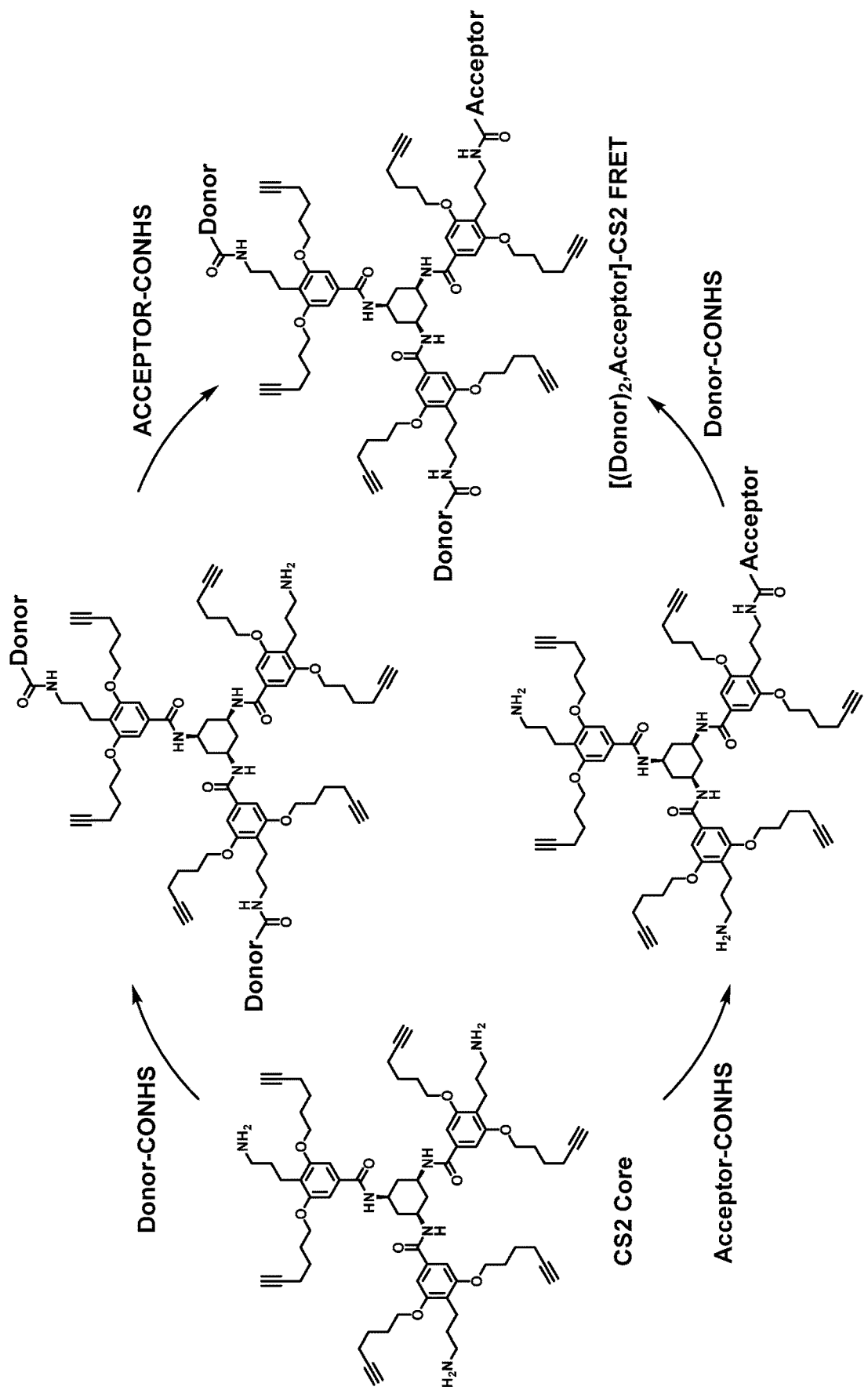
FIG. 19 illustrates an exemplary synthetic route for preparing exemplary intermediate fluorescent core elements.

Intermediate fluorescent core elements comprising FRET donor and acceptor fluorescent dyes may be synthesized, for example, according to the reactions illustrated in Scheme 4 of FIG. 19.

Figure 20:
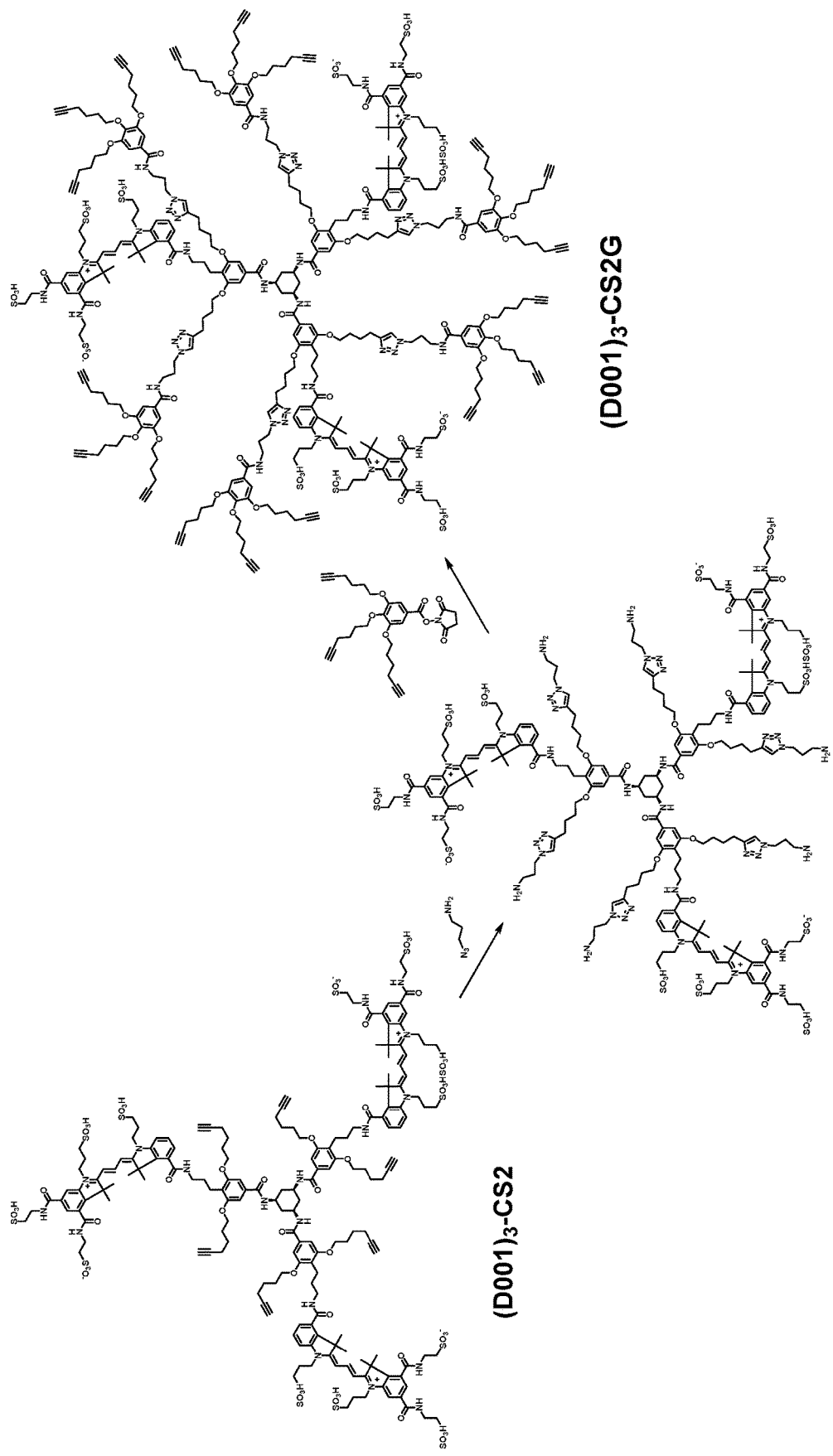
FIG. 20 illustrates increased branching of fluorescent core elements.

Branching of the fluorescent core elements may be increased, for example, as illustrated in Scheme 5 of FIG. 20.

Alternative core elements comprising fluorescent dye elements, optionally FRET donor and acceptor fluorescent dye elements, may be synthesized, for example, according to the reactions illustrated in Schemes 6-1 to 6-4 of FIG. 16, wherein Core 3 and Core 6 have the structures shown in FIG. 17.

Figure 18:
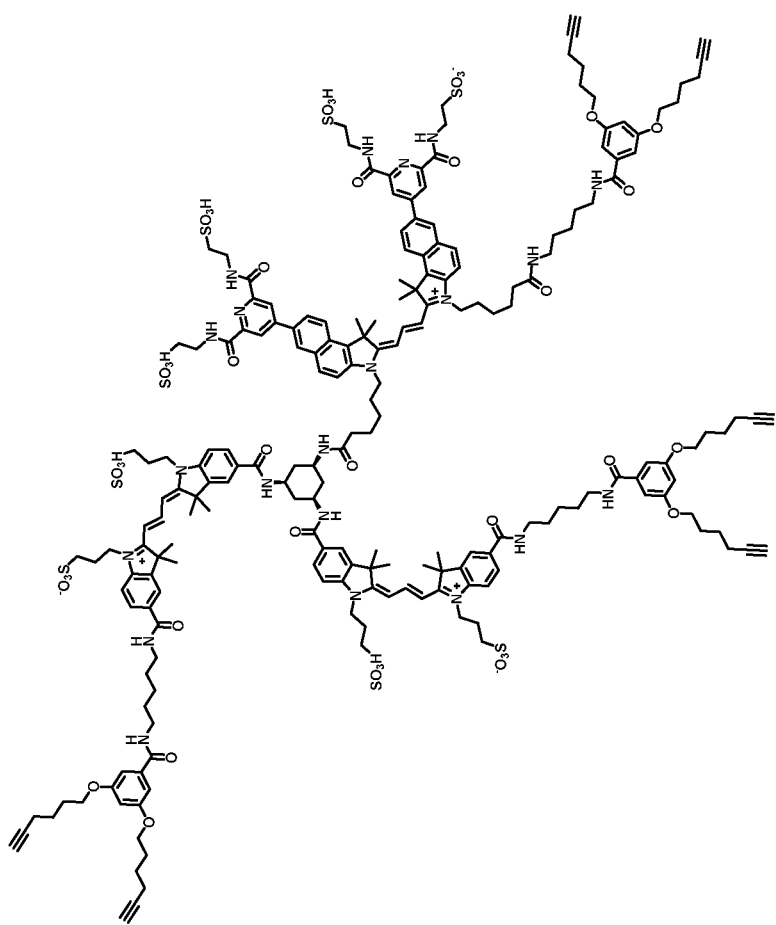
FIG. 18 illustrates an exemplary core element comprising fluorescent dye elements.

Another example of a core element comprising fluorescent dye elements is shown in FIG. 18, where the dyes themselves are bivalent.

Figure 21:
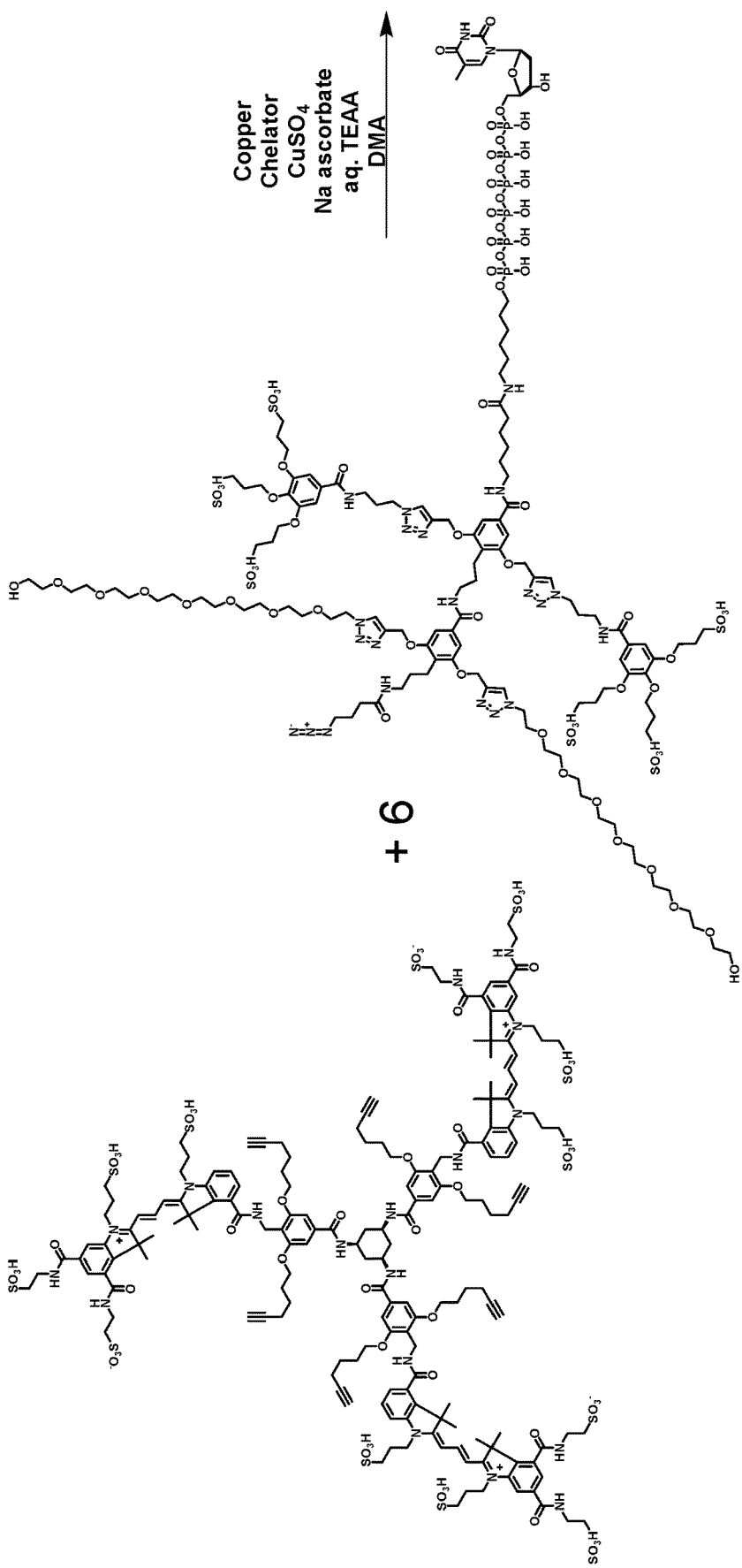
FIG. 21 illustrates an exemplary synthetic route for the assembly of an exemplary protected compound.
Figure 21:
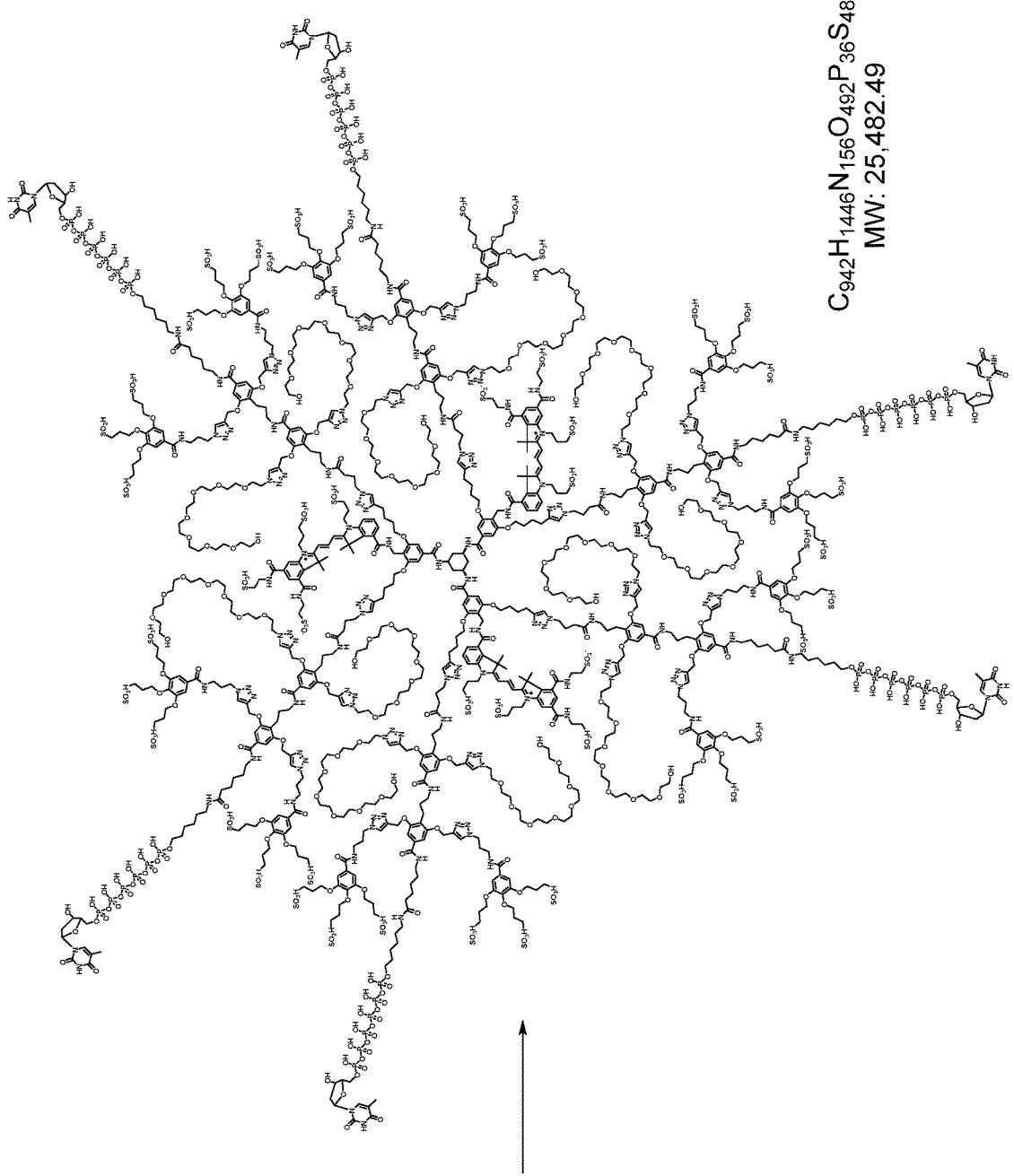
Figure 22A:
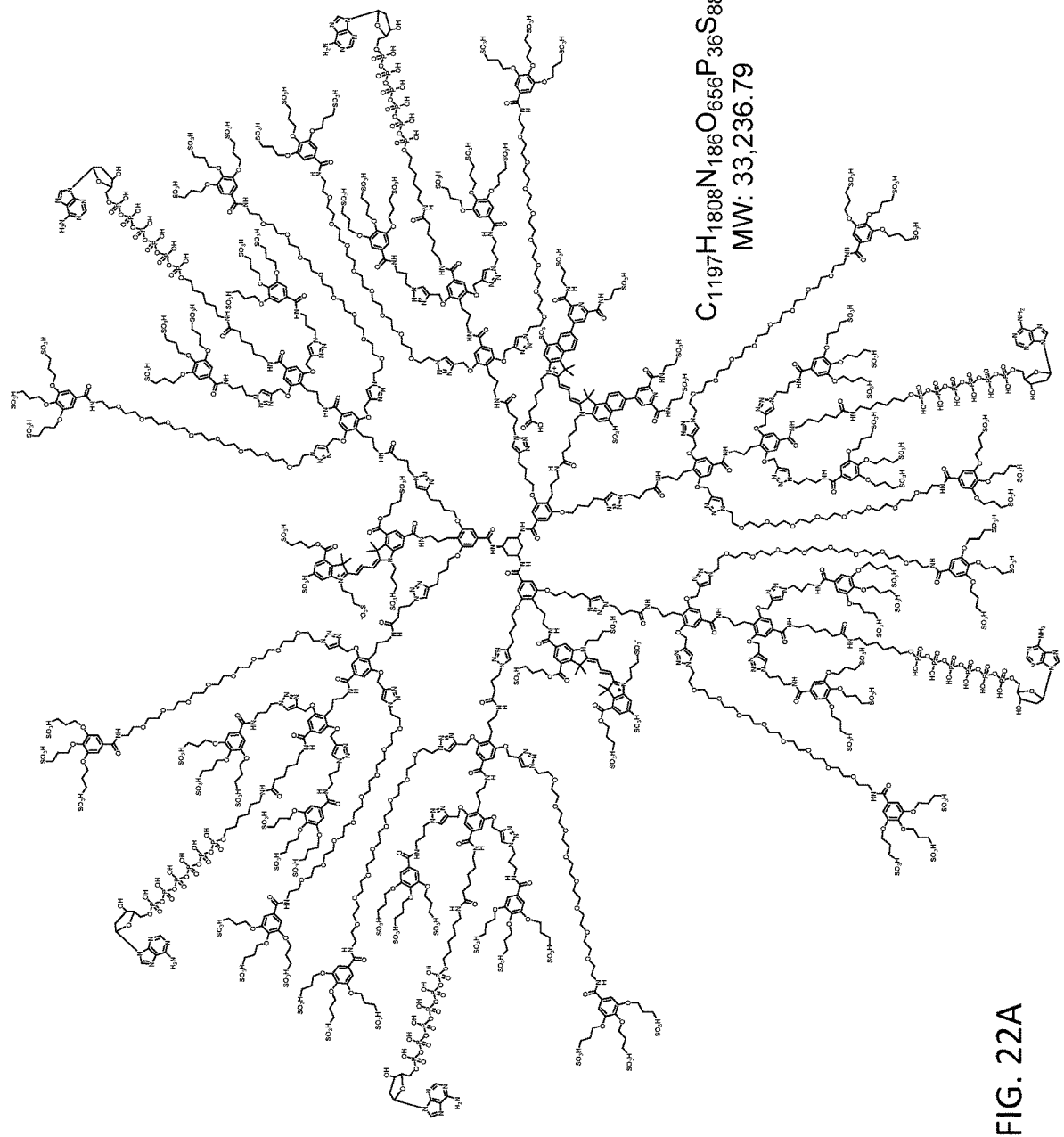
FIGS. 22A-22H illustrate exemplary protected fluorescent reagent compounds.
Figure 22B:
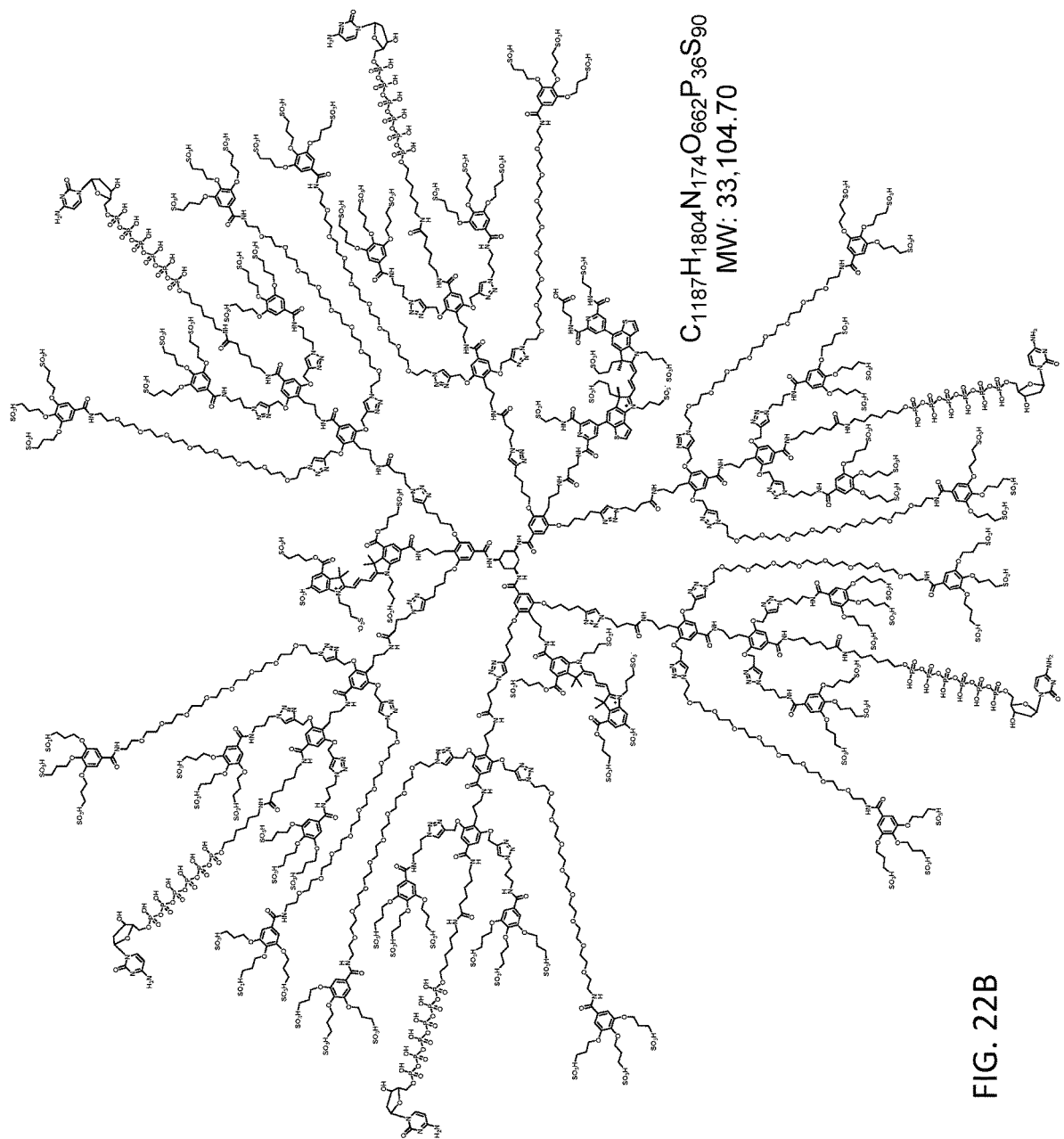
Figure 22C:
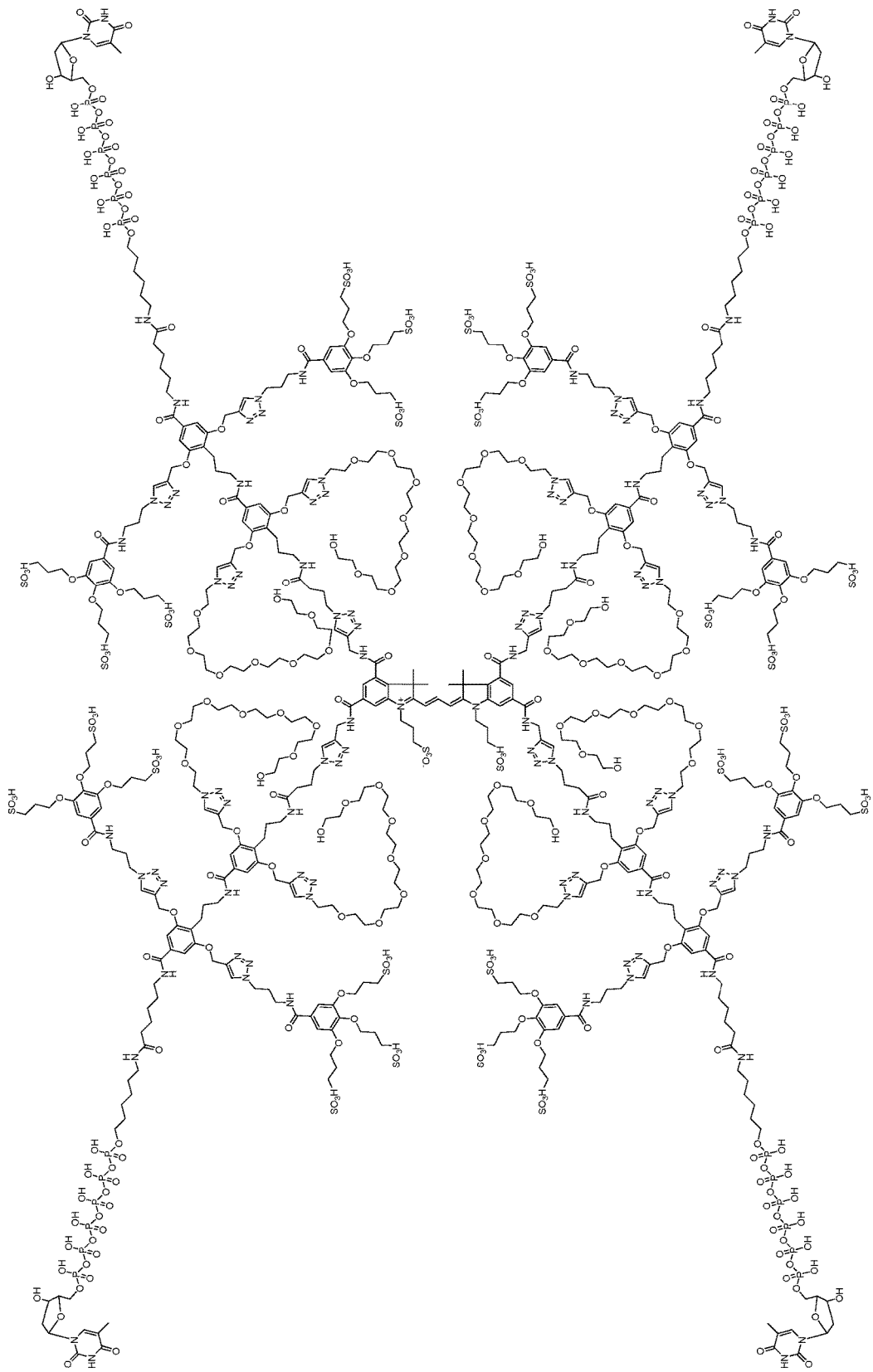
Figure 22D:
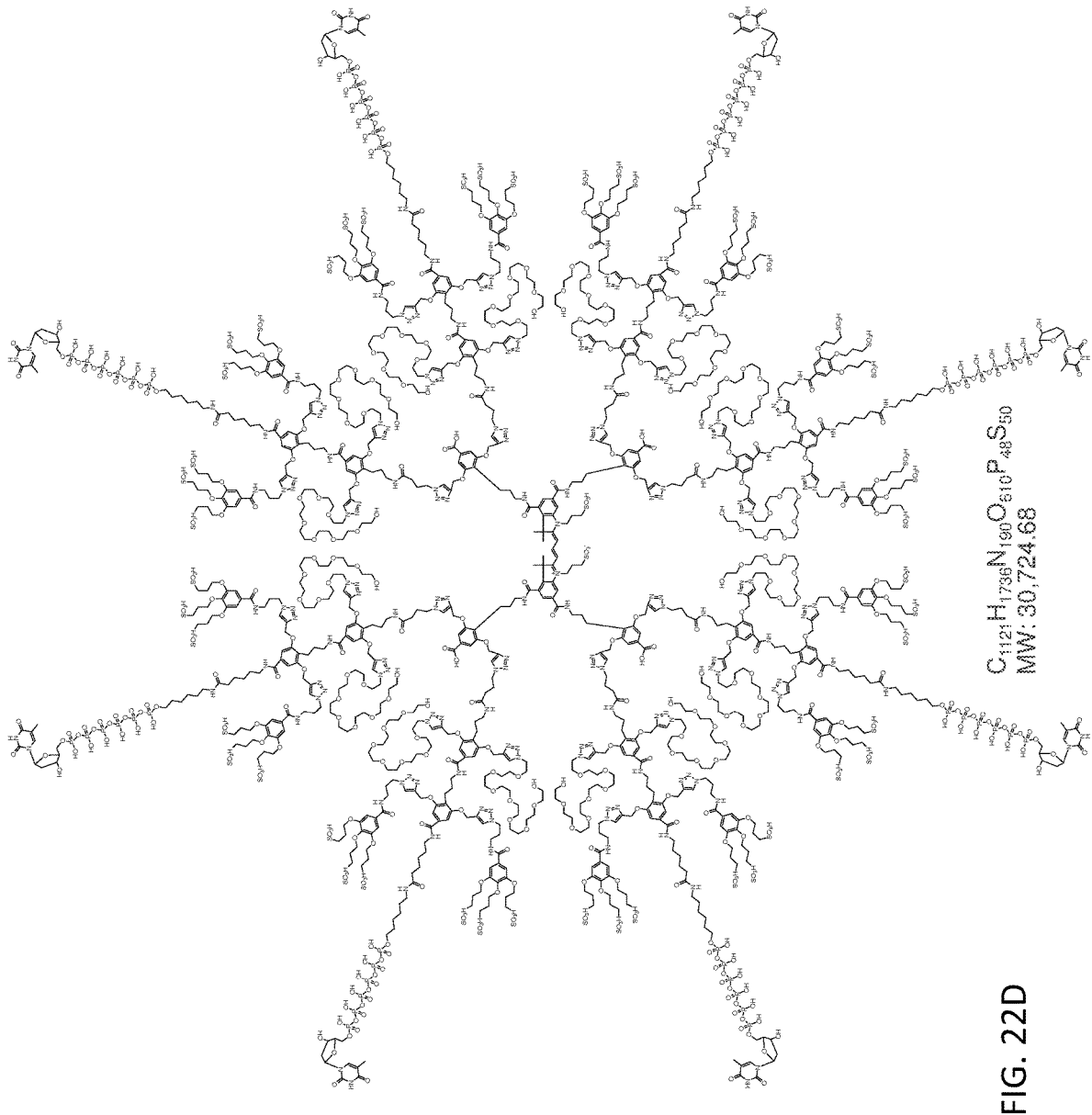
Figure 22E:
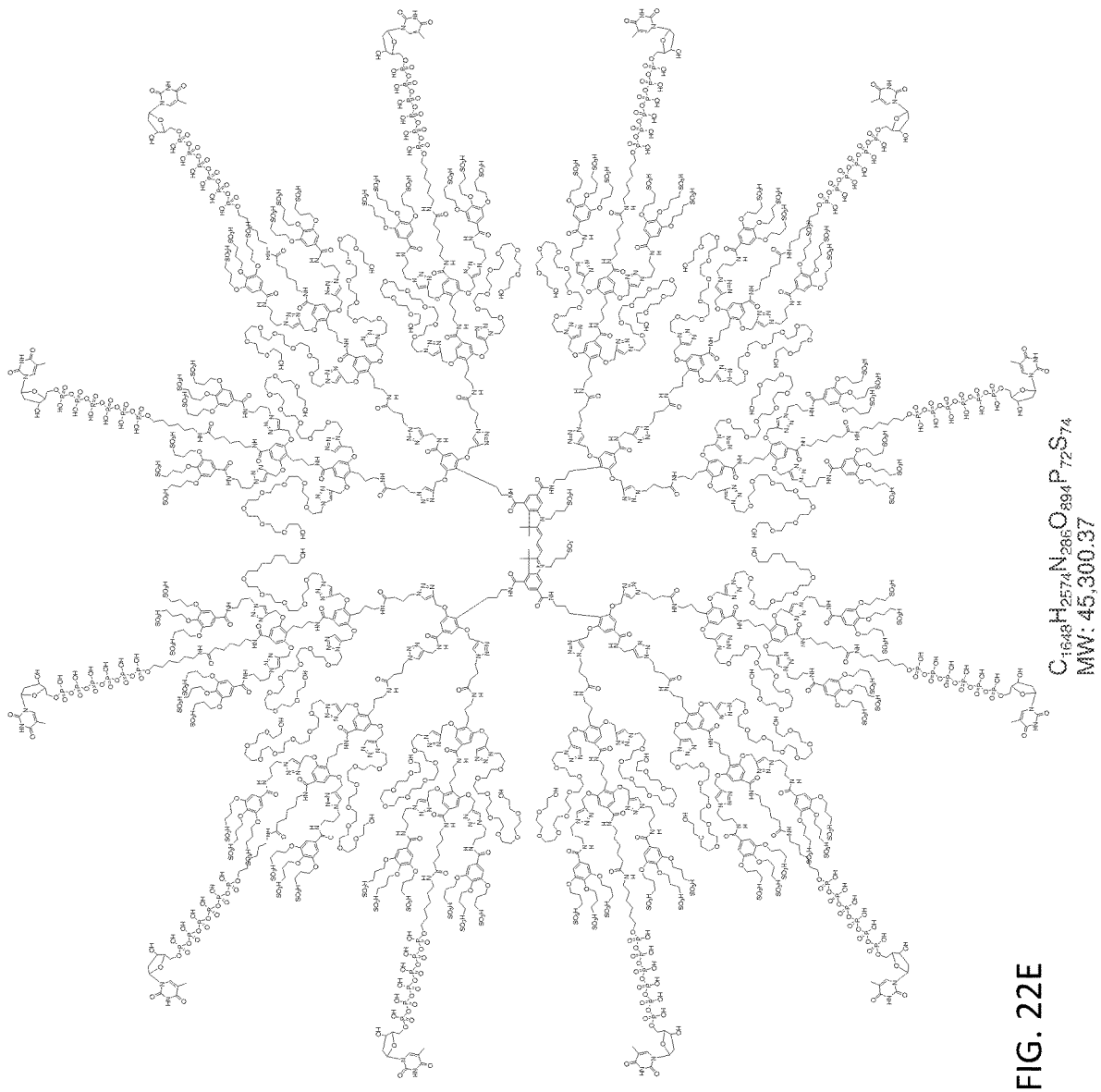
Figure 22F:
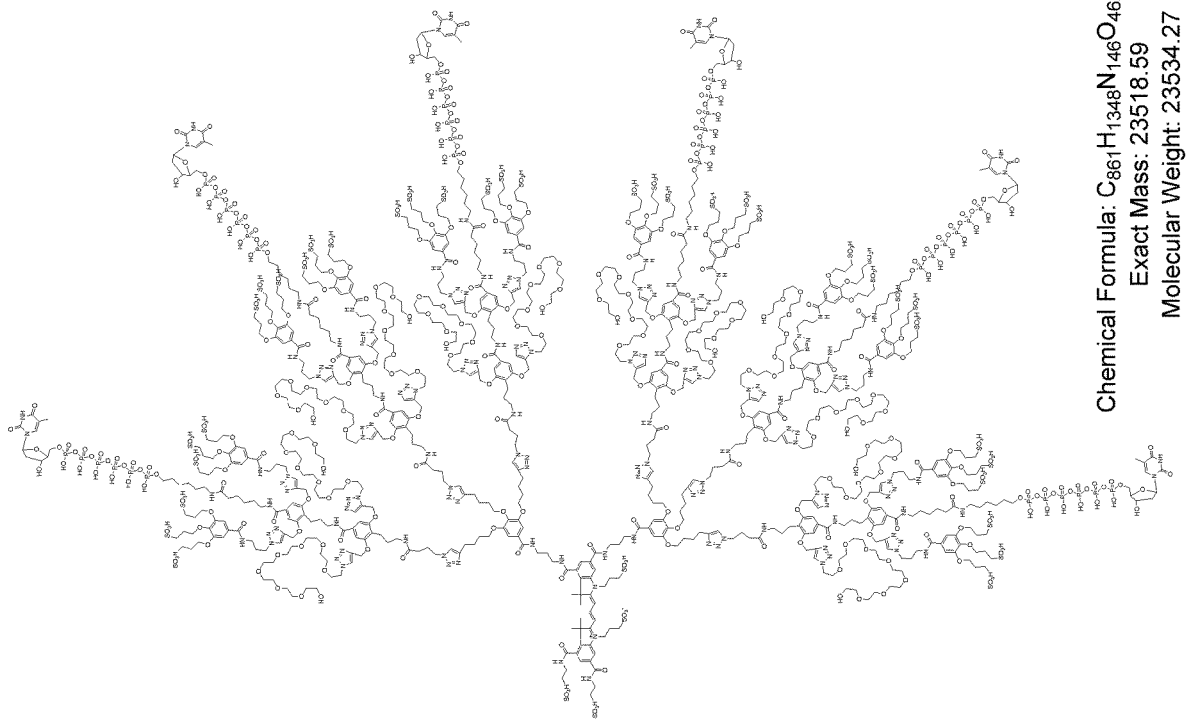
Figure 22G:
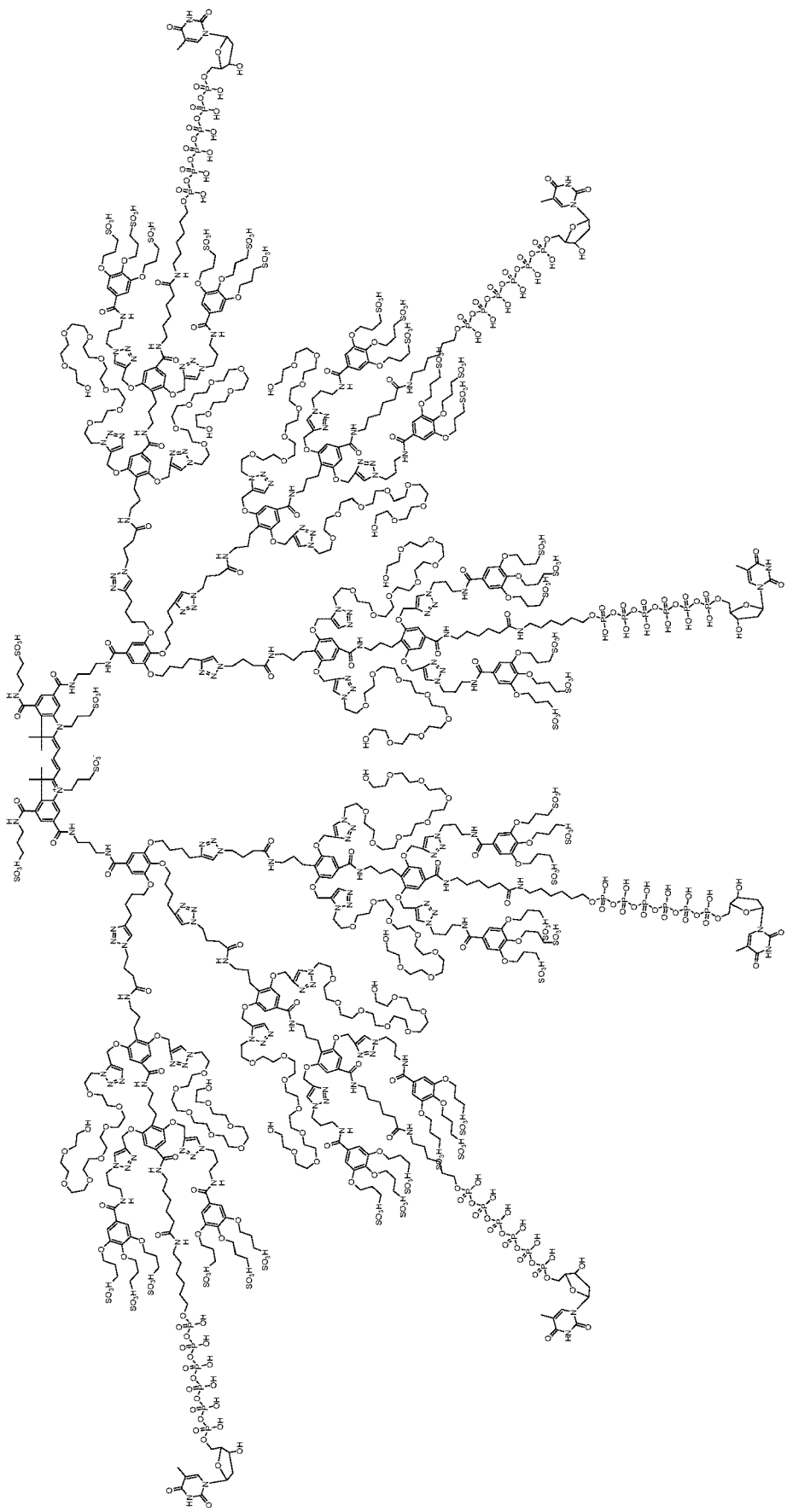
Figure 22H:
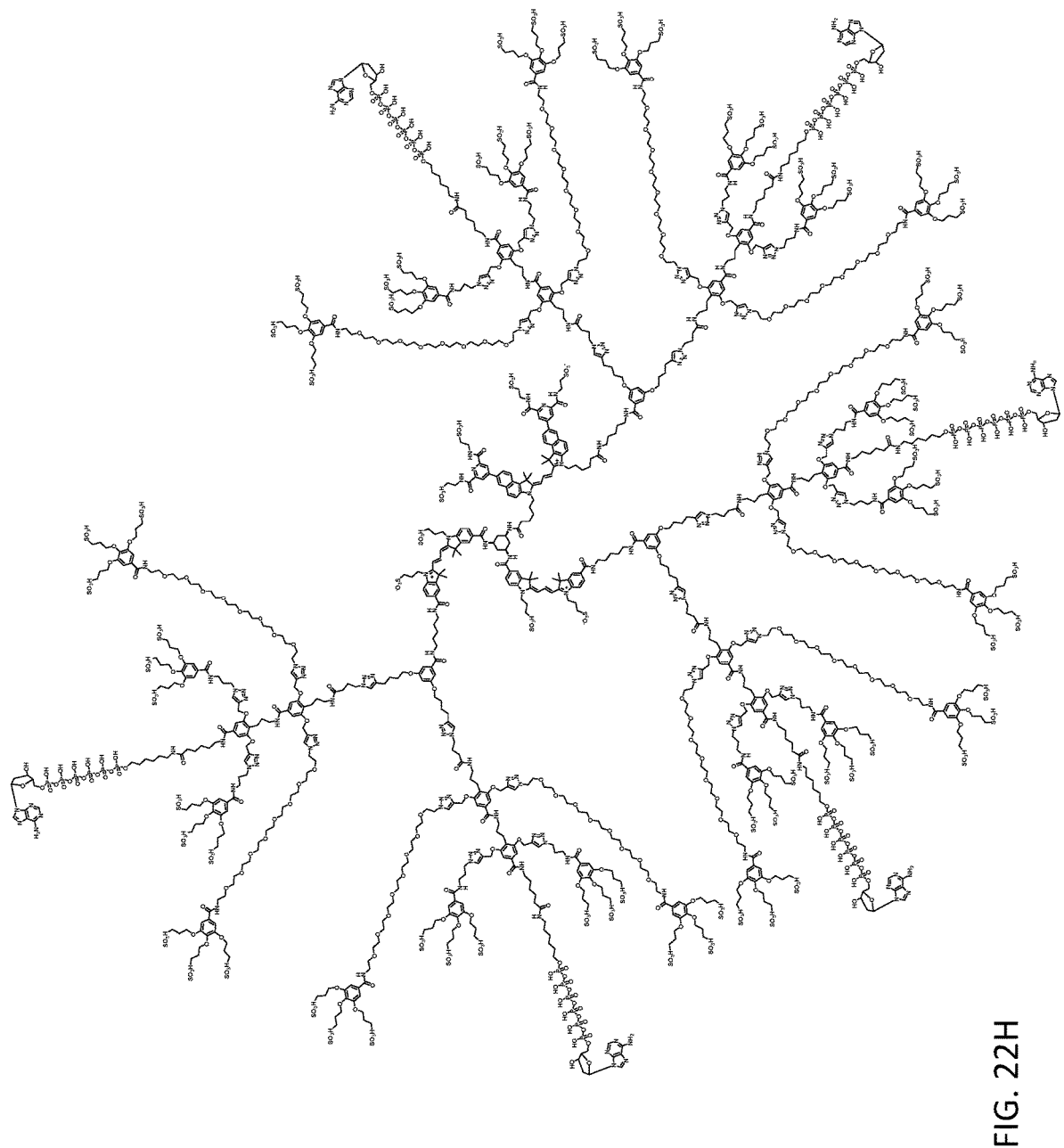

The final fluorescent protected reagent compound products may be generated by reaction of the fluorescently-labeled multivalent central core elements with azide-substituted shield element-binding element ("S'—B'") reagents, for example as shown in Scheme 9 of FIG. 21.

Shield elements modified with a nucleotide hexaphosphate may be synthesized, for example according to Schemes 7-1 or 7-2 (see also Example 5):

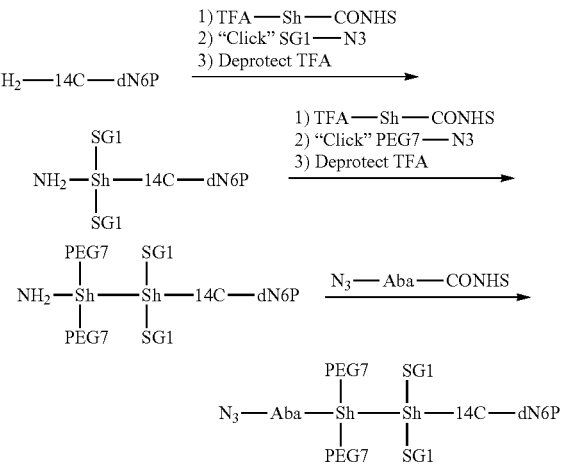

Scheme 7-1

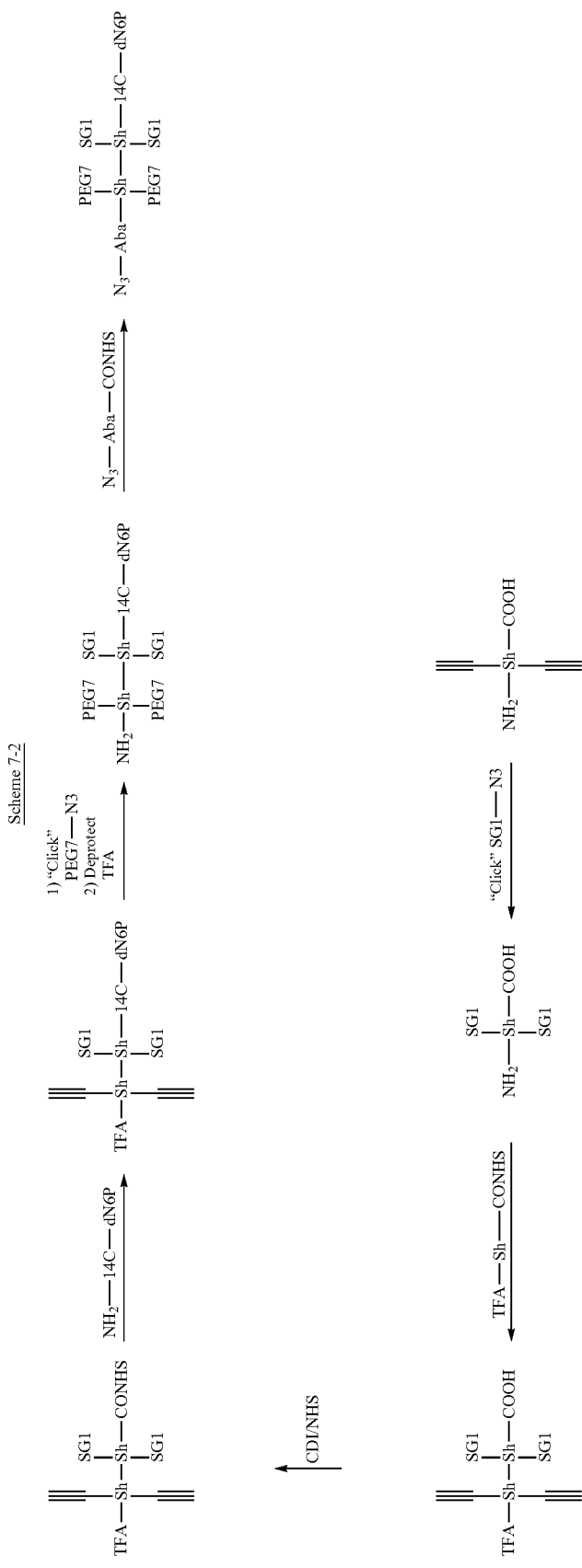

The shield core element reagent, TFA-Sh-CONHS, used in the initial step of the first two reaction cycles of Scheme 7-1, may be generated by reaction of the "Sh" shield core element of Scheme 1 with TFA-NHS to form the following structure:

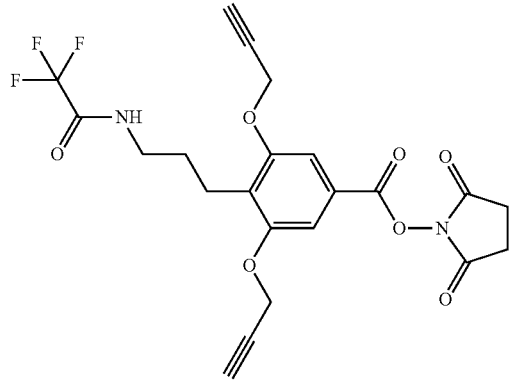 [SMILES: C#CCOc1cc(C(=O)ON2C(=O)CCC2=O)cc(OCC#C)c1CCCNC(=O)C(F)(F)F]

SG1-N₃ has the structure:

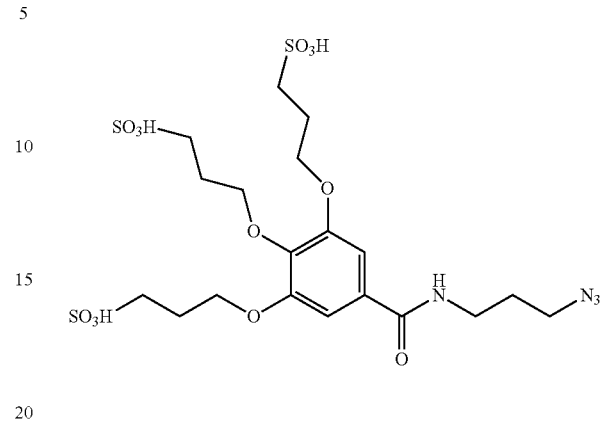

PEG7-N3 has the structure:

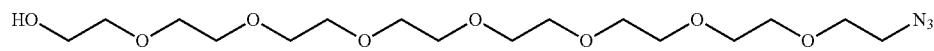 [SMILES: [N-]=[N+]=NCCOCCOCCOCCOCCOCCOCCOCCO]

N3-Aba-CONHS has the structure:

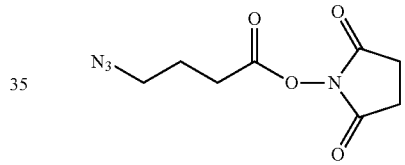

NH₂-14C-dN6P represents a hexaphosphate deoxynucleotide containing a 14-carbon, or equivalent, linker chain terminating in an amino group. An exemplary species of this structure is:

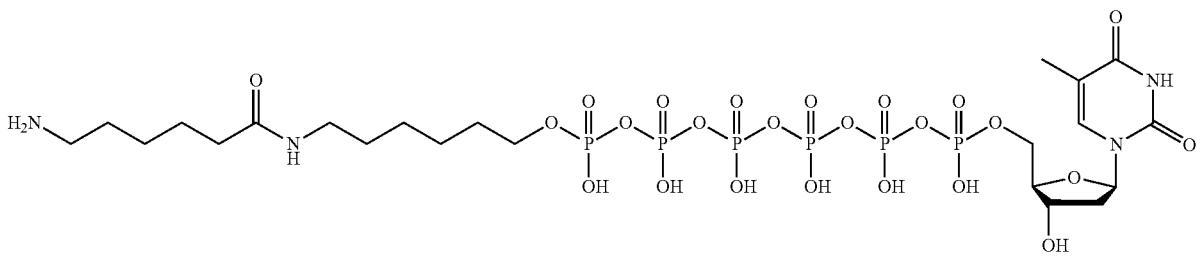

wherein the nucleobase is thymine, and the C14-linker chain includes an amide bond.

Alternative pathways for generating shield element-binding element reagents useful in the synthesis of protected reagent compounds of the instant disclosure are outlined in Schemes 7-3 to 7-5:

Scheme 7-3
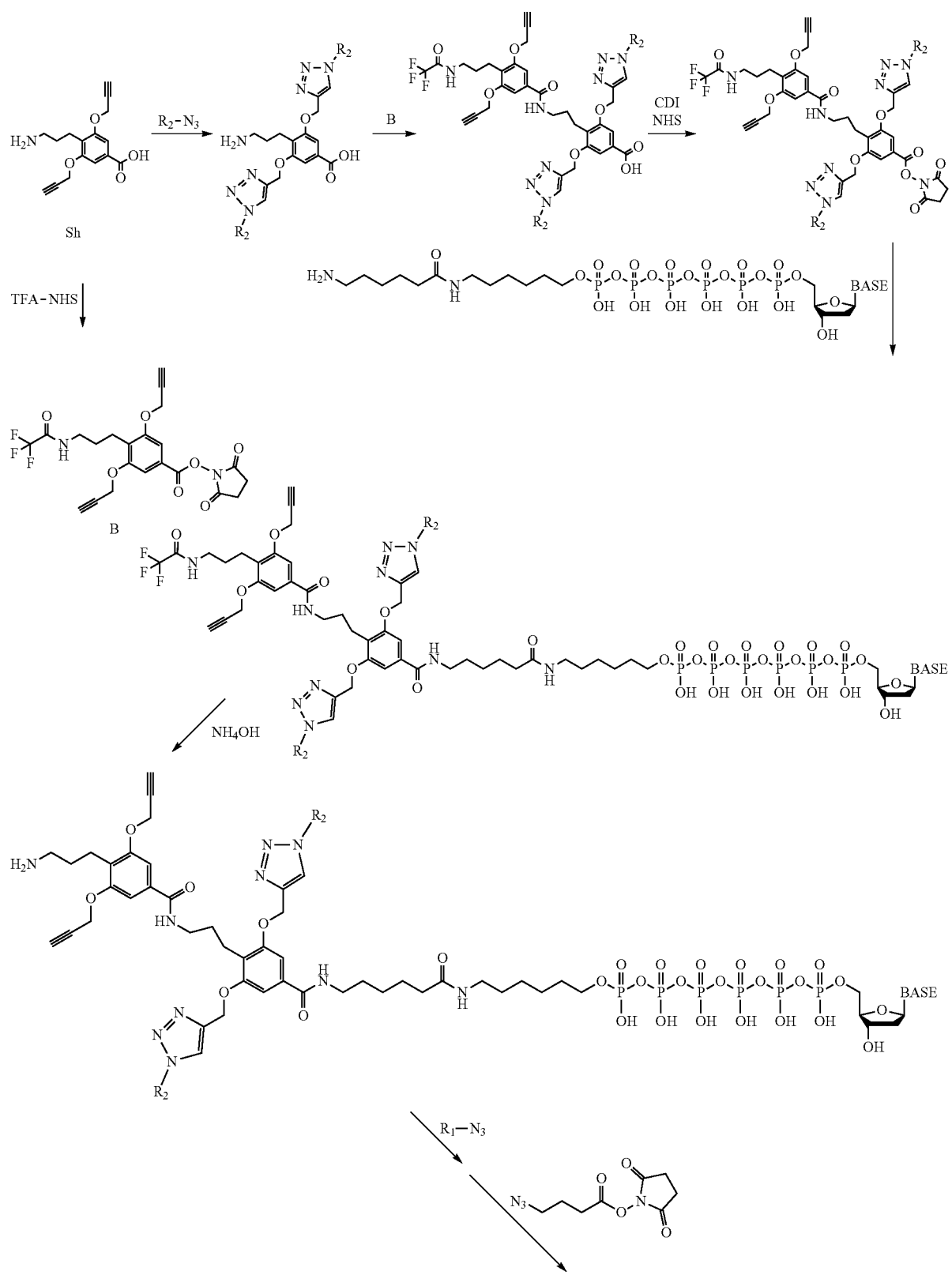

-continued
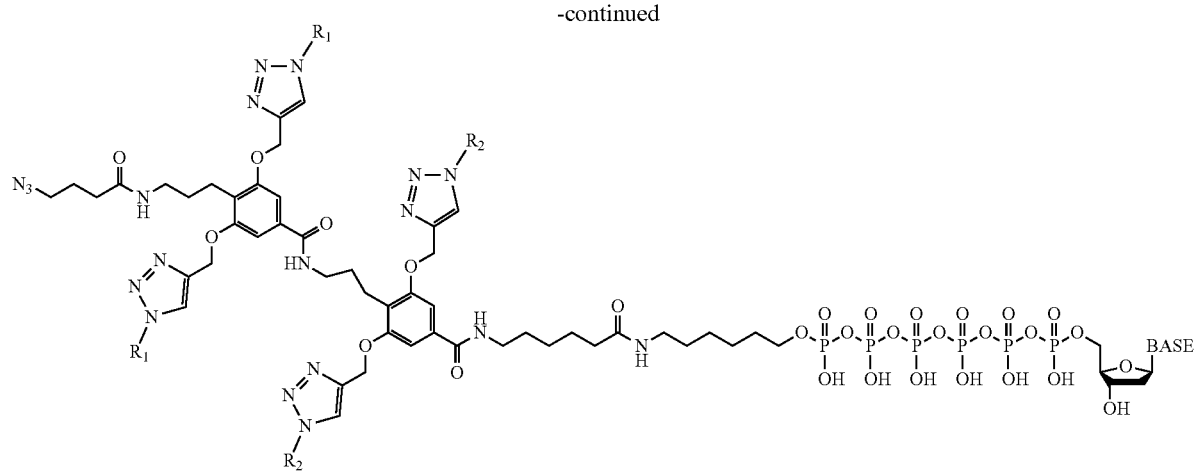
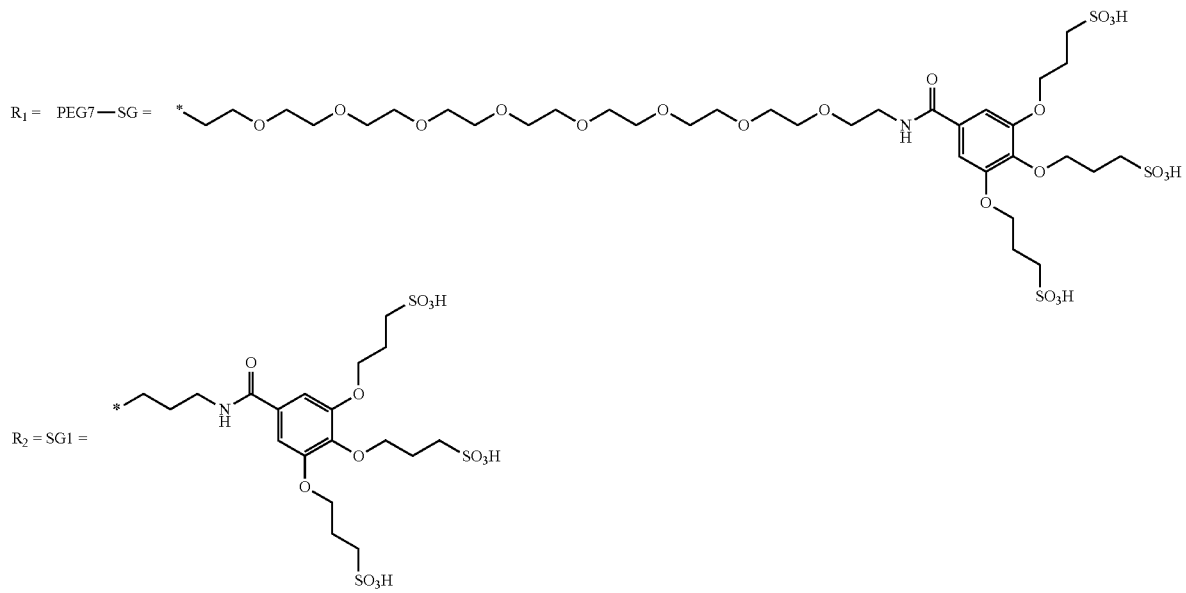
Scheme 7-4
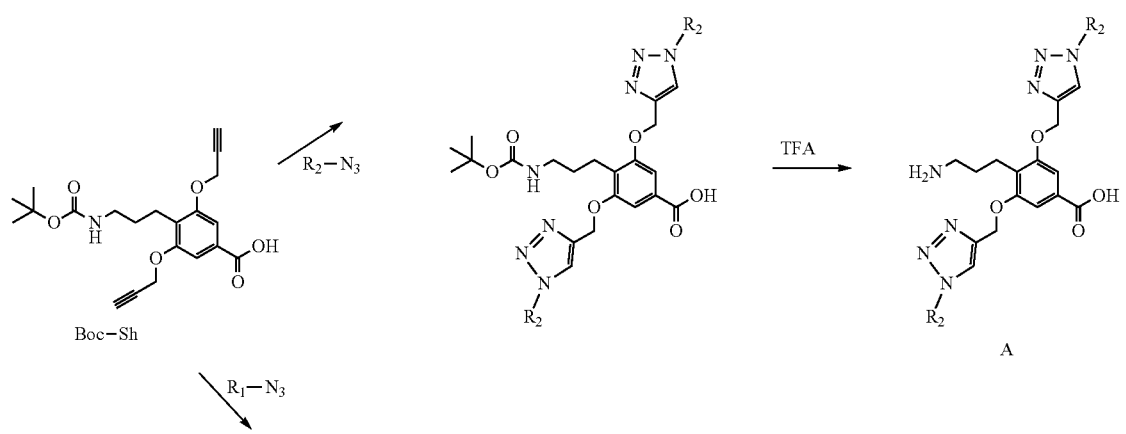

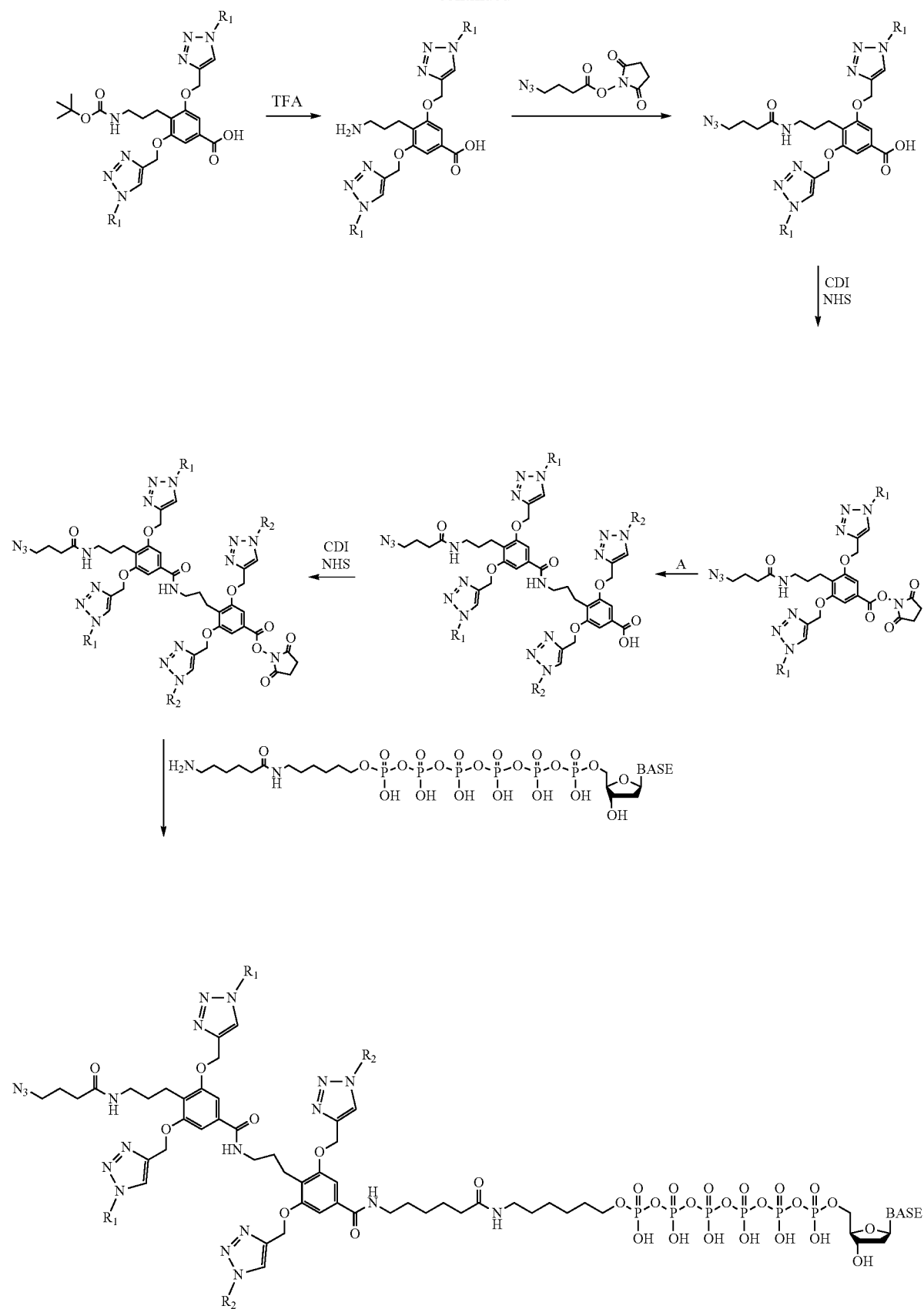

101                                            102
-continued
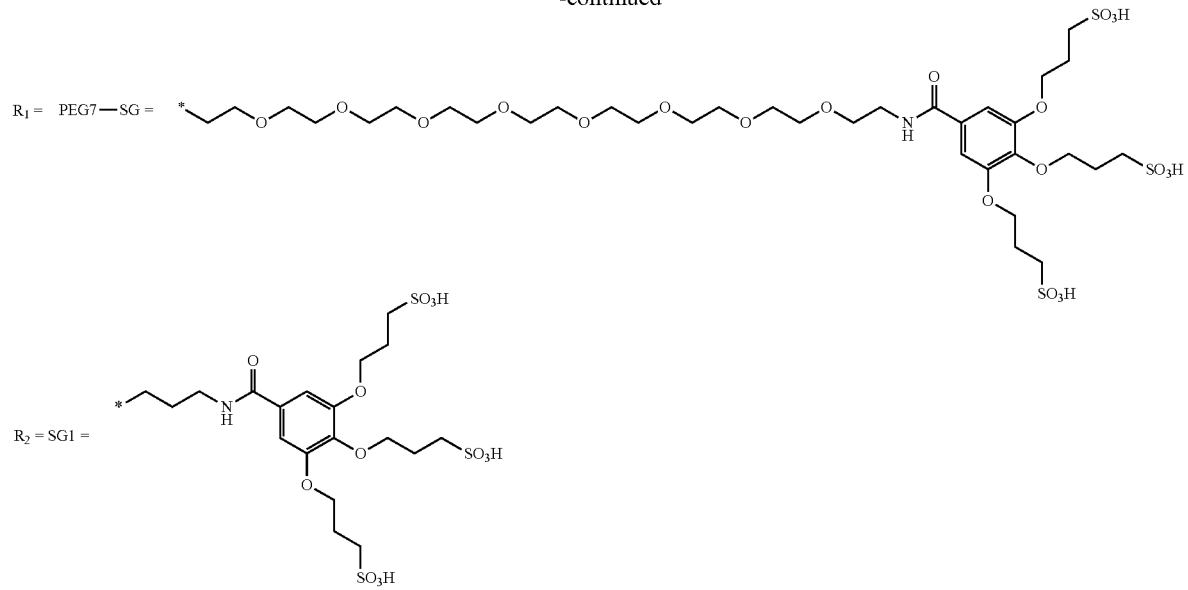
25
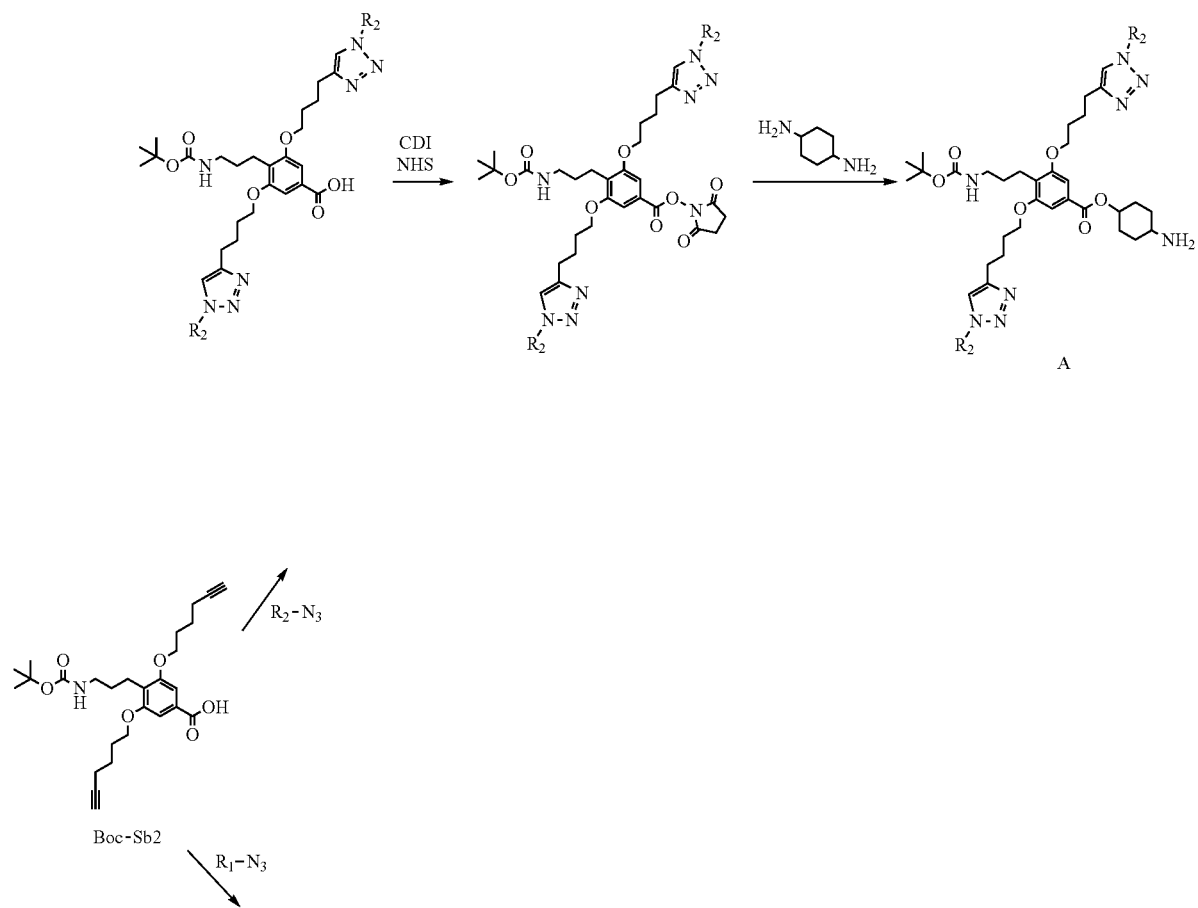

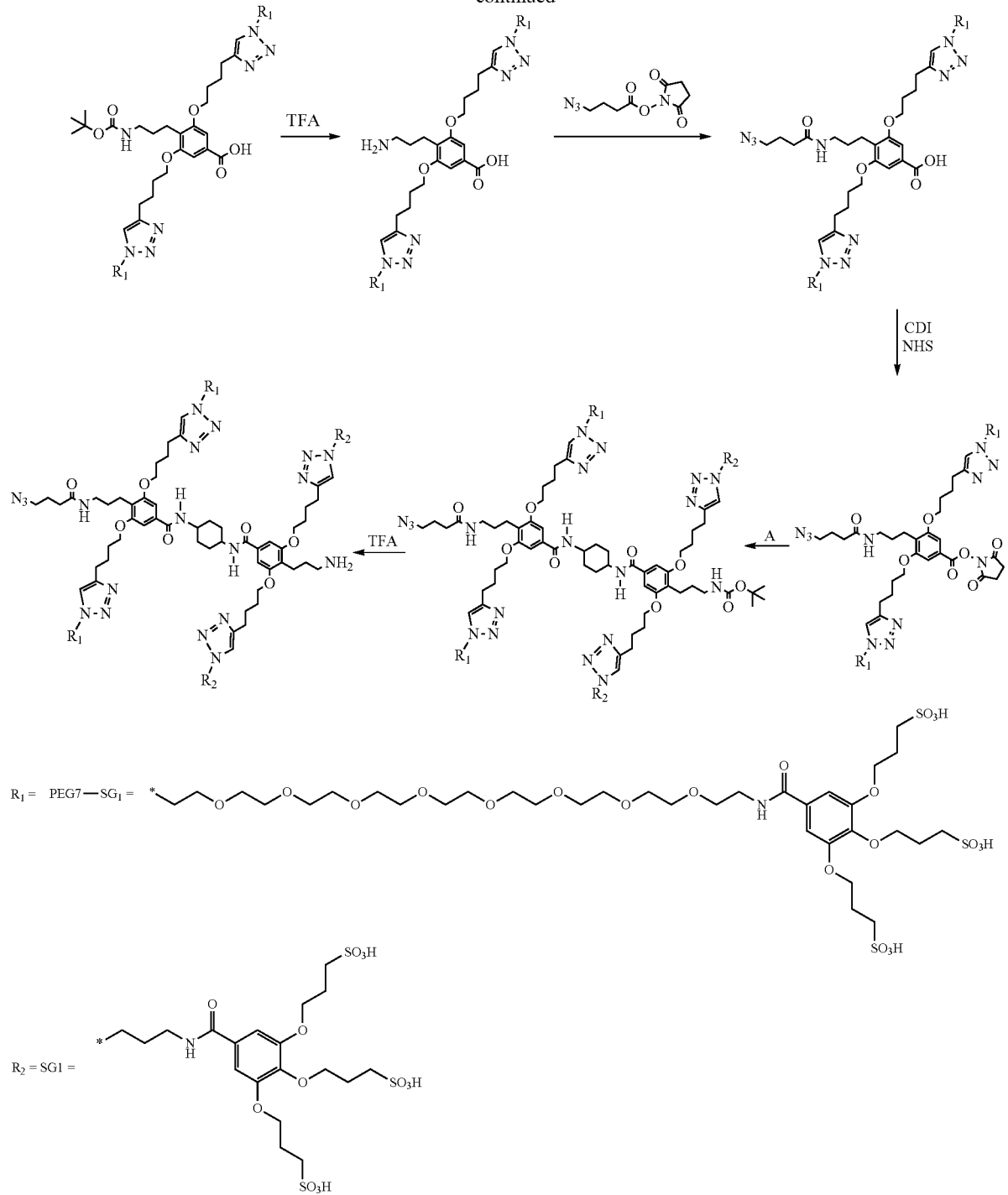
Exemplary synthetic reactions useful in the generation of the azide-containing sidechain reagents of Schemes 7-1 to 7-5 (e.g., $R_1$—$N_3$ and $R_2$—$N_3$ of Schemes 7-3 to 7-5) are outlined in Scheme 8:

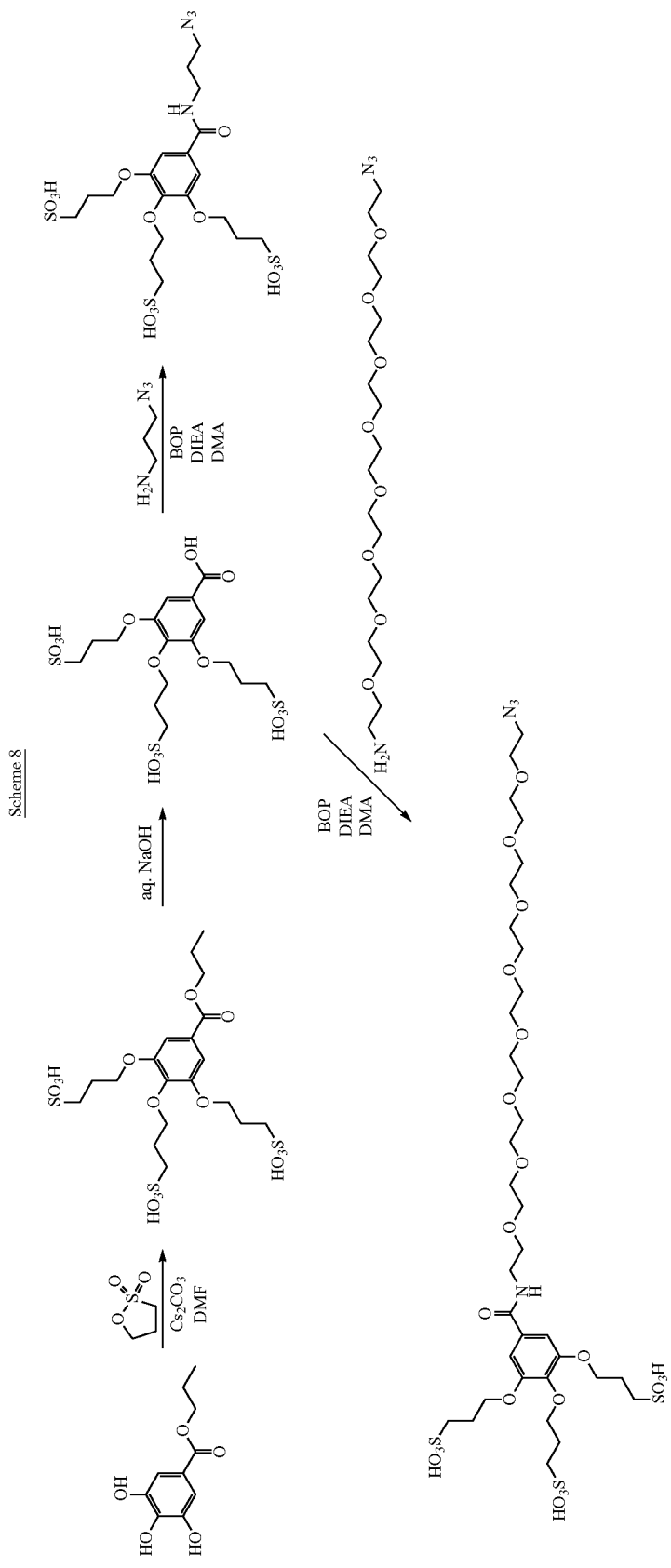

Reasonable variations in all of the above shield component structures should be considered within the scope of the invention.

Exemplary protected compounds of the instant disclosure may be assembled, for example, by the reactions illustrated in Scheme 9 of FIG. 21, wherein the azide-substituted shield element-binding element ("S'—B'") reagent may be abbreviated as follows:

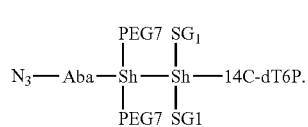

Alternatively, the core elements of the instant compounds may be synthesized, for example, by the reactions exemplified in Scheme 10:

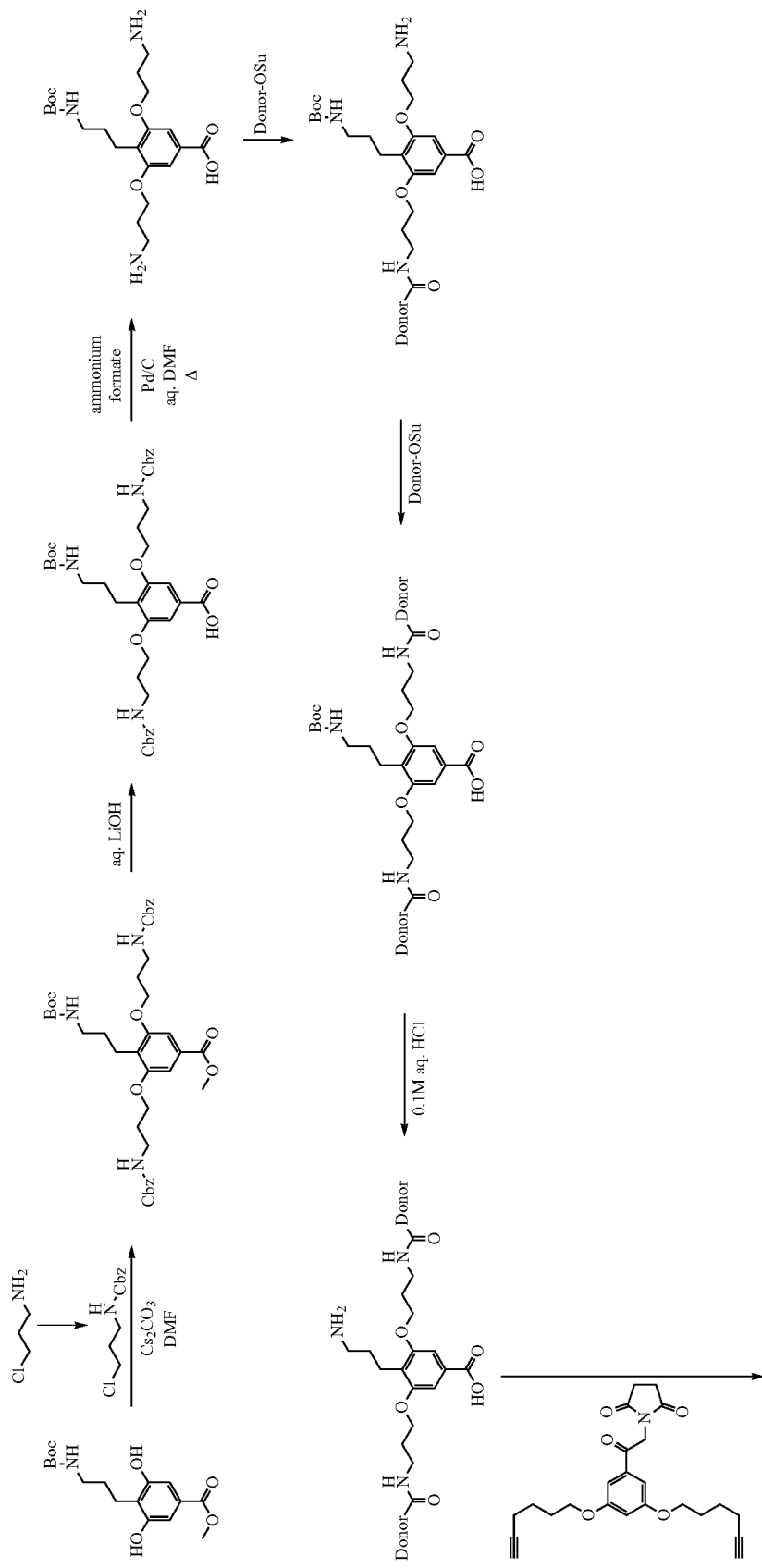
Scheme 10

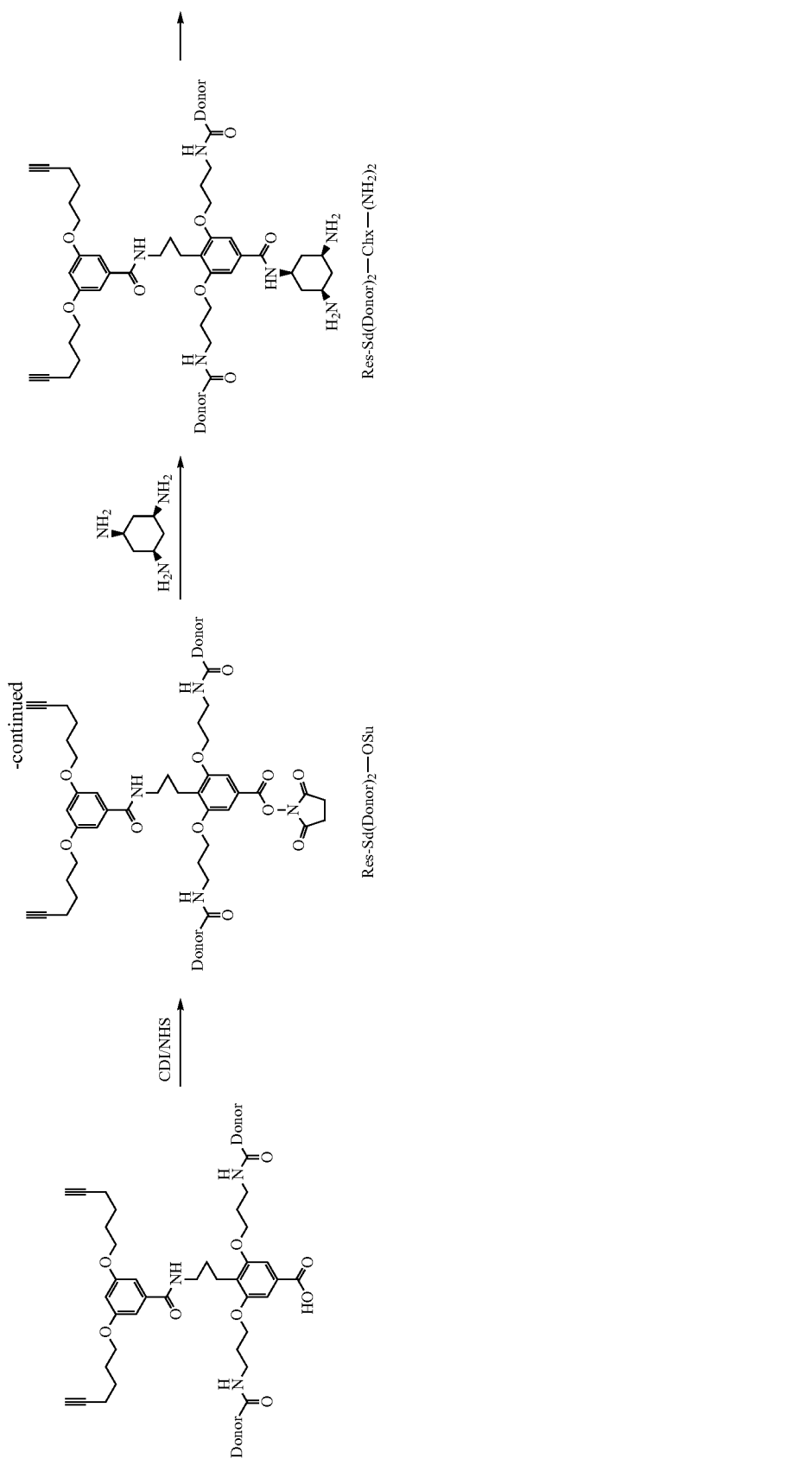

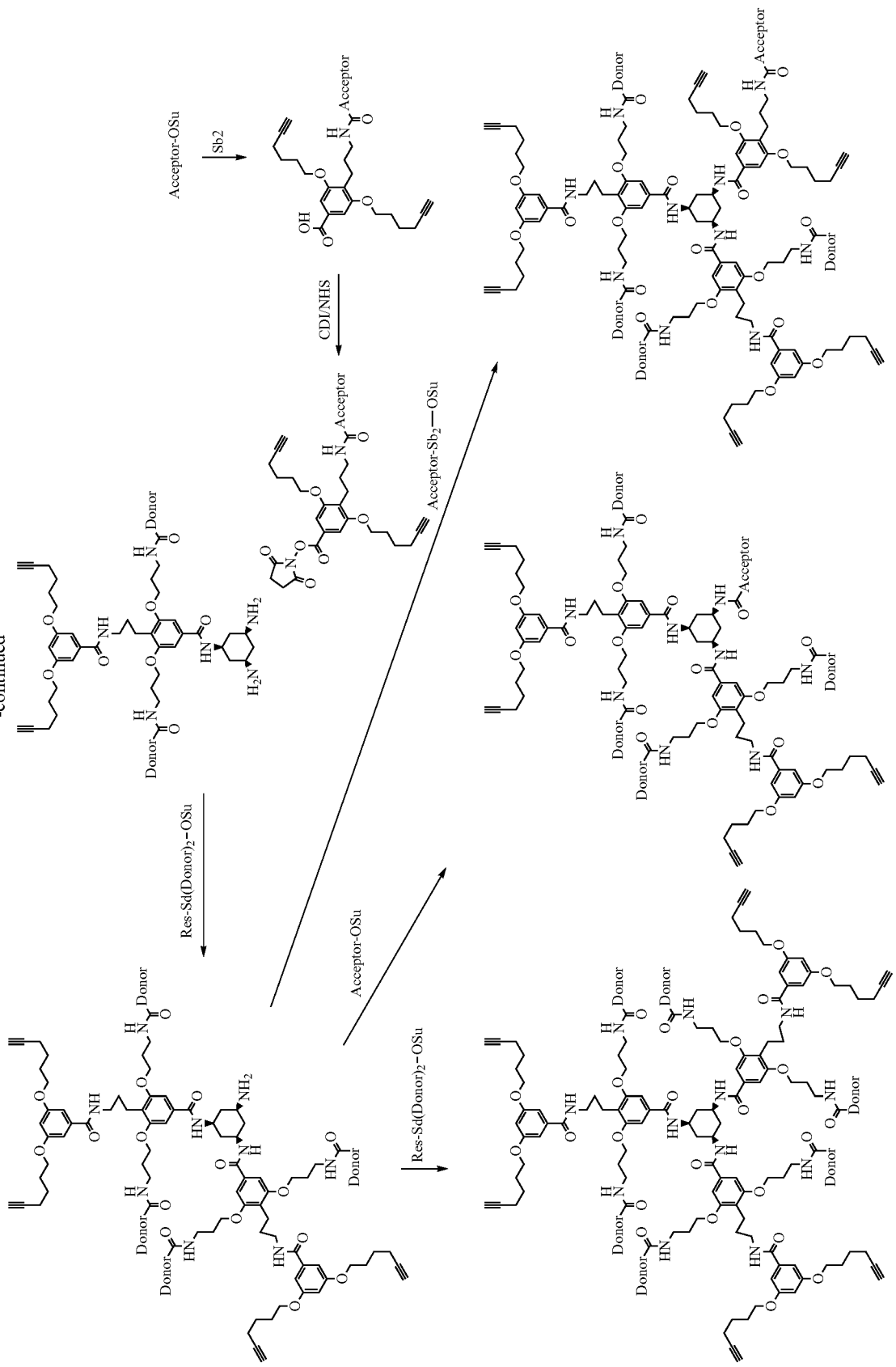

The three products generated according to Scheme 10 illustrate the great flexibility of the instant synthetic methods. In particular, the left-most product contains 6 donor fluorophores attached to the multivalent central core unit, whereas the two right-most products contain 4 donor fluorophores and 1 acceptor fluorophore attached to the multivalent central core unit. The right-most products differ in the spacing between the acceptor fluorophore and the central core element. The synthetic approaches thus provide for the synthesis of a wide variety of protected fluorescent reagents for use in FRET analyses. The final products may be generated by reaction of the fluorescently-labeled multivalent central core elements with a sufficient excess of azide-substituted shield element-binding element ("S'—B'") reagent, for example as shown in Scheme 9 of FIG. 21.

Similar approaches have resulted in the exemplary protected fluorescent reagent compounds of FIGS. 22A-22H, which include adenine and cytosine nucleobases, respectively.

Exemplary synthetic approaches useful in the preparation of dye cores containing 6 and 9 azide terminal groups are shown in Schemes 11 and 12:

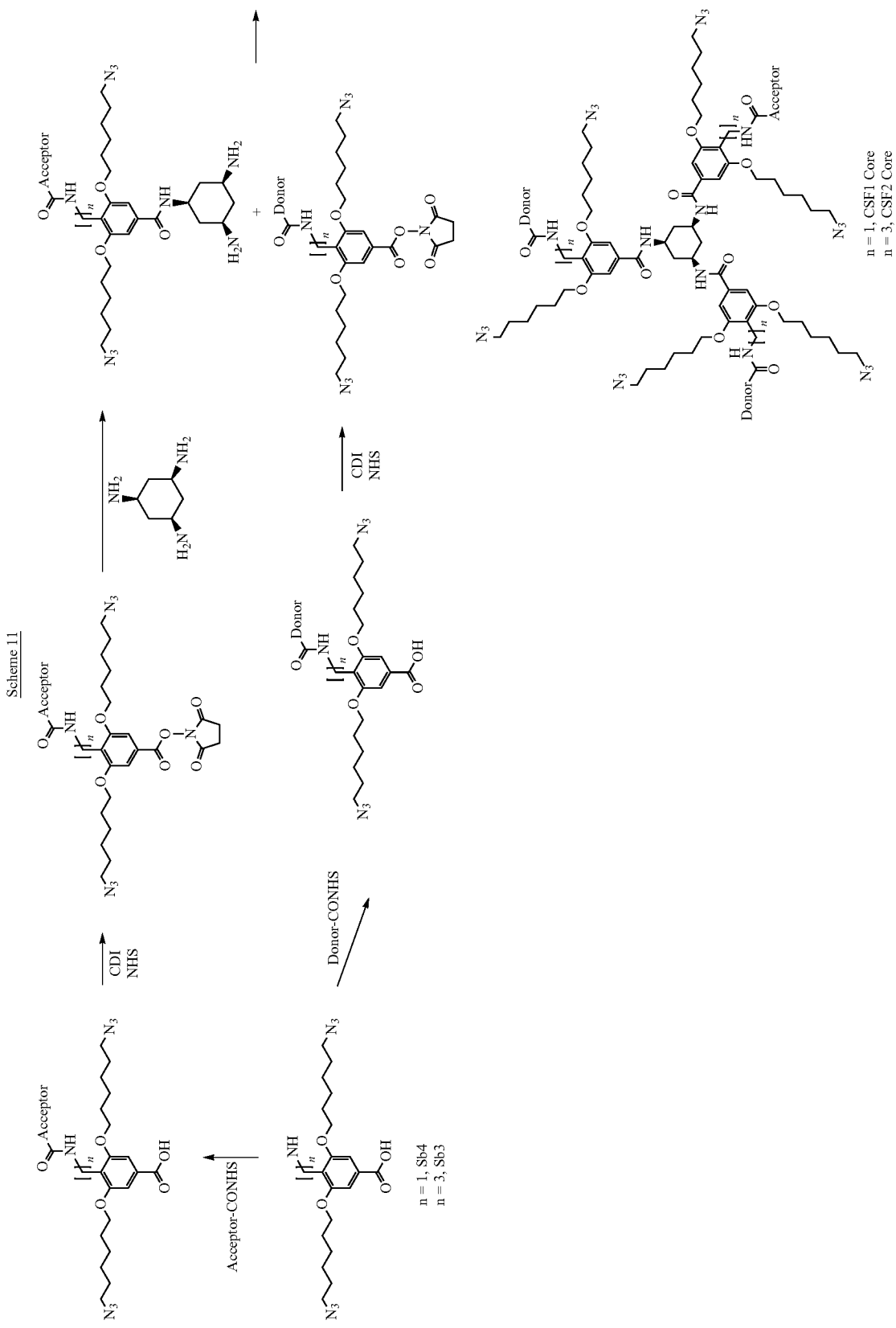

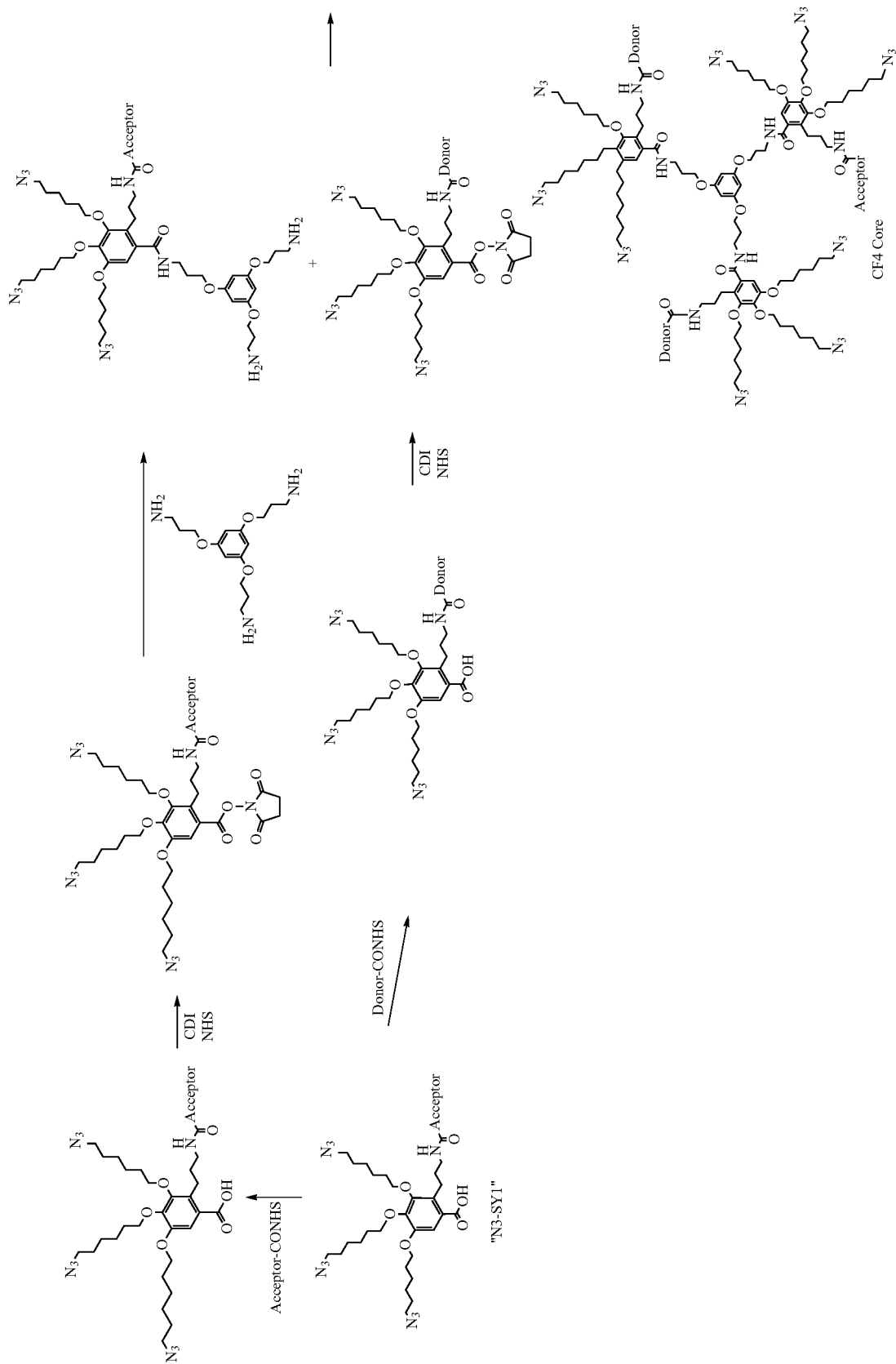
Scheme 12

Such cores may be reacted with alkyne-containing groups, for example using click chemistry or copper-free click chemistry, to generate useful protected fluorescent reagent compounds.

Exemplary synthetic schemes to generate the azide scaffolds employed in the reactions of Schemes 11 and 12 may be prepared as illustrated in Schemes 13 and 14:

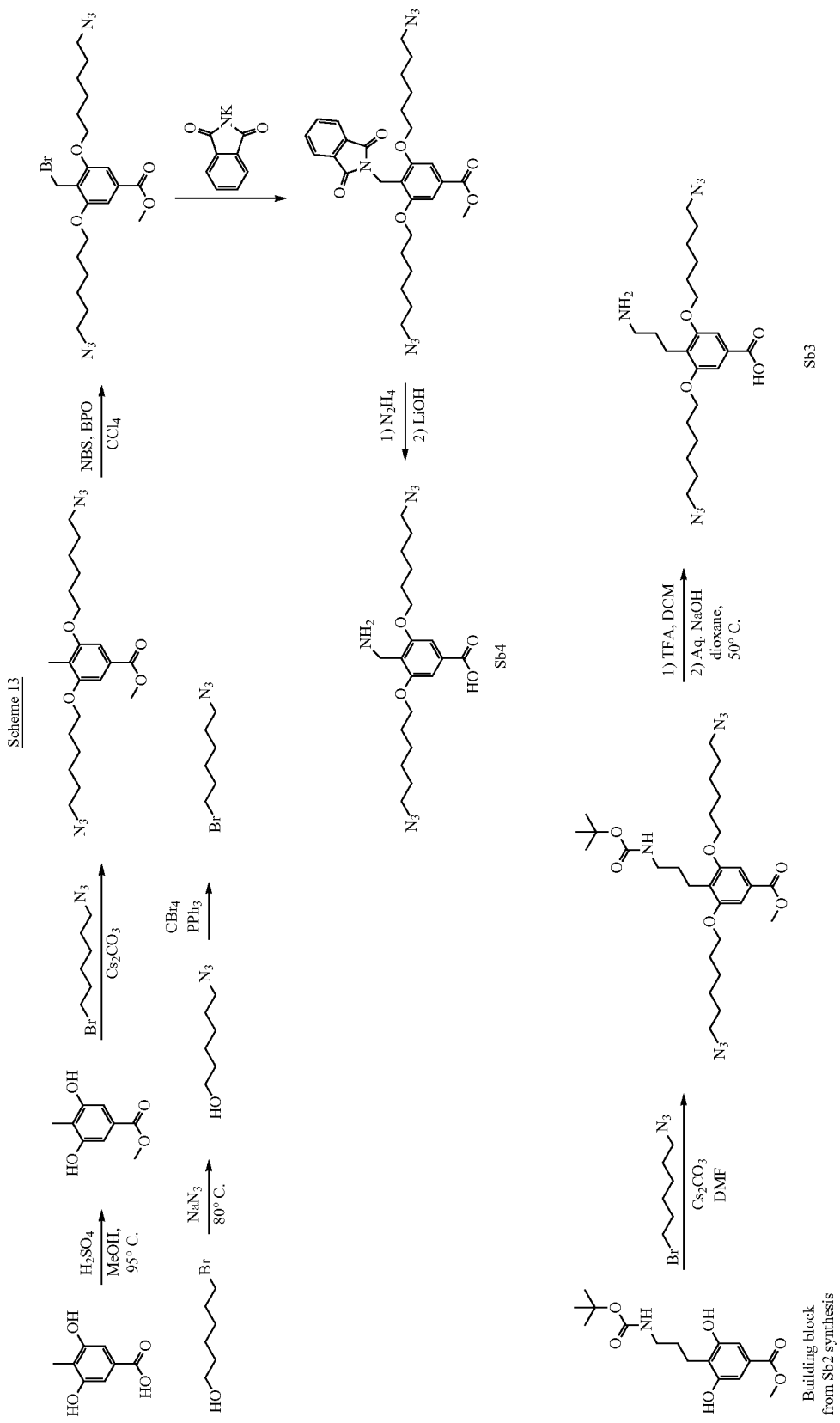

Scheme 14
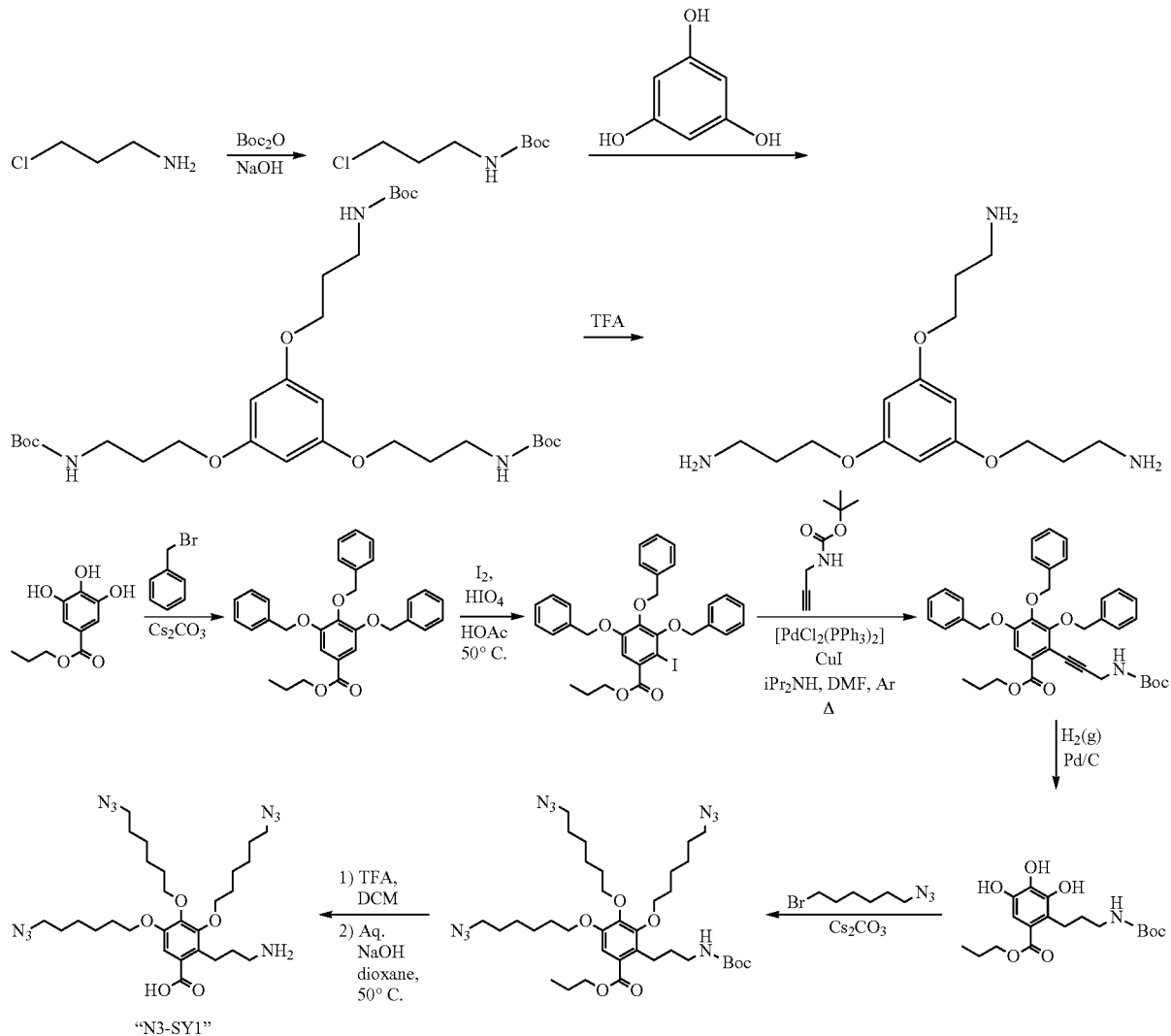
"N3-SY1"
An exemplary synthetic approach for preparing an alkyne-substituted shield element-binding element (S'—B') usefully reacted with, for example, the above-described azide-substituted dye cores is shown in Schemes 15-1 and 15-2, where the $R_1$ and $R_2$ side chain groups are PEG7-SG1 and SG1, respectively, and the binding elements are nucleotide binding elements:

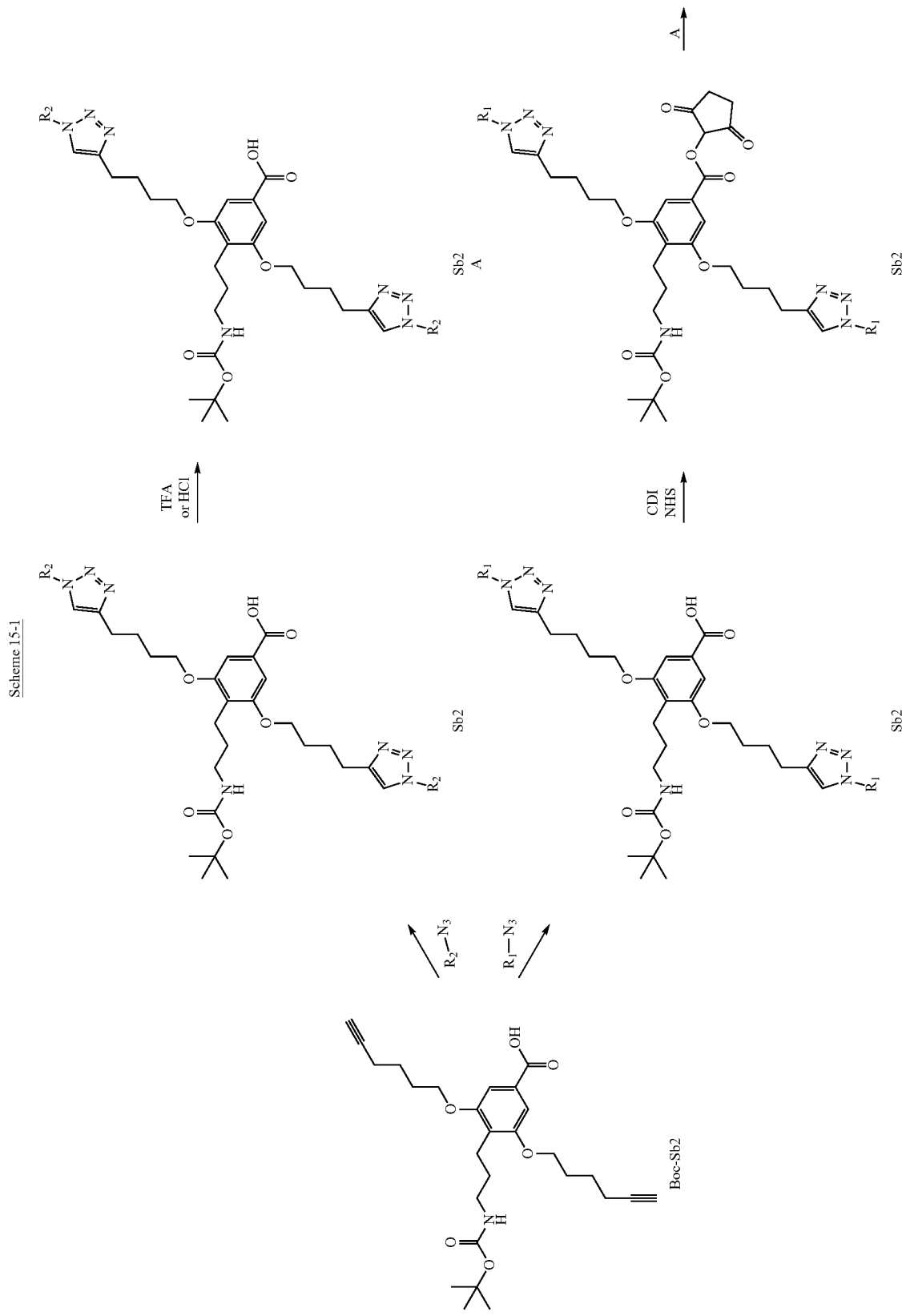

Scheme 15-2
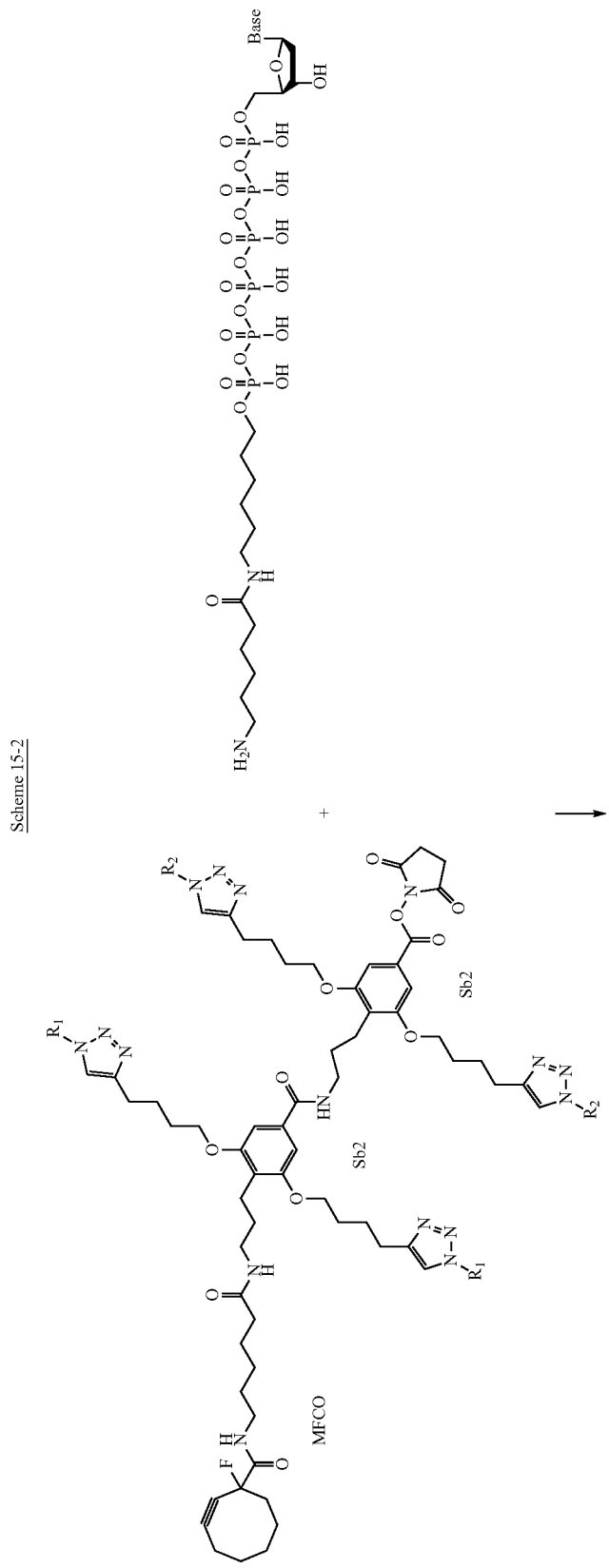

-continued
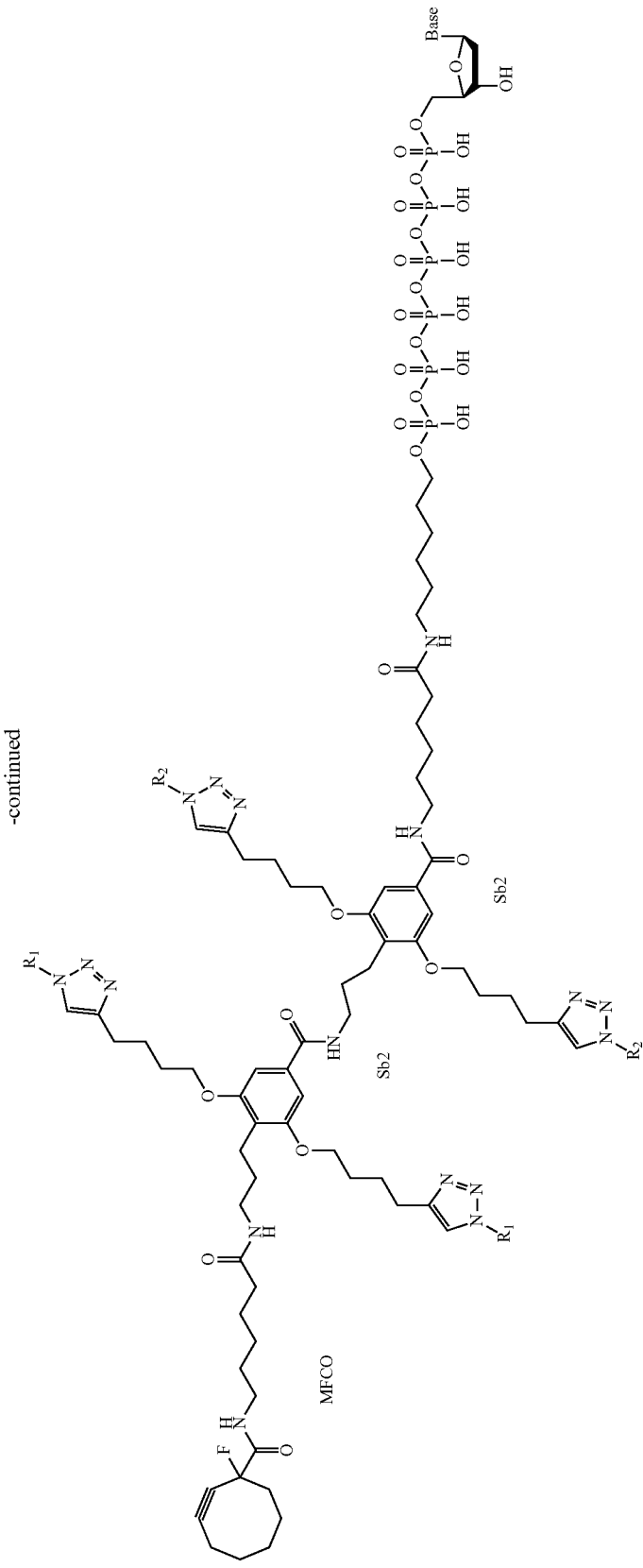

-continued
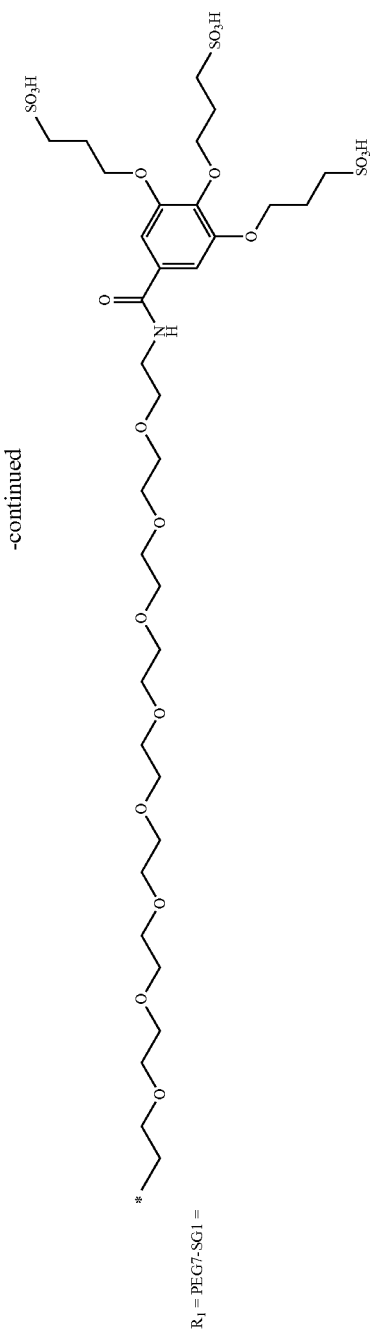
$R_1$ = PEG7-SG1 =
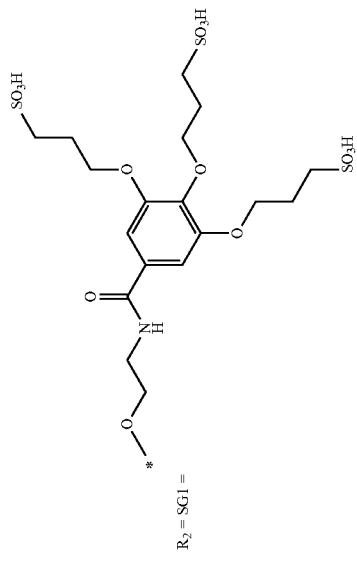
$R_2$ = SG1 =

It should be understood that the shield elements exemplified in Schemes 15-1 and 15-2 correspond to "two-layer" shield elements, but that alternative shield element structures, such as three-layer, four-layer, and so on, may be readily synthesized by routine extension of the disclosed reaction scheme. For example, the triple-layer shield reagent described above could be synthesized by activating the carboxylate group of the two-layer intermediate and reacting with an additional "Sb2" reagent. The $R_1$ and $R_2$ side chain groups, and the side chain groups of any additional layers, may be chosen to provide the desired shielding effects.

Exemplary reactions for preparing components of the just-described shield elements are illustrated in Schemes 16-1 and 16-2:

Scheme 16-1

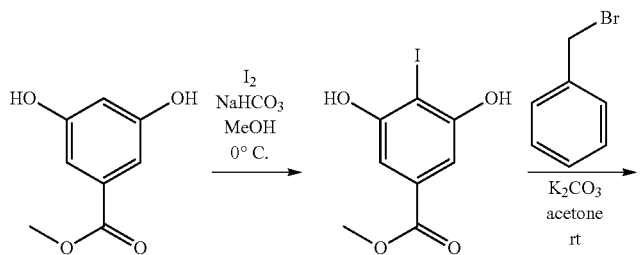

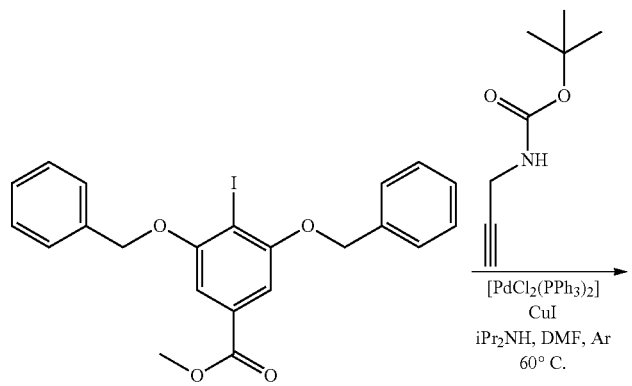

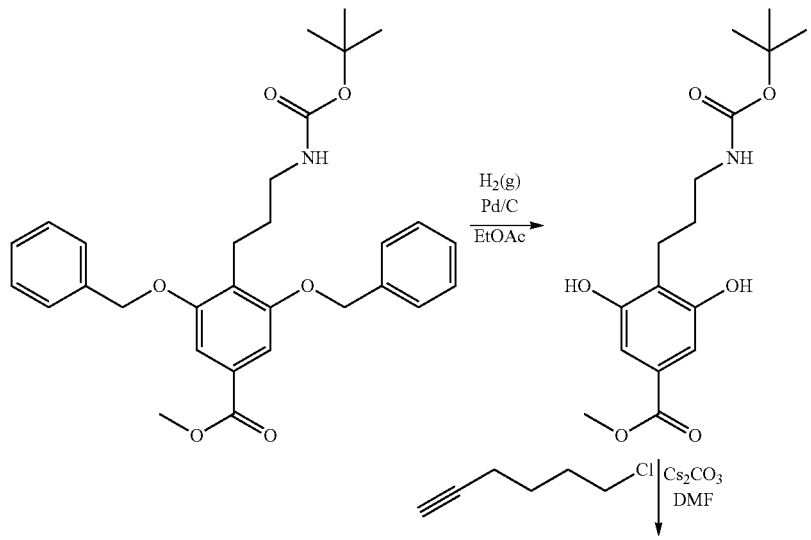

137 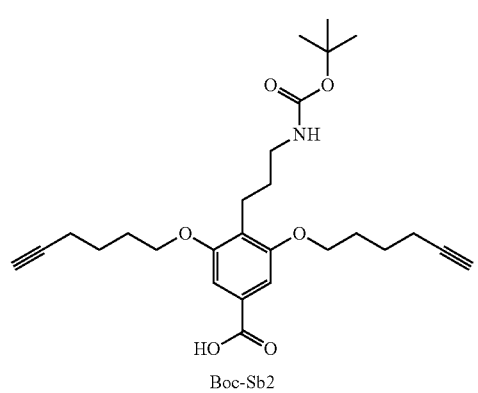 Boc-Sb2
⟵ Aq. NaOH dioxane, 50° C.
138 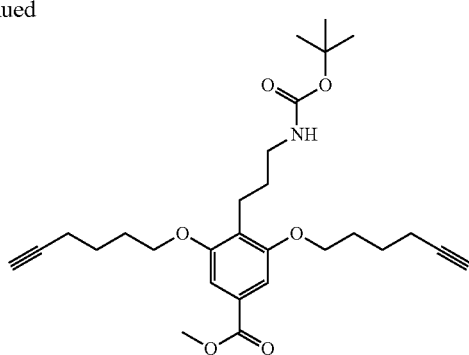

Scheme 16-2
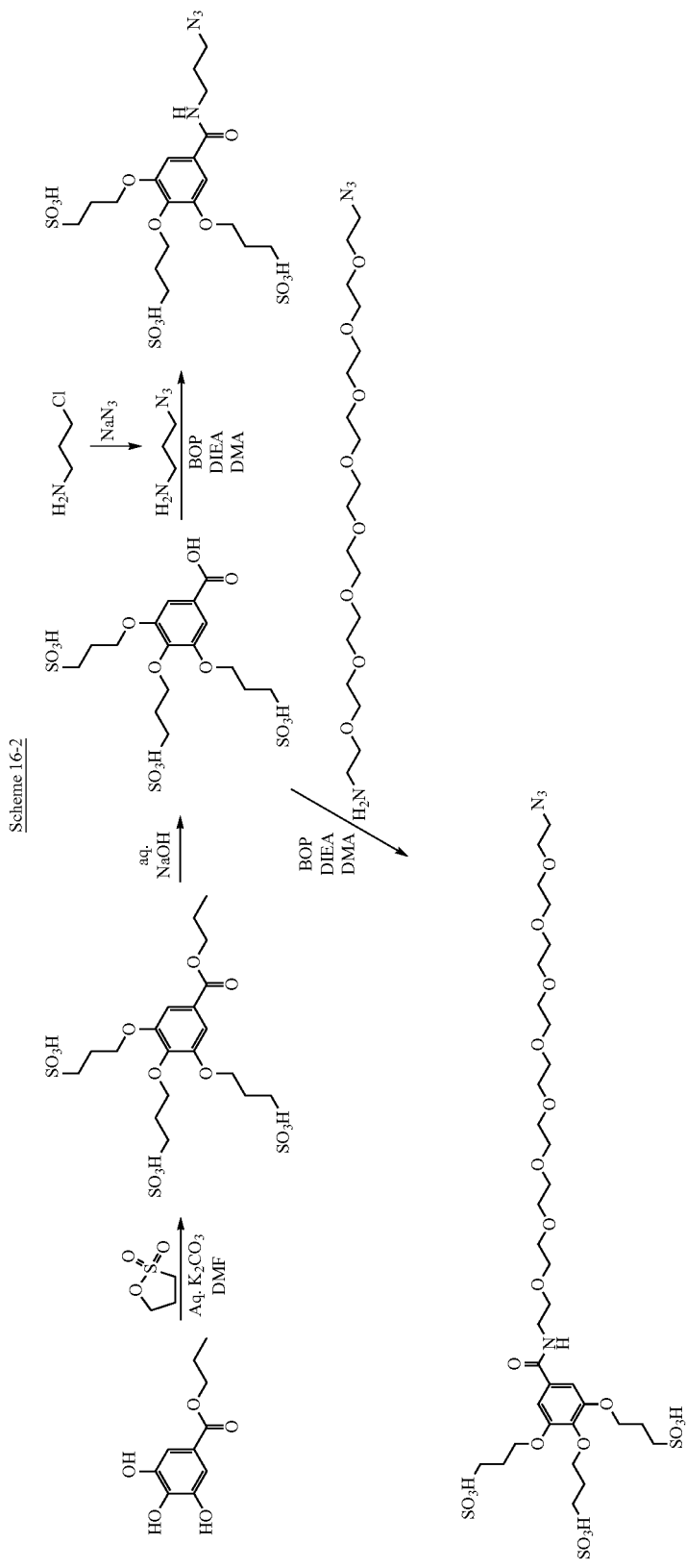

Figure 23:
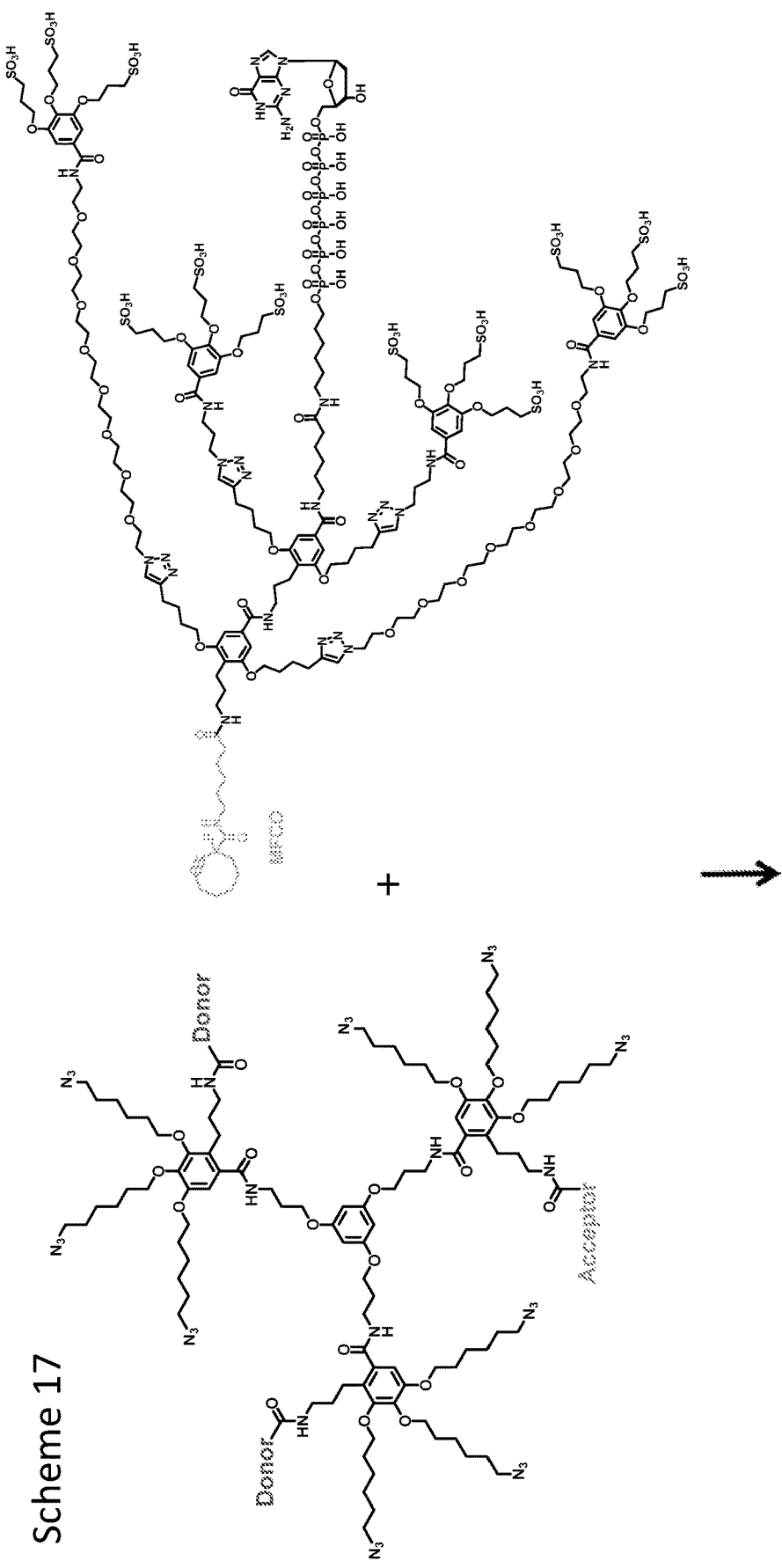
FIG. 23 illustrates an exemplary reaction showing the attachment of alkyne-substituted shield element-binding elements (S'—B's) to an azide-substituted dye core.
Figure 23:
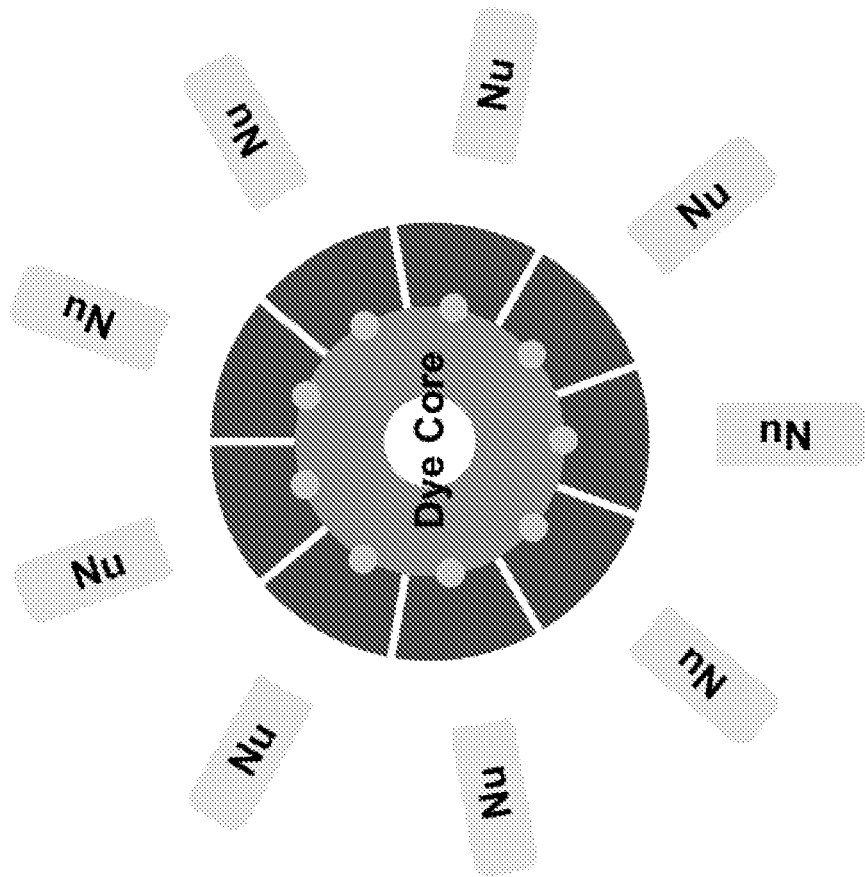

An exemplary reaction showing the attachment of alkyne-substituted shield element-binding elements (S'—B's), to an azide-substituted dye core is illustrated in Scheme 17 of FIG. 23.

As would be understood by those of skill in the art, the dye core reactant in this reaction contains 9 azide groups, and 9 molecular equivalents of the alkyne-substituted shield element-binding element reactant would therefore be provided in order for the reaction to go to completion. It would also be understood that the binding element in the shield element-binding element reactant of this reaction is a nucleotide binding element. The product of the reaction of Scheme 17 in FIG. 23 is shown as a cartoon to illustrate the expected relationship between the central dye core, the shield layers, and the nucleotide binding elements, but no specific three-dimensional structure should be assumed for the product of this reaction or any of the other protected fluorescent reagent compounds of the disclosure.

The above examples provide a representative sample of the structural variety available using the synthetic approaches described herein. In particular, these examples illustrate variation in the multivalent central core element, including fluorescent and non-fluorescent multivalent central core elements, in the fluorescent dye elements, in the branching elements, in the shield core elements, in the shield side chains, and in the binding elements, including linkers and nucleobases. Also illustrated are variation in placement of the reactive groups in the coupling reactions, e.g., the azide group and the alkyne group for click chemistry reactions, on the different precursor components of the protected compounds. Other variants are well within the skill of the ordinary artisan in view of the instant disclosure, in particular in view of the instant synthetic schemes.

It will be readily apparent to one of ordinary skill in the relevant arts that other suitable modifications and adaptations to the methods and applications described herein may be made without departing from the scope of the invention or any embodiment thereof. Having now described the present invention in detail, the same will be more clearly understood by reference to the following Examples, which are included herewith for purposes of illustration only and are not intended to be limiting of the invention.

EXAMPLES

Figure 24:
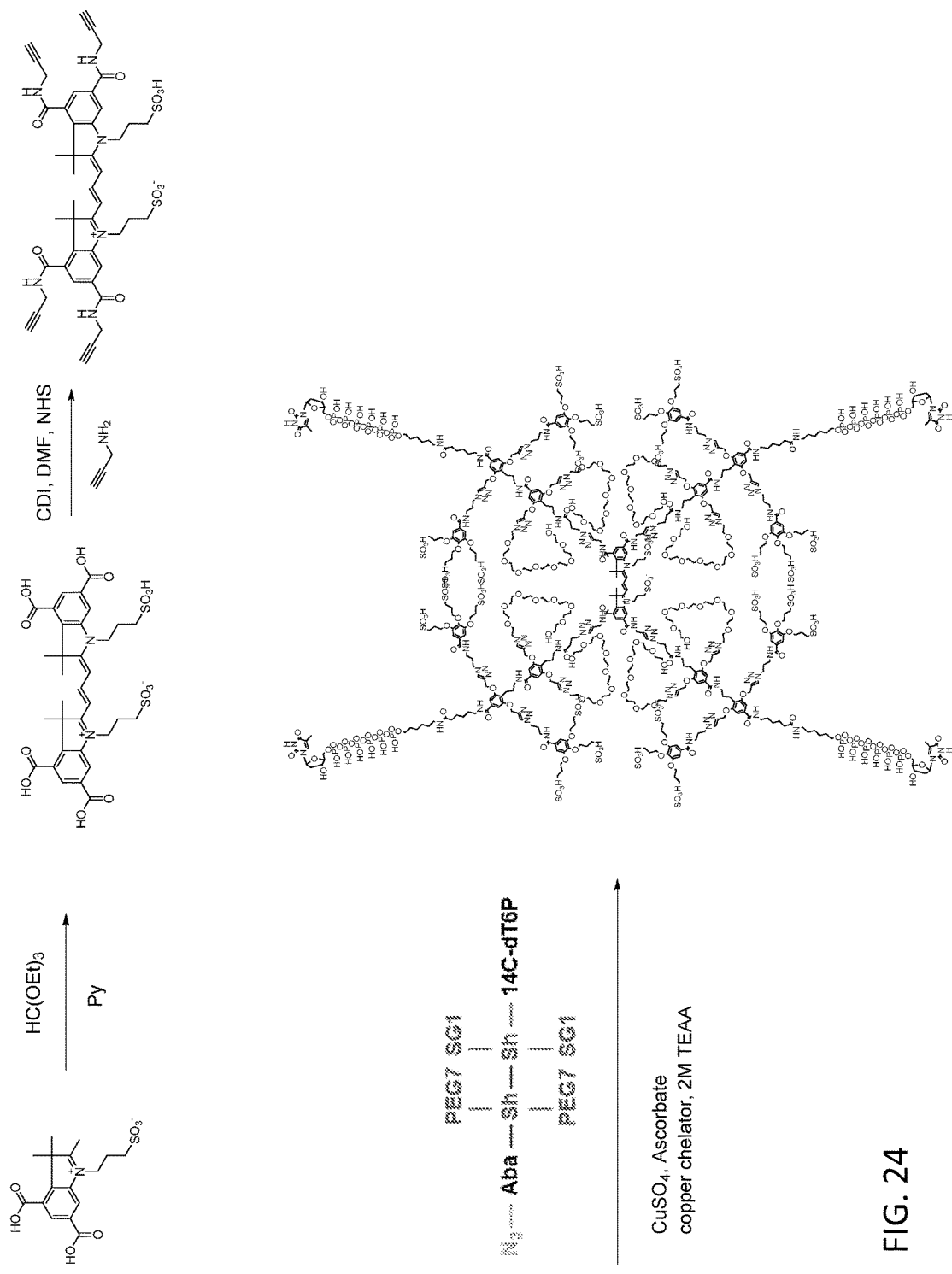
Figure 26:
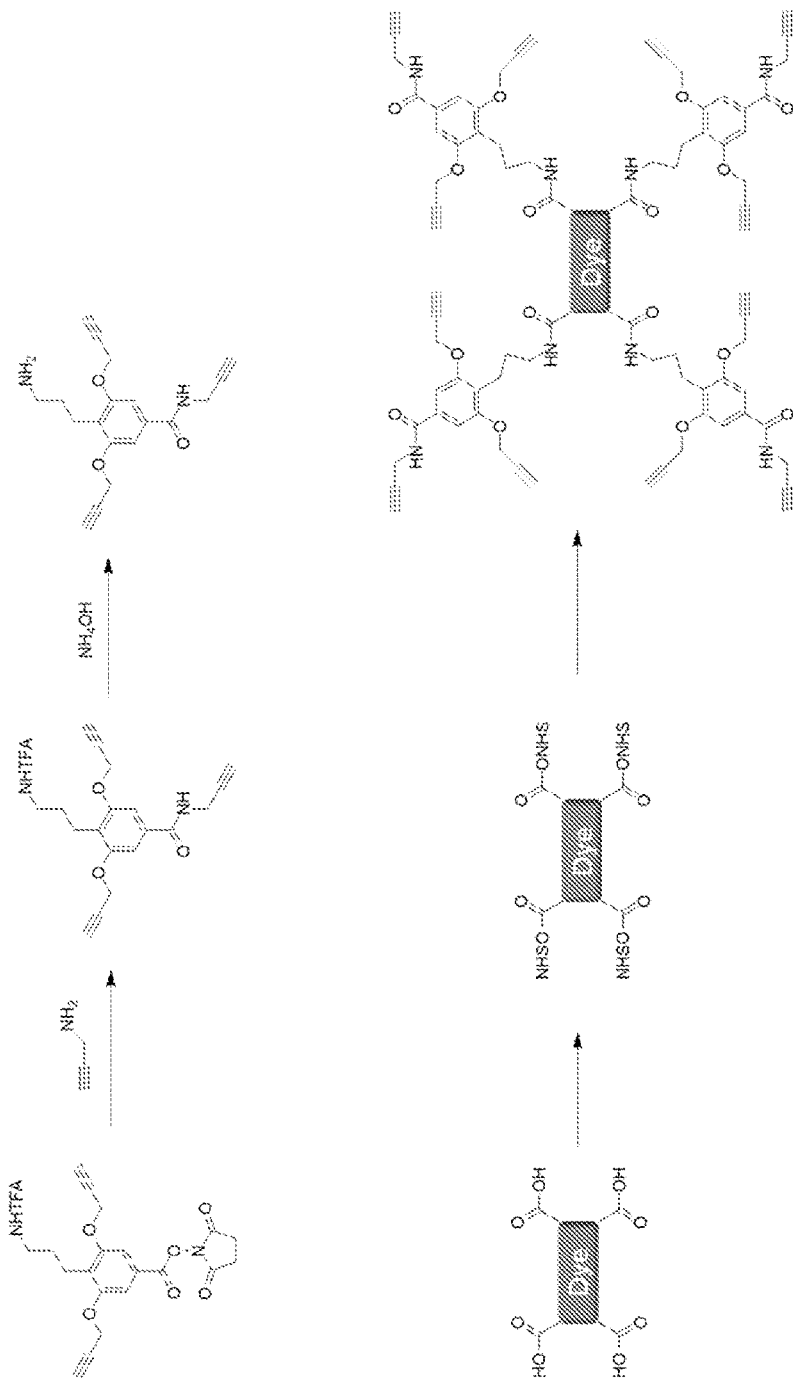
Figure 26:
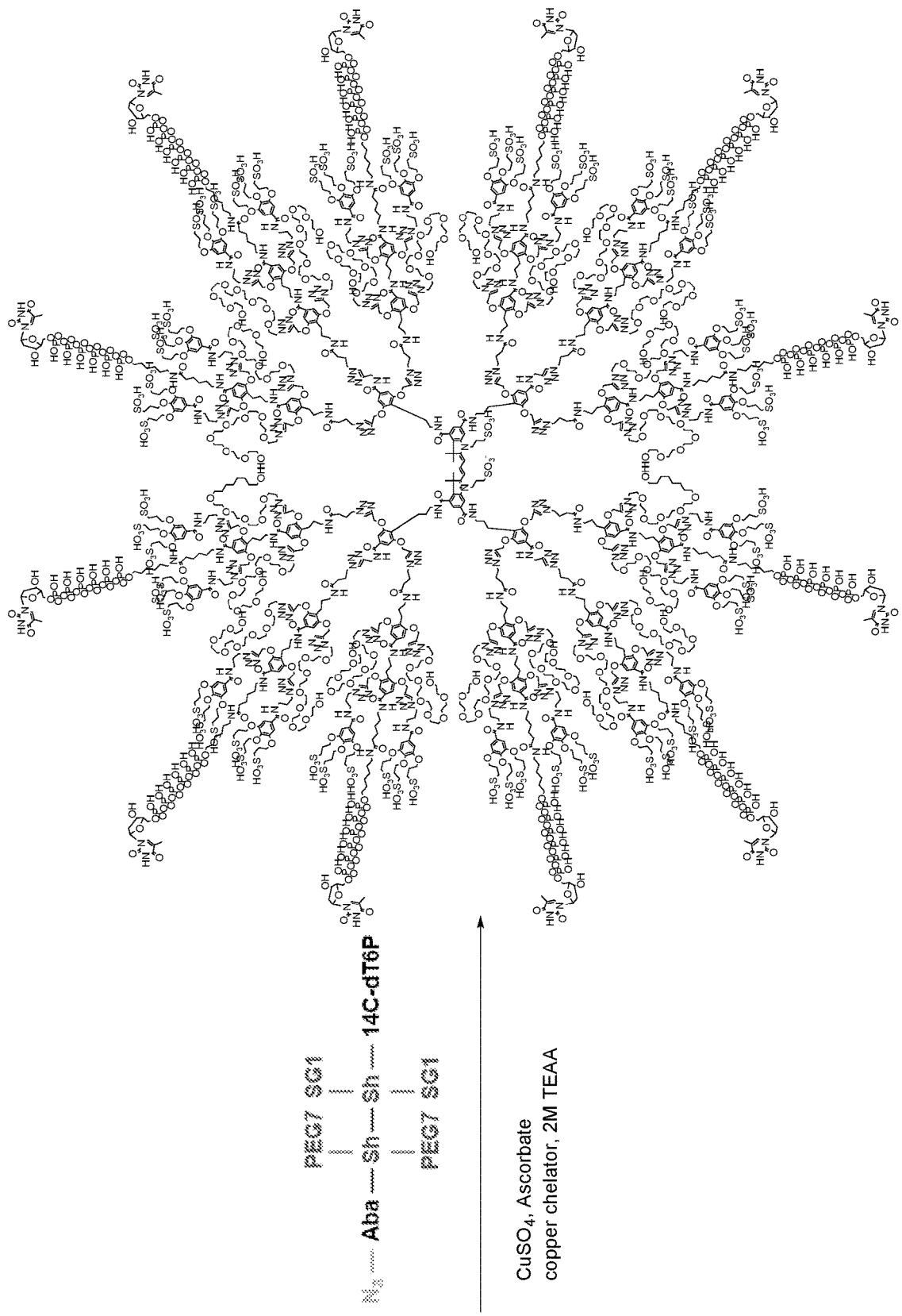

Example 1. Synthesis of Protected Fluorescent Reagent Compounds Comprising Multivalent Fluorescent Dye Elements Three different protected fluorescent reagent compounds comprising tetravalent fluorescent core elements were synthesized according to the following experimental procedures, as outlined in Schemes 18-20 of FIGS. 24-26.

Tetracarboxy Carbocyanine Dye (D010)

A solution of 1-(3-sulfonatopropyl)-2,3,3-trimethylindoleninium carboxylate (85.4 mg, 231 umol, prepared from 1-hydrazinylbenzene-1,3-dicarboxylic acid in 2 steps following the standard Fischer indole synthesis procedures) and ortho-triethylformate (300 µL) in pyridine was heated at 100° C. overnight under nitrogen. Solvent was evaporated off under reduced pressure to give a dark red residue, which was then purified by reverse-phase HPLC (acetonitrile/0.1 M TEAB gradient) to give 122 µmole of the product (53% yield). λmax (545 nm).

Tetraalkyne Carbocyanine Dye (D010-(PA)$_4$)

To a solution of the tetracarboxy dye, D010 (10 µmol) in DMF (300 µL) was added CDI (60 µmol) and NHS (60 µmol) and stirred overnight under nitrogen. To the solution was added diethyl ether (3 mL). The resulting precipitate was collected, washed with diethyl ether (3×1 mL) and dried under high vacuum to give the activated NHS ester. To a solution of the activated NHS ester (4 µmol) in DMF (200 µL) was added DIPEA (20 µL) followed by addition of large excess of propargyl amine (26 µL, 400 µmol). The resultant solution was stirred overnight and the crude product was subjected to reverse-phase HPLC (acetonitrile/0.1 M TEAB gradient) purification to give 1.6 umol of the desired product together with some incomplete reaction adducts (trialkynes and dialkynes).

D010-[Aba-Sh(PEG7)$_2$-Sh(SG1)$_2$-14C-dT6P]$_4$

To a solution of D010-(PA)$_4$ (0.1 µmol) and N3-Aba-Sh (PEG7)$_2$-Sh(SG1)$_2$-14C-dT6P (1.0 µmol) in 2 M TEAA aqueous buffer (20 µL) was added sodium ascorbate (2.5 µL, 200 mM), copper sulfate (2 µL, 100 mM), copper chelator (200 mM, 1 µL) in a vial. After vortexing for 30 seconds the vial was placed in the dark at room temperature overnight. To the vial was added 1M EDTA (10 µL) and the solution was subjected to ion-exchange HPLC (0.05 M TEAA with 20% CH$_3$CN/1.5 M TEAA with 20% CH$_3$CN) followed by reverse-phase HPLC (acetonitrile/0.1 M TEAB gradient) purification to give 0.054 µmol of the desired product.

Octaalkyne Carbocyanine Dye, D010-(Sh)$_4$

To a solution of the activated NHS ester of the tetracarboxy dye, D010-(NHS)$_4$ (1 µmol), in DMF (100 µL) was added DIPEA (5 µL) followed by addition of Sb1 (10 µmol, from Scheme 1) in DMF (50 µL). The resultant solution was stirred overnight and the crude product was subjected to reverse-phase HPLC (acetonitrile/0.1 M TEAB gradient) purification to give 0.56 µmol of the desired product together with some incomplete reaction adducts.

D010-Sh{[Sh(PEG7)$_2$-Sh(SG1)$_2$-14C-dT6P]2}$_4$

To a solution of D010-(Sh)$_4$ (0.06 µmol), N$_3$-Aba-Sh (PEG7)$_2$-Sh(SG1)$_2$-14C-dT6P (1.0 µmol) in 2 M TEAA aqueous buffer (20 µL) was added sodium ascorbate (2.5 µL, 200 mM), copper sulfate (2 µL, 100 mM), copper chelator (200 mM, 1 µL) in a vial. After vortexing for 30 seconds the vial was placed in the dark at room temperature overnight. To the vial was added 1M EDTA (10 µL) and the solution was subjected to ion-exchange HPLC (0.05 M TEAA with 20% CH$_3$CN/1.5 M TEAA with 20% CH$_3$CN) followed by reverse-phase HPLC (acetonitrile/0.1 M TEAB gradient) purification to give 0.036 µmol of the desired product.

Trialkyne Sh compound, Sh-PA

To a solution of TFA-Sh-CONHS (14.1 mg, 29.3 µmol) in DMF (1 mL) was added excess amount of propargyl amine (94 µL, 1.47 mmol) and stirred at room temperature for 2 hours. The crude product was subjected to reverse-phase HPLC (acetonitrile/0.1 M TEAB gradient) purification to give 12.0 mg (quantitative yield) of the TFA protected product. To the TFA protected Sh-PA in acetonitrile (500 µL) was added NH$_4$OH (50%, 500 µL) and stirred overnight. The crude product was purified by reverse-phase HPLC (acetonitrile/0.1 M TEAB gradient) separation to give 5.9 mg (62%) of the desired product.

Dodecaalkyne Carbocyanine Dye, D010-(Sh-PA)$_4$

To a solution of the activated NHS ester of the tetracarboxy dye, D010-(NHS)$_4$ (2.2 µmol), in DMF (165 µL) was added DIPEA (50 µL) followed by addition of Sh-PA (5.9 mg, 18.2 µmol) in DMF (400 µL). The resultant solution was stirred overnight and the crude product was subjected to reverse-phase HPLC (acetonitrile/0.1 M TEAB gradient) purification to give 0.33 µmol of the desired product together with some incomplete reaction adducts.

D010-Sh{[Sh(PEG7)$_2$-Sh(SG1)$_2$-14C-dT6P]2}$_4$

To a solution of D010-(Sh-PA)$_4$ (0.06 μmol) and N$_3$-Aba-Sh(PEG7)$_2$-Sh(SG1)$_2$-14C-dT6P (1.0 μmol) in 2 M TEAA aqueous buffer (20 μL) was added sodium ascorbate (2.5 μL, 200 mM), copper sulfate (2 μL, 100 mM), copper chelator (200 mM, 1 μL) in a vial. After vortexing for 30 seconds the vial was placed in the dark at room temperature overnight. To the vial was added 1M EDTA (10 μL) and the solution was subjected to ion-exchange HPLC (0.05 M TEAA with 20% CH$_3$CN/1.5 M TEAA with 20% CH$_3$CN) followed by reverse-phase HPLC (acetonitrile/0.1 M TEAB gradient) purification to give 0.075 μmol of the desired product.

Example 2. Synthesis of Protected Fluorescent Reagent Compounds Comprising Non-Fluorescent Multivalent Core Elements Protected fluorescent reagent compounds comprising non-fluorescent multivalent core elements were synthesized according to the following experimental procedures. In particular, the non-fluorescent central core was synthesized as outlined in Scheme 21, the dye reagents were prepared as outlined in Scheme 22, and the dyes were attached to the central core as outlined in Schemes 23 and 24.

3,3',3"-(benzene-1,3,5-triyltris(oxy))tris(propan-1-amine) (2-1b)

NaH (108 mg, 4.5 mmol) was added to Phloroglucinol (126 mg, 1 mmol) DMF solution slowly, then tert-butyl (3-chloropropyl)carbamate (935 mg, 4.5 mmol) was added and heated to 55° C. overnight. The resultant solution was diluted in 30 mL ethyl acetate, washed with 20 mL water 4 times. Organic layer was collected, after evaporating the solvent, the residue was further purified with silica gel column to afford 146 mg product 2-1a (24% yield) as a white solid. A mixture of 100 μL TFA and 100 μL dichloromethane was added to 2-1a to remove Boc protection group. All solvents are evaporated off after incubating at room temperature for 2 hr. The triamino derivative 2-1b was directly used without further purification.

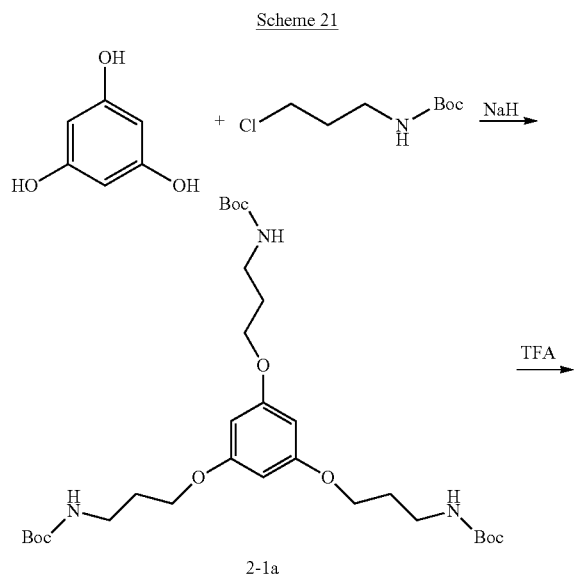

Scheme 21

2-1a

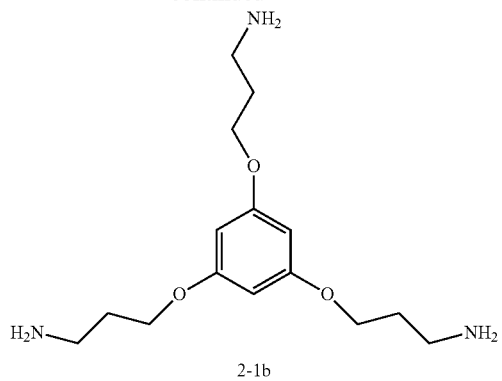

2-1b

N-(5-aminopentyl)-3,4,5-tris(hex-5-yn-1-yloxy)benzamide (2-2b)

3,4,5-tris(hex-5-yn-1-yloxy)benzoic acid (50 mg, 0.12 mmol), EDC·HCl (40 mg, 0.21 mmol), N-Hydroxysuccinimide (25 mg, 0.22 mmol), 72 μL of N,N-Diisopropylethylamine (0.4 mmol) and N-Boc-cadaverine (40 mg, 0.20 mmol) were mixed in 500 μL dichloromethane and stirred overnight, the resultant mixture was purified by silica gel column using ethyl acetate and hexane as eluent to give 26 mg white solid 2-2a (44% yield). Boc protection group was removed by incubating in the mixture of 50 μL TFA and 50 μl dichloromethane for 1 hr. Solvent was evaporated off under high vacuum to give a light yellow residue 2-2b which was used without further purification.

Trihexnyl Gallate-5C-Asp (2-2c)

N-(5-aminopentyl)-3,4,5-tris(hex-5-yn-1-yloxy)benzamide (2-2b, 25 mg, 50 Boc-asp(otbu)-osu (39 mg, 0.1 mmol) were dissolved in 0.5 mL dichloromethane, then 100 μl N,N-Diisopropylethylamine was added and stirred at RT overnight. The reaction mixture was purified by silica gel column to afford 30.4 mg which solids (80% yield). After treatment with 50% TFA in dichlormethane at room temperature for 2 hr, 35 μmol amino acid 2-2c was obtained as a white solid after reverse-phase HPLC purification.

Trihexnyl Gallate-5C-Asp-D005 (2-2d)

5 μmol of D005-OSu, 5 μmol Trihexnyl gallate-5C-Asp and 10 μl DIEA were dissolved in 100 μL DMA and vortexed at room temperature for 2 hr, the reaction mixture was subjected into RP-HPLC to afford 4.5 μmol product 2-2d (90% yield). The same procedure was applied to make Trihexnyl gallate-5C-Asp-X-D002 2-2e. (See Scheme 22.)

Scheme 22
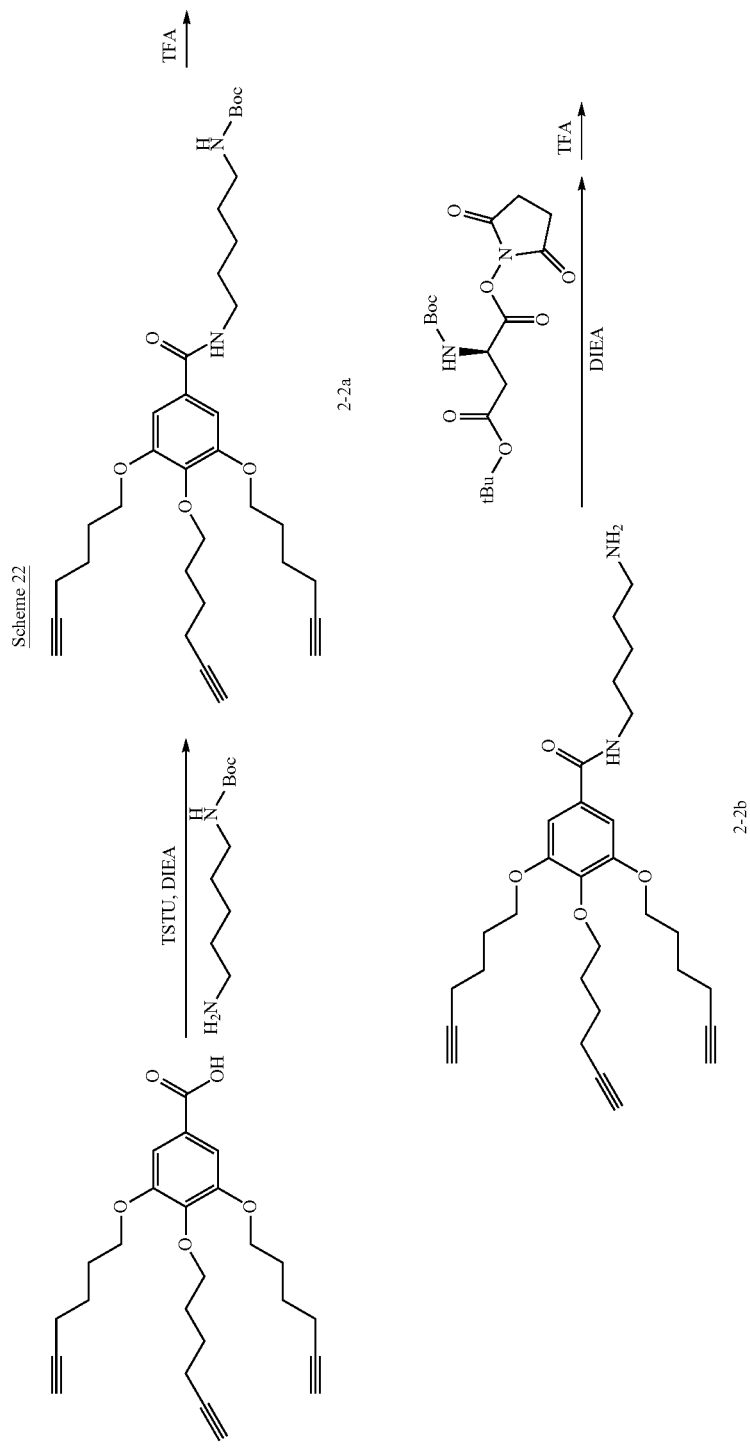

-continued
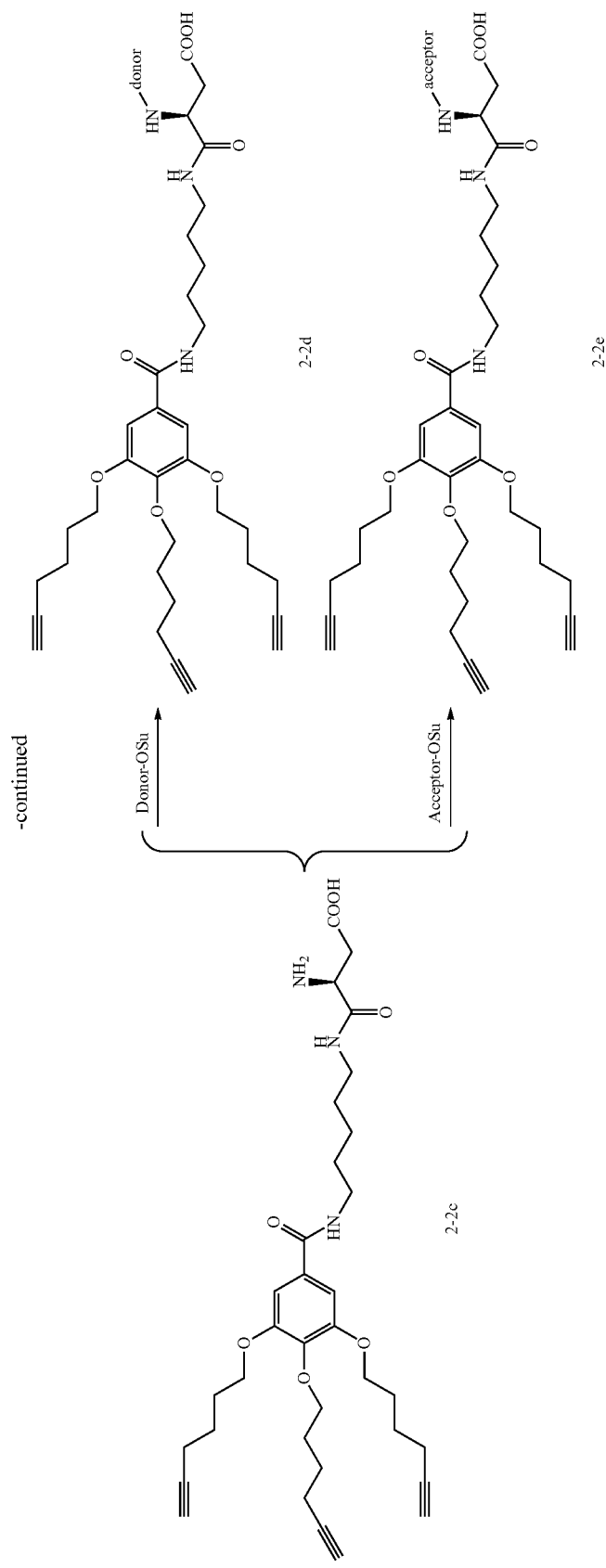

Synthesis of [(D002X)₂D005]-TS6 (2-4b)
Trihexnyl Gallate-5C-Asp-D005-Triamine (2-4a)

1 μmol of Trihexnyl gallate-5C-Asp-D005 (2-2d) was dissolved in 100 μl DMA, 5 μmol of NHS, 5 μL DIEA and 5 μmol of TSTU were added sequentially, after vortexing at RT for 1 hr, to the solution was added ethyl acetate (2 mL). The resulting precipitate was collected, washed with ethyl acetate (3×1 mL) and dried under high vacuum to give the activated NHS ester. To a solution of the activated NHS ester (1 μmol) in DMF (50 μL) was added excess of 3,3',3"-(benzene-1,3,5-triyltris(oxy))tris(propan-1-amine) (2-1b, 50 μL, 3 μmol) in 50 μL 0.2N NaHCO₃. The resultant solution was stirred for 1 hr and the crude product was subjected to reverse-phase HPLC (acetonitrile/0.1 M TEAB gradient) purification to give 0.7 μmol of the desired product 2-4a (70% yield).

[(D002X)₂,D005]-TS6 (2-4b)

2.5 μmol of Trihexnyl gallate-5C-Asp-X-D002 was dissolved in 100 μl DMA, 10 μmol of NHS, 10 μL DIEA and 10 μmol of TSTU were added sequentially after vortexing at RT for 1 hr, to the solution was added ethyl acetate (2 mL). The resulting precipitate was collected, washed with ethyl acetate (3×1 mL) and dried under high vacuum to give the activated NHS ester. To a solution of the activated NHS ester (2.5 μmol) in DMF (50 μL) was added Trihexnyl gallate-5C-Asp-D005-triamine (2-4a, 50 μL, 0.7 μmol) in 20 μL 0.2N NaHCO₃. The resultant solution was stirred for 4 hr and the crude product was subjected to reverse-phase HPLC (acetonitrile/0.1 M TEAB gradient) purification to give 0.4 μmol of the desired product 2-4b (57% yield). (See Scheme 24.)

[(D002X)₂,D005]-TS3 (2-3b)

This compound was synthesized following the same protocol by using triazine instead of 3,3',3"-(benzene-1,3,5-triyltris(oxy))tris(propan-1-amine) 2-1b. (See Scheme 23 of FIG. 27.)

Figure 27:
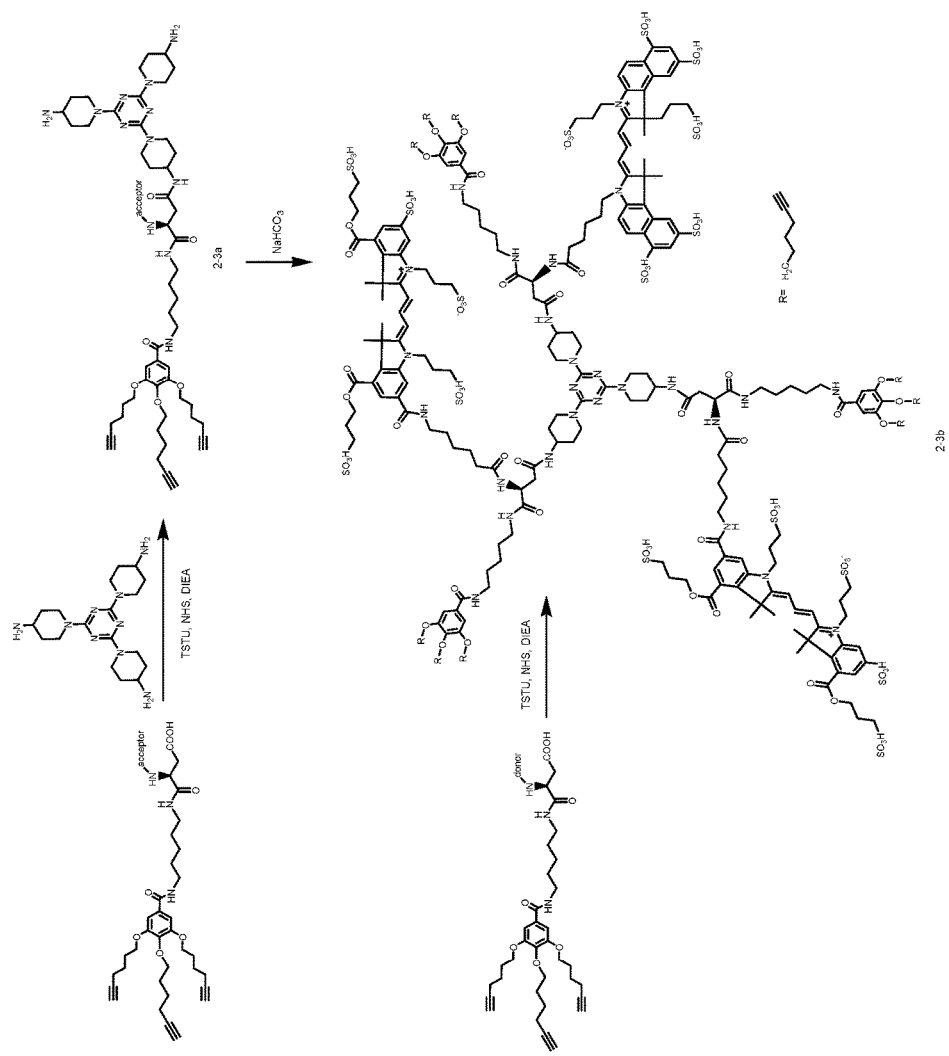
FIG. 27 illustrates the assembly of exemplary compounds.
Figure 27:
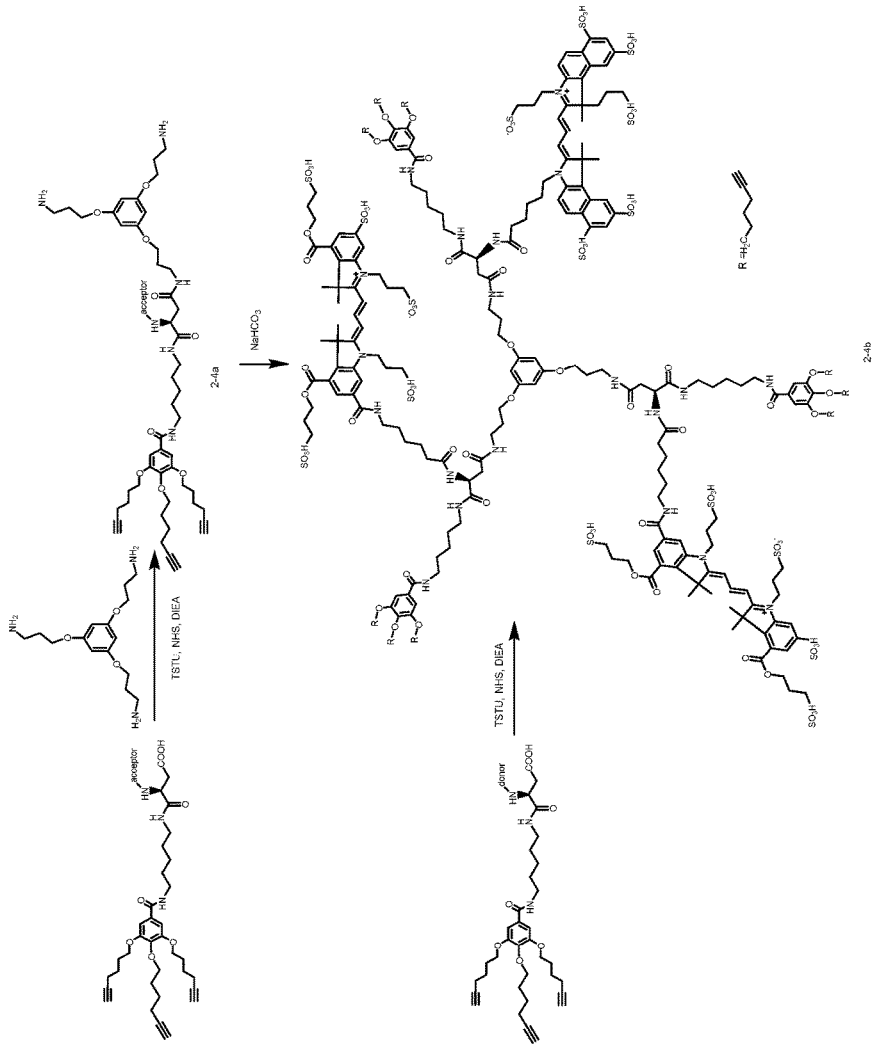

The final compounds were assembled by reacting compounds 2-3b and 2-4b with appropriate azide-substituted shield element-binding element (S'—B') reagents using standard click conditions, as shown in Schemes 23 and 24 of FIG. 27.

Figure 28:
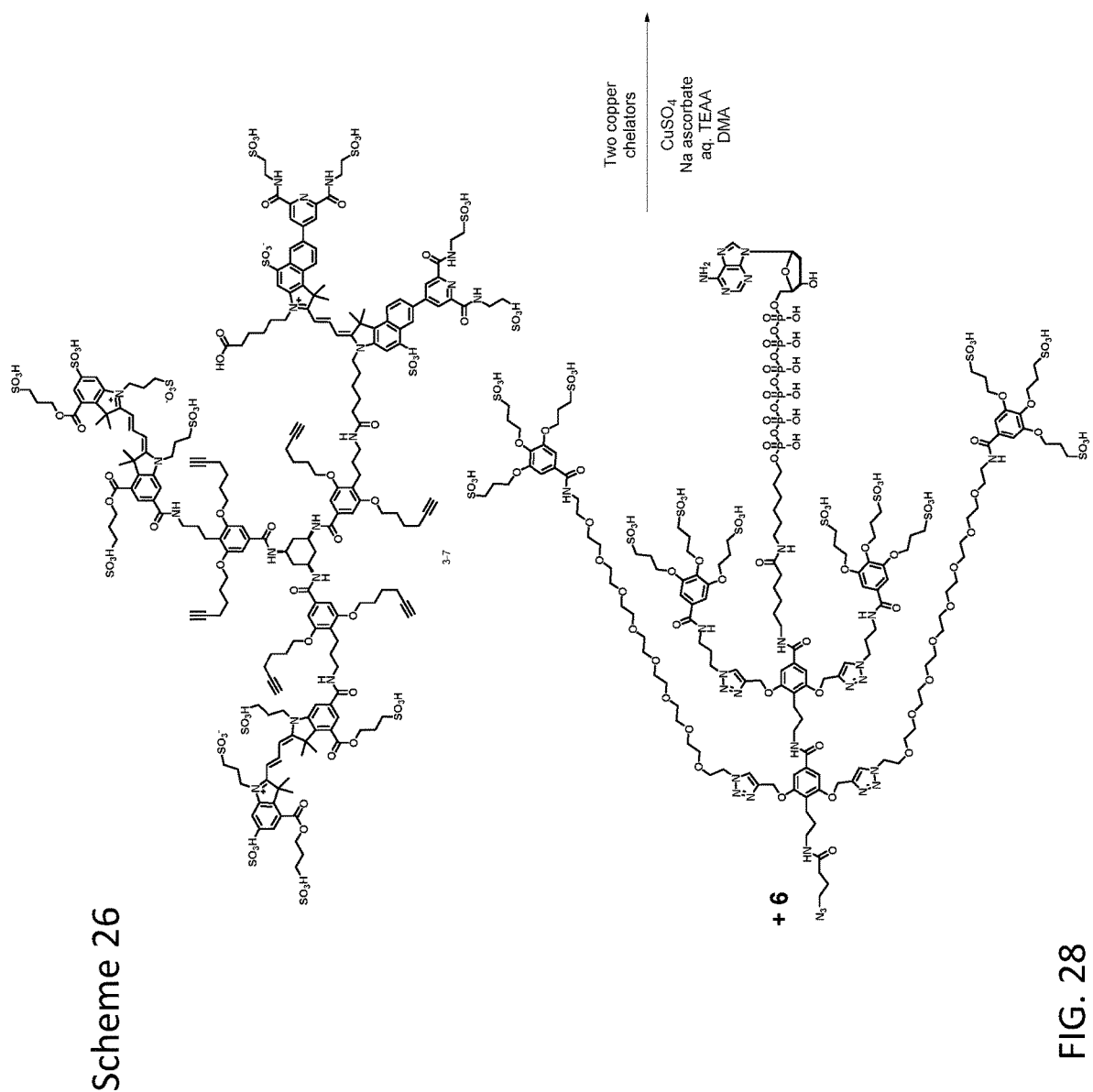
FIG. 28 illustrates the assembly of an exemplary protected fluorescent reagent compound.
Figure 28:
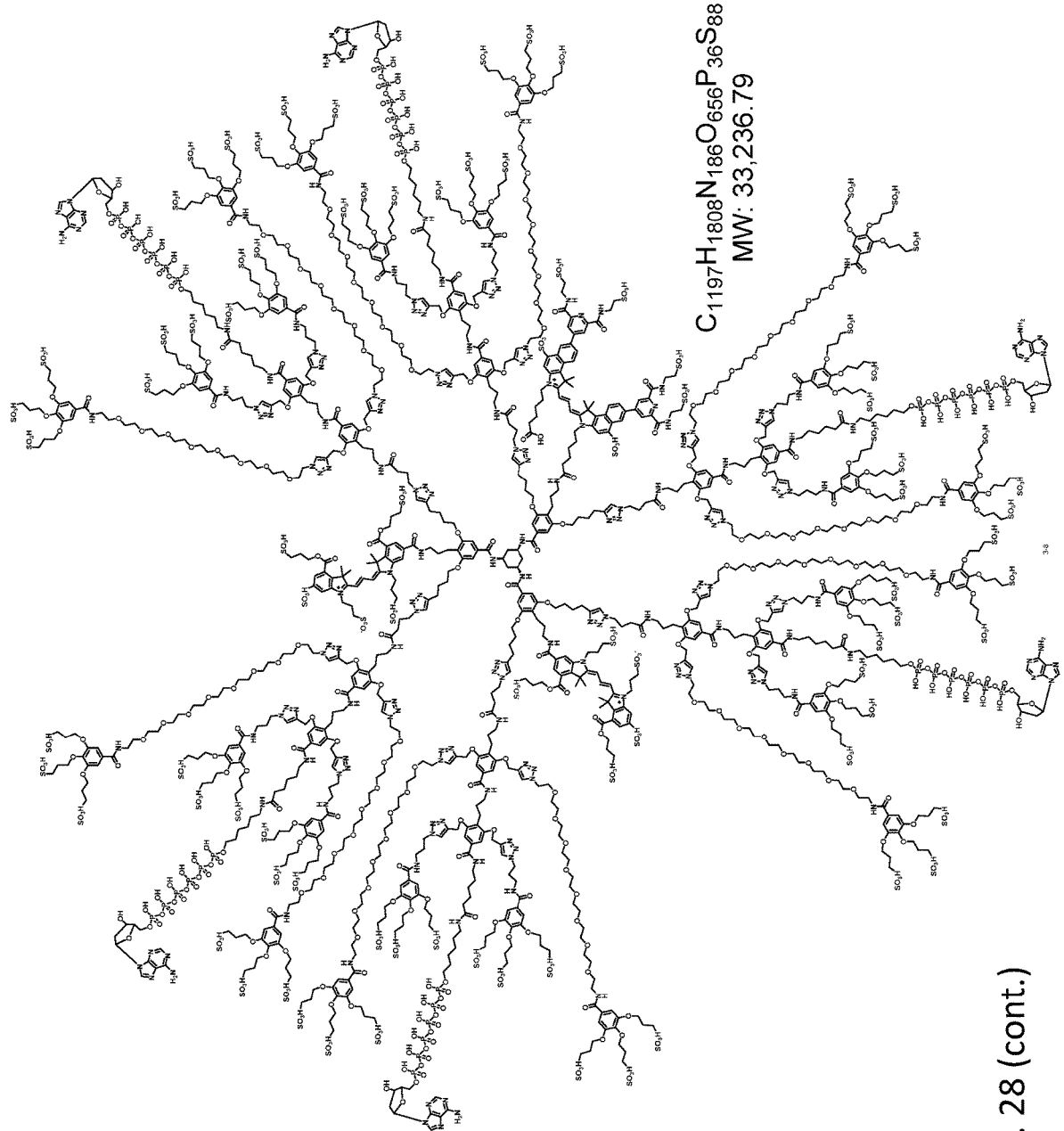

Example 3. Synthesis of Alternative Protected Fluorescent Reagent Compounds Comprising Non-Fluorescent Multivalent Core Elements Alternative protected fluorescent reagent compounds comprising non-fluorescent multivalent core elements were synthesized according to the following experimental procedures. In particular, the non-fluorescent core was synthesized as outlined in Scheme 25. The dye reagents were attached to the non-fluorescent core as described in the experimental methods, and the final products were assembled using click reactions as outlined in Scheme 26 of FIG. 28.

4-(3-Aminopropyl)-N-[3,5-bis({[4-(3-aminopropyl)-3,5-bis(hex-5-yn yloxy)benzene]amido})cyclohexyl]-3,5-bis(hex-5-yn-1-yloxy)benzamide, (NH₂-Sb2)3-Chx, "CS2 core", 3-4)

BOP (35.4 mg, 80 μmol) was added to a vial containing 4-(3-{[(tert-butoxy)carbonyl]amino}propyl)-3,5-bis(hex-5-yn-1-yloxy)benzoic acid (3-1), (77.8 mg, 165 μmol), cyclohexane-1,3,5-triamine (3-2), (5.2 mg, 40 μmol) and DIEA (28 μL). After stirring for 45 min at room temperature the reaction was partitioned between water and ethyl acetate. The organic layer was separated and the aqueous layer extracted with ethyl acetate (2×). The organic layers were combined, washed with sat. aq. NaHCO₃, brine, dried over Na₂SO₄, filtered and concentrated to a yellow oil that was subjected to normal phase purification (12 g silica gel, 0-100% Hex:EtOAc, Combiflash) to give tert-butyl 3,3',3"-(4,4',4"-(cyclohexane-1,3,5-triyltris(azanediyl))tris(oxomethylene)tris(2,6-bis(hex-5-ynyloxy)benzene-4,1-diyl))tris(propane-3,1-diyl)tricarbamate (3-3), (Boc-Sb2)3-Chx. The resulting white residue was dissolved in 30% trifluoroacetic acid in dichloromethane (5 mL) and allowed to stir for 1 h at room temperature. The reaction was then concentrated to give 4-(3-aminopropyl)-N-[3,5-bis({[4-(3-aminopropyl)-3,5-bis(hex-5-yn-1-yloxy)benzene]amido})cyclohexyl]-3,5-bis(hex-5-yn-1-yloxy)benzamide, (NH₂-Sb2)3-Chx, "CS2 core" (3-4) (20.1 mg, 16.9 μmol, 42% yield). LCMS: Calculated Mass 1188.72, Observed Mass 1188.45 (M⁻).

Scheme 25

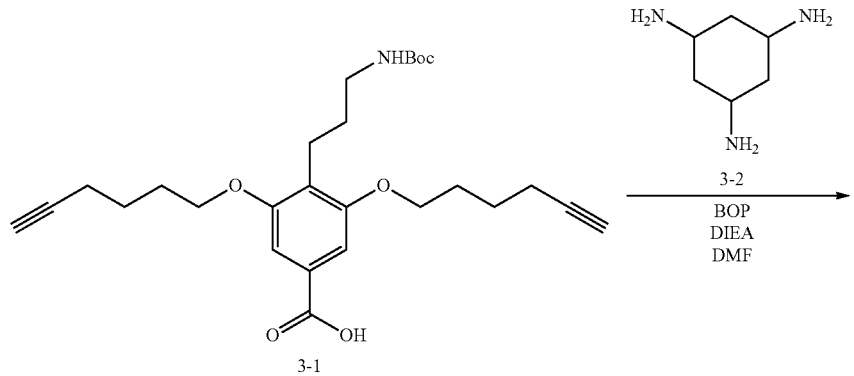

-continued
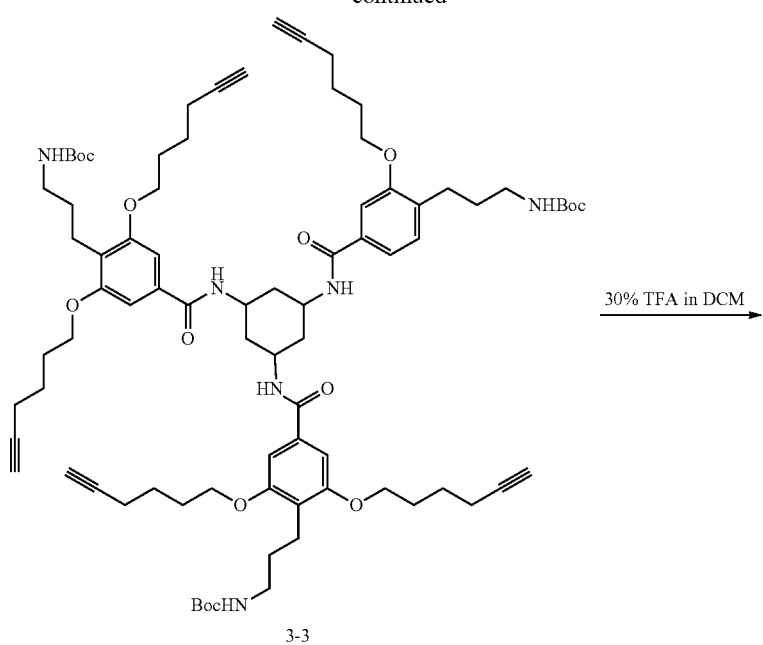
3-3
30% TFA in DCM →
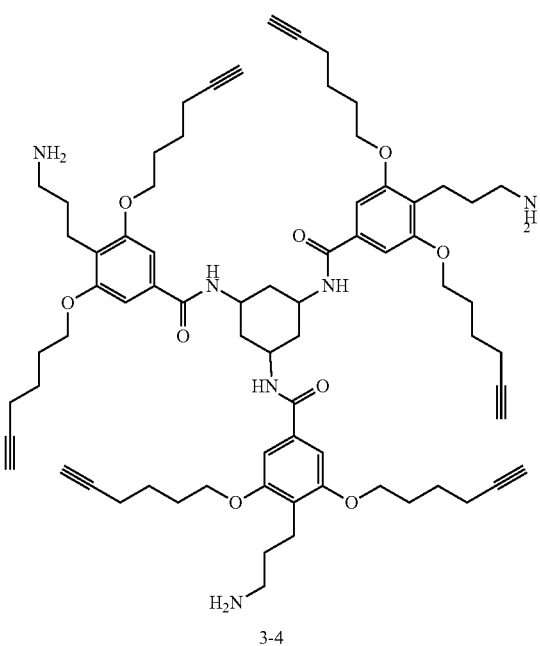
3-4

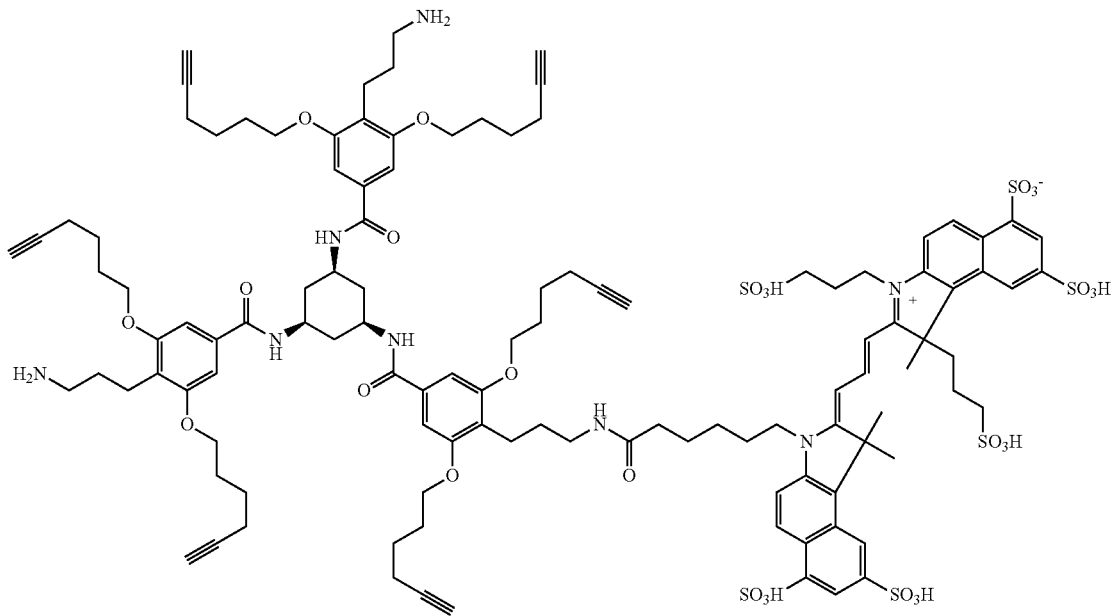
3-5
D005-CS2-(NH₂)₂ (3-5)
DIEA (6.3 μl, 36 μmol, 9 eq) was added to a solution of CS2 core (9.2 mg, 6 μmol, 1.5 eq) and the acceptor dye D005-NHS ester (4 μmol, 1 eq) in DMA (200 μl). The mixture was vortexed at room temperature in dark for 24 h. The product was purified by a reverse phase HPLC (Waters XTerra C18 RP 30×100, 20-54% AcN in 0.1 M TEAB, Akta Purifier) to give compound 3-1 (4.9 mg, 1.9 μmol, 48% yield). LCMS: Calculated Mass 2262.83, Observed Mass 1131.3 (M²⁻/2).
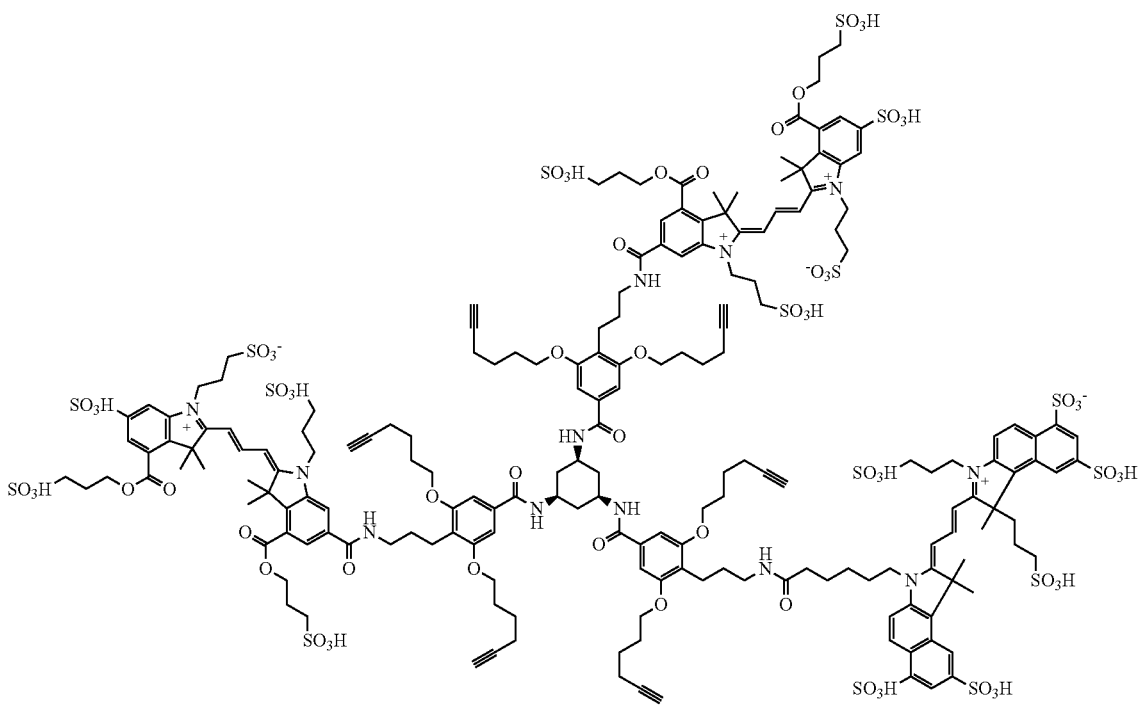
3-6

[(D002)$_2$,D005]-CS2 (3-6)

DIEA (4.0 µl, 23 µmol, 12 eq) was added to a solution of D005-CS2-(NH$_2$)$_2$ (3-5) (4.9 mg, 1.9 µmol, 1 eq) and the donor dye D002 NHS ester (7 µmol, 3.7 eq) in DMF (350 µl). The mixture was vortexed at room temperature in dark for 26 h. The product was purified by a reverse phase HPLC (Waters XTerra C18 RP 30×100, 0-42% AcN in 0.1 M TEAB, Akta Purifier) to give compound 3-6 (0.88 µmol, 46% yield). LCMS: Calculated Mass 4283.08, Observed Mass 1427.55 (M$^{3-}$/3).

[(D002)$_2$,D008]-CS2-[Aba-Sh(PEG7-SG1)$_2$-Sh(SG1)$_2$-14C-dA6P]$_6$ (3-8)

Aqueous solutions of an alternative dye core [(D002)$_2$, D008]-CS2 (3-7) (50 nmol, 1 eq) and the azido shield element-binding element (N$_3$-Aba-Sh(PEG7-SG1)$_2$-Sh(SG1)$_2$-dA6P, 1000 nmol, 20 eq) were lyophilized and dissolved in a mixture of water (15 µl), aqueous TEAA (2 M, 2 µl), and DMA (11 µl). In a separate vial, an aq. solution of sodium ascorbate (1 M, 2.5 µl, 2.5 µmol, 50 eq) was added to a mixture of copper(II) sulfate (100 mM, 1.0 µl, 100 nmol, 2 eq) and two copper chelators (100 mM, 1.0 µl, 100 nmol, 2 eq) and (200 mM, 0.5 µl, 100 nmol, 2 eq) in water. The copper complex solution was added to the solution of both starting materials and the mixture was vortexed at room temperature in dark for 4.7 h. The product was purified by ion exchange chromatography on Q HP Sepharose (GE, 5 ml column, 0.05-1.5 M TEAB in 30% AcN, Akta Purifier) followed by a reverse phase HPLC (Waters XTerra C18 RP 19×100, 0-27% AcN in 0.1 M TEAB, Akta Purifier) to give compound 3-8 (24 nmol, 48% yield, 323 µM, 75 µl).

Example 4. Synthesis of Exemplary Shield Core Elements

Exemplary intermediate compounds useful in the synthesis of the shield core elements are outlined in Scheme 27.

Scheme 27

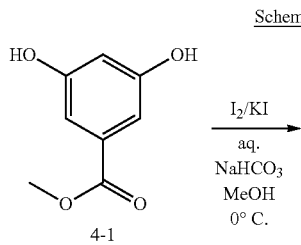

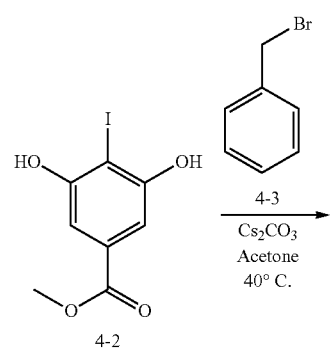

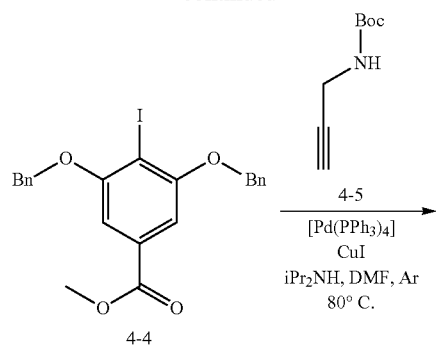

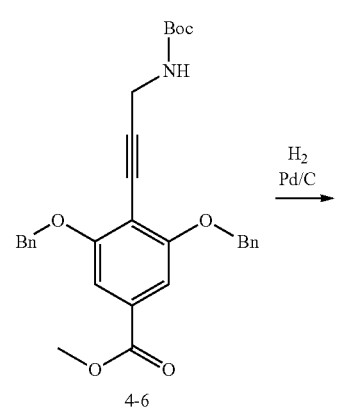

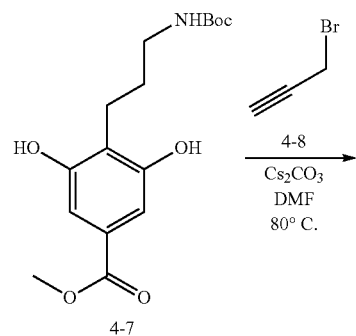

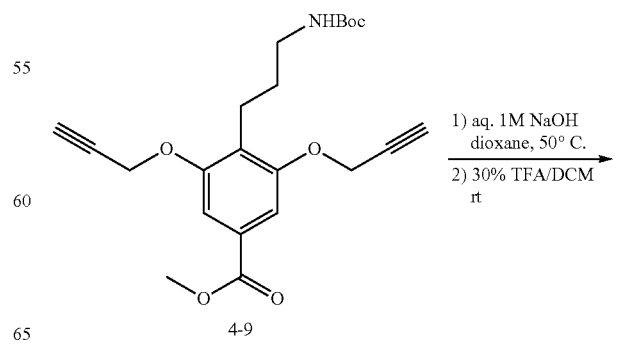

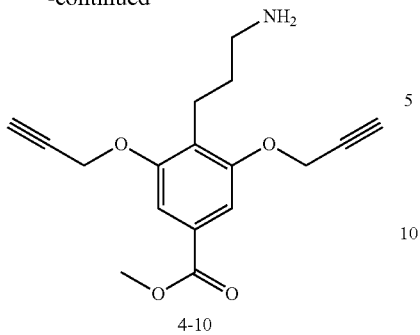

4-10

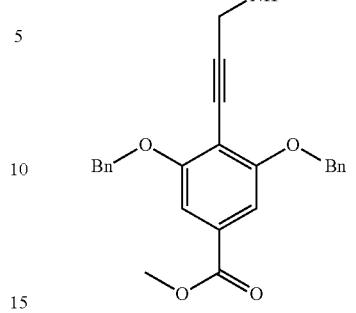

Methyl 3,5-bis(benzyloxy)-4-(3-{[(tert-butoxy)carbonyl]amino}prop-1-yn-1-yl)benzoate (4-6)

To a vial containing methyl 3,5-bis(benzyloxy)-4-iodobenzoate (4-4) (1.3 g, 2.4 mmol), copper(I) iodide (52.3 mg, 275 μmol), and tetrakis(triphenylphosphine)palladium(0) (158.7 mg, 137 μmol) was added diisopropylamine (15 mL) and dimethylformamide (15 mL). The dark brown solution was degassed with Ar and to this was added N-Boc-propargylamine (4-5) (1.3 mg, 8.2 mmol). The reaction was allowed to stir under Ar at 80° C. for 5 h. The reaction was then quenched with aqueous ammonium sulfate (150 mL, saturated) and extracted with ethyl acetate (2×150 mL). The organic layers were combined, washed with brine, dried over sodium sulfate, filtered and concentrated to an orange oil that was subjected to normal phase purification (24 g silica gel, 0-25% Hex:EtOAc, Combiflash). The product was isolated as a pale orange solid which was sonicated in methanol and then filtered to give, methyl 3,5-bis(benzyloxy) (3-{[(tert-butoxy)carbonyl]amino}prop-1-yn-1-yl) benzoate (4-6), as an off white solid (600 mg, 1.2 mmol, 50% yield). $^1$H NMR (CDCl$_3$, 300 MHz): 1.5 (s, 9H); 3.9 (s, 3H); 4.3 (d, 2H); 5.2 (s, 4H); 5.8 (bs, 1H); 7.2-7.5 (m, 12H).

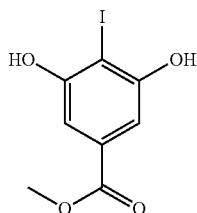

Methyl 3,5-dihydroxy-4-iodobenzoate (4-2)

To a vial containing methyl 3,5-dihydroxybenzoate (4-1) (5.0 g, 30 mmol) in methanol (70 mL) and NaHCO$_3$ (70 mL, 1 M) was added, via syringe pump (12 mL/min) at 0° C., a solution of iodine (7.4 g, 29.3 mmol) in aqueous potassium iodide (10 mL, 3.8 M). After 1 h the reaction was quenched to pH 2 with HCl (37%) and then allowed to warm to room temperature. The reaction was concentrated to dryness and recrystallized from methanol-water. The final product, methyl 3,5-dihydroxy-4-iodobenzoate (4-2), was isolated as yellow crystals (4.4 g, 14.8 mmol, 49% yield). LCMS: Calculated Mass 293.94, Observed Mass 293.03 (M$^-$).

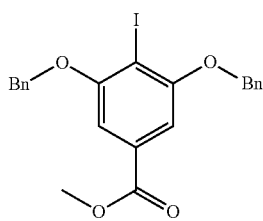 [SMILES: COC(=O)c1cc(OCc2ccccc2)c(I)c(OCc2ccccc2)c1]

Methyl 3,5-bis(benzyloxy)-4-iodobenzoate (4-4)

A mixture of methyl 3,5-dihydroxy-4-iodobenzoate (4-2) (2.94 g, 10.00 mmol), benzyl bromide (3.56 mL, 5.13 g, 30.00 mmol) and cesium carbonate (9.77 g, 30.00 mmol) in acetone (25 mL) was stirred at 40° C. under Ar for 4 h. The mixture was concentrated in vacuo, diluted with water (100 mL) and extracted with ethyl acetate (2×150 mL). The combined organic layers were dried over sodium sulfate, filtered and concentrated. The crude product was purified by column chromatography (silica gel, hexane-ethyl acetate, Combiflash) to give methyl 3,5-bis(benzyloxy)-4-iodobenzoate (4-4) (2.09 g, 4.41 mmol, 44% yield) as a white solid. $^1$H NMR (CDCl$_3$, 300 MHz): 3.92 (s, 3H); 5.22 (s, 4H); 7.23 (s, 2H); 7.33-7.44 (m, 6H); 7.53-7.56 (m, 4H).

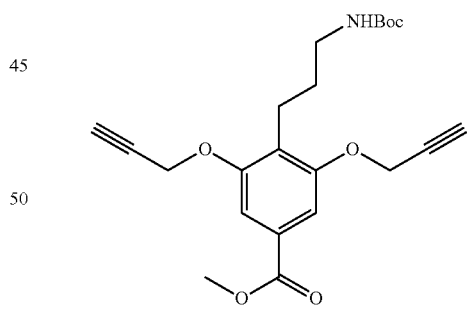

Methyl 4-(3-{[(tert-butoxy)carbonyl]amino}propyl)-3,5-bis(prop-2-yn-1-yloxy)benzoate (4-9)

To a vial containing methyl 3,5-bis(benzyloxy)-4-(3-{[(tert-butoxy)carbonyl]amino}prop-1-yn-1-yl)benzoate (4-6) (5.9 g, 1.2 mmol) in ethyl acetate (4.2 mL) was added palladium on carbon (500 mg, 10% water). The reaction was degassed and allowed to stir under H$_2$ overnight. After stirring overnight the reaction was filtered over Celite to give methyl 4-(3-{[(tert-butoxy)carbonyl]amino}propyl)-3,5-dihydroxybenzoate (4-7), as a clear oil. To the oil was added cesium carbonate (1.4 g, 4.3 mmol) and dimethylformamide (3 mL) followed by propargyl bromide (447.8 mg, 3.0 mmol, 80%). The reaction was sealed and allowed to stir for 5 h at 80° C. The reaction was then quenched with saturated aqueous ammonium sulfate (150 mL) and extracted with ethyl acetate (2×150 mL). The organic layers were combined, washed with brine, dried over sodium sulfate, filtered and concentrated to a dark yellow film that was subjected to normal phase Combiflash purification (24 g silica gel, 0-20% Hex:EtOAc, Combiflash). The isolated product methyl 4-(3-{[(tert-butoxy)carbonyl]amino}propyl)-3,5-bis(prop-2-yn-1-yloxy)benzoate (4-9), appeared as a white solid (358.6 mg 893.3 µmol, 68% yield). $^1$H NMR (CDCl$_3$, 300 MHz): 1.4 (s, 9H); 1.7 (m, 2H); 2.5 (t, 2H); 2.8 (m, 2H); 3.1 (m, 2H); 3.9 (s, 3H); 4.8 (d, 4H); 4.9 (bs, 1H); 7.3 (s, 2H).

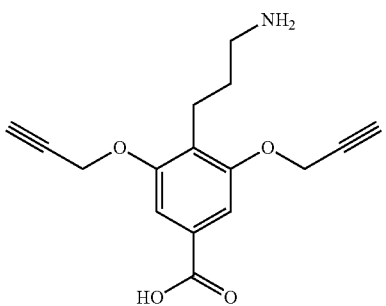 [SMILES: C#CCOc1cc(C(=O)O)cc(OCC#C)c1CCCN]

4-(3-Aminopropyl)-3,5-bis(prop-2-yn-1-yloxy)benzoic acid, "Sh" (4-10)

To a solution of methyl 4-(3-{[(tert-butoxy)carbonyl]amino}propyl)-3,5-bis(prop-2-yn-1-yloxy)benzoate (4-9) (357 mg, 890 mmol) in dioxane (4 mL) was added sodium hydroxide (4.4 mL, 1 M). The reaction was sealed and allowed to stir overnight at 50° C. The reaction was then concentrated, acidified to pH 3.5 with citric acid (5%) and extracted with DCM (3×50 mL). The organic layers were combined, washed with brine, dried over magnesium sulfate, filtered and concentrated to a white solid. To the solid was added 30% trifluoroacetic acid in dichloromethane (5 mL) and the reaction was allowed to stir at room temperature for 2 h. The reaction was then concentrated, redissolved in water, neutralized to pH 7 with NaHCO$_3$ (1 M) and the resulting product was collected by filtration to give the desired product 4-(3-aminopropyl)-3,5-bis(prop-2-yn-1-yloxy)benzoic acid (4-10), as a white solid (256 mg, 890 µmol, 100% yield). LCMS: Calculated Mass 287.12, Observed Mass 285.99 (M$^-$). $^1$H NMR (d6-DMSO, 300 MHz): 1.7 (m, 2H); 2.6 (t, 2H); 2.7 (m, 2H); 3.6 (t, 2H); 4.9 (d, 4H); 7.3 (s, 2H); 7.7 (bs, 3H).

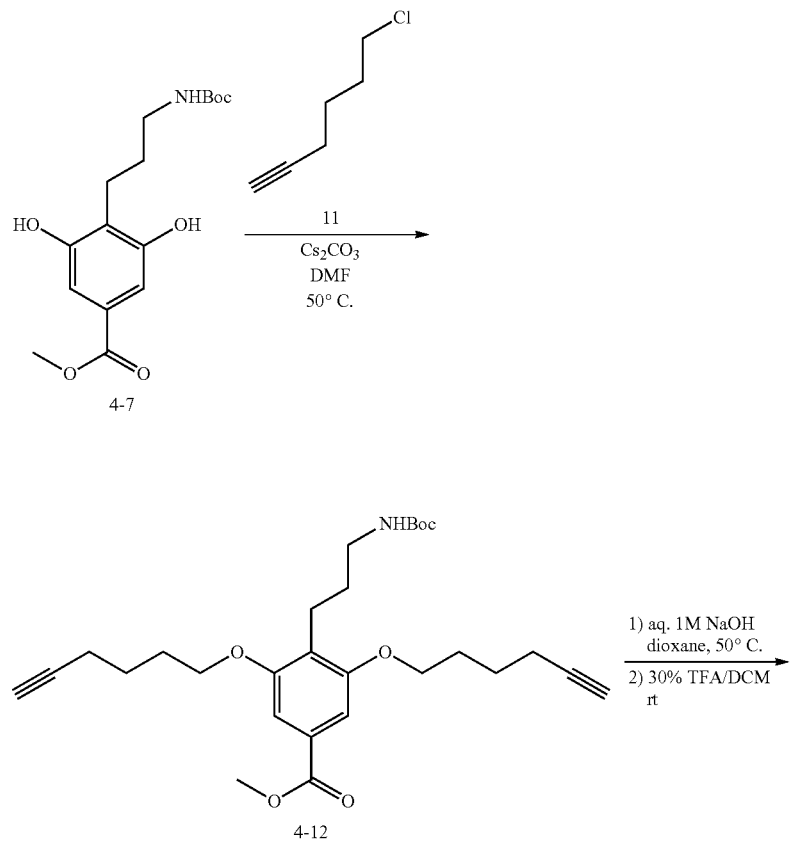

Scheme 28

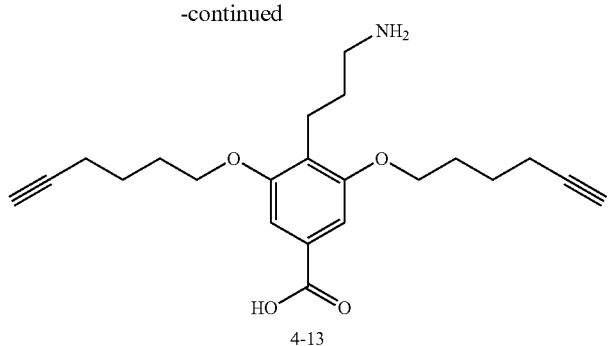

4-13

4-(3-Aminopropyl)-3,5-bis(hex-5-ynyloxy)benzoic acid, "Sb2" (4-13)

4-(3-Aminopropyl)-3,5-bis(hex-5-ynyloxy)benzoic acid, "Sb2" (4-13) was prepared from methyl 4-(3-(tert-butoxycarbonylamino)propyl)-3,5-dihydroxybenzoate (4-7) in a similar synthetic sequence using 6-chloro-1-hexyne instead of propargyl bromide, as outlined in Scheme 28.

Example 5. Synthesis of Exemplary Binding Element-Shield Element Reagents

Figure 29:
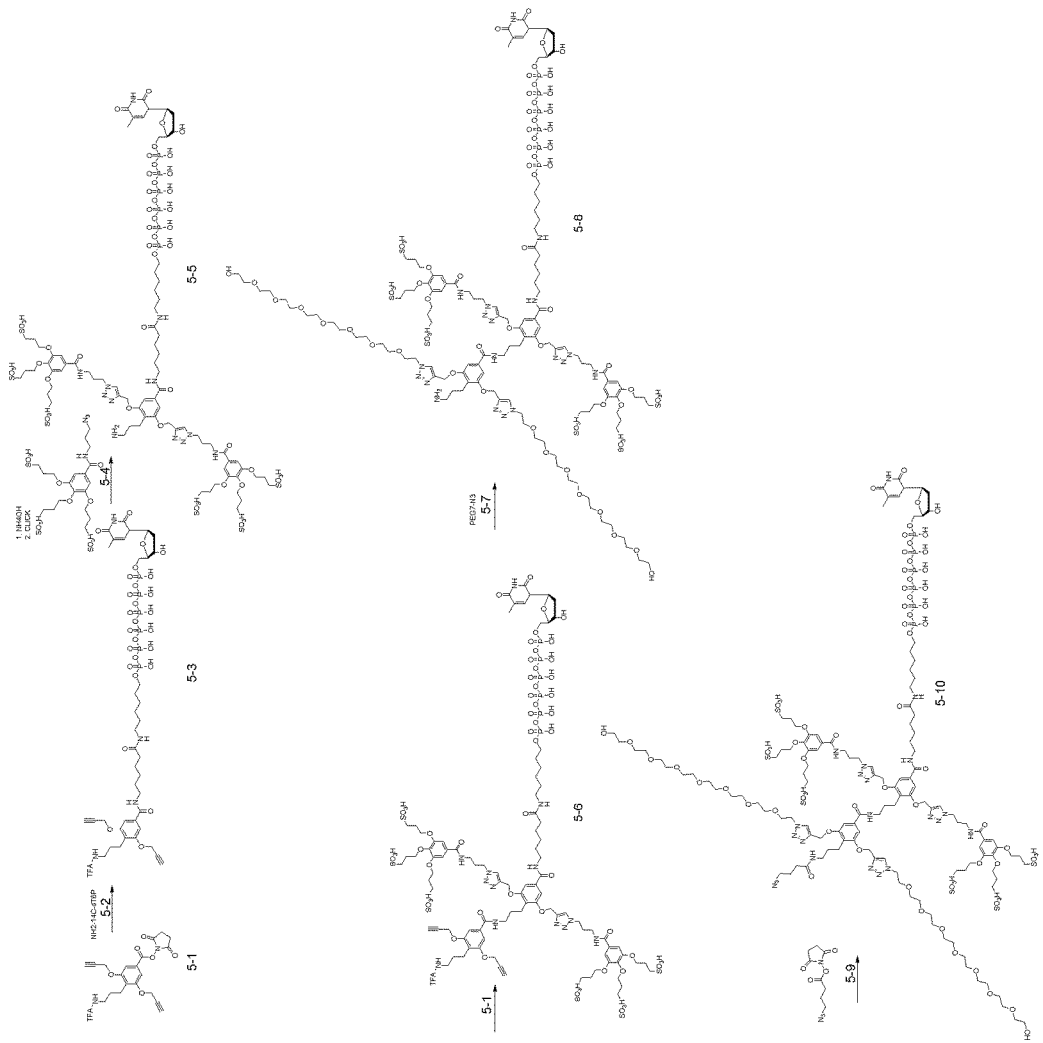
FIG. 29 illustrates exemplary reactions useful in the attachment of binding elements to shield elements.

Exemplary reactions useful in the attachment of binding elements, for example binding elements comprising nucleobases, to shield elements in the generation of binding element-shield element ("S'—B'") reagents are outlined in Scheme 29 of FIG. 29.

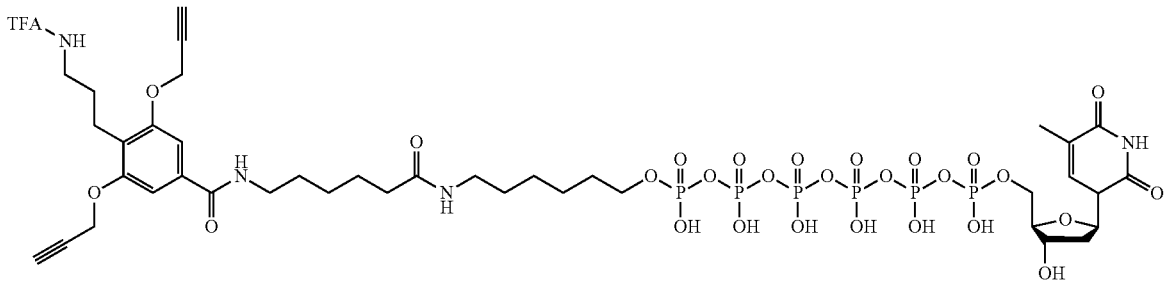

TFA-Sh-14C-dT6P (5-3)

A solution of TFA-Sh-CONHS (5-1), (36.0 mg, 75 μmol) in DMA (1.1 mL) was added to an aq. solution of NH$_2$-14C-dT6P (5-2) (618 μL, 81.0 mM) and NaHCO$_3$ (4.1 mg, 48.8 μmol). The resulting solution was allowed to stir overnight at room temperature and the crude product was subjected to reverse phase HPLC purification (Waters XTerra C18 RP 30×100, 0-37% AcN in 0.1 M TEAB, Akta Purifier) to give intermediate reagent 5-3 (29.7 μmol, 59.5 mM, 59% yield). LCMS: Calculated Mass 1299.16, Observed Mass 1297.78 (M$^2$12).

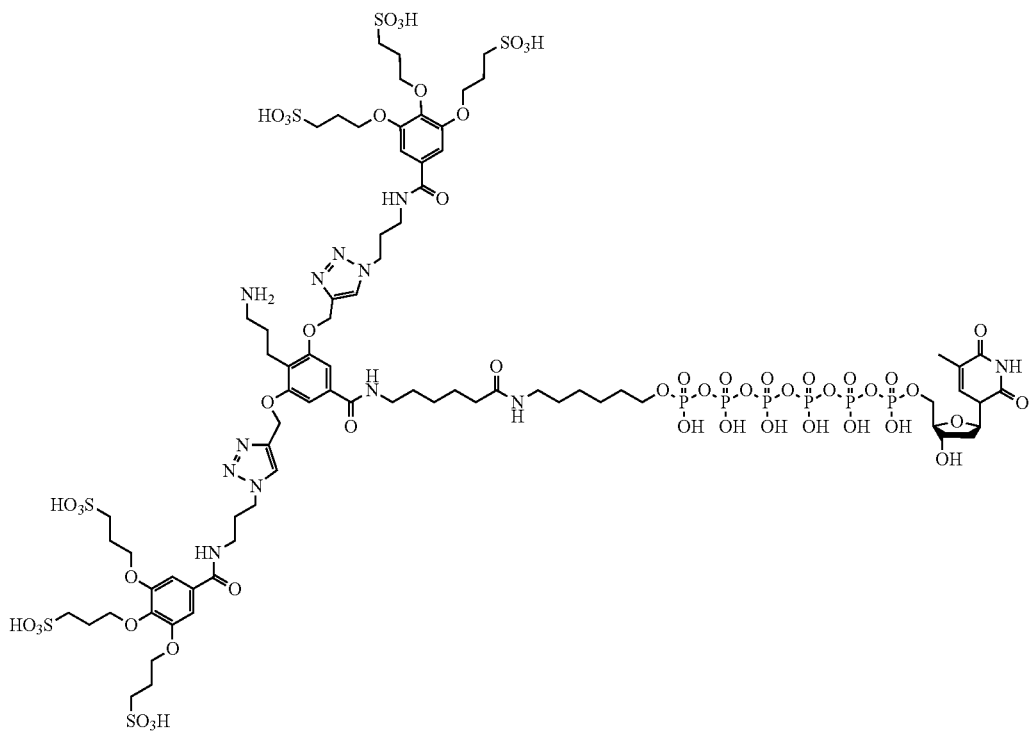

NH$_2$-Sh(SG1)$_2$-14C-dT6P (5-5)

Ammonium hydroxide (2 mL, 14.8 M) was added to a solution of TFA-Sh-14C-dT6P (5-3) (499 μL, 59.5 mM), triethylamine (297 μL) and acetonitrile (500 μL). The reaction was allowed to stir at room temperature for 3 days. The crude product was then evaporated to dryness and subjected to reverse phase HPLC purification (Waters XTerra C18 RP 30×100, 0-37% AcN in 0.1 M TEAB, Akta Purifier). A 100 mM aq. solution of the product was prepared and to this was added TEAA (29.7 μL, 2 M) and 3-{4-[(3-azidopropyl) carbamoyl]-2,6-bis(3-sulfopropoxy)phenoxy}propane-1-sulfonic acid (5-4) (445.5 μL, 200 mM). In a separate vial, an aq. solution of sodium ascorbate (148.5 μL, 1 M) was added to a mixture of copper(II) sulfate (14.8 μl, 1 M). The copper complex solution was added to the solution of both starting materials and the mixture was allowed to stir at room temperature in the dark for 3 h. The crude product was purified by ion exchange chromatography on Q HP Sepharose (GE, 5 ml column, 0.05-1.5 M TEAB in 20% AcN, Akta Purifier) followed by a reverse phase HPLC purification (Waters XTerra C18 RP 30×100, 0-20% AcN in 0.1 M TEAB, Akta Purifier) to give compound 5-5 (9.9 μmol, 49.4 mM, 33% yield). LCMS: Calculated Mass 2439.38, Observed Mass 1219.40 (M$^2$12).

N$_3$-Aba-Sh(PEG7)$_2$-Sh(SG1)$_2$-14C-dT6P (5-10)

Figure 30:
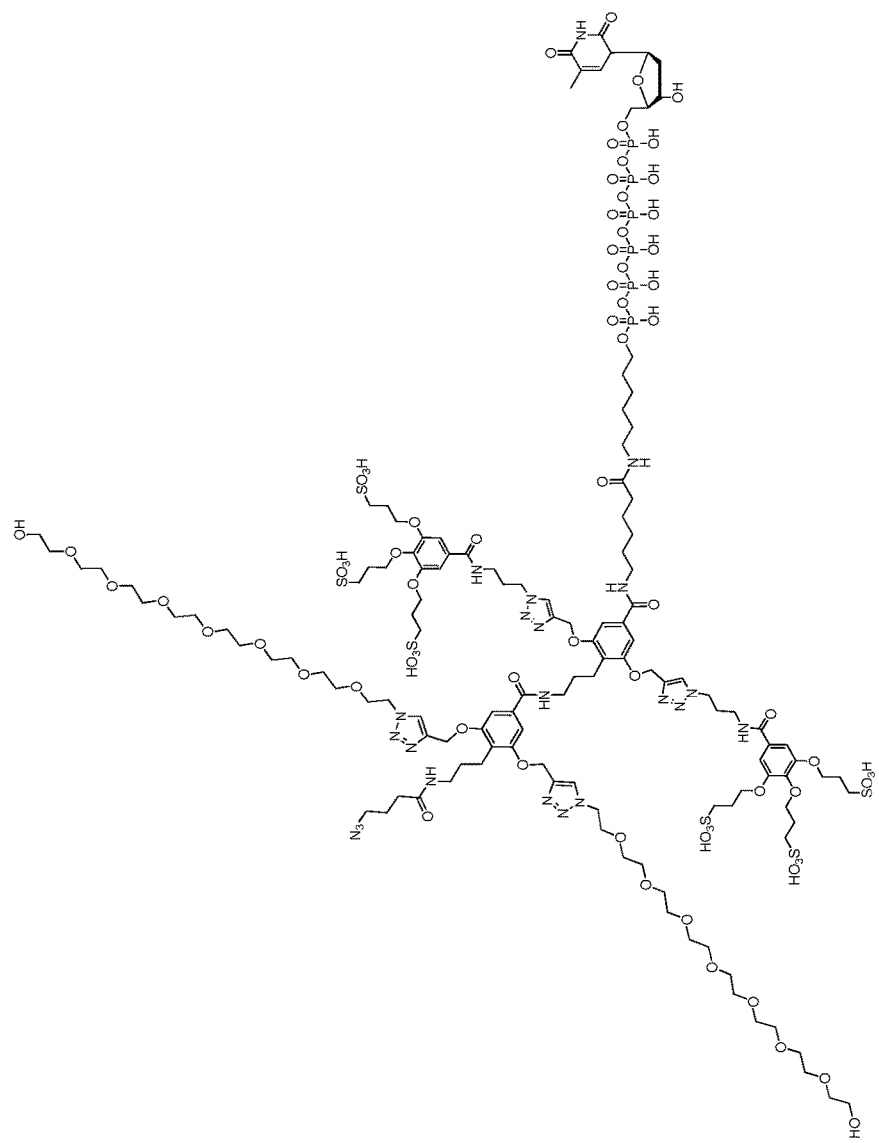
FIG. 30 illustrates the structure of $N_3$-Aba-Sh(PEG7)$_2$-Sh(SG1)$_2$-14C-dT6P (5-10).

A solution of TFA-Sh-CONHS (5-1) (4.9 mg, 10.2 μmol) in DMA (287 μL) was added to an aq. solution of NH$_2$-Sh (SG1)$_2$-14C-dT6P (5-5) (159 μL, 49.4 mM) and NaHCO$_3$ (6.6 mg, 78.7 μmol). The resulting solution was allowed to stir overnight at room temperature and the crude product was subjected to reverse phase HPLC purification (Waters XTerra C18 RP 30×100, 0-20% AcN in 0.1 M TEAB, Akta Purifier). To the product, compound 5-6, was then added ammonium hydroxide (2 mL, 14.8 M) and the solution was allowed to stir overnight at room temperature. The crude product was then evaporated to dryness and subjected to reverse phase HPLC purification (Waters XTerra C18 RP 30×100, 0-28% AcN in 0.1 M TEAB, Akta Purifier). A 39.8 mM aq. stock solution of the product was prepared and to this was added TEAA (20 μL, 2 M) and PEG7 azide (5-7) (21.0 mg, 47.8 μmol). In a separate vial, an aq. solution of sodium ascorbate (39.8 μL, 1 M) was added to copper(II) sulfate (4.0 μL, 1 M). The copper complex solution was added to the solution of both starting materials and the mixture was vortexed at room temperature overnight. The crude product was purified by ion exchange chromatography on Q HP Sepharose (GE, 5 ml column, 0.05-1.5 M TEAB in 20% AcN, Akta Purifier) followed by a reverse phase HPLC purification (Waters XTerra C18 RP 30×100, 0-25% AcN in 0.1 M TEAB, Akta Purifier) to give NH$_2$-Sh(PEG7)$_2$-Sh (SG1)$_2$-14C-dT6P (5-8). A 100 mM aq. solution of the product was prepared and to this was added NaHCO$_3$ (6.6 mg, 78.7 μmol) followed by a solution of 2,5-dioxopyrrolidin-1-yl 4-azidobutanoate (5-9) (59 μL, 58.8 mM) in DMA (200.6 μL). The resulting solution was allowed to stir overnight at room temperature and the crude product was purified by ion exchange chromatography on Q HP Sepharose (GE, 5 ml column, 0.05-1.5 M TEAB in 20% AcN, Akta Purifier) followed by reverse phase HPLC purification (Waters XTerra C18 RP 30×100, 0-28% AcN in 0.1 M TEAB, Akta Purifier) to give N$_3$-Aba-Sh(PEG7)$_2$-Sh(SG1)$_2$-14C-dT6P (5-10) (7.1 μmol, 35.4 mM, 90% yield). LCMS: Calculated Mass 3608.98, Observed Mass 1804.05 (M$^{2-}$/2). See FIG. 30.

Example 6. Use of Protected Fluorescent Reagent Compounds in Sequencing Reactions Sequencing reactions were carried out in a zero-mode waveguide ("ZMW") array having 3000 discrete cores. The reactions were observed using a highly multiplexed confocal fluorescent microscope providing a targeted illumination profile, e.g., a separate spot for each core. See, e.g., U.S. Pat. No. 7,714,303, filed May 9, 2008, which is incorporated herein by reference in its entirety for all purposes. Fluorescent signals from the various ZMWs were detected using an EMCCD camera for 10 minutes, and were subjected to pulse recognition and base calling processes. See, e.g., U.S. Pat. No. 8,182,993, filed Jun. 5, 2008, which is incorporated herein by reference in its entirety for all purposes. The sequencing was carried out generally as described in Eid, J. et al. (2009) *Science* 323:133-138, and the corresponding supplemental information included therewith.

For each of the sequencing reactions the laser power was 1.5 µW/µm$^2$ and a camera frame rate of 100 FPS. The template was a circular vD "SMRTbell" template of about 11000 kb as described in U.S. Pat. No. 8,236,499, filed Mar. 27, 2009. The polymerase enzyme immobilized in the zero mode waveguide was a mutant D29 polymerase as described in U.S. Pat. No. 8,257,954, filed Mar. 30, 2009. The reaction mixture had a Bis-Tris Propane pH 7.5 buffer, antioxidants, 40 mM DTT, 120 mM KOAc to control ionic strength; 30 mM MgOAc and 4% organic solvent additive. The mixture also contained a set of nucleotide analogs corresponding to A, G. C, and T, each present at 150-400 nM, each having a polyphosphate chain with 6 phosphates with a unique fluorescent dyes attached to the terminal phosphate. Ten minute movies of the sequencing reactions were obtained. Data were collected on the brightness, kinetics (pulse width, the interpulse distance (IPD)), photophysical signal stability, sequencing error types, read length, and accuracy. Regular analogs (condition 1) were replaced by a protected compound for A (condition 2), and both A and C analogs (condition 3). G and T analogs remained unchanged throughout the experiment.

Figure 3A:
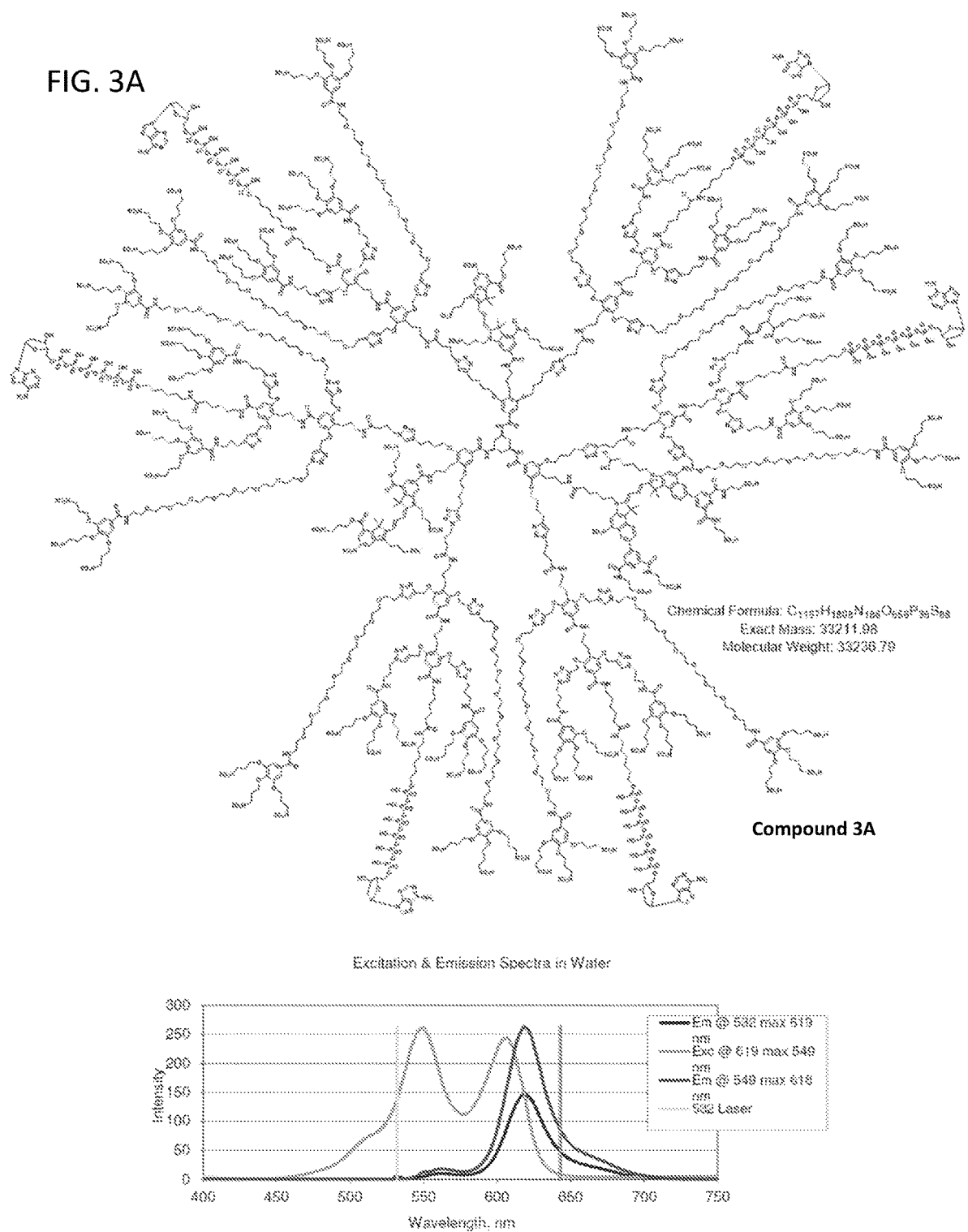
FIGS. 3A-3B display the structures and fluorescence spectra of two exemplary protected fluorescent reagent compounds of the invention.
Figure 3B:
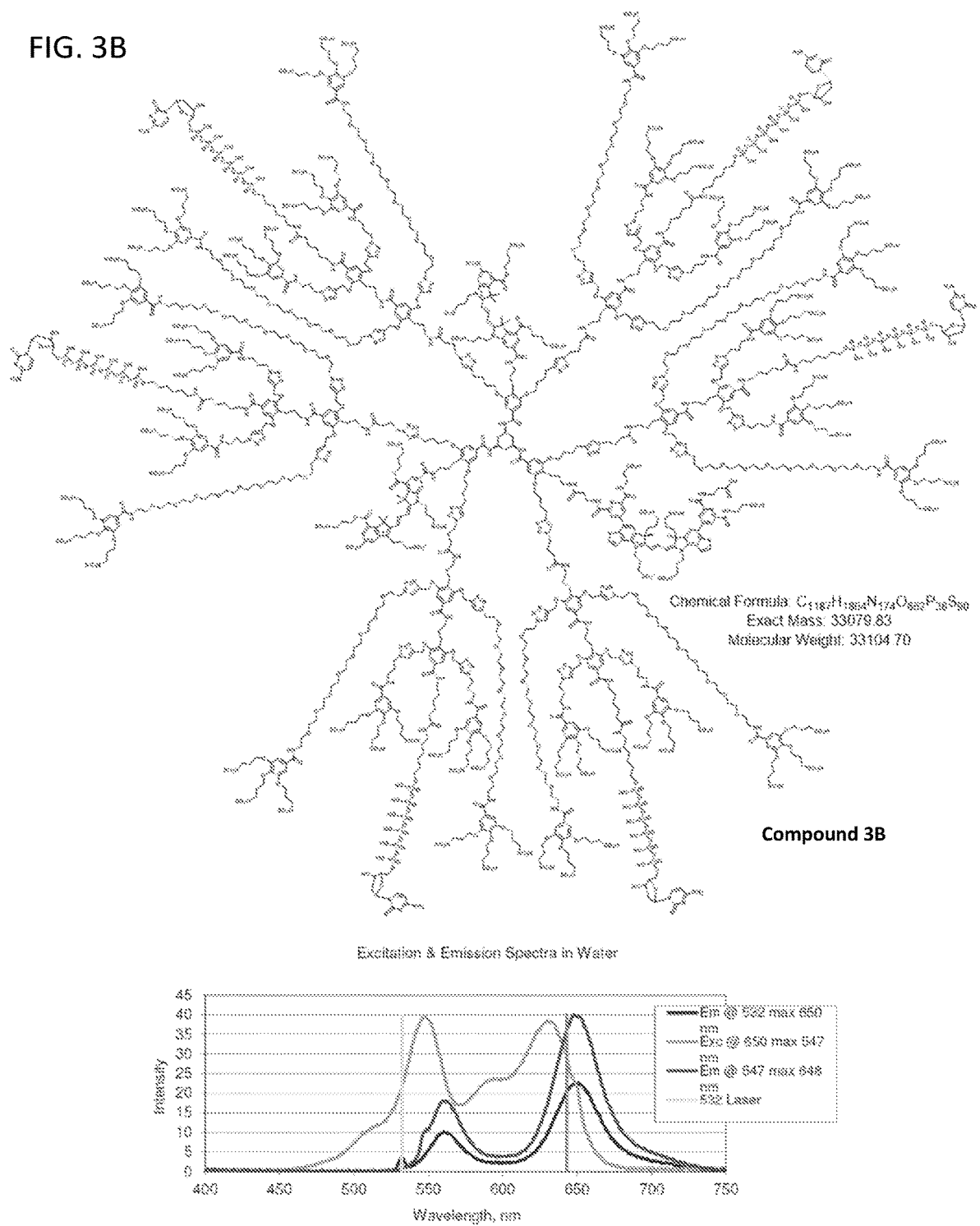

The protected fluorescent reagent compounds shown in FIGS. 3A and 3B were synthesized according the reaction schemes described above. The compound of FIG. 3A ("Compound 3A") has the structure abbreviated as [(D002)$_2$,D008]-CS2-[Aba-Sh(PEG7-SG1)$_2$-Sh(SG1)$_2$-14C-dA6P]$_6$, where D002 is a FRET donor dye, and D008 is a FRET acceptor dye, CS2 is a non-fluorescent multivalent central core element synthesized as described in Example 3 (compound 3-8). The shield elements are attached to the central core element through an Aba group, the inner shield comprises two PEG7-SG1 groups, the outer shield comprises two SG1 groups, and the binding element, adenosine, is coupled through a 14-carbon equivalent and a hexaphosphate. The compound has a maximum emission fluorescence at 618 nm. The compound of FIG. 3B ("Compound 3B") has the structure abbreviated as [(D002)$_2$,D007]-CS2-[Aba-Sh(PEG7-SG1)$_2$-Sh(SG1)$_2$-14C-dC6P]$_6$, which is the same as the structure of FIG. 3A, except that the acceptor dye is D007, and the binding element is cytosine. This compound has a maximum emission fluorescence at 648 nm.

Fluorescence excitation and emission spectra for the compounds shown in FIGS. 3A and 3B are displayed below each structure. In each case, an excitation spectrum was taken near the maximum emission, at either 619 nm for Compound 3A or at 650 nm for Compound 3B. Two emission spectra are shown for each compound (at excitations of 532 nm and 549 nm for Compound 3A and at excitations of 532 nm and 547 nm for Compound 3B). The 532 nm green laser line and the 643 nm red laser line are shown in each panel for reference.

Figure 4:
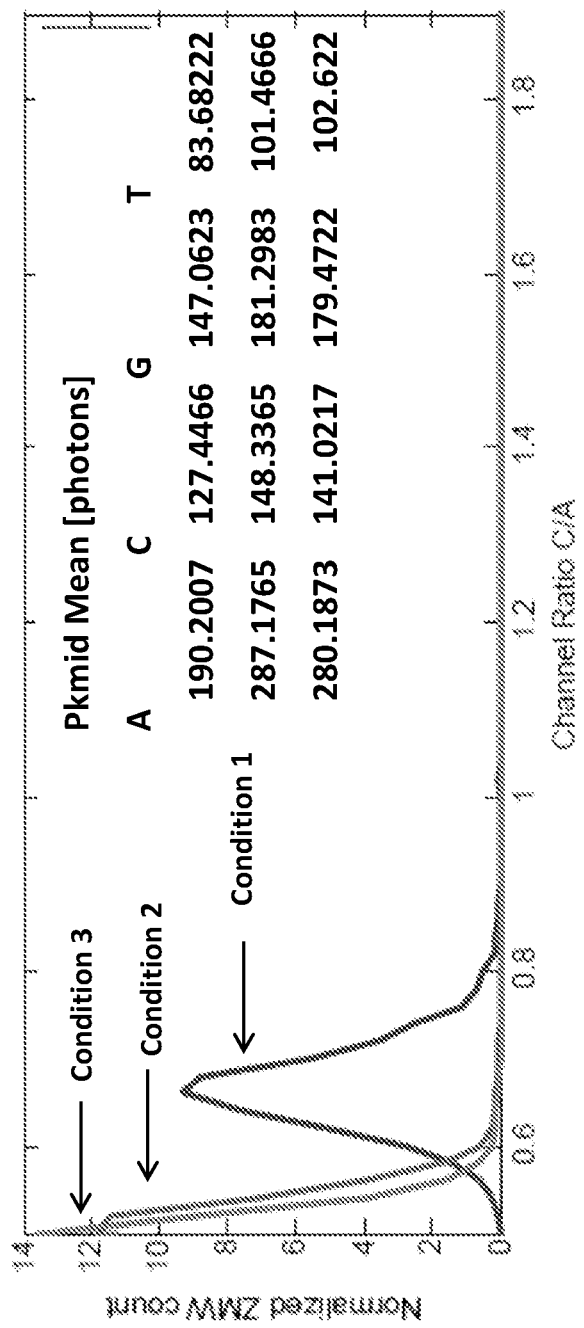
FIG. 4 illustrates the brightness of two exemplary protected fluorescent reagent compounds under sequencing conditions compared to control, unprotected compounds.

FIG. 4 shows the relative brightness of Compounds 3A and 3B compared to a control unprotected compound containing dye D002 (see below). Cumulative ZMW distribution is plotted as a function of C/A channel ratio of pkmid fluorescence intensities. Pkmid represents a peak median brightness, which is derived as follows. For each incorporation signal pulse, first and last frames are taken out, and the mean number of emitted photons detected by the camera is computed. These values are presented in the table insert for control (condition 1), Compound 3A substituted for A (condition 2), and both Compound 3A substituted for A and Compound 3B substituted for C (condition 3), respectively. Compound 3A is approximately 1.25 times brighter than the unprotected compound. Compound 3B is approximately 1.5 times brighter than the unprotected compound. According to the pkmid values, Compound 3A is ~1.5× brighter than the control, and Compound 3B has about the same brightness as the control. The unprotected control reagent for the A nucleotide had the following structure:

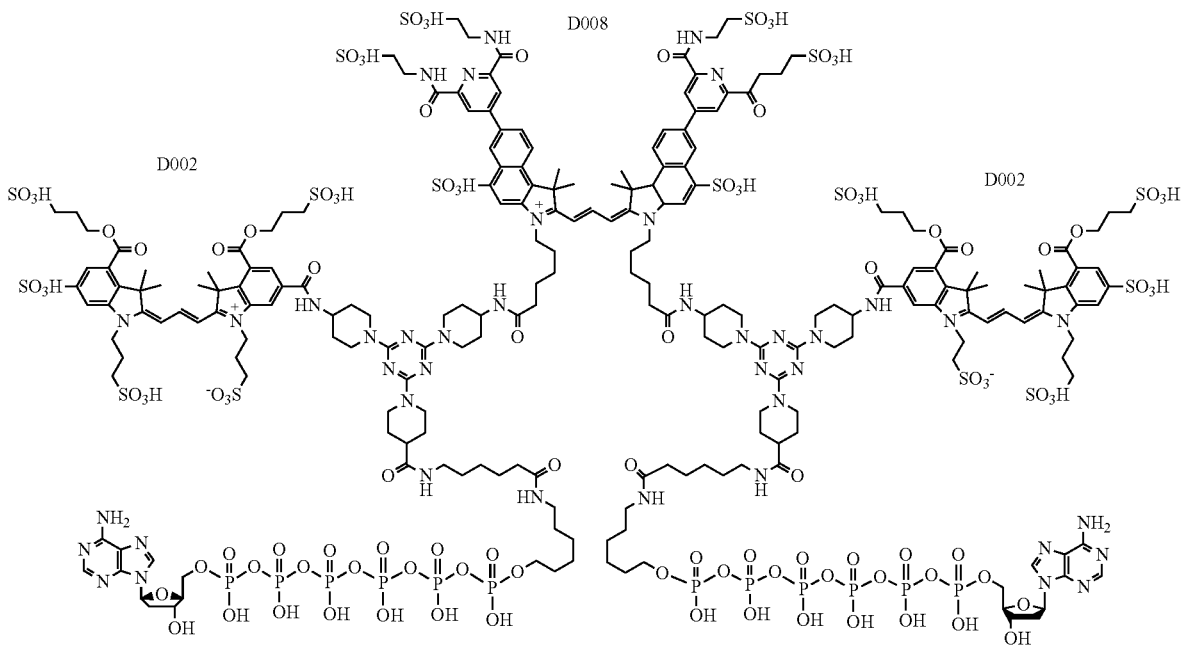

Figure 5:
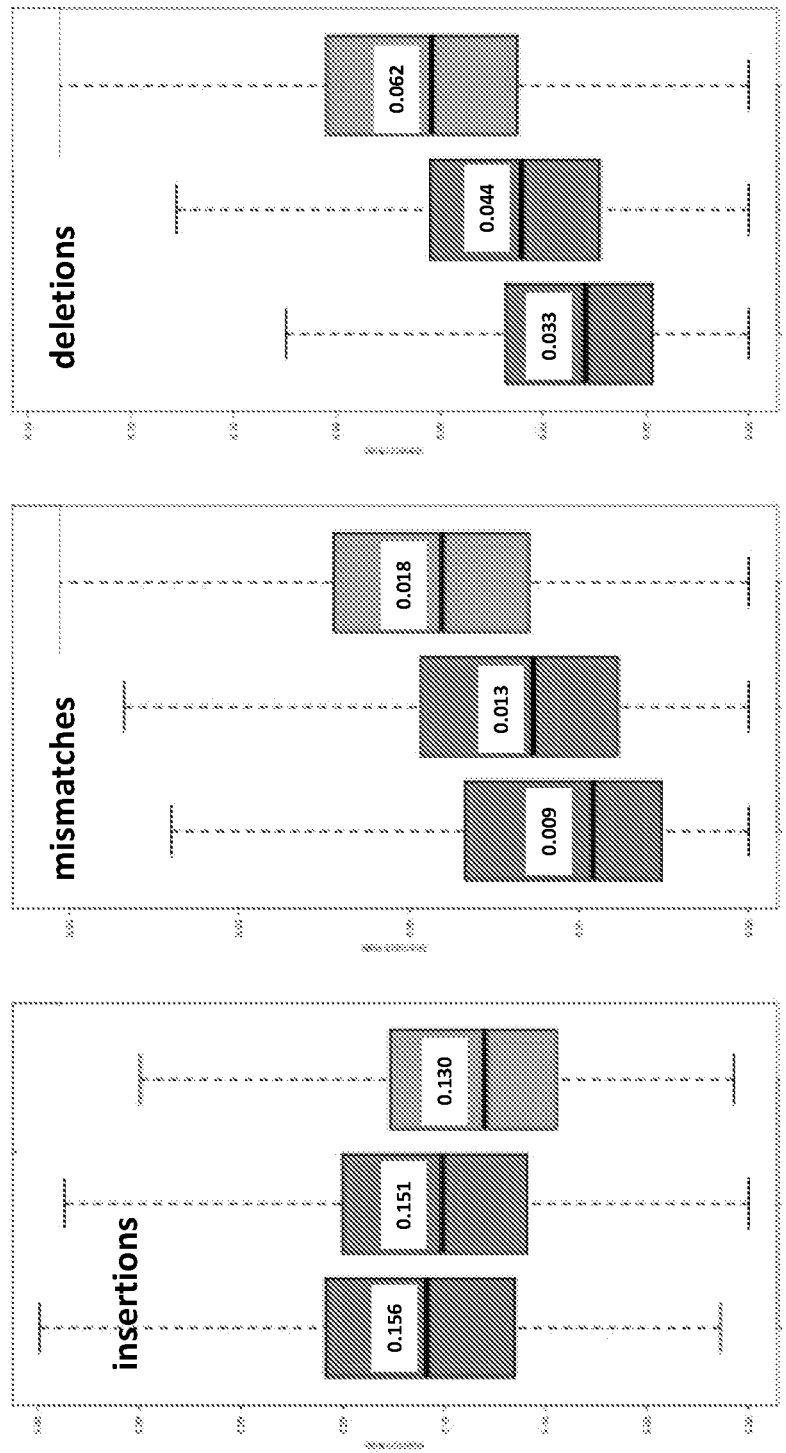
FIG. 5 shows a comparison of error types of two exemplary protected fluorescent reagent compounds compared to control, unprotected compounds.

FIG. 5 shows the error profile of sequencing reactions using the exemplary protected compounds under the above-described conditions. The left panel compares insertion rates, the middle panel compares mismatch rates, and the right panel compares deletion rates. Within each panel, results are shown for condition 1 (i.e., control unprotected compounds) (left bar), for condition 2 (i.e., Compound 3A replacing A) (middle bar), and for condition 3 (i.e., Compound 3A replacing A and Compound 3B replacing C) (right bar). As shown in the figure, insertions were lower for the protected compounds, while mismatches and deletions were somewhat higher. This result confirms that the bulkiness of the protected compounds does not significantly affect the reliability of sequencing using these reagents. The result also demonstrates that enclosure of the dyes inside the protective macroscaffold reduces undesirable interactions of the dyes with ZMW surface and/or the DNA polymerase.

Figures 6A, 6B:
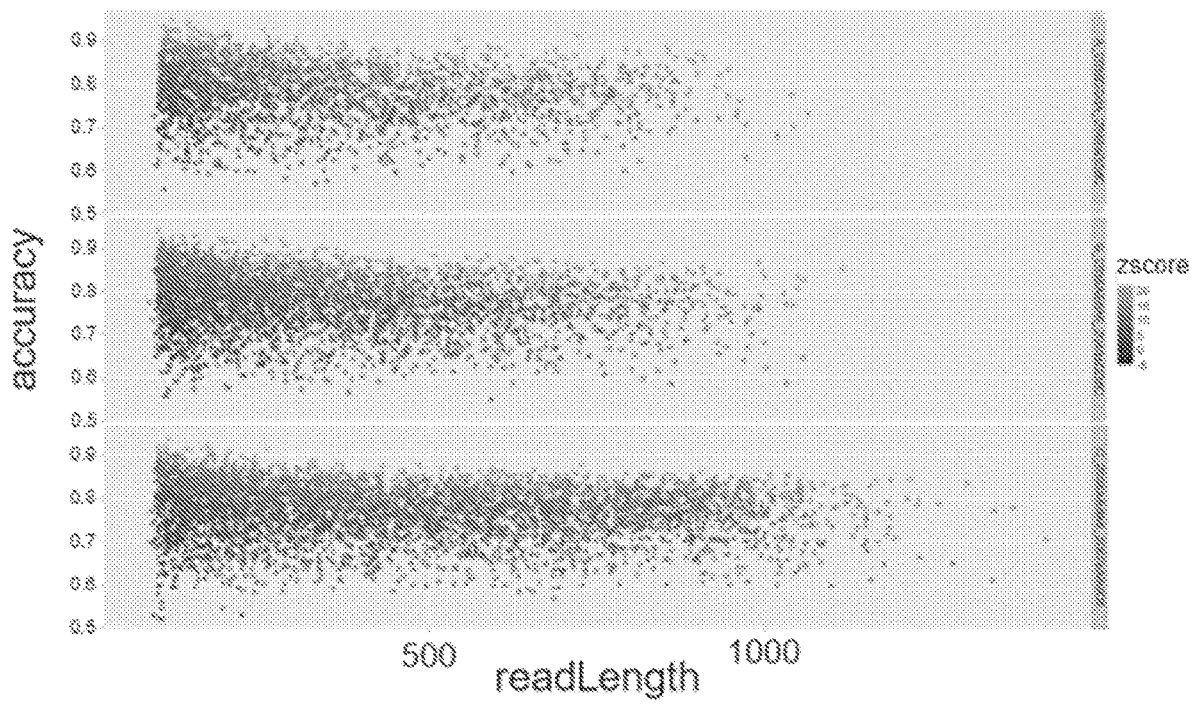

FIGS. 6A-6D show an analysis of readlength and accuracy for the protected compounds. FIG. 6A compares accuracy as a function of readlength, wherein each dot is an aligned ZMW read, for the three conditions (top: condition 1; middle: condition 2; bottom: condition 3). FIG. 6B provides a summary of the overall sequencing results using the three different conditions. FIG. 6C plots the probability distribution function (y-axis) versus accuracy (x-axis) for the three different conditions. FIG. 6D plots the probability distribution function (y-axis) versus readlength for the three different conditions. The results shown in FIGS. 6A-6D demonstrate that accuracies are comparable for the three different conditions (using 0, 1, or 2 protected fluorescent compounds). The differences in readlengths are driven primarily by variations in interpulse distance.

Example 7. Photostability of Protected Fluorescent Reagent Compounds in Sequencing Reactions Sequencing reactions were carried out as described in Example 6, except that 45 minute movies of the sequencing reactions were obtained at laser power 2.5 $\mu W/\mu m^2$, and one additional combination of protected and unprotected fluorescent reagent compounds was tested. Data corresponding to the brightness, kinetics (pulse width, the interpulse distance (IPD)), photophysical signal stability, sequencing error types, read length, and accuracy were collected for each reaction. Non-protected fluorescent reagent analogs (condition 1) were replaced by Compound 3A for A (condition 2), by Compound 3B for C (condition 3), and by both Compound 3A and Compound 3B for A and C (condition 4). G and T analogs remained unchanged throughout the experiment.

Figure 7:
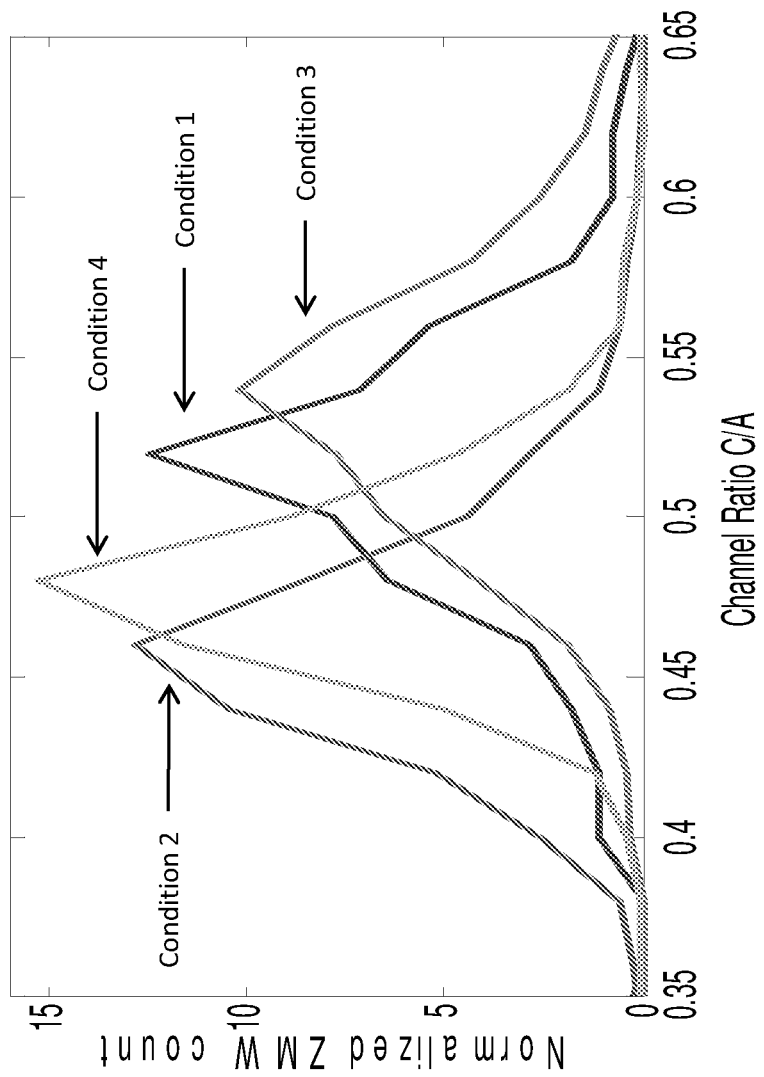
FIG. 7 illustrates the brightness of two exemplary protected fluorescent reagent compounds under longer sequencing conditions compared to control, unprotected compounds.

FIG. 7 shows a comparison of the brightness of the samples under the four tested conditions. The results indicate that Compound 3A is approximately 15% brighter than an unprotected compound containing the same dye, and Compound 3B has approximately the same brightness as an unprotected compound containing the same dye. Use of the protected compounds in sequencing reactions is therefore expected to result in comparable or lower rate of missing pulses compared to unprotected compounds.

FIGS. 8A and 8B show a comparison of peak height variance for the various dye mixtures as measured in the A channel (FIG. 8A) and in the C channel (FIG. 8B). In particular, the peak height variance decreases for Compound 3A in the A channel (conditions 2 and 4, FIG. 8A) and for Compound 3B in the C channel (conditions 3 and 4, FIG. 8B). A sample containing both Compound 3A and Compound 3B shows lower peak height variance in both A and C channels (condition 4, FIGS. 8A and 8B). These data demonstrate an increased photophysical signal stability for the protected compounds compared to the unprotected control compounds. The increased stability improves the accuracy of incorporation pulse calling through reduction of photophysical pulse splitting.

Figure 9A:
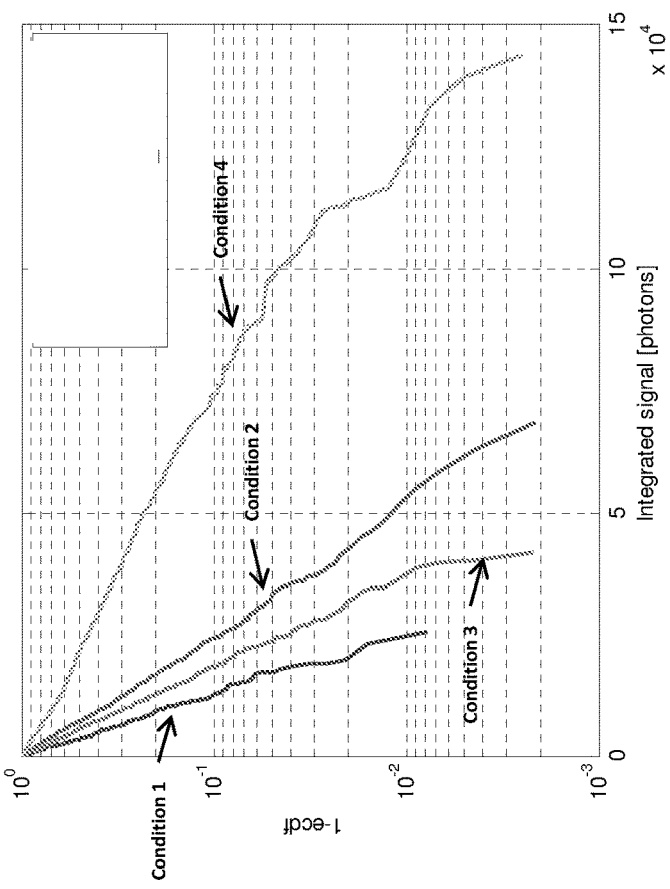
FIGS. 9A-9C illustrate a decrease in the occurrence of photodamage for protected compounds under longer sequencing times.
Figure 9B:
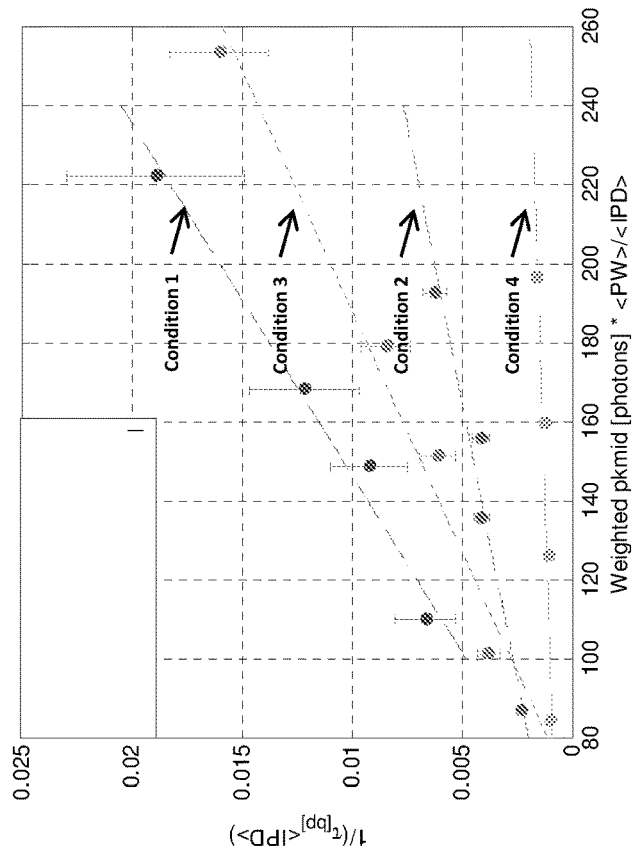
Figure 9C:
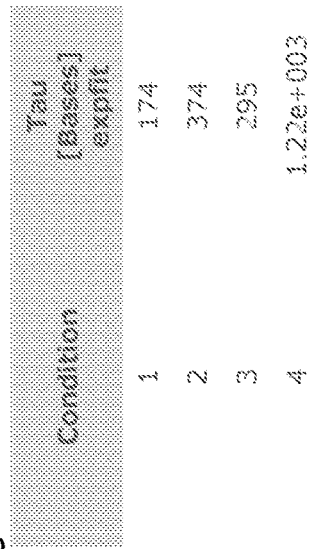

FIGS. 9A-9C demonstrate a decrease in the occurrence of photodamage in the sequencing reactions when using the protective compounds. In particular, these results demonstrate a decrease in photodamage to DNA polymerase, a critical factor in obtaining maximal readlengths with single-molecule real-time sequencing methods. FIG. 9A shows a plot of the inverse of the photodamage component of the overall polymerase lifetime (in bases incorporated) as a function of the photons received by the system (normalized by the difference in kinetics (pulsewidths and IPDs) between conditions). The slope of the resulting lines represents the overall rate of photodamage for particular condition. FIG. 9B shows a plot of the probability of polymerase survival (logarithmic scale) as a function of the photons received by the system (linear scale). These results demonstrate a mitigation of photodamage in the system through the use of the protected fluorescent compounds and, in particular, an improved probability of survival for the DNA polymerase when using the protected compounds. An exponential fit of overall polymerase lifetime in bases is summarized in FIG. 9C for each condition. These results demonstrate that photodamage resulting from the fluorescent dye is significantly mitigated in the protected reagent compounds. Specifically, the overall photodamage tau improvement using protected versions of the A and C nucleotides (i.e., Compounds 3A and 3B, respectively) is approximately 7-fold.

Figure 10A:
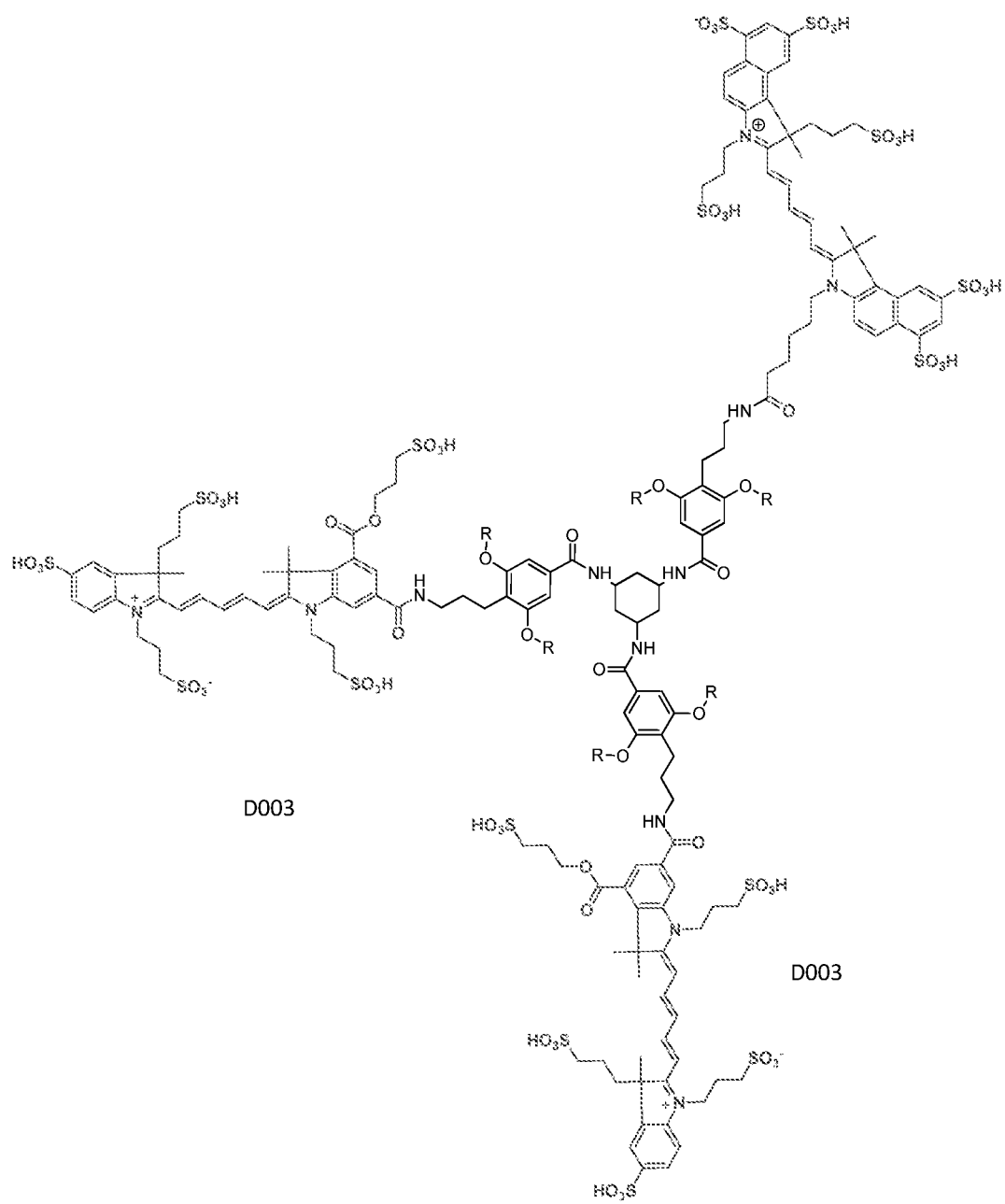
FIGS. 10A-10C demonstrate the effect of increased substitution of a protected compound containing a triple-layer shield on photodamage.
Figure 10A:
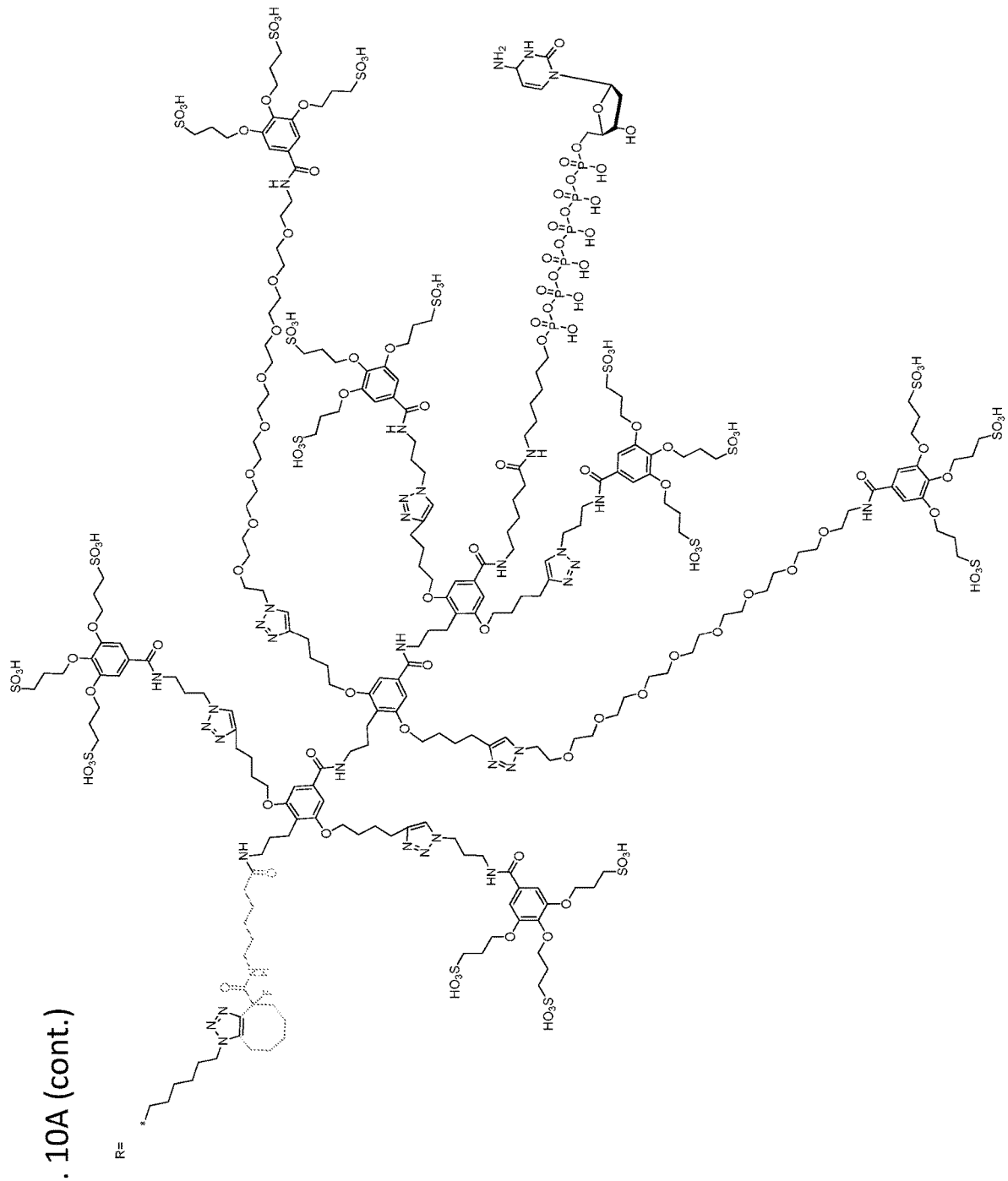
Figures 10B, 10C:
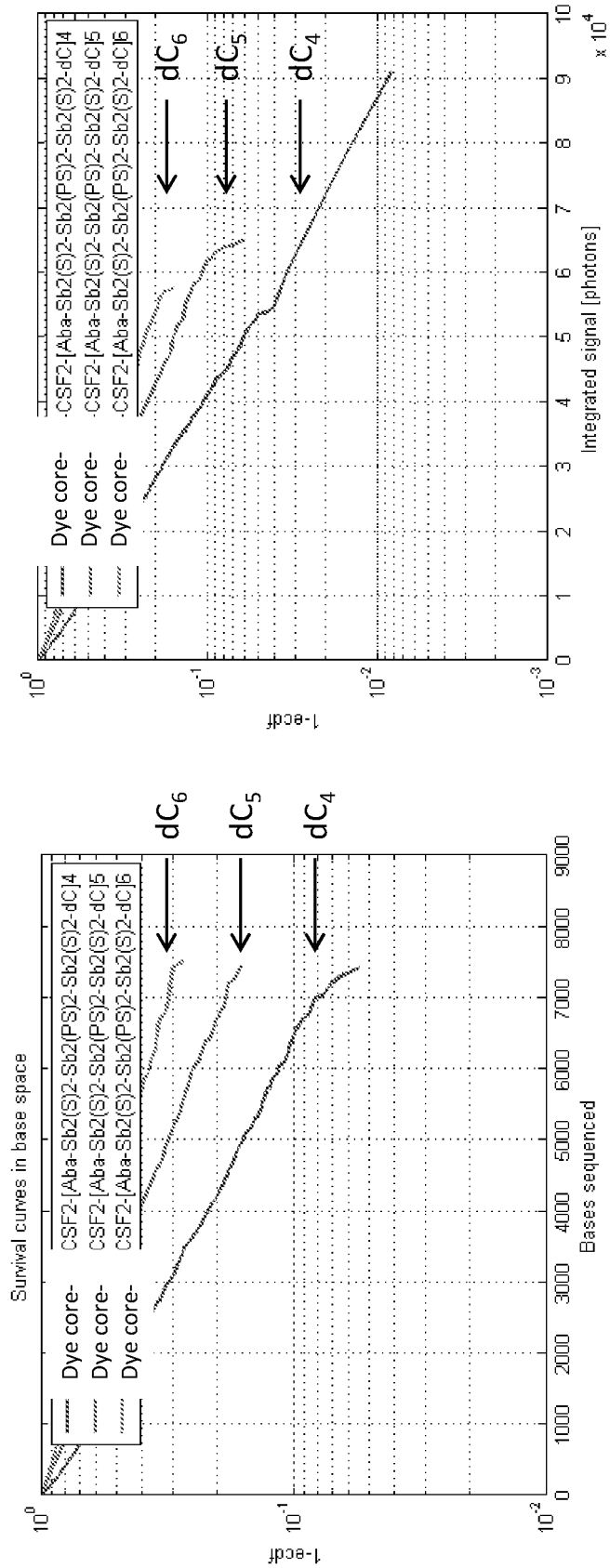

Example 8. Decreased Photodamage in Sequencing Reactions Using Protected Fluorescent Reagent Compounds with Increased Triple-Layer Shield Number FIGS. 10A-10C illustrate the protective effects of increasing numbers of a triple-layered shield element in protected reagent compounds used for single-molecule real-time DNA sequencing reactions. FIG. 10A shows the common structural features of the tested protected compounds. Specifically, the tested compounds contained a dye core comprising two donor fluorophores ("D003") and one acceptor fluorophore ("D006"), as shown on the left side of the figure. The six "R" groups in the dye core structure represent the shield element-binding element component of the structures, as shown on the right side of the figure. Cycloalkyne-substituted shield element-binding element components were coupled to an azide-substituted dye core precursor compound using a copper-free click reaction. As shown, the compounds comprise a "triple-layer" shield element that is terminated with a deoxycytosine binding element. The tested compounds contained either 4, 5, or 6 of the shown R groups attached to the dye core. These compounds were purified from one another following the click reaction using ion-exchange chromatography. The purified compounds were characterized by a combination of enzymatic digestion (to determine nucleotide concentration) and absorbance (to determine dye core concentration).

FIG. 10B shows the results of sequencing reactions, performed as described in Example 6, but with 100 nM of the above-described protected deoxycytosine reagent compounds and 150 nM of protected sequencing reagents corresponding to the other three bases. As shown, the compounds with higher substitution of the shield elements show an increased probability of polymerase survival (logarithmic scale) as a function of bases sequenced (left panel) and photons received (right panel). FIG. 10C shows an exponential fit of overall polymerase lifetime for each of the compounds from the experiments of FIG. 10B. These results demonstrate a mitigation of photodamage in the system through the use of the compounds with increased substitution of shield layers.

All patents, patent publications, and other published references mentioned herein are hereby incorporated by reference in their entireties as if each had been individually and specifically incorporated by reference herein.

While specific examples have been provided, the above description is illustrative and not restrictive. Any one or more of the features of the previously described embodiments can be combined in any manner with one or more features of any other embodiments in the present invention. Furthermore, many variations of the invention will become apparent to those skilled in the art upon review of the specification. The scope of the invention should, therefore, be determined by reference to the appended claims, along with their full scope of equivalents.

What is claimed is:

1. A compound of structural formula (I):

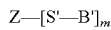  (I); wherein

Z is a multivalent central core element comprising a non-fluorescent multivalent central core element and a fluorescent dye element;

each S' is independently an intermediate chemical group, wherein at least one S' comprises a shield element, wherein the shield element comprises a shield core element and a side chain;

each B' is independently a terminal chemical group, wherein at least one B' comprises a binding element; and m is an integer from 2 to 24.

2. The compound of claim 1, wherein the shield element decreases photodamage of the compound or of a biomolecule associated with the binding element.

3. The compound of claim 1, wherein the shield element decreases contact between the fluorescent dye element and the binding element.

4. The compound of claim 1, wherein the shield element comprises a plurality of side chains.

5. The compound of claim 4, wherein at least one side chain has a molecular weight of at least 300.

6. The compound of claim 4, wherein at least one side chain comprises a dendrimer.

7. The compound of claim 4, wherein at least one side chain comprises a negatively-charged component.

8. The compound of claim 1, wherein the shield element comprises an inner layer and an outer layer.

9. The compound of claim 1, wherein the binding element comprises a nucleotide.

10. The compound of claim 1, wherein the binding element comprises biotin.

11. The compound of claim 1, wherein the binding element comprises a polyphosphate.

12. The compound of claim 1, wherein Z comprises a branching element.

13. The compound of claim 1, wherein m is an integer from 2 to 12.

14. The compound of claim 1, wherein the fluorescent dye element is a cyanine dye.

15. The compound of claim 1, wherein Z comprises a linker group.

16. The compound of claim 1 having structural formula (IIa) or (IIb):

wherein
X is the non-fluorescent multivalent central core element;
at least one D is the fluorescent dye element;
at least one W, if present, is a branching element;
n is an integer from 2 to 6;
each o is independently an integer from 1 to 4; and
each p is independently an integer from 1 to 4.

17. The compound of claim 16, wherein X comprises a polyamine.

18. The compound of claim 16, comprising at least one donor fluorophore and at least one acceptor fluorophore.

19. The compound of claim 16, wherein the shield element comprises a plurality of side chains.

20. The compound of claim 16, wherein the shield element comprises an inner layer and an outer layer.

21. The compound of claim 16, wherein n is an integer from 2 to 4.

22. The compound of claim 16, wherein each o is independently an integer from 1 to 3.

23. The compound of claim 16, wherein each p is independently an integer from 1 to 3.

24. The compound of claim 1 having structural formula (III):

wherein
X is the non-fluorescent multivalent central core element;
at least one D is the fluorescent dye element;
at least one W is a branching element;
n is an integer from 2 to 6;
each p' is independently an integer from 1 to 4; and
each p" is independently an integer from 1 to 4.

25. The compound of claim 24, wherein X comprises a polyamine.

26. The compound of claim 24, comprising at least one donor fluorophore and at least one acceptor fluorophore.

27. The compound of claim 24, wherein the shield element comprises a plurality of side chains.

28. The compound of claim 24, wherein the shield element comprises an inner layer and an outer layer.

29. The compound of claim 24, wherein n is an integer from 2 to 4.

30. The compound of claim 24, wherein each p' is independently an integer from 1 to 3.

31. The compound of claim 24, wherein each p" is independently an integer from 1 to 3.

* * * * *